(12) United States Patent
Simmons et al.

(10) Patent No.: US 11,771,123 B2
(45) Date of Patent: *Oct. 3, 2023

(54) METHODS FOR TREATING BIOMASS TO PRODUCE OLIGOSACCHARIDES AND RELATED COMPOSITIONS

(71) Applicant: Cambridge Glycoscience Ltd, Cambridge (GB)

(72) Inventors: Thomas J. Simmons, Cambridge (GB); Jeremy Bartosiak-Jentys, Chester (GB); Aleksandra Wlodek, Sawston (GB); Gustavo Valente, Newcastle upon Tyne (GB)

(73) Assignee: CAMBRIDGE GLYCOSCIENCE LTD, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/846,188

(22) Filed: Jun. 22, 2022

(65) Prior Publication Data

US 2022/0408775 A1    Dec. 29, 2022

Related U.S. Application Data

(63) Continuation of application No. 17/691,931, filed on Mar. 10, 2022, which is a continuation of application (Continued)

(30) Foreign Application Priority Data

Aug. 16, 2019  (GB) ..................................... 1911762
Aug. 16, 2019  (GB) ..................................... 1911764
Feb. 19, 2020  (GB) ..................................... 2002315

(51) Int. Cl.
*A23K 20/189*  (2016.01)
*A23L 29/30*   (2016.01)
(Continued)

(52) U.S. Cl.
CPC .............. *A23L 29/30* (2016.08); *A23L 7/126* (2016.08); *A23L 7/135* (2016.08); *A23L 27/33* (2016.08);
(Continued)

(58) Field of Classification Search
CPC .......... A23L 29/30; A23L 7/135; A23L 7/126; A23L 27/33; A23L 27/63; A23L 29/262;
(Continued)

(56) References Cited

U.S. PATENT DOCUMENTS 6,667,066 B2  12/2003  Labeille et al.
7,033,626 B2  4/2006  Spendler et al.
(Continued)

FOREIGN PATENT DOCUMENTS

CA    2831543 A1    10/2012
CN    101899488 A    12/2010
(Continued)

OTHER PUBLICATIONS

Translation of JP-2008120789-A (Year: 2008).*
(Continued)

*Primary Examiner* — Brent T O'Hern
(74) *Attorney, Agent, or Firm* — Wilson Sonsini Goodrich & Rosati

(57) ABSTRACT

Methods of forming an ingredient for human consumption are provided herein. The methods may include isolating one or more soluble polysaccharides from a biomass, generating one or more oligosaccharides from the biomass, and combining the one or more isolated soluble polysaccharides with the generated oligosaccharides to form the ingredient. Methods of pretreating a biomass are also provided. The methods may include administering a physical pretreatment to a biomass, administering a gentle pretreatment to the physically pretreated biomass, and administering a strong pre-
(Continued)

treatment to the gently pretreated biomass. Ingredients for human consumption are also provided.

17 Claims, 15 Drawing Sheets

Specification includes a Sequence Listing.

Related U.S. Application Data

No. 17/083,121, filed on Oct. 28, 2020, now Pat. No. 11,297,865, which is a continuation of application No. PCT/EP2020/072929, filed on Aug. 14, 2020.

(51) Int. Cl.
| | | |
|---|---|---|
| *A23L 7/135* | (2016.01) | |
| *A23L 7/126* | (2016.01) | |
| *A23L 27/30* | (2016.01) | |
| *A23L 27/60* | (2016.01) | |
| *A23L 29/262* | (2016.01) | |
| *C12P 19/02* | (2006.01) | |
| *C12P 19/12* | (2006.01) | |
| *C12P 19/14* | (2006.01) | |

(52) U.S. Cl.
CPC ............. *A23L 27/63* (2016.08); *A23L 29/262* (2016.08); *C12P 19/02* (2013.01); *C12P 19/12* (2013.01); *C12P 19/14* (2013.01); *A23V 2002/00* (2013.01)

(58) Field of Classification Search
CPC ........... C12P 19/02; C12P 19/12; C12P 19/14; A23V 2002/00
USPC .......................................................... 426/5
See application file for complete search history.

(56) References Cited

U.S. PATENT DOCUMENTS

| | | |
|---|---|---|
| 7,151,079 B2 | 12/2006 | Fack et al. |
| 7,378,103 B2 | 5/2008 | Kanji et al. |
| 7,598,069 B2 | 10/2009 | Felby et al. |
| 7,754,456 B2 | 7/2010 | Penttila et al. |
| 7,993,463 B2 | 8/2011 | Griffin et al. |
| 7,993,890 B2 | 8/2011 | Soerensen et al. |
| 8,057,840 B2 | 11/2011 | Harrison et al. |
| 8,202,842 B2 | 6/2012 | Sinclair et al. |
| 8,247,200 B2 | 8/2012 | Foody et al. |
| 8,663,952 B2 | 3/2014 | He et al. |
| 8,679,794 B2 | 3/2014 | Muniglia et al. |
| 8,709,763 B2 | 4/2014 | Lali et al. |
| 8,894,771 B2 | 11/2014 | Floyd et al. |
| 8,927,038 B2 | 1/2015 | Broekaert et al. |
| 8,956,846 B2 | 2/2015 | Ben Chaabane et al. |
| 9,062,328 B2 | 6/2015 | Medoff |
| 9,090,916 B2 | 7/2015 | Casanave et al. |
| 9,113,652 B2 | 8/2015 | Pilling et al. |
| 9,150,895 B2 | 10/2015 | Kurihara et al. |
| 9,410,216 B2 | 8/2016 | Eyal et al. |
| 9,458,482 B2 | 10/2016 | Bals et al. |
| 9,580,729 B2 | 2/2017 | Noda et al. |
| 9,605,291 B2 | 3/2017 | Yamada et al. |
| 9,663,836 B2 | 5/2017 | Jansen et al. |
| 9,670,516 B2 | 6/2017 | Minamino et al. |
| 9,783,860 B2 | 10/2017 | Floyd et al. |
| 9,797,021 B2 | 10/2017 | Floyd et al. |
| 9,920,309 B2 | 3/2018 | Reisinger et al. |
| 9,920,346 B2 | 3/2018 | Funada et al. |
| 9,955,707 B2 | 5/2018 | Delbaere |
| 9,963,725 B2 | 5/2018 | Lali et al. |
| 9,963,728 B2 | 5/2018 | Minamino et al. |
| 9,982,280 B2 | 5/2018 | Noordam et al. |
| 9,988,657 B2 | 6/2018 | Nagy et al. |
| 10,041,138 B1 | 8/2018 | Eyal et al. |
| 10,131,923 B2 | 11/2018 | Noordam et al. |
| 10,167,576 B2 | 1/2019 | Chao et al. |
| 10,174,351 B2 | 1/2019 | Smits et al. |
| 10,253,343 B2 | 4/2019 | Yamada et al. |
| 10,351,633 B2 | 7/2019 | Cheng et al. |
| 10,368,569 B2 | 8/2019 | Toksoz et al. |
| 10,426,791 B2 | 10/2019 | Speelmans et al. |
| 10,428,362 B2 | 10/2019 | Nagy et al. |
| 10,472,657 B2 | 11/2019 | Nagy et al. |
| 10,487,369 B2 | 11/2019 | Floyd et al. |
| 10,557,153 B2 | 2/2020 | De et al. |
| 10,563,238 B2 | 2/2020 | Yamada et al. |
| 10,570,432 B2 | 2/2020 | Nishino et al. |
| 10,633,461 B2 | 4/2020 | Richard et al. |
| 10,752,705 B2 | 8/2020 | Geremia et al. |
| 10,858,712 B2 | 12/2020 | Kilambi et al. |
| 11,006,658 B2 | 5/2021 | Simmons |
| 11,134,709 B2 | 10/2021 | Hofmekler |
| 11,151,848 B2 | 10/2021 | Strong et al. |
| 11,180,786 B2 | 11/2021 | Cao et al. |
| 11,193,005 B2 | 12/2021 | Behabtu |
| 11,208,674 B2 | 12/2021 | Konishi et al. |
| 11,248,247 B2 | 2/2022 | Simmons |
| 11,253,818 B2 | 2/2022 | Kurihara et al. |
| 11,254,957 B2 | 2/2022 | Retsina et al. |
| 11,279,960 B2 | 3/2022 | Kasahara et al. |
| 11,297,865 B2 | 4/2022 | Simmons et al. |
| 11,596,165 B2 | 3/2023 | Simmons |
| 2003/0091691 A1 | 5/2003 | Olsen et al. |
| 2004/0258829 A1 | 12/2004 | Zheng et al. |
| 2007/0248649 A1 | 10/2007 | Sawatzki et al. |
| 2008/0102163 A1 | 5/2008 | O'Toole et al. |
| 2009/0042266 A1 | 2/2009 | Vehmaanpera et al. |
| 2009/0062232 A1 | 3/2009 | Fujikawa et al. |
| 2009/0305935 A1 | 12/2009 | Cascao-Pereira et al. |
| 2011/0143402 A1 | 6/2011 | De Laat et al. |
| 2011/0171710 A1 | 7/2011 | Yu et al. |
| 2012/0035127 A1 | 2/2012 | Goffin et al. |
| 2012/0115192 A1 | 5/2012 | Lali et al. |
| 2012/0135500 A1 | 5/2012 | Aehle et al. |
| 2012/0231147 A1 | 9/2012 | Srinivasan et al. |
| 2012/0264873 A1 | 10/2012 | Eyal et al. |
| 2013/0095531 A1 | 4/2013 | Schooneveld-Bergmans et al. |
| 2013/0157318 A1 | 6/2013 | Ishikawa et al. |
| 2013/0164420 A1 | 6/2013 | Catani et al. |
| 2015/0065454 A1 | 3/2015 | Dupasquier et al. |
| 2016/0007642 A1 | 1/2016 | Geremia et al. |
| 2016/0081381 A1 | 3/2016 | Medoff |
| 2016/0082022 A1 | 3/2016 | Medoff |
| 2016/0208300 A1 | 7/2016 | Yamada et al. |
| 2016/0326559 A1 | 11/2016 | Funada et al. |
| 2016/0340705 A1 | 11/2016 | Lali et al. |
| 2017/0114371 A1 | 4/2017 | Pedersen et al. |
| 2017/0295805 A1 | 10/2017 | Abu-Hardan et al. |
| 2017/0303548 A1 | 10/2017 | Krogh et al. |
| 2017/0303550 A1 | 10/2017 | Abu-Hardan et al. |
| 2018/0134741 A1 | 5/2018 | Falck |
| 2019/0029272 A1 | 1/2019 | Niemann |
| 2019/0153555 A1 | 5/2019 | Eyal et al. |
| 2019/0233862 A1 | 8/2019 | Cao et al. |
| 2019/0281874 A1 | 9/2019 | Davidek et al. |
| 2020/0071736 A1 | 3/2020 | Hammerer et al. |
| 2020/0113215 A1 | 4/2020 | Hofmekler |
| 2020/0123577 A1 | 4/2020 | De Laat et al. |
| 2020/0128860 A1 | 4/2020 | Hofmekler |
| 2020/0216574 A1 | 7/2020 | Richard et al. |
| 2020/0263265 A1 | 8/2020 | Wu et al. |
| 2020/0299791 A1 | 9/2020 | McKay et al. |
| 2020/0308212 A1 | 10/2020 | Falck |
| 2020/0352203 A1 | 11/2020 | Simmons |
| 2021/0010043 A1 | 1/2021 | Simmons |
| 2021/0120855 A1 | 4/2021 | Park et al. |
| 2021/0177021 A1 | 6/2021 | Simmons |
| 2021/0207321 A1 | 7/2021 | Loureiro et al. |
| 2021/0227853 A1 | 7/2021 | Pia |
| 2021/0253977 A1 | 8/2021 | Huang et al. |
| 2021/0315245 A1 | 10/2021 | Simmons |
| 2021/0347694 A1 | 11/2021 | Havenith et al. |

(56) References Cited

U.S. PATENT DOCUMENTS

| | | |
|---|---|---|
| 2021/0392931 A1 | 12/2021 | Simmons et al. |
| 2021/0395284 A1 | 12/2021 | Baur et al. |
| 2022/0017766 A1 | 1/2022 | Kalb |
| 2022/0132896 A1 | 5/2022 | Kannar et al. |
| 2022/0132897 A1 | 5/2022 | Simmons |
| 2022/0408775 A1* | 12/2022 | Simmons ............... A23L 29/30 |

FOREIGN PATENT DOCUMENTS

| | | |
|---|---|---|
| CN | 102925516 A | 2/2013 |
| CN | 106367449 A | 2/2017 |
| CN | 107746866 A | 3/2018 |
| CN | 108157664 A | 6/2018 |
| CN | 108588144 A | 9/2018 |
| EP | 1228098 B1 | 9/2006 |
| EP | 1466926 B1 | 8/2007 |
| EP | 1751296 B1 | 4/2009 |
| EP | 1699974 B1 | 7/2009 |
| EP | 2256208 A1 | 12/2010 |
| EP | 2235195 B1 | 7/2011 |
| EP | 2076271 B1 | 9/2011 |
| EP | 1871400 B1 | 10/2011 |
| EP | 1811038 B1 | 2/2012 |
| EP | 2225387 B1 | 9/2012 |
| EP | 2265127 B1 | 10/2013 |
| EP | 2665823 A1 | 11/2013 |
| EP | 2427565 B1 | 1/2014 |
| EP | 1977652 B1 | 3/2015 |
| EP | 3010352 A1 | 4/2016 |
| EP | 3013155 A1 | 5/2016 |
| EP | 3037005 A1 | 6/2016 |
| EP | 1706477 B1 | 10/2016 |
| EP | 2313514 B1 | 11/2016 |
| EP | 2784156 B1 | 6/2017 |
| EP | 2817374 B1 | 6/2017 |
| EP | 2996492 B1 | 7/2017 |
| EP | 3041941 B1 | 12/2017 |
| EP | 2548966 B1 | 7/2018 |
| EP | 2548965 B1 | 8/2018 |
| EP | 3374315 A1 | 9/2018 |
| EP | 2117322 B1 | 10/2018 |
| EP | 3177728 B1 | 10/2018 |
| EP | 3177729 B1 | 10/2018 |
| EP | 3182830 B1 | 10/2018 |
| EP | 3190189 B1 | 12/2018 |
| EP | 3415632 A1 | 12/2018 |
| EP | 3438272 A1 | 2/2019 |
| EP | 2734633 B1 | 5/2019 |
| EP | 2917359 B1 | 7/2019 |
| EP | 3511418 A1 | 7/2019 |
| EP | 3530743 A1 | 8/2019 |
| EP | 3541870 A1 | 9/2019 |
| EP | 2917355 B1 | 10/2019 |
| EP | 3088530 B1 | 4/2020 |
| EP | 3511418 B1 | 7/2020 |
| EP | 3737769 A1 | 11/2020 |
| EP | 3010352 B1 | 12/2020 |
| EP | 3784045 A1 | 3/2021 |
| EP | 3815540 A1 | 5/2021 |
| EP | 3960772 A1 | 3/2022 |
| EP | 3981379 A2 | 4/2022 |
| EP | 3993644 A1 | 5/2022 |
| EP | 3438272 B1 | 6/2022 |
| JP | 2003334000 A | 11/2003 |
| JP | 2006087319 A | 4/2006 |
| JP | 2008120789 A * | 5/2008 |
| JP | 2009089626 A | 4/2009 |
| JP | 2009125064 A | 6/2009 |
| JP | 2010200720 A | 9/2010 |
| JP | 2010215556 A | 9/2010 |
| JP | 2010226995 A | 10/2010 |
| JP | 2012527886 A | 11/2012 |
| JP | 2017502701 A | 1/2017 |
| KR | 20190133438 A | 12/2019 |
| WO | WO-2012133495 A1 | 10/2012 |
| WO | WO-2012141256 A1 | 10/2012 |
| WO | WO-2013016115 A1 | 1/2013 |
| WO | WO-2013096603 A2 | 6/2013 |
| WO | WO-2013159005 A2 | 10/2013 |
| WO | WO-2014170498 A1 | 10/2014 |
| WO | WO-2015107413 A1 | 7/2015 |
| WO | WO-2017057718 A1 | 4/2017 |
| WO | WO-2017107527 A1 | 6/2017 |
| WO | WO-2018106656 A1 | 6/2018 |
| WO | WO-2019010336 A1 | 1/2019 |
| WO | WO-2019055717 A1 | 3/2019 |
| WO | WO-2019102218 A2 | 5/2019 |
| WO | WO-2019138024 A1 | 7/2019 |
| WO | WO-2019162416 A1 | 8/2019 |
| WO | WO-2019227525 A1 | 12/2019 |
| WO | WO-2019229228 A1 | 12/2019 |
| WO | WO-2019239366 A1 | 12/2019 |
| WO | WO-2020009964 A1 | 1/2020 |
| WO | WO-2020035599 A1 | 2/2020 |
| WO | WO-2020097458 A1 | 5/2020 |
| WO | WO-2021032647 A1 | 2/2021 |
| WO | WO-2021074271 A1 | 4/2021 |
| WO | WO-2021074316 A1 | 4/2021 |
| WO | WO-2021116437 A2 | 6/2021 |
| WO | WO-2021116437 A3 | 7/2021 |
| WO | WO-2021140225 A1 | 7/2021 |
| WO | WO-2021243151 A1 | 12/2021 |
| WO | WO-2021257921 A1 | 12/2021 |
| WO | WO-2022034078 A1 | 2/2022 |
| WO | WO-2022060726 A1 | 3/2022 |
| WO | WO-2022067131 A1 | 3/2022 |
| WO | WO-2022069084 A1 | 4/2022 |
| WO | WO-2022073646 A1 | 4/2022 |

OTHER PUBLICATIONS

Basholli-Salihu et al. The Use of Cellobiose and Fructooligosaccharide on Growth and Stability of Bifidobacterium infantis in Fermented Milk. Food and Nutrition Sciences, 2013, 4, 1301-1306. Published Online Dec. 2013. DOI: http://dx.doi.org/10.4236/fns. 2013.412167.

Beldman et al. Application of cellulase and pectinase from fungal origin for the liquefaction and saccharification of biomass. Enzyme and Microbial Technology, vol. 6, Issue 11, pp. 503-507 (Nov. 1984). DOI: https://doi.org/10.1016/0141-0229(84)90004-8.

Brijwani et al. Production of a cellulolytic enzyme system in mixed-culture solid-state fermentation of soybean hulls supplemented with wheat bran. Process Biochemistry, vol. 45, No. 1, 120-128 (2010).

Chen et al. Characterization of a novel xylanase from Aspergillus flavus with the unique properties in production of xylooligosaccharides. J Basic Microbiol. Apr. 2019;59(4):351-358. doi: 10.1002/jobm.201800545. Epub Feb. 12, 2019.

Chica, et al. Semi-rational approaches to engineering enzyme activity: combining the benefits of directed evolution and rational design. Curr Opin Biotechnol. Aug. 2005;16(4):378-84.

Dallabernardina et al. Mixed-Linkage Glucan Oligosaccharides Produced by Automated Glycan Assembly Serve as Tools To Determine the Substrate Specificity of Lichenase. Chemistry. Mar. 2, 2017;23(13):3191-3196. doi: 10.1002/chem.201605479. Epub Feb. 3, 2017.

Danneels et al. A quantitative indicator diagram for lytic polysaccharide monooxygenases reveals the role of aromatic surface residues in HjLPMO9A regioselectivity. PLoS One. 2017; 12(5): e0178446. Published online May 31, 2017. doi: 10.1371/journal.pone. 0178446.

De La Fuente et al. Development of a robust method for the quantitative determination of disaccharides in honey by gas chromatography. J Chromatogr A, 1135 (2006) 212-218.

Dos Santos et al. Structural basis for xyloglucan specificity and α-d-Xylp(1 → 6)-D-Glcp recognition at the −1 subsite within the GH5 family. Biochemistry. Mar. 17, 2015;54(10):1930-42. doi: 10.1021/acs.biochem.5b00011. Epub Mar. 6, 2015.

(56) References Cited

OTHER PUBLICATIONS

EFSA Panel on Dietetic Products, Nutrition and Allergies (NDA) (2018). Safety of xylo-oligosaccharides (XOS) as a novel food pursuant to Regulation (EU) 2015/2283: (Scientific Opinion). E F S A Journal, 16(7), [5361]. DOI: https://doi.org/10.2903/j.efsa.2018. 5361. 20 pages.
El Khoury et al. Beta Glucan: Health Benefits in Obesity and Metabolic Syndrome. J Nutr Metab. 2012; 2012: 851362. Published online Dec. 11, 2011. doi: 10.1155/2012/851362. 28 pages.
EP18157957.4 Extended European Search Report dated Jul. 13, 2018.
Falck et al. Arabinoxylanase from glycoside hydrolase family 5 is a selective enzyme for production of specific arabinoxylooligosaccharides. Food Chem. Mar. 1, 2018;242:579-584. doi: 10.1016/j. foodchem.2017.09.048. Epub Sep. 12, 2017.
Fanuel et al. The Podospora anserina lytic polysaccharide monooxygenase PaLPMO9H catalyzes oxidative cleavage of diverse plant cell wall matrix glycans. Biotechnol Biofuels. 2017; 10: 63. Published online Mar. 11, 2017. doi: 10.1186/s13068-017-0749-5.
Gorton. Spare the sugar, bakingbusiness.com. Mar. 31, 2013. Retrieved Sep. 16, 2020 from: https://www.bakingbusiness.com/articles/34774-spare-the-sugar. 8 pages.
Goubet et al. Polysaccharide analysis using carbohydrate gel electrophoresis: a method to study plant cell wall polysaccharides and polysaccharide hydrolases. Anal Biochem. Jan. 1, 2002;300(1):53-68.
GRAS Notification—Claim of GRAS Status (Revised May 21, 2010), Claim of Exemption from the Requirement for Premarket Approval Requirements Pursuant to Proposed 21 CFR § 170. 36(c)(1), pp. 000007 and 000015. EAS Consulting Group, LLC, Alexandria, Virginia, USA. Retrieved Dec. 2 from URL: http://wayback.archive-it.org/7993/20171031045331/https://www.fda.gov/downloads/Food/IngredientsPackagingLabeling/GRAS/NoticeInventory/UCM269544.pdf.
Greek Yogurt with Honey Base, Database Accession No. 4046243, Database GNPD online (Jun. 6, 2016). Mintel. 4 pages.
Gupta et al. Xylooligosaccharide—A Valuable Material from Waste to Taste: A Review. J Environ Res Develop, vol. 10, No. 3, pp. 555-563 (Jan.-Mar. 2016).
Hakala et al. Enzyme-aided alkaline extraction of oligosaccharides and polymeric xylan from hardwood kraft pulp. Carbohydr Polym. Mar. 1, 2013;93(1):102-8. doi: 10.1016/j.carbpol.2012.05.013. Epub May 11, 2012.
Hang et al. Enzymatic Production of Soluble Sugars from Corn Husks. LWT—Food Science and Technology, vol. 32, Issue 4, pp. 208-210 (Jun. 1999). DOI: https://doi.org/10.1006/fstl.1998.0530.
Jayapal et al. Value addition to sugarcane bagasse: Xylan extraction and its process optimization for xylooligosaccharides production. Industrial Crops and Products, vol. 42, pp. 14-24 (2013).
Karadeniz et al. Sugar composition of apple juices. European Food Research and Technology, vol. 215, pp. 145-148 (2002).
Kracher et al. Active-site copper reduction promotes substrate binding of fungal lytic polysaccharide monooxygenase and reduces stability. J Biol Chem. Feb. 2, 2018; 293(5): 1676-1687. Published online Dec. 19, 2017. doi: 10.1074/jbc.RA117.000109.
Kuhad et al. Microbial Cellulases and Their Industrial Applications. Enzyme Res. 2011; 2011: 280696. Published online Sep. 7, 2011. doi: 10.4061/2011/280696.
Lecumberri et al. A diet rich in dietary fiber from cocoa improves lipid profile and reduces malondialdehyde in hypercholesterolemic rats. Nutrition. Apr. 2007;23(4):332-41. doi: 10.1016/j.nut.2007.01. 013. Epub Mar. 23, 2007.
Linares-Pastén et al. Structural Considerations on the Use of Endo-Xylanases for the Production of prebiotic Xylooligosaccharides from Biomass. Curr Protein Pept Sci. Jan. 2018; 19(1): 48-67. Published online Jan. 2018. doi: 10.2174/1389203717666160923155209.
Loose et al. Activation of bacterial lytic polysaccharide monooxygenases with cellobiose dehydrogenase. Protein Sci. Dec. 2016; 25(12): 2175-2186. Published online Sep. 26, 2016. doi: 10.1002/pro.3043.

Maehara et al. GH30 Glucuronoxylan-Specific Xylanase from Streptomyces turgidiscabies C56. Appl Environ Microbiol. Feb. 15, 2018; 84(4): e01850-17. Published online Jan. 31, 2018. Prepublished online Nov. 27, 2017.
Mathew et al. Xylo- and arabinoxylooligosaccharides from wheat bran by endoxylanases, utilisation by probiotic bacteria, and structural studies of the enzymes. Appl Microbiol Biotechnol. Apr. 2018;102(7):3105-3120. doi: 10.1007/s00253-018-8823-x. Epub Feb. 14, 2018.
Meier et al. Oxygen Activation by Cu LPMOs in Recalcitrant Carbohydrate Polysaccharide Conversion to Monomer Sugars. Chem Rev. Mar. 14, 2018; 118(5): 2593-2635. Published online Nov. 20, 2017. doi: 10.1021/acs.chemrev.7b00421.
Motta et al. Chapter 10: "A Review of Xylanase Production by the Fermentation of Xylan: Classification, Characterization and Applications," pp. 251-275. In Sustainable Degradation of Lignocellulosic Biomass, Chandel and Da Silva, eds. (May 15, 2013).
Nordberg Karlsson et al. Endo-xylanases as tools for production of substituted xylooligosaccharides with prebiotic properties. Appl Microbiol Biotechnol. 2018; 102(21): 9081-9088. Published online Sep. 8, 2018. doi: 10.1007/S00253-018-9343-4.
Park et al. Effect of fructo-oligosaccharide and isomalto-oligosaccharide addition on baking quality of frozen dough. Food Chem. Dec. 15, 2016;213:157-162. doi: 10.1016/j.foodchem.2016. 06.067. Epub Jun. 21, 2016.
PCT/EP2019/054380 International Search Report and Written Opinion dated Jun. 27, 2019.
PCT/EP2019/072026 International Search Report and Written Opinion dated Dec. 2, 2019.
PCT/EP2020/072929 International Search Report and Written Opinion dated Dec. 8, 2020.
PCT/EP2020/085810 International Search Report and Written Opinion dated Jun. 9, 2021.
PCT/EP2021/050311 International Search Report and Written Opinion dated May 3, 2021.
Qi et al. Application of ultrafiltration and nanofiltration for recycling cellulase and concentrating glucose from enzymatic hydrolyzate of steam exploded wheat straw. Bioresour Technol. Jan. 2012;104:466-72. doi: 10.1016/j.biortech.2011.10.049. Epub Oct. 31, 2011.
Qing et al. "Chapter 19: Xylooligosaccharides Production, Quantification, and Characterization in Context of Lignocellulosic Biomass Pretreatment," pp. 391-415. In Aqueous Pretreatment of Plant Biomass for Biological and Chemical Conversion to Fuels and Chemicals, First Edition. Edited by Charles E. Wyman (2013).
Schmiele et al. Mixolab™ for rheological evaluation of wheat flour partially replaced by soy protein hydrolysate and fructooligosaccharides for bread production. LWT—Food Science and Technology, vol. 76, Part B, pp. 259-269 (Mar. 2017). Available online Jul. 5, 2016. DOI: https://doi.org/10.1016/j.lwt.2016.07.014.
Short-Chain Fructooligosaccharides: Handling/Processing. Technical Evaluation Report. U.S. Department of Agriculture (USDA) Agricultural Marketing Service (AMS). Aug. 11, 2006. Retrieved Sep. 16, 2020 from URL: https://www.ams.usda.gov/sites/default/files/media/Fructooligosaccharides%20TR.pdf, 7 pages.
Simmons et al. An unexpectedly lichenase-stable hexasaccharide from cereal, horsetail and lichen mixed-linkage β-glucans (MLGs): implications for MLG subunit distribution. Phytochemistry. Nov. 2013;95:322-32. doi: 10.1016/j.phytochem.2013.08.003. Epub Sep. 8, 2013.
Simmons et al. Bonds broken and formed during the mixed-linkage glucan : xyloglucan endotransglucosylase reaction catalysed by Equisetum hetero-trans-β-glucanase.Biochem J. Apr. 1, 2017; 474(7): 1055-1070. Published online Mar. 8, 2017. Prepublished online Jan. 20, 2017. doi: 10.1042/BCJ20160935.
Simmons et al. Structural and electronic determinants of lytic polysaccharide monooxygenase reactivity on polysaccharide substrates. Nat Commun. 2017; 8: 1064. Published online Oct. 20, 2017. doi: 10.1038/s41467-017-01247-3.
Singh et al. Protein Engineering Approaches in the Post-Genomic Era. Curr Protein Pept Sci. 18: 1-11 (2017).
Sun et al. Hydrolysis of lignocellulosic materials for ethanol production: a review. Bioresour Technol. May 2002;83(1):1-11. doi: 10.1016/s0960-8524(01)00212-7.

(56) References Cited

OTHER PUBLICATIONS

Tanaka et al. Creation of cellobiose and xylooligosaccharides-coutilizing *Escherichia coli* displaying both β-glucosidase and β-xylosidase on its cell surface. ACS Synth. Biol. 2014, 3, 7, 446-453. Published online Oct. 24, 2013. DOI: https://doi.org/10.1021/sb400070q.
U.S. Appl. No. 16/844,960 Notice of Allowance dated Feb. 3, 2021.
U.S. Appl. No. 16/844,960 Office Action dated Sep. 22, 2020.
U.S. Appl. No. 17/033,321 Office Action dated Aug. 2, 2021.
U.S. Appl. No. 17/033,321 Office Action dated Jan. 11, 2021.
Villares et al. Lytic polysaccharide monooxygenases disrupt the cellulose fibers structure. Sci Rep. 2017; 7: 40262. Published online Jan. 10, 2017. doi: 10.1038/srep40262.
Wang et al. Relative fermentation of oligosaccharides from human milk and plants by gut microbes. European Food Research and Technology, vol. 243, pp. 133-146 (2017). Published online Jun. 20, 2016.
Watanabe, Eiichi. Membrane Separation in Cellulose Saccharification and Mixed Enzyme Culture Liquid Recycling. [Medicine and Biology, vol. No. 119, Issue No. 3, Sep. 10, 1989]. 7 pages.
Xiao et al. Application of Xylo-oligosaccharide in modifying human intestinal function. African Journal of Microbiology Research 6(9):2116-2119 (Mar. 9, 2012).
Zhang et al. Hemicellulose isolation, characterization, and the production of xylo-oligosaccharides from the wastewater of a viscose fiber mill. Carbohydr Polym. May 5, 2016;141:238-43. doi: 10.1016/j.carbpol.2016.01.022. Epub Jan. 12, 2016.
Aachary et al. Xylooligosaccharides (XOS) as an Emerging Prebiotic: Microbial Synthesis, Utilization, Structural Characterization, Bioactive Properties, and Applications. Comprehensive Reviews in Food Science and Food Safety, vol. 10, pp. 2-16 (2011).
Bhale et al. Enzymatic activity of *Trichoderma* species. Novus Natural Science Research, 2012, vol. 1, No. 4. 8 pages.
Co-pending U.S. Appl. No. 17/691,931, inventors Simmons; Thomas J. et al., filed Mar. 10, 2022.
Co-pending U.S. Appl. No. 17/837,868, inventor Simmons; Thomas J., filed Jun. 10, 2022.
Co-pending U.S. Appl. No. 17/858,609, inventors Simmons; Thomas J. et al., filed Jul. 6, 2022.
Co-pending U.S. Appl. No. 17/865,142, inventors Bartosiak-jentys; Jeremy et al., filed Jul. 14, 2022.
Green et al. Industrial Fungal Enzymes: An Occupational Allergen Perspective. Journal of Allergy, vol. 2011, Article ID 682574, 11 pages.
Jousse et al. Simplified Kinetic Scheme of Flavor Formation by the Maillard Reaction. Journal of Food Science, vol. 67, No. 7, pp. 2534-2542 (2002).
Lu et al. Extraction and modification of hemicellulose from lignocellulosic biomass: A review. Green Processing and Synthesis 2021; 10: 779-804.
Réhault-Godbert et al. The Golden Egg: Nutritional Value, Bioactivities, and Emerging Benefits for Human Health. Nutrients 11, 684 (Mar. 22, 2019). 26 pages.
U.S. Appl. No. 17/033,321 Notice of Allowance dated Oct. 6, 2021.
U.S. Appl. No. 17/083,121 Notice of Allowance dated Aug. 23, 2021.
U.S. Appl. No. 17/083,121 Notice of Allowance dated Dec. 8, 2021.
U.S. Appl. No. 17/083,121 Office Action dated May 14, 2021.
U.S. Appl. No. 17/571,199 Office Action dated Apr. 28, 2022.
U.S. Appl. No. 17/229,628 Office Action dated Nov. 10, 2022.
U.S. Appl. No. 17/571,199 Notice of Allowance dated Feb. 7, 2023.
U.S. Appl. No. 17/571,199 Notice of Allowance dated Oct. 14, 2022.
U.S. Appl. No. 17/571,199 Office Action dated Sep. 7, 2022.
U.S. Appl. No. 17/837,868 Office Action dated Feb. 8, 2023.
U.S. Appl. No. 17/837,868 Office Action dated Oct. 5, 2022.
U.S. Appl. No. 17/229,628 Office Action dated Apr. 5, 2023.
U.S. Appl. No. 17/837,868 Office Action dated Jun. 5, 2023.
Maple et al. Detailed Tautomeric Equilibrium of Aqueous D-Glucose. Observation of Six Tautomers by Ultrahigh Resolution Carbon-13 Nmr. J Am Chem Soc 1987, 109, 3168-3169.
Senevirathne et al. Effect of Mixed Microbial Culture Treatment on the Nutritive Value of Coffee, Green Tea and Oolong Tea Residues and the Effect of the Fermented Residues on in Vitro Rumen Fermentation. APCBEE Procedia 4 (2012) 66-72.
U.S. Appl. No. 16/999,483 Office Action dated Jul. 28, 2023.
U.S. Appl. No. 17/229,628 Notice of Allowance dated Jun. 20, 2023.
Zivkovic et al. Bovine Milk as a Source of Functional Oligosaccharides for Improving Human Health. Adv Nutr 2:284-289 (2011).

\* cited by examiner

FIG. 10A

SEQUENCE LISTING

<160> NUMBER OF SEQ ID NOS: 25

<210> SEQ ID NO 1
<211> LENGTH: 293
<212> TYPE: PRT
<213> ORGANISM: Podospora anserina

```
<400> SEQUENCE: 1

Met Lys Gly Leu Leu Ser Val Ala Ala Leu Ser Leu Ala Val Ser Glu
1               5                   10                  15

Val Ser Ala His Tyr Ile Phe Gln Gln Leu Ser Thr Gly Ser Thr Lys
            20                  25                  30

His Gly Val Phe Gln Tyr Ile Arg Gln Asn Thr Asn Tyr Asn Ser Pro
        35                  40                  45

Val Thr Asp Leu Ser Ser Asn Asp Leu Arg Cys Asn Glu Gly Gly Ala
    50                  55                  60

Ser Gly Ala Asn Thr Gln Thr Val Thr Val Arg Ala Gly Asp Ser Phe
65                  70                  75                  80

Thr Phe His Leu Asp Thr Pro Val Tyr His Gln Gly Pro Val Ser Val
                85                  90                  95

Tyr Leu Ser Lys Ala Pro Gly Ser Ala Ser Ser Tyr Asp Gly Ser Gly
            100                 105                 110

Thr Trp Phe Lys Ile Lys Asp Trp Gly Pro Thr Phe Pro Gly Gly Gln
        115                 120                 125

Trp Thr Leu Ala Gly Ser Tyr Thr Ala Gln Leu Pro Ser Cys Ile Thr
    130                 135                 140

Asp Gly Glu Tyr Leu Leu Arg Ile Gln Ser Leu Gly Ile His Asn Pro
145                 150                 155                 160

Tyr Pro Ala Gly Thr Pro Gln Phe Tyr Ile Ser Cys Ala Gln Ile Lys
                165                 170                 175

Val Thr Gly Gly Gly Ser Val Asn Pro Ser Gly Val Ala Ile Pro Gly
            180                 185                 190

Ala Phe Lys Ala Thr Asp Pro Gly Tyr Thr Ala Asn Ile Tyr Ser Asn
        195                 200                 205

Phe Asn Ser Tyr Thr Val Pro Gly Pro Ser Val Phe Ser Cys Gly Ser
    210                 215                 220

Asn Gly Gly Gly Ser Ser Pro Val Glu Pro Gln Pro Gln Pro Thr Thr
225                 230                 235                 240

Thr Leu Val Thr Ser Thr Arg Ala Pro Val Ala Thr Gln Pro Ala Gly
                245                 250                 255

Cys Ala Val Ala Lys Trp Gly Gln Cys Gly Gly Asn Gly Trp Thr Gly
            260                 265                 270

Cys Thr Thr Cys Ala Ala Gly Ser Thr Cys Asn Thr Gln Asn Ala Tyr
        275                 280                 285

Tyr His Gln Cys Val
    290

<210> SEQ ID NO 2
<211> LENGTH: 242
<212> TYPE: PRT
<213> ORGANISM: Bacillus subtilis subsp. subtilis str. 168

<400> SEQUENCE: 2

Met Pro Tyr Leu Lys Arg Val Leu Leu Leu Leu Val Thr Gly Leu Phe
1               5                   10                  15

Met Ser Leu Phe Ala Val Thr Ala Thr Ala Ser Ala Gln Thr Gly Gly
            20                  25                  30

Ser Phe Phe Asp Pro Phe Asn Gly Tyr Asn Ser Gly Phe Trp Gln Lys
        35                  40                  45

Ala Asp Gly Tyr Ser Asn Gly Asn Met Phe Asn Cys Thr Trp Arg Ala
    50                  55                  60
```

```
Asn Asn Val Ser Met Thr Ser Leu Gly Glu Met Arg Leu Ala Leu Thr
 65                  70                  75                  80

Ser Pro Ala Tyr Asn Lys Phe Asp Cys Gly Glu Asn Arg Ser Val Gln
                 85                  90                  95

Thr Tyr Gly Tyr Gly Leu Tyr Glu Val Arg Met Lys Pro Ala Lys Asn
            100                 105                 110

Thr Gly Ile Val Ser Ser Phe Phe Thr Tyr Thr Gly Pro Thr Asp Gly
        115                 120                 125

Thr Pro Trp Asp Glu Ile Asp Ile Glu Phe Leu Gly Lys Asp Thr Thr
130                 135                 140

Lys Val Gln Phe Asn Tyr Tyr Thr Asn Gly Ala Gly Asn His Glu Lys
145                 150                 155                 160

Ile Val Asp Leu Gly Phe Asp Ala Ala Asn Ala Tyr His Thr Tyr Ala
                165                 170                 175

Phe Asp Trp Gln Pro Asn Ser Ile Lys Trp Tyr Val Asp Gly Gln Leu
                180                 185                 190

Lys His Thr Ala Thr Asn Gln Ile Pro Thr Thr Pro Gly Lys Ile Met
                195                 200                 205

Met Asn Leu Trp Asn Gly Thr Gly Val Asp Glu Trp Leu Gly Ser Tyr
210                 215                 220

Asn Gly Val Asn Pro Leu Tyr Ala His Tyr Asp Trp Val Arg Tyr Thr
225                 230                 235                 240

Lys Lys

<210> SEQ ID NO 3
<211> LENGTH: 948
<212> TYPE: PRT
<213> ORGANISM: Ruminiclostridium thermocellum

<400> SEQUENCE: 3

Met Gly Ala Ser Ile Lys Thr Ser Ile Lys Ile Arg Thr Val Ala Phe
 1               5                  10                  15

Val Ser Ile Ile Ala Ile Ala Leu Ser Ile Leu Ser Phe Ile Pro Asn
                20                  25                  30

Arg Ala Tyr Ala Ser Pro Gln Arg Gly Arg Pro Arg Leu Asn Ala Ala
            35                  40                  45

Arg Thr Thr Phe Val Gly Asp Asn Gly Gln Pro Leu Arg Gly Pro Tyr
 50                 55                  60

Thr Ser Thr Glu Trp Thr Ala Ala Pro Tyr Asp Gln Ile Ala Arg
 65                 70                  75                  80

Val Lys Glu Leu Gly Phe Asn Ala Val His Leu Tyr Ala Glu Cys Phe
                85                  90                  95

Asp Pro Arg Tyr Pro Ala Pro Gly Ser Lys Ala Pro Gly Tyr Ala Val
            100                 105                 110

Asn Glu Ile Asp Lys Ile Val Glu Arg Thr Arg Glu Leu Gly Leu Tyr
            115                 120                 125

Leu Val Ile Thr Ile Gly Asn Gly Ala Asn Asn Gly Asn His Asn Ala
        130                 135                 140

Gln Trp Ala Arg Asp Phe Trp Lys Phe Tyr Ala Pro Arg Tyr Ala Lys
145                 150                 155                 160

Glu Thr His Val Leu Tyr Glu Ile His Asn Glu Pro Val Ala Trp Gly
                165                 170                 175

Pro Pro Tyr Ser Ser Thr Ala Asn Pro Pro Gly Ala Val Asp Met
                180                 185                 190
```

```
Glu Ile Asp Val Tyr Arg Ile Ile Arg Thr Tyr Ala Pro Glu Thr Pro
        195                 200                 205
Val Leu Leu Phe Ser Tyr Ala Val Phe Gly Gly Lys Gly Gly Ala Ala
210                 215                 220
Glu Ala Leu Lys Asp Ile Arg Ala Phe Asn Lys Ala Val Phe Gly Asn
225                 230                 235                 240
Glu Asn Ala Val Trp Thr Asn Glu Ala Val Ala Phe His Gly Tyr Ala
                245                 250                 255
Gly Trp Gln Glu Thr Thr Ile Ala Val Glu Glu Leu Leu Lys Ala Gly
                260                 265                 270
Tyr Pro Cys Phe Met Thr Glu Tyr Ala Gly Gly Ala Trp Gly Ser Gly
                275                 280                 285
Met Gly Gly Leu Asp Val Glu Leu Thr Tyr Glu Leu Glu Arg Leu Gly
                290                 295                 300
Val Ser Trp Leu Thr Phe Gln Tyr Ile Pro Pro Thr Gly Val Ser Asp
305                 310                 315                 320
Asp Val Thr Lys Pro Glu Tyr Phe Ser Ala Leu Val Glu Asn Ser Gly
                325                 330                 335
Leu Ser Trp Thr Pro Asp Tyr Gly Asn Trp Pro Ala Ala Arg Gly Val
                340                 345                 350
Tyr Gly Asn Gly Gly Leu Ala Arg Glu Thr Ala Thr Trp Ile Asn Asn
                355                 360                 365
Phe Leu Thr Gly Thr Thr Arg Ile Glu Ala Glu Asp Phe Asp Trp Gly
                370                 375                 380
Gly Asn Gly Val Ser Tyr Tyr Asp Thr Asp Ser Val Asn Val Gly Gly
385                 390                 395                 400
Gln Tyr Arg Pro Asp Glu Gly Val Asp Ile Glu Lys Thr Ser Asp Thr
                405                 410                 415
Gly Gly Gly Tyr Asn Val Gly Trp Ile Ser Glu Gly Glu Trp Leu Glu
                420                 425                 430
Tyr Thr Ile Arg Val Arg Asn Pro Gly Tyr Tyr Asn Leu Ser Leu Arg
                435                 440                 445
Val Ala Gly Ile Ser Gly Ser Arg Val Gln Val Ser Phe Gly Asn Gln
                450                 455                 460
Asp Lys Thr Gly Val Trp Glu Leu Pro Ala Thr Gly Gly Phe Gln Thr
465                 470                 475                 480
Trp Thr Thr Ala Thr Arg Gln Val Phe Leu Gly Ala Gly Leu Gln Lys
                485                 490                 495
Leu Arg Ile Asn Ala Leu Ser Gly Gly Phe Asn Leu Asn Trp Ile Glu
                500                 505                 510
Leu Ser Pro Ile Ser Thr Gly Thr Ile Pro Asp Gly Thr Tyr Lys Phe
                515                 520                 525
Leu Asn Arg Ala Asn Gly Lys Thr Leu Gln Glu Val Thr Gly Asn Asn
                530                 535                 540
Ser Ile Ile Thr Ala Asp Tyr Lys Gly Ile Thr Glu Gln His Trp Lys
545                 550                 555                 560
Ile Gln His Ile Gly Gly Gly Gln Tyr Arg Ile Ser Ser Ala Gly Arg
                565                 570                 575
Gly Trp Asn Trp Asn Trp Trp Met Gly Phe Gly Thr Val Gly Trp Trp
                580                 585                 590
Gly Thr Gly Ser Ser Thr Cys Phe Ile Ile Ser Pro Thr Gly Asp Gly
                595                 600                 605
```

Tyr Tyr Arg Ile Val Leu Val Gly Asp Gly Thr Asn Leu Gln Ile Ser
610                 615                 620

Ser Gly Asp Pro Ser Lys Ile Glu Gly Lys Ala Phe His Gly Ala
625                 630                 635                 640

Asn Gln Gln Trp Ala Ile Leu Pro Val Ser Ala Pro Ala Phe Pro Thr
            645                 650                 655

Gly Leu Ser Ala Val Leu Asp Ser Ser Gly Asn Thr Ala Asn Leu Thr
            660                 665                 670

Trp Asn Ala Ala Pro Gly Ala Asn Ser Tyr Asn Val Lys Arg Ser Thr
            675                 680                 685

Lys Ser Gly Gly Pro Tyr Thr Thr Ile Ala Thr Asn Ile Thr Ser Thr
690                 695                 700

Asn Tyr Thr Asp Thr Gly Val Ala Thr Gly Thr Lys Tyr Tyr Tyr Val
705                 710                 715                 720

Val Ser Ala Val Ser Asn Gly Val Glu Thr Leu Asn Ser Ala Glu Ala
                725                 730                 735

Ile Leu Gln Tyr Pro Lys Leu Thr Gly Thr Val Ile Gly Thr Gln Gly
            740                 745                 750

Ser Trp Asn Asn Ile Gly Asn Thr Ile His Lys Ala Phe Asp Gly Asp
            755                 760                 765

Leu Asn Thr Phe Phe Asp Gly Pro Thr Ala Asn Gly Cys Trp Leu Gly
770                 775                 780

Leu Asp Phe Gly Glu Gly Val Arg Asn Val Ile Thr Gln Ile Lys Phe
785                 790                 795                 800

Cys Pro Arg Ser Gly Tyr Glu Gln Arg Met Ile Gly Ile Phe Gln
                805                 810                 815

Gly Ala Asn Lys Glu Asp Phe Ser Asp Ala Val Thr Leu Phe Thr Ile
            820                 825                 830

Thr Ser Leu Pro Gly Ser Gly Thr Leu Thr Ser Val Asp Val Asp Asn
            835                 840                 845

Pro Thr Gly Phe Arg Tyr Val Arg Tyr Leu Ser Pro Asp Gly Ser Asn
850                 855                 860

Gly Asn Ile Ala Glu Leu Gln Phe Phe Gly Thr Pro Ala Gly Glu Glu
865                 870                 875                 880

Asn Asp Asp Val His Leu Gly Asp Ile Asn Asp Gly Asn Ile Asn
                885                 890                 895

Ser Thr Asp Leu Gln Met Leu Lys Arg His Leu Arg Ser Ile Arg
            900                 905                 910

Leu Thr Glu Lys Gln Leu Leu Asn Ala Asp Thr Asn Arg Asp Gly Arg
            915                 920                 925

Val Asp Ser Thr Asp Leu Ala Leu Leu Lys Arg Tyr Ile Leu Arg Val
930                 935                 940

Ile Thr Thr Leu
945

<210> SEQ ID NO 4
<211> LENGTH: 443
<212> TYPE: PRT
<213> ORGANISM: Gonapodya prolifera

<400> SEQUENCE: 4

Met Ala Arg Leu Ser Ser Leu Ile Ala Leu Val Leu Ala Phe Val Ala
1               5                   10                  15

Val Ser Ala Pro Ala Leu Ala Ala Arg Gly Arg Pro Arg Leu Asn Gly
            20                  25                  30

```
Lys Thr Phe Val Ala Asp Ser Gly Val Pro Leu Arg Gly Pro Phe Thr
         35                  40                  45

Ser Thr Glu Trp Thr Pro Ala Val Pro Ala Ala Asn Ile Ala Asn Met
     50                  55                  60

Arg Asn Tyr Asn Phe Asn Ala Ile His Leu Tyr Ala Glu Thr Phe Asp
 65              70                  75                      80

Pro Asn Tyr Pro Ala Ala Gly Ser Gln Lys Pro Gly Tyr Ala Ala Thr
                 85                  90                  95

Arg Val Asp Gln Ile Val Ala Ala Thr Lys Ala Ala Asn Met Tyr Val
             100                 105                 110

Val Ile Val Leu Ala Asn Gly Ala Asn Asn Gly Lys Phe Asn Leu Asn
             115                 120                 125

Tyr Ala Lys Asp Phe Trp Ser Phe Tyr Ala Ala Arg Tyr Lys Asn Glu
         130                 135                 140

Thr His Val Ile Tyr Glu Ile His Asn Glu Pro Val Gln Trp Gly Pro
145                 150                 155                 160

Pro Tyr Ile Ser Ser Thr Gln Ser Pro Gly Ala Val Ser Met Asn Ala
                 165                 170                 175

Asp Cys Tyr Lys Ile Ile Arg Ala Val Ala Pro Asp Thr Pro Val Leu
             180                 185                 190

Leu Phe Thr Tyr Ala Ser Ile Gly Gly Gly Ser Ser Ala Ala Gly Ala
         195                 200                 205

Val Lys Asp Ala Gln Ser Phe Asn Thr Ala Val Phe Gly Asn Ala Asn
     210                 215                 220

Ala Gln Trp Thr Asn Glu Ala Ile Ala Ile His Gly Tyr Trp Gly Ala
225                 230                 235                 240

Gln Gly Ala Ser Asp Ala Ala Lys Ala Leu Asn Ala Ala Gly Phe Ser
             245                 250                 255

Val Val Leu Thr Glu Phe Ala Ala Ala Thr Ser Pro Thr Ser Pro Asn
             260                 265                 270

Gly Gly Gln Asp Thr Val Leu Thr Gly Phe Met Glu Gln Gln Gly Val
         275                 280                 285

Ser Trp Leu Thr Phe Leu His Val Pro Pro Thr Gly Val Ser Gly Asp
     290                 295                 300

Val Thr Asp Pro Asn Gln Tyr Thr Asn Arg Met Thr Ala Ala Gly Ile
305                 310                 315                 320

Gly Phe Asp Arg Asp Pro Gly Leu Asn Ala Val Gly Gly Gln Ala
                 325                 330                 335

Ala Pro Val Pro Val Pro Ala Pro Val Pro Ser Pro Val Pro
             340                 345                 350

Ala Pro Val Pro Ala Val Pro Ala Val Arg Thr Thr Ala Arg Pro
             355                 360                 365

Ala Pro Ser Pro Ser Pro Val Pro Ala Pro Val Pro Ala Pro
         370                 375                 380

Val Pro Ala Pro Val Pro Ala Pro Val Pro Ala Pro Val Pro Ala Pro
385                 390                 395                 400

Val Pro Ala Pro Val Pro Ala Ser Pro Ala Thr Thr Thr Arg Arg
                 405                 410                 415

His Arg Thr Arg Pro Pro Arg Thr Thr Thr Ala Pro Ala Val Pro Ala
             420                 425                 430

Pro Pro Pro Ala Ala Thr Pro Lys Val Cys Gly
             435                 440
```

<210> SEQ ID NO 5
<211> LENGTH: 413
<212> TYPE: PRT
<213> ORGANISM: Dickeya chrysanthemi

<400> SEQUENCE: 5

```
Met Asn Gly Asn Val Ser Leu Trp Val Arg His Cys Leu His Ala Ala
1               5                   10                  15

Leu Phe Val Ser Ala Thr Ala Gly Ser Phe Ser Val Tyr Ala Asp Thr
            20                  25                  30

Val Lys Ile Asp Ala Asn Val Asn Tyr Gln Ile Ile Gln Gly Phe Gly
        35                  40                  45

Gly Met Ser Gly Val Gly Trp Ile Asn Asp Leu Thr Thr Glu Gln Ile
    50                  55                  60

Asn Thr Ala Tyr Gly Ser Gly Val Gly Gln Ile Gly Leu Ser Ile Met
65                  70                  75                  80

Arg Val Arg Ile Asp Pro Asp Ser Ser Lys Trp Asn Ile Gln Leu Pro
                85                  90                  95

Ser Ala Arg Gln Ala Val Ser Leu Gly Ala Lys Ile Met Ala Thr Pro
            100                 105                 110

Trp Ser Pro Pro Ala Tyr Met Lys Ser Asn Asn Ser Leu Ile Asn Gly
        115                 120                 125

Gly Arg Leu Leu Pro Ala Asn Tyr Ser Ala Tyr Thr Ser His Leu Leu
    130                 135                 140

Asp Phe Ser Lys Tyr Met Gln Thr Asn Gly Ala Pro Leu Tyr Ala Ile
145                 150                 155                 160

Ser Ile Gln Asn Glu Pro Asp Trp Lys Pro Asp Tyr Glu Ser Cys Glu
                165                 170                 175

Trp Ser Gly Asp Glu Phe Lys Ser Tyr Leu Lys Ser Gln Gly Ser Lys
            180                 185                 190

Phe Gly Ser Leu Lys Val Ile Val Ala Glu Ser Leu Gly Phe Asn Pro
        195                 200                 205

Ala Leu Thr Asp Pro Val Leu Lys Asp Ser Asp Ala Ser Lys Tyr Val
    210                 215                 220

Ser Ile Ile Gly Gly His Leu Tyr Gly Thr Thr Pro Lys Pro Tyr Pro
225                 230                 235                 240

Leu Ala Gln Asn Ala Gly Lys Gln Leu Trp Met Thr Glu His Tyr Val
                245                 250                 255

Asp Ser Lys Gln Ser Ala Asn Asn Trp Thr Ser Ala Ile Glu Val Gly
            260                 265                 270

Thr Glu Leu Asn Ala Ser Met Val Ser Asn Tyr Ser Ala Tyr Val Trp
        275                 280                 285

Trp Tyr Ile Arg Arg Ser Tyr Gly Leu Leu Thr Glu Asp Gly Lys Val
    290                 295                 300

Ser Lys Arg Gly Tyr Val Met Ser Gln Tyr Ala Arg Phe Val Arg Pro
305                 310                 315                 320

Gly Ala Leu Arg Ile Gln Ala Thr Glu Asn Pro Gln Ser Asn Val His
                325                 330                 335

Leu Thr Ala Tyr Lys Asn Thr Asp Gly Lys Met Val Ile Val Ala Val
            340                 345                 350

Asn Thr Asn Asp Ser Asp Gln Met Leu Ser Leu Asn Ile Ser Asn Ala
        355                 360                 365

Asn Val Thr Lys Phe Glu Lys Tyr Ser Thr Ser Ala Ser Leu Asn Val
    370                 375                 380
```

Glu Tyr Gly Gly Ser Ser Gln Val Asp Ser Ser Gly Lys Ala Thr Val
385                 390                 395                 400

Trp Leu Asn Pro Leu Ser Val Thr Thr Phe Val Ser Lys
            405                 410

<210> SEQ ID NO 6
<211> LENGTH: 422
<212> TYPE: PRT
<213> ORGANISM: Bacillus subtilis subsp. subtilis str. 168

<400> SEQUENCE: 6

Met Ile Pro Arg Ile Lys Lys Thr Ile Cys Val Leu Val Cys Phe
1               5                   10                  15

Thr Met Leu Ser Val Met Leu Gly Pro Gly Ala Thr Glu Val Leu Ala
            20                  25                  30

Ala Ser Asp Val Thr Val Asn Val Ser Ala Glu Lys Gln Val Ile Arg
            35                  40                  45

Gly Phe Gly Gly Met Asn His Pro Ala Trp Ala Gly Asp Leu Thr Ala
    50                  55                  60

Ala Gln Arg Glu Thr Ala Phe Gly Asn Gly Gln Asn Gln Leu Gly Phe
65                  70                  75                  80

Ser Ile Leu Arg Ile His Val Asp Glu Asn Arg Asn Asn Trp Tyr Lys
                85                  90                  95

Glu Val Glu Thr Ala Lys Ser Ala Val Lys His Gly Ala Ile Val Phe
            100                 105                 110

Ala Ser Pro Trp Asn Pro Pro Ser Asp Met Val Glu Thr Phe Asn Arg
        115                 120                 125

Asn Gly Asp Thr Ser Ala Lys Arg Leu Lys Tyr Asn Lys Tyr Ala Ala
    130                 135                 140

Tyr Ala Gln His Leu Asn Asp Phe Val Thr Phe Met Lys Asn Asn Gly
145                 150                 155                 160

Val Asn Leu Tyr Ala Ile Ser Val Gln Asn Glu Pro Asp Tyr Ala His
                165                 170                 175

Glu Trp Thr Trp Trp Thr Pro Gln Glu Ile Leu Arg Phe Met Arg Glu
            180                 185                 190

Asn Ala Gly Ser Ile Asn Ala Arg Val Ile Ala Pro Glu Ser Phe Gln
        195                 200                 205

Tyr Leu Lys Asn Leu Ser Asp Pro Ile Leu Asn Asp Pro Gln Ala Leu
    210                 215                 220

Ala Asn Met Asp Ile Leu Gly Thr His Leu Tyr Gly Thr Gln Val Ser
225                 230                 235                 240

Gln Phe Pro Tyr Pro Leu Phe Lys Gln Lys Gly Ala Gly Lys Asp Leu
                245                 250                 255

Trp Met Thr Glu Val Tyr Tyr Pro Asn Ser Asp Thr Asn Ser Ala Asp
            260                 265                 270

Arg Trp Pro Glu Ala Leu Asp Val Ser Gln His Ile His Asn Ala Met
        275                 280                 285

Val Glu Gly Asp Phe Gln Ala Tyr Val Trp Trp Tyr Ile Arg Arg Ser
    290                 295                 300

Tyr Gly Pro Met Lys Glu Asp Gly Thr Ile Ser Lys Arg Gly Tyr Asn
305                 310                 315                 320

Met Ala His Phe Ser Lys Phe Val Arg Pro Gly Tyr Val Arg Ile Asp
                325                 330                 335

Ala Thr Lys Asn Pro Asn Ala Asn Val Tyr Val Ser Ala Tyr Lys Gly

```
                340                 345                 350
Asp Asn Lys Val Val Ile Val Ala Ile Asn Lys Ser Asn Thr Gly Val
            355                 360                 365

Asn Gln Asn Phe Val Leu Gln Asn Gly Ser Ala Ser Asn Val Ser Arg
        370                 375                 380

Trp Ile Thr Ser Ser Ser Ser Asn Leu Gln Pro Gly Thr Asn Leu Thr
385                 390                 395                 400

Val Ser Gly Asn His Phe Trp Ala His Leu Pro Ala Gln Ser Val Thr
            405                 410                 415

Thr Phe Val Val Asn Arg
            420

<210> SEQ ID NO 7
<211> LENGTH: 547
<212> TYPE: PRT
<213> ORGANISM: Bacteroides ovatus

<400> SEQUENCE: 7

Met Lys Asn Ile Thr Leu Leu Phe Cys Leu Phe Leu Ala Asn Ile Leu
1               5                   10                  15

Leu Gly Ala Cys Ser Gly Gly Glu Asp Glu Lys Lys Glu Met Asp Glu
            20                  25                  30

Gly Lys Gly Ala Tyr Ala Leu Phe Leu Lys Lys Ser Ile Thr Val Ser
        35                  40                  45

Thr Gly Glu Ser Gln Thr Asp Val Val Glu Trp Ala Lys Thr Ser
    50                  55                  60

Trp Glu Ile Thr Leu Gly Glu Gly Asp Ile Val Lys Ser Val Thr Pro
65                  70                  75                  80

Thr Ser Gly Gly Ser Asn Thr Gly Glu Lys Gln Tyr Thr Lys Val Arg
            85                  90                  95

Val Ser Cys Gly Ala Asn Ser Thr Met Lys Lys Arg Thr Gln Thr Ile
            100                 105                 110

His Leu Phe Asp Lys Thr Asn Glu Thr Thr Val Asp Leu Leu Val Glu
            115                 120                 125

Gln Glu Pro Pro Phe Lys Ser Val Thr Leu Thr Val Asp Pro Ser Val
        130                 135                 140

Lys Tyr Gln Pro Val Val Gly Phe Gly Gly Met Tyr Asn Pro Lys Ile
145                 150                 155                 160

Trp Cys Gly Asp Asn Leu Ile Ser Ala Ser Gln Leu Asp Lys Met Tyr
            165                 170                 175

Gly Ala Gly Gly Leu Gly Tyr Ser Ile Leu Arg Leu Met Ile Tyr Pro
            180                 185                 190

Asn Glu Ser Asp Trp Ser Ala Asp Val Glu Ala Ala Lys Ala Ala Gln
        195                 200                 205

Ala Asn Gly Ala Ile Ile Phe Ala Cys Pro Trp Asp Cys Thr Asp Ala
    210                 215                 220

Leu Ala Asp Lys Ile Thr Val Asn Gly Lys Glu Met Lys His Leu Lys
225                 230                 235                 240

Lys Glu Asn Tyr Glu Ala Tyr Ala Asn His Leu Ile Arg Tyr Val Thr
            245                 250                 255

Phe Met Lys Glu Lys Gly Val Asn Leu Tyr Ala Ile Ser Val Gln Asn
            260                 265                 270

Glu Pro Asp Met Glu Phe Thr Tyr Trp Thr Pro Ser Glu Val Val Asp
        275                 280                 285
```

```
Phe Val Lys Gln Tyr Gly Ala Arg Ile Arg Glu Thr Gly Val Lys Leu
    290                 295                 300

Met Ser Pro Glu Ala Cys Gly Met Gln Pro Glu Tyr Thr Asp Pro Ile
305                 310                 315                 320

Ile Asn Asn Ala Glu Ala Phe Ala Gln Thr Asp Ile Leu Ala Gly His
                325                 330                 335

Leu Tyr Gln Gly Phe Thr Asp Leu Ser Ser Gly Tyr Val Lys Asn Arg
            340                 345                 350

His Asp Tyr Ile Cys Gly Val Tyr Ser Arg Ile Gln Gly Lys Thr Trp
        355                 360                 365

Trp Met Thr Glu His Leu Phe Asn Asp Gly Glu Asn Ser Asp Asp Ser
370                 375                 380

Ser Lys Trp Glu Phe Leu Lys Trp Gln Tyr Ser Leu Asn His Leu Gly
385                 390                 395                 400

Lys Glu Ile His Met Cys Met Glu Gly Tyr Cys Ser Ala Tyr Ile Tyr
                405                 410                 415

Trp Tyr Leu Lys Arg Phe Tyr Gly Leu Met Gly Asp Thr Asp Lys Arg
            420                 425                 430

Ser Pro Thr Ser Glu Gly Glu Ile Thr Lys Asn Gly Tyr Ile Met Ala
        435                 440                 445

His Tyr Ala Gln Tyr Ala Thr Glu Thr Thr Arg Ile Lys Val Val Thr
450                 455                 460

Asn Asn Glu Glu Val Cys Ala Thr Ala Tyr Trp Asp Glu Lys Thr Gly
465                 470                 475                 480

Glu Val Thr Ile Val Leu Leu Asn Leu Asn Gly Ala Ser Gln Trp Leu
                485                 490                 495

Glu Ile Pro Leu Ala Gly Ile Lys Lys Ala Ser Ala Val Glu Thr Asn
            500                 505                 510

Glu Thr Lys Asn Met Glu Val Ile Asp Thr Gly Leu Met Glu Ser Ala
        515                 520                 525

Glu Gly Ile Thr Val Leu Leu Ser Ala Asn Ser Ile Thr Ser Val Arg
        530                 535                 540

Leu Thr Phe
545

<210> SEQ ID NO 8
<211> LENGTH: 502
<212> TYPE: PRT
<213> ORGANISM: Bacteroides ovatus

<400> SEQUENCE: 8

Met Glu Lys Gln Ser Phe Ser Asp Gly Leu Phe Ser Pro Leu Gly Ile
1               5                   10                  15

Lys Arg Val Ile Phe Met Leu Val Leu Leu Thr Thr Ser Phe Ile Ser
            20                  25                  30

Cys Ser Asn Ser Asp Glu Lys Gly Gly Ser Leu Glu Val Ala Gln Glu
        35                  40                  45

Tyr Arg Asn Leu Glu Phe Asp Ala Arg Gly Ser Arg Gln Thr Ile Gln
    50                  55                  60

Ile Asp Gly Pro Ala Glu Trp His Ile Ser Thr Ser Glu Ser Trp Cys
65                  70                  75                  80

Lys Ser Ser His Thr Ile Gly Glu Gly Lys Gln Tyr Val Asn Ile Thr
                85                  90                  95

Val Glu Ala Asn Asp Thr Gln Lys Glu Arg Thr Ala Thr Val Thr Val
            100                 105                 110
```

Ser Ala Ser Gly Ala Pro Asp Ile Ile Asn Val Lys Gln Ser Leu
            115                 120                 125
Tyr Ser Val Pro Ala Tyr Asp Glu Tyr Ile Ala Pro Asp Asn Thr Gly
            130                 135                 140
Met Arg Asp Leu Thr Ser Met Gln Leu Ser Ala Leu Met Lys Ala Gly
145                 150                 155                 160
Val Asn Val Gly Asn Thr Phe Glu Ala Val Ile Val Gly Asn Asp Gly
                165                 170                 175
Ser Leu Ser Gly Asp Glu Thr Cys Trp Gly Asn Pro Thr Pro Asn Lys
            180                 185                 190
Val Leu Phe Glu Gly Ile Lys Ala Ala Gly Phe Asp Val Val Arg Ile
            195                 200                 205
Pro Val Ala Tyr Ser His Gln Phe Glu Asp Ala Ala Thr Tyr Lys Ile
            210                 215                 220
Lys Ser Ala Trp Met Asp Lys Val Glu Ala Val Lys Ala Ala Leu
225                 230                 235                 240
Asp Ala Gly Leu Tyr Val Ile Ile Asn Ile His Trp Glu Gly Gly Trp
                245                 250                 255
Leu Asn His Pro Val Asp Ala Asn Lys Glu Ala Leu Asp Glu Arg Leu
            260                 265                 270
Glu Ala Met Trp Lys Gln Ile Ala Leu Arg Phe Arg Asp Tyr Asp Asp
            275                 280                 285
Arg Leu Leu Phe Ala Gly Thr Asn Glu Val Asn Asn Asp Ala Asn
290                 295                 300
Gly Ala Gln Pro Thr Glu Asn Tyr Arg Val Gln Asn Gly Phe Asn
305                 310                 315                 320
Gln Val Phe Val Asn Thr Val Arg Ala Thr Gly Gly Arg Asn His Tyr
                325                 330                 335
Arg His Leu Ile Val Gln Ala Tyr Asn Thr Asp Val Ala Lys Ala Val
            340                 345                 350
Ala His Phe Thr Met Pro Leu Asp Ile Val Gln Asn Arg Ile Phe Leu
            355                 360                 365
Glu Cys His Tyr Tyr Asp Pro Tyr Asp Phe Thr Ile Met Pro Asn Asp
            370                 375                 380
Glu Asn Phe Lys Ser Gln Trp Gly Ala Ala Phe Ala Gly Gly Asp Val
385                 390                 395                 400
Ser Ala Thr Gly Gln Glu Gly Asp Ile Glu Ala Thr Leu Ser Ser Leu
                405                 410                 415
Asn Val Phe Ile Asn Asn Val Pro Val Ile Gly Glu Tyr Gly
            420                 425                 430
Pro Thr Leu Arg Asp Gln Leu Thr Gly Glu Ala Leu Glu Asn His Leu
            435                 440                 445
Lys Ser Arg Asn Asp Tyr Ile Glu Tyr Val Val Lys Thr Cys Val Lys
450                 455                 460
Asn Lys Leu Val Pro Leu Tyr Trp Asp Ala Gly Tyr Thr Glu Lys Leu
465                 470                 475                 480
Phe Asp Arg Thr Thr Gly Gln Pro His Asn Ala Ala Ser Ile Ala Ala
                485                 490                 495
Ile Met Lys Gly Leu Asn
            500

<210> SEQ ID NO 9
<211> LENGTH: 838

<212> TYPE: PRT
<213> ORGANISM: Trichoderma reesei

<400> SEQUENCE: 9

Met Lys Val Ser Arg Val Leu Ala Leu Val Leu Gly Ala Val Ile Pro
1               5                   10                  15

Ala His Ala Ala Phe Ser Trp Lys Asn Val Lys Leu Gly Gly Gly Gly
            20                  25                  30

Gly Phe Val Pro Gly Ile Ile Phe His Pro Lys Thr Lys Gly Val Ala
        35                  40                  45

Tyr Ala Arg Thr Asp Ile Gly Gly Leu Tyr Arg Leu Asn Ala Asp Asp
50                  55                  60

Ser Trp Thr Ala Val Thr Asp Gly Ile Ala Asp Asn Ala Gly Trp His
65                  70                  75                  80

Asn Trp Gly Ile Asp Ala Val Ala Leu Asp Pro Gln Asp Asp Gln Lys
                85                  90                  95

Val Tyr Ala Ala Val Gly Met Tyr Thr Asn Ser Trp Asp Pro Ser Asn
            100                 105                 110

Gly Ala Ile Ile Arg Ser Ser Asp Arg Gly Ala Thr Trp Ser Phe Thr
        115                 120                 125

Asn Leu Pro Phe Lys Val Gly Gly Asn Met Pro Gly Arg Gly Ala Gly
130                 135                 140

Glu Arg Leu Ala Val Asp Pro Ala Asn Ser Asn Ile Ile Tyr Phe Gly
145                 150                 155                 160

Ala Arg Ser Gly Asn Gly Leu Trp Lys Ser Thr Asp Gly Gly Val Thr
                165                 170                 175

Phe Ser Lys Val Ser Ser Phe Thr Ala Thr Gly Thr Tyr Ile Pro Asp
            180                 185                 190

Pro Ser Asp Ser Asn Gly Tyr Asn Ser Asp Lys Gln Gly Leu Met Trp
        195                 200                 205

Val Thr Phe Asp Ser Thr Ser Ser Thr Thr Gly Gly Ala Thr Ser Arg
210                 215                 220

Ile Phe Val Gly Thr Ala Asp Asn Ile Thr Ala Ser Val Tyr Val Ser
225                 230                 235                 240

Thr Asn Ala Gly Ser Thr Trp Ser Ala Val Pro Gly Gln Pro Gly Lys
                245                 250                 255

Tyr Phe Pro His Lys Ala Lys Leu Gln Pro Ala Glu Lys Ala Leu Tyr
            260                 265                 270

Leu Thr Tyr Ser Asp Gly Thr Gly Pro Tyr Asp Gly Thr Leu Gly Ser
        275                 280                 285

Val Trp Arg Tyr Asp Ile Ala Gly Gly Thr Trp Lys Asp Ile Thr Pro
290                 295                 300

Val Ser Gly Ser Asp Leu Tyr Phe Gly Phe Gly Gly Leu Gly Leu Asp
305                 310                 315                 320

Leu Gln Lys Pro Gly Thr Leu Val Val Ala Ser Leu Asn Ser Trp Trp
                325                 330                 335

Pro Asp Ala Gln Leu Phe Arg Ser Thr Asp Ser Gly Thr Thr Trp Ser
            340                 345                 350

Pro Ile Trp Ala Trp Ala Ser Tyr Pro Thr Glu Thr Tyr Tyr Tyr Ser
        355                 360                 365

Ile Ser Thr Pro Lys Ala Pro Trp Ile Lys Asn Asn Phe Ile Asp Val
        370                 375                 380

Thr Ser Glu Ser Pro Ser Asp Gly Leu Ile Lys Arg Leu Gly Trp Met
385                 390                 395                 400

```
Ile Glu Ser Leu Glu Ile Asp Pro Thr Asp Ser Asn His Trp Leu Tyr
                405                 410                 415
Gly Thr Gly Met Thr Ile Phe Gly Gly His Asp Leu Thr Asn Trp Asp
            420                 425                 430
Thr Arg His Asn Val Ser Ile Gln Ser Leu Ala Asp Gly Ile Glu Glu
        435                 440                 445
Phe Ser Val Gln Asp Leu Ala Ser Ala Pro Gly Gly Ser Glu Leu Leu
450                 455                 460
Ala Ala Val Gly Asp Asp Asn Gly Phe Thr Phe Ala Ser Arg Asn Asp
465                 470                 475                 480
Leu Gly Thr Ser Pro Gln Thr Val Trp Ala Thr Pro Thr Trp Ala Thr
                485                 490                 495
Ser Thr Ser Val Asp Tyr Ala Gly Asn Ser Val Lys Ser Val Val Arg
            500                 505                 510
Val Gly Asn Thr Ala Gly Thr Gln Gln Val Ala Ile Ser Ser Asp Gly
        515                 520                 525
Gly Ala Thr Trp Ser Ile Asp Tyr Ala Ala Asp Thr Ser Met Asn Gly
    530                 535                 540
Gly Thr Val Ala Tyr Ser Ala Asp Gly Asp Thr Ile Leu Trp Ser Thr
545                 550                 555                 560
Ala Ser Ser Gly Val Gln Arg Ser Gln Phe Gln Gly Ser Phe Ala Ser
                565                 570                 575
Val Ser Ser Leu Pro Ala Gly Ala Val Ile Ala Ser Asp Lys Lys Thr
            580                 585                 590
Asn Ser Val Phe Tyr Ala Gly Ser Gly Ser Thr Phe Tyr Val Ser Lys
        595                 600                 605
Asp Thr Gly Ser Ser Phe Thr Arg Gly Pro Lys Leu Gly Ser Ala Gly
    610                 615                 620
Thr Ile Arg Asp Ile Ala Ala His Pro Thr Thr Ala Gly Thr Leu Tyr
625                 630                 635                 640
Val Ser Thr Asp Val Gly Ile Phe Arg Ser Thr Asp Ser Gly Thr Thr
                645                 650                 655
Phe Gly Gln Val Ser Thr Ala Leu Thr Asn Thr Tyr Gln Ile Ala Leu
            660                 665                 670
Gly Val Gly Ser Gly Ser Asn Trp Asn Leu Tyr Ala Phe Gly Thr Gly
        675                 680                 685
Pro Ser Gly Ala Arg Leu Tyr Ala Ser Gly Asp Ser Gly Ala Ser Trp
    690                 695                 700
Thr Asp Ile Gln Gly Ser Gln Gly Phe Gly Ser Ile Asp Ser Thr Lys
705                 710                 715                 720
Val Ala Gly Ser Gly Ser Thr Ala Gly Gln Val Tyr Val Gly Thr Asn
                725                 730                 735
Gly Arg Gly Val Phe Tyr Ala Gln Gly Thr Val Gly Gly Thr Gly Thr
            740                 745                 750
Gly Thr Ser Ser Ser Thr Lys Gln Ser Ser Ser Thr Ser Ser Ala
        755                 760                 765
Ser Ser Ser Thr Thr Leu Arg Ser Ser Val Val Ser Thr Thr Arg Ala
    770                 775                 780
Ser Thr Val Thr Ser Ser Arg Thr Ser Ser Ala Ala Gly Pro Thr Gly
785                 790                 795                 800
Ser Gly Val Ala Gly His Tyr Ala Gln Cys Gly Gly Ile Gly Trp Thr
                805                 810                 815
```

```
Gly Pro Thr Gln Cys Val Ala Pro Tyr Val Cys Gln Lys Gln Asn Asp
            820                 825                 830

Tyr Tyr Tyr Gln Cys Val
        835
```

<210> SEQ ID NO 10
<211> LENGTH: 513
<212> TYPE: PRT
<213> ORGANISM: Trichoderma reesei

<400> SEQUENCE: 10

```
Met Tyr Arg Lys Leu Ala Val Ile Ser Ala Phe Leu Ala Thr Ala Arg
1               5                   10                  15

Ala Gln Ser Ala Cys Thr Leu Gln Ser Glu Thr His Pro Pro Leu Thr
            20                  25                  30

Trp Gln Lys Cys Ser Ser Gly Gly Thr Cys Thr Gln Gln Thr Gly Ser
        35                  40                  45

Val Val Ile Asp Ala Asn Trp Arg Trp Thr His Ala Thr Asn Ser Ser
50                  55                  60

Thr Asn Cys Tyr Asp Gly Asn Thr Trp Ser Ser Thr Leu Cys Pro Asp
65                  70                  75                  80

Asn Glu Thr Cys Ala Lys Asn Cys Cys Leu Asp Gly Ala Ala Tyr Ala
                85                  90                  95

Ser Thr Tyr Gly Val Thr Thr Ser Gly Asn Ser Leu Ser Ile Gly Phe
            100                 105                 110

Val Thr Gln Ser Ala Gln Lys Asn Val Gly Ala Arg Leu Tyr Leu Met
        115                 120                 125

Ala Ser Asp Thr Thr Tyr Gln Glu Phe Thr Leu Leu Gly Asn Glu Phe
130                 135                 140

Ser Phe Asp Val Asp Val Ser Gln Leu Pro Cys Gly Leu Asn Gly Ala
145                 150                 155                 160

Leu Tyr Phe Val Ser Met Asp Ala Asp Gly Gly Val Ser Lys Tyr Pro
                165                 170                 175

Thr Asn Thr Ala Gly Ala Lys Tyr Gly Thr Gly Tyr Cys Asp Ser Gln
            180                 185                 190

Cys Pro Arg Asp Leu Lys Phe Ile Asn Gly Gln Ala Asn Val Glu Gly
        195                 200                 205

Trp Glu Pro Ser Ser Asn Asn Ala Asn Thr Gly Ile Gly Gly His Gly
210                 215                 220

Ser Cys Cys Ser Glu Met Asp Ile Trp Glu Ala Asn Ser Ile Ser Glu
225                 230                 235                 240

Ala Leu Thr Pro His Pro Cys Thr Thr Val Gly Gln Glu Ile Cys Glu
                245                 250                 255

Gly Asp Gly Cys Gly Gly Thr Tyr Ser Asp Asn Arg Tyr Gly Gly Thr
            260                 265                 270

Cys Asp Pro Asp Gly Cys Asp Trp Asn Pro Tyr Arg Leu Gly Asn Thr
        275                 280                 285

Ser Phe Tyr Gly Pro Gly Ser Ser Phe Thr Leu Asp Thr Thr Lys Lys
290                 295                 300

Leu Thr Val Val Thr Gln Phe Glu Thr Ser Gly Ala Ile Asn Arg Tyr
305                 310                 315                 320

Tyr Val Gln Asn Gly Val Thr Phe Gln Gln Pro Asn Ala Glu Leu Gly
                325                 330                 335

Ser Tyr Ser Gly Asn Glu Leu Asn Asp Asp Tyr Cys Thr Ala Glu Glu
            340                 345                 350
```

```
Ala Glu Phe Gly Gly Ser Ser Phe Ser Asp Lys Gly Gly Leu Thr Gln
            355                 360                 365

Phe Lys Lys Ala Thr Ser Gly Gly Met Val Leu Val Met Ser Leu Trp
    370                 375                 380

Asp Asp Tyr Tyr Ala Asn Met Leu Trp Leu Asp Ser Thr Tyr Pro Thr
385                 390                 395                 400

Asn Glu Thr Ser Ser Thr Pro Gly Ala Val Arg Gly Ser Cys Ser Thr
                405                 410                 415

Ser Ser Gly Val Pro Ala Gln Val Glu Ser Gln Ser Pro Asn Ala Lys
            420                 425                 430

Val Thr Phe Ser Asn Ile Lys Phe Gly Pro Ile Gly Ser Thr Gly Asn
            435                 440                 445

Pro Ser Gly Gly Asn Pro Pro Gly Gly Asn Arg Gly Thr Thr Thr
            450                 455                 460

Arg Arg Pro Ala Thr Thr Thr Gly Ser Ser Pro Gly Pro Thr Gln Ser
465                 470                 475                 480

His Tyr Gly Gln Cys Gly Gly Ile Gly Tyr Ser Gly Pro Thr Val Cys
                485                 490                 495

Ala Ser Gly Thr Thr Cys Gln Val Leu Asn Pro Tyr Tyr Ser Gln Cys
            500                 505                 510

Leu

<210> SEQ ID NO 11
<211> LENGTH: 471
<212> TYPE: PRT
<213> ORGANISM: Trichoderma reesei

<400> SEQUENCE: 11

Met Ile Val Gly Ile Leu Thr Thr Leu Ala Thr Leu Ala Thr Leu Ala
1               5                   10                  15

Ala Ser Val Pro Leu Glu Glu Arg Gln Ala Cys Ser Ser Val Trp Gly
            20                  25                  30

Gln Cys Gly Gly Gln Asn Trp Ser Gly Pro Thr Cys Cys Ala Ser Gly
        35                  40                  45

Ser Thr Cys Val Tyr Ser Asn Asp Tyr Tyr Ser Gln Cys Leu Pro Gly
    50                  55                  60

Ala Ala Ser Ser Ser Ser Ser Thr Arg Ala Ala Ser Thr Thr Ser Arg
65                  70                  75                  80

Val Ser Pro Thr Thr Ser Arg Ser Ser Ser Ala Thr Pro Pro Pro Gly
                85                  90                  95

Ser Thr Thr Thr Arg Val Pro Pro Val Gly Ser Gly Thr Ala Thr Tyr
            100                 105                 110

Ser Gly Asn Pro Phe Val Gly Val Thr Pro Trp Ala Asn Ala Tyr Tyr
        115                 120                 125

Ala Ser Glu Val Ser Ser Leu Ala Ile Pro Ser Leu Thr Gly Ala Met
    130                 135                 140

Ala Thr Ala Ala Ala Ala Val Ala Lys Val Pro Ser Phe Met Trp Leu
145                 150                 155                 160

Asp Thr Leu Asp Lys Thr Pro Leu Met Glu Gln Thr Leu Ala Asp Ile
                165                 170                 175

Arg Thr Ala Asn Lys Asn Gly Gly Asn Tyr Ala Gly Gln Phe Val Val
            180                 185                 190

Tyr Asp Leu Pro Asp Arg Asp Cys Ala Ala Leu Ala Ser Asn Gly Glu
        195                 200                 205
```

```
Tyr Ser Ile Ala Asp Gly Gly Val Ala Lys Tyr Lys Asn Tyr Ile Asp
            210                 215                 220

Thr Ile Arg Gln Ile Val Glu Tyr Ser Asp Ile Arg Thr Leu Leu
225                 230                 235                 240

Val Ile Glu Pro Asp Ser Leu Ala Asn Leu Val Thr Asn Leu Gly Thr
                245                 250                 255

Pro Lys Cys Ala Asn Ala Gln Ser Ala Tyr Leu Glu Cys Ile Asn Tyr
            260                 265                 270

Ala Val Thr Gln Leu Asn Leu Pro Asn Val Ala Met Tyr Leu Asp Ala
        275                 280                 285

Gly His Ala Gly Trp Leu Gly Trp Pro Ala Asn Gln Asp Pro Ala Ala
        290                 295                 300

Gln Leu Phe Ala Asn Val Tyr Lys Asn Ala Ser Ser Pro Arg Ala Leu
305                 310                 315                 320

Arg Gly Leu Ala Thr Asn Val Ala Asn Tyr Asn Gly Trp Asn Ile Thr
                325                 330                 335

Ser Pro Pro Ser Tyr Thr Gln Gly Asn Ala Val Tyr Asn Glu Lys Leu
            340                 345                 350

Tyr Ile His Ala Ile Gly Pro Leu Leu Ala Asn His Gly Trp Ser Asn
        355                 360                 365

Ala Phe Phe Ile Thr Asp Gln Gly Arg Ser Gly Lys Gln Pro Thr Gly
        370                 375                 380

Gln Gln Gln Trp Gly Asp Trp Cys Asn Val Ile Gly Thr Gly Phe Gly
385                 390                 395                 400

Ile Arg Pro Ser Ala Asn Thr Gly Asp Ser Leu Leu Asp Ser Phe Val
                405                 410                 415

Trp Val Lys Pro Gly Gly Glu Cys Asp Gly Thr Ser Asp Ser Ser Ala
                420                 425                 430

Pro Arg Phe Asp Ser His Cys Ala Leu Pro Asp Ala Leu Gln Pro Ala
                435                 440                 445

Pro Gln Ala Gly Ala Trp Phe Gln Ala Tyr Phe Val Gln Leu Leu Thr
        450                 455                 460

Asn Ala Asn Pro Ser Phe Leu
465                 470

<210> SEQ ID NO 12
<211> LENGTH: 239
<212> TYPE: PRT
<213> ORGANISM: Aspergillus niger

<400> SEQUENCE: 12

Met Lys Leu Pro Val Thr Leu Ala Met Leu Ala Ala Thr Ala Met Gly
1               5                   10                  15

Gln Thr Met Cys Ser Gln Tyr Asp Ser Ala Ser Ser Pro Pro Tyr Ser
            20                  25                  30

Val Asn Gln Asn Leu Trp Gly Glu Tyr Gln Gly Thr Gly Ser Gln Cys
        35                  40                  45

Val Tyr Val Asp Lys Leu Ser Ser Ser Gly Ala Ser Trp His Thr Glu
    50                  55                  60

Trp Thr Trp Ser Gly Gly Glu Gly Thr Val Lys Ser Tyr Ser Asn Ser
65                  70                  75                  80

Gly Val Thr Phe Asn Lys Lys Leu Val Ser Asp Val Ser Ser Ile Pro
                85                  90                  95

Thr Ser Val Glu Trp Lys Gln Asp Asn Thr Asn Val Asn Ala Asp Val
```

```
                  100                 105                 110
Ala Tyr Asp Leu Phe Thr Ala Ala Asn Val Asp His Ala Thr Ser Ser
            115                 120                 125

Gly Asp Tyr Glu Leu Met Ile Trp Leu Ala Arg Tyr Gly Asn Ile Gln
130                 135                 140

Pro Ile Gly Lys Gln Ile Ala Thr Ala Thr Val Gly Gly Lys Ser Trp
145                 150                 155                 160

Glu Val Trp Tyr Gly Ser Thr Thr Gln Ala Gly Ala Glu Gln Arg Thr
                165                 170                 175

Tyr Ser Phe Val Ser Glu Ser Pro Ile Asn Ser Tyr Ser Gly Asp Ile
            180                 185                 190

Asn Ala Phe Phe Ser Tyr Leu Thr Gln Asn Gln Gly Phe Pro Ala Ser
        195                 200                 205

Ser Gln Tyr Leu Ile Asn Leu Gln Phe Gly Thr Glu Ala Phe Thr Gly
    210                 215                 220

Gly Pro Ala Thr Phe Thr Val Asp Asn Trp Thr Ala Ser Val Asn
225                 230                 235
```

<210> SEQ ID NO 13
<211> LENGTH: 416
<212> TYPE: PRT
<213> ORGANISM: Aspergillus niger

<400> SEQUENCE: 13

```
Met Arg Ile Ser Asn Leu Ile Val Ala Ala Ser Ala Ala Ser Met Val
1               5                   10                  15

Ser Ala Leu Pro Ser Arg Gln Met Lys Lys Arg Asp Ser Gly Phe Lys
            20                  25                  30

Trp Val Gly Thr Ser Glu Ser Gly Ala Glu Phe Gly Ser Ala Leu Pro
        35                  40                  45

Gly Thr Leu Gly Thr Asp Tyr Thr Trp Pro Glu Thr Ser Lys Ile Gln
    50                  55                  60

Val Leu Arg Asn Lys Gly Met Asn Ile Phe Arg Ile Pro Phe Leu Met
65                  70                  75                  80

Glu Arg Leu Thr Pro Asp Gly Leu Thr Ser Ser Phe Ala Ser Thr Tyr
                85                  90                  95

Leu Ser Asp Leu Lys Ser Thr Val Glu Phe Val Thr Asn Ser Gly Ala
            100                 105                 110

Tyr Ala Val Leu Asp Pro His Asn Tyr Gly Arg Phe Asp Gly Ser Ile
        115                 120                 125

Ile Thr Ser Thr Ser Asp Phe Lys Thr Trp Trp Lys Asn Val Ala Thr
    130                 135                 140

Glu Phe Ala Asp Asn Asp Lys Val Ile Phe Asp Thr Asn Asn Glu Tyr
145                 150                 155                 160

His Asp Met Glu Gln Ser Leu Val Leu Asp Leu Asn Gln Ala Ala Ile
                165                 170                 175

Asn Gly Ile Arg Ala Ala Gly Ala Thr Thr Gln Tyr Ile Phe Val Glu
            180                 185                 190

Gly Asn Ala Tyr Thr Gly Ala Trp Asp Trp Thr Thr Tyr Asn Asp Asn
        195                 200                 205

Leu Ser Gly Leu Thr Asp Ser Glu Asp Lys Ile Ile Tyr Glu Met His
    210                 215                 220

Gln Tyr Leu Asp Ser Asp Ser Ser Gly Thr Ser Glu Thr Cys Val Ser
225                 230                 235                 240
```

```
Ser Thr Ile Gly Gln Glu Arg Leu Glu Lys Ala Thr Glu Trp Leu Lys
            245                 250                 255

Thr Asn Asn Lys Gln Gly Ile Val Gly Glu Phe Ala Gly Gly Val Asn
        260                 265                 270

Ser Val Cys Glu Glu Ala Val Glu Gly Met Leu Ala Tyr Met Ser Glu
    275                 280                 285

Asn Ser Asp Val Trp Val Gly Ala Ser Trp Trp Ser Ala Gly Pro Trp
290                 295                 300

Trp Gly Thr Tyr Met Tyr Ser Leu Glu Pro Thr Asp Gly Thr Ala Tyr
305                 310                 315                 320

Ser Thr Tyr Leu Pro Ile Leu Glu Lys Tyr Phe Pro Ser Gly Asp Ala
                325                 330                 335

Ser Ala Ser Ser Ser Ala Ser Val Ser Val Ala Ala Ala Thr Ser Thr
            340                 345                 350

Ala Ser Thr Thr Thr Ala Ala Phe Glu Gln Thr Thr Thr Pro Ala Thr
        355                 360                 365

Gln Gly Pro Ser Ala Thr Asn Ser Ala Gly Glu Val Asn Gln Tyr Tyr
    370                 375                 380

Gln Cys Gly Gly Ile Asn Trp Thr Gly Pro Thr Val Cys Ala Ser Pro
385                 390                 395                 400

Tyr Thr Cys Lys Val Gln Asn Asp Tyr Tyr Gln Cys Val Ala Glu
                405                 410                 415

<210> SEQ ID NO 14
<211> LENGTH: 331
<212> TYPE: PRT
<213> ORGANISM: Aspergillus niger

<400> SEQUENCE: 14

Met Lys Phe Gln Ser Thr Leu Leu Ala Ala Ala Ala Gly Ser Ala
1               5                   10                  15

Leu Ala Val Pro His Gly Ser Gly His Lys Lys Arg Ala Ser Val Phe
            20                  25                  30

Glu Trp Phe Gly Ser Asn Glu Ser Gly Ala Glu Phe Gly Thr Asn Ile
        35                  40                  45

Pro Gly Val Trp Gly Thr Asp Tyr Ile Phe Pro Asp Pro Ser Thr Ile
    50                  55                  60

Ser Thr Leu Ile Gly Lys Gly Met Asn Phe Phe Arg Val Gln Phe Met
65                  70                  75                  80

Met Glu Arg Leu Leu Pro Asp Ser Met Thr Gly Ser Tyr Asp Glu Glu
                85                  90                  95

Tyr Leu Ala Asn Leu Thr Thr Val Val Lys Ala Val Thr Asp Gly Gly
            100                 105                 110

Ala His Ala Leu Ile Asp Pro His Asn Tyr Gly Arg Tyr Asn Gly Glu
        115                 120                 125

Ile Ile Ser Ser Thr Ser Asp Phe Gln Thr Phe Trp Gln Asn Leu Ala
    130                 135                 140

Gly Gln Tyr Lys Asp Asn Asp Leu Val Met Phe Asp Thr Asn Asn Glu
145                 150                 155                 160

Tyr Tyr Asp Met Asp Gln Asp Leu Val Leu Asn Leu Asn Gln Ala Ala
                165                 170                 175

Ile Asn Gly Ile Arg Ala Ala Gly Ala Ser Gln Tyr Ile Phe Val Glu
            180                 185                 190

Gly Asn Ser Trp Thr Gly Ala Trp Thr Trp Val Asp Val Asn Asp Asn
        195                 200                 205
```

```
Met Lys Asn Leu Thr Asp Pro Glu Asp Lys Ile Val Tyr Glu Met His
            210                 215                 220

Gln Tyr Leu Asp Ser Asp Gly Ser Gly Thr Ser Glu Thr Cys Val Ser
225                 230                 235                 240

Gly Thr Ile Gly Lys Glu Arg Ile Thr Asp Ala Thr Gln Trp Leu Lys
                245                 250                 255

Asp Asn Lys Lys Val Gly Phe Ile Gly Glu Tyr Ala Gly Gly Ser Asn
            260                 265                 270

Asp Val Cys Arg Ser Ala Val Ser Gly Met Leu Glu Tyr Met Ala Asn
            275                 280                 285

Asn Thr Asp Val Trp Lys Gly Ala Ser Trp Ala Ala Gly Pro Trp
290                 295                 300

Trp Gly Asp Tyr Ile Phe Ser Leu Glu Pro Pro Asp Gly Thr Ala Tyr
305                 310                 315                 320

Thr Gly Met Leu Asp Ile Leu Glu Thr Tyr Leu
                325                 330

<210> SEQ ID NO 15
<211> LENGTH: 465
<212> TYPE: PRT
<213> ORGANISM: Trichoderma reesei

<400> SEQUENCE: 15

Met Lys Ser Ser Ile Ser Val Val Leu Ala Leu Leu Gly His Ser Ala
1               5                   10                  15

Ala Trp Ser Tyr Ala Thr Lys Ser Gln Tyr Arg Ala Asn Ile Lys Ile
            20                  25                  30

Asn Ala Arg Gln Thr Tyr Gln Thr Met Ile Gly Gly Gly Cys Ser Gly
        35                  40                  45

Ala Phe Gly Ile Ala Cys Gln Gln Phe Gly Ser Ser Gly Leu Ser Pro
50                  55                  60

Glu Asn Gln Gln Lys Val Thr Gln Ile Leu Phe Asp Glu Asn Ile Gly
65                  70                  75                  80

Gly Leu Ser Ile Val Arg Asn Asp Ile Gly Ser Ser Pro Gly Thr Thr
                85                  90                  95

Ile Leu Pro Thr Cys Pro Ala Thr Pro Gln Asp Lys Phe Asp Tyr Val
            100                 105                 110

Trp Asp Gly Ser Asp Asn Cys Gln Phe Asn Leu Thr Lys Thr Ala Leu
        115                 120                 125

Lys Tyr Asn Pro Asn Leu Tyr Val Tyr Ala Asp Ala Trp Ser Ala Pro
130                 135                 140

Gly Cys Met Lys Thr Val Gly Thr Glu Asn Leu Gly Gly Gln Ile Cys
145                 150                 155                 160

Gly Val Arg Gly Thr Asp Cys Lys His Asp Trp Arg Gln Ala Tyr Ala
                165                 170                 175

Asp Tyr Leu Val Gln Tyr Val Arg Phe Tyr Lys Glu Glu Gly Ile Asp
            180                 185                 190

Ile Ser Leu Leu Gly Ala Trp Asn Glu Pro Asp Phe Asn Pro Phe Thr
        195                 200                 205

Tyr Glu Ser Met Leu Ser Asp Gly Tyr Gln Ala Lys Asp Phe Leu Glu
            210                 215                 220

Val Leu Tyr Pro Thr Leu Lys Lys Ala Phe Pro Lys Val Asp Val Ser
225                 230                 235                 240

Cys Cys Asp Ala Thr Gly Ala Arg Gln Glu Arg Asn Ile Leu Tyr Glu
```

```
                       245                 250                 255
Leu Gln Gln Ala Gly Gly Glu Arg Tyr Phe Asp Ile Ala Thr Trp His
                260                 265                 270

Asn Tyr Gln Ser Asn Pro Glu Arg Pro Phe Asn Ala Gly Gly Lys Pro
            275                 280                 285

Asn Ile Gln Thr Glu Trp Ala Asp Gly Thr Gly Pro Trp Asn Ser Thr
        290                 295                 300

Trp Asp Tyr Ser Gly Gln Leu Ala Glu Gly Leu Gln Trp Ala Leu Tyr
305                 310                 315                 320

Met His Asn Ala Phe Val Asn Ser Asp Thr Ser Gly Tyr Thr His Trp
                325                 330                 335

Trp Cys Ala Gln Asn Thr Asn Gly Asp Asn Ala Leu Ile Arg Leu Asp
            340                 345                 350

Arg Asp Ser Tyr Glu Val Ser Ala Arg Leu Trp Ala Phe Ala Gln Tyr
        355                 360                 365

Phe Arg Phe Ala Arg Pro Gly Ser Val Arg Ile Gly Ala Thr Ser Asp
370                 375                 380

Val Glu Asn Val Tyr Val Thr Ala Tyr Val Asn Lys Asn Gly Thr Val
385                 390                 395                 400

Ala Ile Pro Val Ile Asn Ala Ala His Phe Pro Tyr Asp Leu Thr Ile
                405                 410                 415

Asp Leu Glu Gly Ile Lys Lys Arg Lys Leu Ser Glu Tyr Leu Thr Asp
            420                 425                 430

Asn Ser His Asn Val Thr Leu Gln Ser Arg Tyr Lys Val Ser Gly Ser
        435                 440                 445

Ser Leu Lys Val Thr Val Glu Pro Arg Ala Met Lys Thr Phe Trp Leu
    450                 455                 460

Glu
465

<210> SEQ ID NO 16
<211> LENGTH: 211
<212> TYPE: PRT
<213> ORGANISM: Aspergillus niger

<400> SEQUENCE: 16

Met Lys Val Thr Ala Ala Phe Ala Gly Leu Leu Val Thr Ala Phe Ala
1               5                   10                  15

Ala Pro Val Pro Glu Pro Val Leu Val Ser Arg Ser Ala Gly Ile Asn
            20                  25                  30

Tyr Val Gln Asn Tyr Asn Gly Asn Leu Gly Asp Phe Thr Tyr Asp Glu
        35                  40                  45

Ser Ala Gly Thr Phe Ser Met Tyr Trp Glu Asp Gly Val Ser Ser Asp
    50                  55                  60

Phe Val Val Gly Leu Gly Trp Thr Thr Gly Ser Ser Lys Ala Ile Thr
65                  70                  75                  80

Tyr Ser Ala Glu Tyr Ser Ala Ser Gly Ser Ser Tyr Leu Ala Val
                85                  90                  95

Tyr Gly Trp Val Asn Tyr Pro Gln Ala Glu Tyr Tyr Ile Val Glu Asp
            100                 105                 110

Tyr Gly Asp Tyr Asn Pro Cys Ser Ser Ala Thr Ser Leu Gly Thr Val
        115                 120                 125

Tyr Ser Asp Gly Ser Thr Tyr Gln Val Cys Thr Asp Thr Arg Thr Asn
    130                 135                 140
```

Glu Pro Ser Ile Thr Gly Thr Ser Thr Phe Thr Gln Tyr Phe Ser Val
145                 150                 155                 160

Arg Glu Ser Thr Arg Thr Ser Gly Thr Val Thr Val Ala Asn His Phe
                165                 170                 175

Asn Phe Trp Ala Gln His Gly Phe Gly Asn Ser Asp Phe Asn Tyr Gln
            180                 185                 190

Val Met Ala Val Glu Ala Trp Ser Gly Ala Gly Ser Ala Ser Val Thr
        195                 200                 205

Ile Ser Ser
    210

<210> SEQ ID NO 17
<211> LENGTH: 437
<212> TYPE: PRT
<213> ORGANISM: Trichoderma reesei

<400> SEQUENCE: 17

Met Met Met Leu Ser Lys Ser Leu Leu Ser Ala Ala Thr Ala Ala Ser
1               5                   10                  15

Ala Leu Ala Ala Val Leu Gln Pro Val Pro Arg Ala Ser Ser Phe Val
            20                  25                  30

Thr Ile Ser Gly Thr Gln Phe Asn Ile Asp Gly Lys Val Gly Tyr Phe
        35                  40                  45

Ala Gly Thr Asn Cys Tyr Trp Cys Ser Phe Leu Thr Asn His Ala Asp
    50                  55                  60

Val Asp Ser Thr Phe Ser His Ile Ser Ser Gly Leu Lys Val Val
65                  70                  75                  80

Arg Val Trp Gly Phe Asn Asp Val Asn Thr Gln Pro Ser Pro Gly Gln
                85                  90                  95

Ile Trp Phe Gln Lys Leu Ser Ala Thr Gly Ser Thr Ile Asn Thr Gly
            100                 105                 110

Ala Asp Gly Leu Gln Thr Leu Asp Tyr Val Val Gln Ser Ala Glu Gln
        115                 120                 125

His Asn Leu Lys Leu Ile Ile Pro Phe Val Asn Asn Trp Ser Asp Tyr
130                 135                 140

Gly Gly Ile Asn Ala Tyr Val Asn Ala Phe Gly Gly Asn Ala Thr Thr
145                 150                 155                 160

Trp Tyr Thr Asn Thr Ala Ala Gln Thr Gln Tyr Arg Lys Tyr Val Gln
                165                 170                 175

Ala Val Val Ser Arg Tyr Ala Asn Ser Thr Ala Ile Phe Ala Trp Glu
            180                 185                 190

Leu Gly Asn Glu Pro Arg Cys Asn Gly Cys Ser Thr Asp Val Ile Val
        195                 200                 205

Gln Trp Ala Thr Ser Val Ser Gln Tyr Val Lys Ser Leu Asp Ser Asn
    210                 215                 220

His Leu Val Thr Leu Gly Asp Glu Gly Leu Gly Leu Ser Thr Gly Asp
225                 230                 235                 240

Gly Ala Tyr Pro Tyr Thr Tyr Gly Glu Gly Thr Asp Phe Ala Lys Asn
                245                 250                 255

Val Gln Ile Lys Ser Leu Asp Phe Gly Thr Phe His Leu Tyr Pro Asp
            260                 265                 270

Ser Trp Gly Thr Asn Tyr Thr Trp Gly Asn Gly Trp Ile Gln Thr His
        275                 280                 285

Ala Ala Ala Cys Leu Ala Ala Gly Lys Pro Cys Val Phe Glu Glu Tyr
    290                 295                 300

```
Gly Ala Gln Gln Asn Pro Cys Thr Asn Glu Ala Pro Trp Gln Thr Thr
305                 310                 315                 320

Ser Leu Thr Thr Arg Gly Met Gly Gly Asp Met Phe Trp Gln Trp Gly
            325                 330                 335

Asp Thr Phe Ala Asn Gly Ala Gln Ser Asn Ser Asp Pro Tyr Thr Val
        340                 345                 350

Trp Tyr Asn Ser Ser Asn Trp Gln Cys Leu Val Lys Asn His Val Asp
    355                 360                 365

Ala Ile Asn Gly Gly Thr Thr Thr Pro Pro Val Ser Ser Thr Thr
370                 375                 380

Thr Thr Ser Ser Arg Thr Ser Ser Thr Pro Pro Pro Gly Gly Ser
385                 390                 395                 400

Cys Ser Pro Leu Tyr Gly Gln Cys Gly Gly Ser Gly Tyr Thr Gly Pro
            405                 410                 415

Thr Cys Cys Ala Gln Gly Thr Cys Ile Tyr Ser Asn Tyr Trp Tyr Ser
            420                 425                 430

Gln Cys Leu Asn Thr
            435

<210> SEQ ID NO 18
<211> LENGTH: 335
<212> TYPE: PRT
<213> ORGANISM: Aspergillus niger

<400> SEQUENCE: 18

Met Phe Ala Lys Leu Ser Leu Leu Ser Leu Phe Ser Ser Ala Ala
1               5                   10                  15

Leu Gly Ala Ser Asn Gln Thr Leu Ser Tyr Gly Asn Ile Asp Lys Ser
            20                  25                  30

Ala Thr Pro Glu Ala Arg Ala Leu Leu Lys Tyr Ile Gln Leu Gln Tyr
        35                  40                  45

Gly Ser His Tyr Ile Ser Gly Gln Gln Asp Ile Asp Ser Trp Asn Trp
    50                  55                  60

Val Glu Lys Asn Ile Gly Val Ala Pro Ala Ile Leu Gly Ser Asp Phe
65                  70                  75                  80

Thr Tyr Tyr Ser Pro Ser Ala Val Ala His Gly Gly Lys Ser His Ala
                85                  90                  95

Val Glu Asp Val Ile Gln His Ala Gly Arg Asn Gly Ile Asn Ala Leu
            100                 105                 110

Val Trp His Trp Tyr Ala Pro Thr Cys Leu Leu Asp Thr Ala Lys Glu
        115                 120                 125

Pro Trp Tyr Lys Gly Phe Tyr Thr Glu Ala Thr Cys Phe Asn Val Ser
    130                 135                 140

Glu Ala Val Asn Asp His Gly Asn Gly Thr Asn Tyr Lys Leu Leu Leu
145                 150                 155                 160

Arg Asp Ile Asp Ala Ile Ala Ala Gln Ile Lys Arg Leu Asp Gln Ala
                165                 170                 175

Lys Val Pro Ile Leu Phe Arg Pro Leu His Glu Pro Glu Gly Gly Trp
            180                 185                 190

Phe Trp Trp Gly Ala Gln Gly Pro Ala Pro Phe Lys Lys Leu Trp Asp
        195                 200                 205

Ile Leu Tyr Asp Arg Ile Thr Arg Tyr His Asn Leu His Asn Met Val
    210                 215                 220

Trp Val Cys Asn Thr Ala Asp Pro Ala Trp Tyr Pro Gly Asn Asp Lys
```

```
                225                 230                 235                 240

Cys Asp Ile Ala Thr Ile Asp His Tyr Pro Ala Val Gly Asp His Gly
                245                 250                 255

Val Ala Ala Asp Gln Tyr Lys Lys Leu Gln Thr Val Thr Asn Asn Glu
            260                 265                 270

Arg Val Leu Ala Met Ala Glu Val Gly Pro Ile Pro Asp Pro Asp Lys
        275                 280                 285

Gln Ala Arg Glu Asn Val Asn Trp Ala Tyr Trp Met Val Trp Ser Gly
    290                 295                 300

Asp Phe Ile Glu Asp Gly Lys Gln Asn Pro Asn Gln Phe Leu His Lys
305                 310                 315                 320

Val Tyr Asn Asp Thr Arg Val Val Ala Leu Asn Trp Glu Gly Ala
                325                 330                 335

<210> SEQ ID NO 19
<211> LENGTH: 383
<212> TYPE: PRT
<213> ORGANISM: Aspergillus niger

<400> SEQUENCE: 19

Met Lys Leu Ser Asn Ala Leu Leu Thr Leu Ala Ser Leu Ala Leu Ala
1               5                   10                  15

Asn Val Ser Thr Ala Leu Pro Lys Ala Ser Pro Ala Pro Ser Thr Ser
            20                  25                  30

Ser Ser Ala Ala Ser Thr Ser Phe Ala Ser Thr Ser Gly Leu Gln Phe
        35                  40                  45

Thr Ile Asp Gly Glu Thr Gly Tyr Phe Ala Gly Thr Asn Ser Tyr Trp
    50                  55                  60

Ile Gly Phe Leu Thr Asp Asn Ala Asp Val Asp Leu Val Met Gly His
65                  70                  75                  80

Leu Lys Ser Ser Gly Leu Lys Ile Leu Arg Val Trp Gly Phe Asn Asp
                85                  90                  95

Val Thr Ser Gln Pro Ser Ser Gly Thr Val Trp Tyr Gln Leu His Gln
            100                 105                 110

Asp Gly Lys Ser Thr Ile Asn Thr Gly Ala Asp Gly Leu Gln Arg Leu
        115                 120                 125

Asp Tyr Val Val Ser Ser Ala Glu Gln His Asp Ile Lys Leu Ile Ile
    130                 135                 140

Asn Phe Val Asn Tyr Trp Thr Asp Tyr Gly Gly Met Ser Ala Tyr Val
145                 150                 155                 160

Ser Ala Tyr Gly Gly Ser Gly Glu Thr Asp Phe Tyr Thr Ser Asp Thr
                165                 170                 175

Met Gln Ser Ala Tyr Gln Thr Tyr Ile Lys Thr Val Val Glu Arg Tyr
            180                 185                 190

Ser Asn Ser Ser Ala Val Phe Ala Trp Glu Leu Ala Asn Glu Pro Arg
        195                 200                 205

Cys Pro Ser Cys Asp Thr Ser Val Leu Tyr Asn Trp Ile Glu Lys Thr
    210                 215                 220

Ser Lys Phe Ile Lys Gly Leu Asp Ala Asp Arg Met Val Cys Ile Gly
225                 230                 235                 240

Asp Glu Gly Phe Gly Leu Asn Ile Asp Ser Asp Gly Ser Tyr Pro Tyr
                245                 250                 255

Gln Phe Ser Glu Gly Leu Asn Phe Thr Met Asn Leu Gly Ile Asp Thr
            260                 265                 270
```

```
Ile Asp Phe Gly Thr Leu His Leu Tyr Pro Asp Ser Trp Gly Thr Ser
            275                 280                 285

Asp Asp Trp Gly Asn Gly Trp Ile Thr Ala His Gly Ala Ala Cys Lys
290                 295                 300

Ala Ala Gly Lys Pro Cys Leu Leu Glu Glu Tyr Gly Val Thr Ser Asn
305                 310                 315                 320

His Cys Ser Val Glu Gly Ser Trp Gln Lys Thr Ala Leu Ser Thr Thr
                325                 330                 335

Gly Val Gly Ala Asp Leu Phe Trp Gln Tyr Gly Asp Asp Leu Ser Thr
                340                 345                 350

Gly Lys Ser Pro Asp Asp Gly Asn Thr Ile Tyr Tyr Gly Thr Ser Asp
            355                 360                 365

Tyr Gln Cys Leu Val Thr Asp His Val Ala Ala Ile Gly Ser Ala
370                 375                 380

<210> SEQ ID NO 20
<211> LENGTH: 452
<212> TYPE: PRT
<213> ORGANISM: Aspergillus niger

<400> SEQUENCE: 20

Met His Gln Arg Ala Leu Leu Phe Ser Ala Leu Leu Thr Ala Val Arg
1               5                   10                  15

Ala Gln Gln Ala Gly Thr Leu Thr Glu Glu Val His Pro Ser Leu Thr
                20                  25                  30

Trp Gln Lys Cys Thr Ser Glu Gly Ser Cys Thr Glu Gln Ser Gly Ser
            35                  40                  45

Val Val Ile Asp Ser Asn Trp Arg Trp Thr His Ser Val Asn Asp Ser
50                  55                  60

Thr Asn Cys Tyr Thr Gly Asn Thr Trp Asp Ala Thr Leu Cys Pro Asp
65                  70                  75                  80

Asp Glu Thr Cys Ala Ala Asn Cys Ala Leu Asp Gly Ala Asp Tyr Glu
                85                  90                  95

Ser Thr Tyr Gly Val Thr Thr Asp Gly Asp Ser Leu Thr Leu Lys Phe
                100                 105                 110

Val Thr Gly Ser Asn Val Gly Ser Arg Leu Tyr Leu Met Asp Thr Ser
            115                 120                 125

Asp Glu Gly Tyr Gln Thr Phe Asn Leu Leu Asp Ala Glu Phe Thr Phe
130                 135                 140

Asp Val Asp Val Ser Asn Leu Pro Cys Gly Leu Asn Gly Ala Leu Tyr
145                 150                 155                 160

Phe Thr Ala Met Asp Ala Asp Gly Gly Val Ser Lys Tyr Pro Ala Asn
                165                 170                 175

Lys Ala Gly Ala Lys Tyr Gly Thr Gly Tyr Cys Asp Ser Gln Cys Pro
            180                 185                 190

Arg Asp Leu Lys Phe Ile Asp Gly Gln Ala Asn Val Asp Gly Trp Glu
        195                 200                 205

Pro Ser Ser Asn Asn Asp Asn Thr Gly Ile Gly Asn His Gly Ser Cys
    210                 215                 220

Cys Pro Glu Met Asp Ile Trp Glu Ala Asn Lys Ile Ser Thr Ala Leu
225                 230                 235                 240

Thr Pro His Pro Cys Asp Ser Ser Glu Gln Thr Met Cys Glu Gly Asn
                245                 250                 255

Asp Cys Gly Gly Thr Tyr Ser Asp Asp Arg Tyr Gly Gly Thr Cys Asp
                260                 265                 270
```

```
Pro Asp Gly Cys Asp Phe Asn Pro Tyr Arg Met Gly Asn Asp Ser Phe
        275                 280                 285

Tyr Gly Pro Gly Lys Thr Ile Asp Thr Gly Ser Lys Met Thr Val Val
    290                 295                 300

Thr Gln Phe Ile Thr Asp Gly Ser Gly Ser Leu Ser Glu Ile Lys Arg
305                 310                 315                 320

Tyr Tyr Val Gln Asn Gly Asn Val Ile Ala Asn Ala Asp Ser Asn Ile
                325                 330                 335

Ser Gly Val Thr Gly Asn Ser Ile Thr Thr Asp Phe Cys Thr Ala Gln
            340                 345                 350

Lys Lys Ala Phe Gly Asp Glu Asp Ile Phe Ala Glu His Asn Gly Leu
        355                 360                 365

Ala Gly Ile Ser Asp Ala Met Ser Ser Met Val Leu Ile Leu Ser Leu
    370                 375                 380

Trp Asp Asp Tyr Tyr Ala Ser Met Glu Trp Leu Asp Ser Asp Tyr Pro
385                 390                 395                 400

Glu Asn Ala Thr Ala Thr Asp Pro Gly Val Ala Arg Gly Thr Cys Asp
                405                 410                 415

Ser Glu Ser Gly Val Pro Ala Thr Val Glu Gly Ala His Pro Asp Ser
            420                 425                 430

Ser Val Thr Phe Ser Asn Ile Lys Phe Gly Pro Ile Asn Ser Thr Phe
        435                 440                 445

Ser Ala Ser Ala
    450

<210> SEQ ID NO 21
<211> LENGTH: 536
<212> TYPE: PRT
<213> ORGANISM: Aspergillus niger

<400> SEQUENCE: 21

Met Ser Ser Phe Gln Ile Tyr Arg Ala Ala Leu Leu Leu Ser Ile Leu
1               5                   10                  15

Ala Thr Ala Asn Ala Gln Gln Val Gly Thr Tyr Thr Thr Glu Thr His
            20                  25                  30

Pro Ser Leu Thr Trp Gln Thr Cys Thr Ser Asp Gly Ser Cys Thr Thr
        35                  40                  45

Asn Asp Gly Glu Val Val Ile Asp Ala Asn Trp Arg Trp Val His Ser
    50                  55                  60

Thr Ser Ser Ala Thr Asn Cys Tyr Thr Gly Asn Glu Trp Asp Thr Ser
65                  70                  75                  80

Ile Cys Thr Asp Asp Val Thr Cys Ala Ala Asn Cys Ala Leu Asp Gly
                85                  90                  95

Ala Thr Tyr Glu Ala Thr Tyr Gly Val Thr Thr Ser Gly Ser Glu Leu
            100                 105                 110

Arg Leu Asn Phe Val Thr Gln Gly Ser Ser Lys Asn Ile Gly Ser Arg
        115                 120                 125

Leu Tyr Leu Met Ser Asp Asp Ser Asn Tyr Glu Leu Phe Lys Leu Leu
    130                 135                 140

Gly Gln Glu Phe Thr Phe Asp Val Asp Val Ser Asn Leu Pro Cys Gly
145                 150                 155                 160

Leu Asn Gly Ala Leu Tyr Phe Val Ala Met Asp Ala Asp Gly Gly Thr
                165                 170                 175

Ser Glu Tyr Ser Gly Asn Lys Ala Gly Ala Lys Tyr Gly Thr Gly Tyr
```

```
                180                 185                 190
Cys Asp Ser Gln Cys Pro Arg Asp Leu Lys Phe Ile Asn Gly Glu Ala
            195                 200                 205
Asn Cys Asp Gly Trp Glu Pro Ser Ser Asn Val Asn Thr Gly Val
        210                 215                 220
Gly Asp His Gly Ser Cys Cys Ala Glu Met Asp Val Trp Glu Ala Asn
225                 230                 235                 240
Ser Ile Ser Asn Ala Phe Thr Ala His Pro Cys Asp Ser Val Ser Gln
            245                 250                 255
Thr Met Cys Asp Gly Asp Ser Cys Gly Gly Thr Tyr Ser Ala Ser Gly
            260                 265                 270
Asp Arg Tyr Ser Gly Thr Cys Asp Pro Asp Gly Cys Asp Tyr Asn Pro
        275                 280                 285
Tyr Arg Leu Gly Asn Thr Asp Phe Tyr Gly Pro Gly Leu Thr Val Asp
        290                 295                 300
Thr Asn Ser Pro Phe Thr Val Val Thr Gln Phe Ile Thr Asp Asp Gly
305                 310                 315                 320
Thr Ser Ser Gly Thr Leu Thr Glu Ile Lys Arg Leu Tyr Val Gln Asn
            325                 330                 335
Gly Glu Val Ile Ala Asn Gly Ala Ser Thr Tyr Ser Ser Val Asn Gly
            340                 345                 350
Ser Ser Ile Thr Ser Ala Phe Cys Glu Ser Glu Lys Thr Leu Phe Gly
            355                 360                 365
Asp Glu Asn Val Phe Asp Lys His Gly Gly Leu Glu Gly Met Gly Glu
        370                 375                 380
Ala Met Ala Lys Gly Met Val Leu Val Leu Ser Leu Trp Asp Asp Tyr
385                 390                 395                 400
Ala Ala Asp Met Leu Trp Leu Asp Ser Asp Tyr Pro Val Asn Ser Ser
            405                 410                 415
Ala Ser Thr Pro Gly Val Ala Arg Gly Thr Cys Ser Thr Asp Ser Gly
            420                 425                 430
Val Pro Ala Thr Val Glu Ala Glu Ser Pro Asn Ala Tyr Val Thr Tyr
            435                 440                 445
Ser Asn Ile Lys Phe Gly Pro Ile Gly Ser Thr Tyr Ser Ser Gly Ser
        450                 455                 460
Ser Ser Gly Ser Gly Ser Ser Ser Ser Ser Ser Thr Thr Thr Lys
465                 470                 475                 480
Ala Thr Ser Thr Thr Leu Lys Thr Thr Ser Thr Ser Ser Gly Ser
            485                 490                 495
Ser Ser Thr Ser Ala Ala Gln Ala Tyr Gly Gln Cys Gly Gly Gln Gly
            500                 505                 510
Trp Thr Gly Pro Thr Thr Cys Val Ser Gly Tyr Thr Cys Thr Tyr Glu
        515                 520                 525
Asn Ala Tyr Tyr Ser Gln Cys Leu
    530                 535

<210> SEQ ID NO 22
<211> LENGTH: 744
<212> TYPE: PRT
<213> ORGANISM: Trichoderma reesei

<400> SEQUENCE: 22

Met Arg Tyr Arg Thr Ala Ala Leu Ala Leu Ala Thr Gly Pro Phe
1               5                   10                  15
```

-continued

```
Ala Arg Ala Asp Ser His Ser Thr Ser Gly Ala Ser Ala Glu Ala Val
         20                  25                  30

Val Pro Pro Ala Gly Thr Pro Trp Gly Thr Ala Tyr Asp Lys Ala Lys
         35                  40                  45

Ala Ala Leu Ala Lys Leu Asn Leu Gln Asp Lys Val Gly Ile Val Ser
 50                  55                  60

Gly Val Gly Trp Asn Gly Gly Pro Cys Val Gly Asn Thr Ser Pro Ala
 65                  70                  75                  80

Ser Lys Ile Ser Tyr Pro Ser Leu Cys Leu Gln Asp Gly Pro Leu Gly
                 85                  90                  95

Val Arg Tyr Ser Thr Gly Ser Thr Ala Phe Thr Pro Gly Val Gln Ala
                100                 105                 110

Ala Ser Thr Trp Asp Val Asn Leu Ile Arg Glu Arg Gly Gln Phe Ile
            115                 120                 125

Gly Glu Glu Val Lys Ala Ser Gly Ile His Val Ile Leu Gly Pro Val
130                 135                 140

Ala Gly Pro Leu Gly Lys Thr Pro Gln Gly Gly Arg Asn Trp Glu Gly
145                 150                 155                 160

Phe Gly Val Asp Pro Tyr Leu Thr Gly Ile Ala Met Gly Gln Thr Ile
                165                 170                 175

Asn Gly Ile Gln Ser Val Gly Val Gln Ala Thr Ala Lys His Tyr Ile
            180                 185                 190

Leu Asn Glu Gln Glu Leu Asn Arg Glu Thr Ile Ser Ser Asn Pro Asp
        195                 200                 205

Asp Arg Thr Leu His Glu Leu Tyr Thr Trp Pro Phe Ala Asp Ala Val
210                 215                 220

Gln Ala Asn Val Ala Ser Val Met Cys Ser Tyr Asn Lys Val Asn Thr
225                 230                 235                 240

Thr Trp Ala Cys Glu Asp Gln Tyr Thr Leu Gln Thr Val Leu Lys Asp
                245                 250                 255

Gln Leu Gly Phe Pro Gly Tyr Val Met Thr Asp Trp Asn Ala Gln His
            260                 265                 270

Thr Thr Val Gln Ser Ala Asn Ser Gly Leu Asp Met Ser Met Pro Gly
        275                 280                 285

Thr Asp Phe Asn Gly Asn Asn Arg Leu Trp Gly Pro Ala Leu Thr Asn
290                 295                 300

Ala Val Asn Ser Asn Gln Val Pro Thr Ser Arg Val Asp Asp Met Val
305                 310                 315                 320

Thr Arg Ile Leu Ala Ala Trp Tyr Leu Thr Gly Gln Asp Gln Ala Gly
                325                 330                 335

Tyr Pro Ser Phe Asn Ile Ser Arg Asn Val Gln Gly Asn His Lys Thr
            340                 345                 350

Asn Val Arg Ala Ile Ala Arg Asp Gly Ile Val Leu Leu Lys Asn Asp
        355                 360                 365

Ala Asn Ile Leu Pro Leu Lys Lys Pro Ala Ser Ile Ala Val Val Gly
370                 375                 380

Ser Ala Ala Ile Ile Gly Asn His Ala Arg Asn Ser Pro Ser Cys Asn
385                 390                 395                 400

Asp Lys Gly Cys Asp Asp Gly Ala Leu Gly Met Gly Trp Gly Ser Gly
                405                 410                 415

Ala Val Asn Tyr Pro Tyr Phe Val Ala Pro Tyr Asp Ala Ile Asn Thr
            420                 425                 430

Arg Ala Ser Ser Gln Gly Thr Gln Val Thr Leu Ser Asn Thr Asp Asn
```

```
                    435                 440                 445
        Thr Ser Ser Gly Ala Ser Ala Arg Gly Lys Asp Val Ala Ile Val
        450                 455                 460

Phe Ile Thr Ala Asp Ser Gly Glu Gly Tyr Ile Thr Val Glu Gly Asn
        465                 470                 475                 480

Ala Gly Asp Arg Asn Asn Leu Asp Pro Trp His Asn Gly Asn Ala Leu
                        485                 490                 495

Val Gln Ala Val Ala Gly Ala Asn Ser Asn Val Ile Val Val His
                    500                 505                 510

Ser Val Gly Ala Ile Ile Leu Glu Gln Ile Leu Ala Leu Pro Gln Val
                    515                 520                 525

Lys Ala Val Val Trp Ala Gly Leu Pro Ser Gln Glu Ser Gly Asn Ala
        530                 535                 540

Leu Val Asp Val Leu Trp Gly Asp Val Ser Pro Ser Gly Lys Leu Val
        545                 550                 555                 560

Tyr Thr Ile Ala Lys Ser Pro Asn Asp Tyr Asn Thr Arg Ile Val Ser
                        565                 570                 575

Gly Gly Ser Asp Ser Phe Ser Glu Gly Leu Phe Ile Asp Tyr Lys His
                    580                 585                 590

Phe Asp Asp Ala Asn Ile Thr Pro Arg Tyr Glu Phe Gly Tyr Gly Leu
                    595                 600                 605

Ser Tyr Thr Lys Phe Asn Tyr Ser Arg Leu Ser Val Leu Ser Thr Ala
                    610                 615                 620

Lys Ser Gly Pro Ala Thr Gly Ala Val Val Pro Gly Gly Pro Ser Asp
        625                 630                 635                 640

Leu Phe Gln Asn Val Ala Thr Val Thr Val Asp Ile Ala Asn Ser Gly
                        645                 650                 655

Gln Val Thr Gly Ala Glu Val Ala Gln Leu Tyr Ile Thr Tyr Pro Ser
                    660                 665                 670

Ser Ala Pro Arg Thr Pro Pro Lys Gln Leu Arg Gly Phe Ala Lys Leu
                    675                 680                 685

Asn Leu Thr Pro Gly Gln Ser Gly Thr Ala Thr Phe Asn Ile Arg Arg
        690                 695                 700

Arg Asp Leu Ser Tyr Trp Asp Thr Ala Ser Gln Lys Trp Val Val Pro
        705                 710                 715                 720

Ser Gly Ser Phe Gly Ile Ser Val Gly Ala Ser Ser Arg Asp Ile Arg
                        725                 730                 735

Leu Thr Ser Thr Leu Ser Val Ala
                    740

<210> SEQ ID NO 23
<211> LENGTH: 344
<212> TYPE: PRT
<213> ORGANISM: Trichoderma reesei

<400> SEQUENCE: 23

Met Ile Gln Lys Leu Ser Asn Leu Leu Val Thr Ala Leu Ala Val Ala
1               5                   10                  15

Thr Gly Val Val Gly His Gly His Ile Asn Asp Ile Val Ile Asn Gly
                20                  25                  30

Val Trp Tyr Gln Ala Tyr Asp Pro Thr Thr Phe Pro Tyr Glu Ser Asn
            35                  40                  45

Pro Pro Ile Val Val Gly Trp Thr Ala Ala Asp Leu Asp Asn Gly Phe
        50                  55                  60
```

```
Val Ser Pro Asp Ala Tyr Gln Asn Pro Asp Ile Ile Cys His Lys Asn
 65                  70                  75                  80

Ala Thr Asn Ala Lys Gly His Ala Ser Val Lys Ala Gly Asp Thr Ile
             85                  90                  95

Leu Phe Gln Trp Val Pro Val Pro Trp Pro His Pro Gly Pro Ile Val
            100                 105                 110

Asp Tyr Leu Ala Asn Cys Asn Gly Asp Cys Glu Thr Val Asp Lys Thr
            115                 120                 125

Thr Leu Glu Phe Phe Lys Ile Asp Gly Val Gly Leu Leu Ser Gly Gly
130                 135                 140

Asp Pro Gly Thr Trp Ala Ser Asp Val Leu Ile Ser Asn Asn Asn Thr
145                 150                 155                 160

Trp Val Val Lys Ile Pro Asp Asn Leu Ala Pro Gly Asn Tyr Val Leu
                165                 170                 175

Arg His Glu Ile Ile Ala Leu His Ser Ala Gly Gln Ala Asn Gly Ala
            180                 185                 190

Gln Asn Tyr Pro Gln Cys Phe Asn Ile Ala Val Ser Gly Ser Gly Ser
            195                 200                 205

Leu Gln Pro Ser Gly Val Leu Gly Thr Asp Leu Tyr His Ala Thr Asp
210                 215                 220

Pro Gly Val Leu Ile Asn Ile Tyr Thr Ser Pro Leu Asn Tyr Ile Ile
225                 230                 235                 240

Pro Gly Pro Thr Val Val Ser Gly Leu Pro Thr Ser Val Ala Gln Gly
                245                 250                 255

Ser Ser Ala Ala Thr Ala Thr Ala Ser Ala Thr Val Pro Gly Gly Gly
            260                 265                 270

Ser Gly Pro Thr Ser Arg Thr Thr Thr Ala Arg Thr Thr Gln Ala
            275                 280                 285

Ser Ser Arg Pro Ser Ser Thr Pro Pro Ala Thr Thr Ser Ala Pro Ala
290                 295                 300

Gly Gly Pro Thr Gln Thr Leu Tyr Gly Gln Cys Gly Gly Ser Gly Tyr
305                 310                 315                 320

Ser Gly Pro Thr Arg Cys Ala Pro Pro Ala Thr Cys Ser Thr Leu Asn
                325                 330                 335

Pro Tyr Tyr Ala Gln Cys Leu Asn
            340

<210> SEQ ID NO 24
<211> LENGTH: 459
<212> TYPE: PRT
<213> ORGANISM: Trichoderma reesei

<400> SEQUENCE: 24

Met Ala Pro Ser Val Thr Leu Pro Leu Thr Thr Ala Ile Leu Ala Ile
 1               5                  10                  15

Ala Arg Leu Val Ala Ala Gln Gln Pro Gly Thr Ser Thr Pro Glu Val
             20                  25                  30

His Pro Lys Leu Thr Thr Tyr Lys Cys Thr Lys Ser Gly Gly Cys Val
             35                  40                  45

Ala Gln Asp Thr Ser Val Val Leu Asp Trp Asn Tyr Arg Trp Met His
 50                  55                  60

Asp Ala Asn Tyr Asn Ser Cys Thr Val Asn Gly Gly Val Asn Thr Thr
 65                  70                  75                  80

Leu Cys Pro Asp Glu Ala Thr Cys Gly Lys Asn Cys Phe Ile Glu Gly
             85                  90                  95
```

Val Asp Tyr Ala Ala Ser Gly Val Thr Thr Ser Gly Ser Leu Thr
            100                 105                 110

Met Asn Gln Tyr Met Pro Ser Ser Gly Gly Tyr Ser Ser Val Ser
            115                 120                 125

Pro Arg Leu Tyr Leu Asp Ser Asp Gly Glu Tyr Val Met Leu Lys
            130                 135                 140

Leu Asn Gly Gln Glu Leu Ser Phe Asp Val Asp Leu Ser Ala Leu Pro
145                 150                 155                 160

Cys Gly Glu Asn Gly Ser Leu Tyr Leu Ser Gln Met Asp Glu Asn Gly
                165                 170                 175

Gly Ala Asn Gln Tyr Asn Thr Ala Gly Ala Asn Tyr Gly Ser Gly Tyr
            180                 185                 190

Cys Asp Ala Gln Cys Pro Val Gln Thr Trp Arg Asn Gly Thr Leu Asn
            195                 200                 205

Thr Ser His Gln Gly Phe Cys Cys Asn Glu Met Asp Ile Leu Glu Gly
        210                 215                 220

Asn Ser Arg Ala Asn Ala Leu Thr Pro His Ser Cys Thr Ala Thr Ala
225                 230                 235                 240

Cys Asp Ser Ala Gly Cys Gly Phe Asn Pro Tyr Gly Ser Gly Tyr Lys
                245                 250                 255

Ser Tyr Tyr Gly Pro Gly Asp Thr Val Asp Thr Ser Lys Thr Phe Thr
            260                 265                 270

Ile Ile Thr Gln Phe Asn Thr Asp Asn Gly Ser Pro Ser Gly Asn Leu
        275                 280                 285

Val Ser Ile Thr Arg Lys Tyr Gln Gln Asn Gly Val Asp Ile Pro Ser
        290                 295                 300

Ala Gln Pro Gly Gly Asp Thr Ile Ser Ser Cys Pro Ser Ala Ser Ala
305                 310                 315                 320

Tyr Gly Gly Leu Ala Thr Met Gly Lys Ala Leu Ser Ser Gly Met Val
                325                 330                 335

Leu Val Phe Ser Ile Trp Asn Asp Asn Ser Gln Tyr Met Asn Trp Leu
            340                 345                 350

Asp Ser Gly Asn Ala Gly Pro Cys Ser Ser Thr Glu Gly Asn Pro Ser
            355                 360                 365

Asn Ile Leu Ala Asn Asn Pro Asn Thr His Val Val Phe Ser Asn Ile
        370                 375                 380

Arg Trp Gly Asp Ile Gly Ser Thr Thr Asn Ser Thr Ala Pro Pro Pro
385                 390                 395                 400

Pro Pro Ala Ser Ser Thr Thr Phe Ser Thr Thr Arg Arg Ser Ser Thr
                405                 410                 415

Thr Ser Ser Ser Pro Ser Cys Thr Gln Thr His Trp Gly Gln Cys Gly
            420                 425                 430

Gly Ile Gly Tyr Ser Gly Cys Lys Thr Cys Thr Ser Gly Thr Thr Cys
            435                 440                 445

Gln Tyr Ser Asn Asp Tyr Tyr Ser Gln Cys Leu
        450                 455

<210> SEQ ID NO 25
<211> LENGTH: 418
<212> TYPE: PRT
<213> ORGANISM: Trichoderma reesei

<400> SEQUENCE: 25

Met Asn Lys Ser Val Ala Pro Leu Leu Leu Ala Ala Ser Ile Leu Tyr

-continued

```
1               5                   10                  15
Gly Gly Ala Val Ala Gln Gln Thr Val Trp Gly Gln Cys Gly Gly Ile
                20                  25                  30
Gly Trp Ser Gly Pro Thr Asn Cys Ala Pro Gly Ser Ala Cys Ser Thr
            35                  40                  45
Leu Asn Pro Tyr Tyr Ala Gln Cys Ile Pro Gly Ala Thr Thr Ile Thr
        50                  55                  60
Thr Ser Thr Arg Pro Pro Ser Gly Pro Thr Thr Thr Arg Ala Thr
65                  70                  75                  80
Ser Thr Ser Ser Thr Pro Pro Thr Ser Ser Gly Val Arg Phe Ala
                85                  90                  95
Gly Val Asn Ile Ala Gly Phe Asp Phe Gly Cys Thr Thr Asp Gly Thr
                100                 105                 110
Cys Val Thr Ser Lys Val Tyr Pro Pro Leu Lys Asn Phe Thr Gly Ser
            115                 120                 125
Asn Asn Tyr Pro Asp Gly Ile Gly Gln Met Gln His Phe Val Asn Glu
        130                 135                 140
Asp Gly Met Thr Ile Phe Arg Leu Pro Val Gly Trp Gln Tyr Leu Val
145                 150                 155                 160
Asn Asn Asn Leu Gly Gly Asn Leu Asp Ser Thr Ser Ile Ser Lys Tyr
                165                 170                 175
Asp Gln Leu Val Gln Gly Cys Leu Ser Leu Gly Ala Tyr Cys Ile Val
            180                 185                 190
Asp Ile His Asn Tyr Ala Arg Trp Asn Gly Gly Ile Ile Gly Gln Gly
        195                 200                 205
Gly Pro Thr Asn Ala Gln Phe Thr Ser Leu Trp Ser Gln Leu Ala Ser
        210                 215                 220
Lys Tyr Ala Ser Gln Ser Arg Val Trp Phe Gly Ile Met Asn Glu Pro
225                 230                 235                 240
His Asp Val Asn Ile Asn Thr Trp Ala Ala Thr Val Gln Glu Val Val
                245                 250                 255
Thr Ala Ile Arg Asn Ala Gly Ala Thr Ser Gln Phe Ile Ser Leu Pro
            260                 265                 270
Gly Asn Asp Trp Gln Ser Ala Gly Ala Phe Ile Ser Asp Gly Ser Ala
        275                 280                 285
Ala Ala Leu Ser Gln Val Thr Asn Pro Asp Gly Ser Thr Thr Asn Leu
        290                 295                 300
Ile Phe Asp Val His Lys Tyr Leu Asp Ser Asp Asn Ser Gly Thr His
305                 310                 315                 320
Ala Glu Cys Thr Thr Asn Asn Ile Asp Gly Ala Phe Ser Pro Leu Ala
                325                 330                 335
Thr Trp Leu Arg Gln Asn Asn Arg Gln Ala Ile Leu Thr Glu Thr Gly
            340                 345                 350
Gly Gly Asn Val Gln Ser Cys Ile Gln Asp Met Cys Gln Gln Ile Gln
        355                 360                 365
Tyr Leu Asn Gln Asn Ser Asp Val Tyr Leu Gly Tyr Val Gly Trp Gly
        370                 375                 380
Ala Gly Ser Phe Asp Ser Thr Tyr Val Leu Thr Glu Thr Pro Thr Gly
385                 390                 395                 400
Ser Gly Asn Ser Trp Thr Asp Thr Ser Leu Val Ser Ser Cys Leu Ala
                405                 410                 415
Arg Lys
```

METHODS FOR TREATING BIOMASS TO PRODUCE OLIGOSACCHARIDES AND RELATED COMPOSITIONS

CROSS REFERENCE

This application is a continuation of U.S. patent application Ser. No. 17/691,931, filed Mar. 10, 2022, which is a continuation of U.S. patent application Ser. No. 17/083,121, filed Oct. 28, 2020, which is a continuation of International Patent Application PCT/EP2020/072929, filed Aug. 14, 2020, which this application claims the benefit of UK Patent Application No. 1911762.1, filed Aug. 16, 2019, UK Patent Application No. 1911764.7, filed Aug. 16, 2019, and UK Patent Application No. 2002315.6, filed Feb. 19, 2020, each of which is hereby incorporated by reference in its entirety.

SEQUENCE LISTING

The instant application contains a Sequence Listing which has been submitted in ASCII format via EFS-Web and is hereby incorporated by in its entirety. Said ASCII copy, created Oct. 26, 2020, is named 56406_709_302_ST.txt and is 97.0 kilobytes in size

BACKGROUND

Sugary foods and drinks are an important part of cultural and lifestyle habits across the world, but the sugar they contain has been linked to obesity, diabetes, poor dental health, and disruptive behavior in people. Because of this, consumer preferences have been shifting away from sugar-containing foods, and governments are increasingly implementing regulation to encourage the consumption of less sugar.

As such, industry has been searching for suitable low-calorie sweeteners for many decades to substitute for sugar in food and beverages. Unfortunately, many sugar substitutes are produced from non-natural resources, and often offer bitter undertones or other unpleasant tastes along with their sweetness, both of which consumers find unappealing. Moreover, while many sweeteners are able to mimic the sweetness of sugar in food and drinks, few are able to mimic the broad range of roles that sugar plays in food, such as adding bulk, modulating texture, providing structure, acting as a preservative, and modulating color and flavor through caramelization and Maillard reactions. In addition, many bulking sweeteners that are able to mimic these physical properties of sugar have gastrointestinal tolerance issues that limit their use to levels well below the amount required to replace sugar in a standard Western diet.

Dietary fiber is an important part of a positive diet and helps maintain digestive health and a well-regulated gut flora. Such fiber includes saccharides of varying chain lengths and types. In addition to being found naturally in a wide spectrum of foods, fiber can also be produced separately and added to other foods during their manufacture.

SUMMARY

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

In some embodiments, described herein are methods of producing ingredients for human consumption. A method of producing an ingredient for human consumption may comprise (a) isolating one or more soluble polysaccharides from a biomass; (b) contacting the remaining biomass with one or more enzymes to form one or more oligosaccharides; (c) isolating the one or more oligosaccharides; and (d) combining a portion of the one or more soluble polysaccharides from step (a) with a portion of the one or more oligosaccharides from step (c) to form the ingredient.

In some cases, the method may comprise purifying the isolated one or more soluble polysaccharides.

In some cases, the method may comprise purifying the isolated one or more oligosaccharides.

In some cases, the method may comprise treating the biomass to solubilize the one or more soluble polysaccharides.

In some cases, the method may comprise purifying the isolated one or more soluble polysaccharides.

In some cases, the treating comprises a thermochemical treatment.

In some cases, the thermochemical treatment comprises at least one of a hot water treatment or a hot alkali treatment.

In some cases, the hot alkali treatment uses an alkali with a pH of from 10 to 14.

In some cases, the hot alkali treatment uses at least one of sodium hydroxide, potassium hydroxide, sodium carbonate, calcium carbonate, calcium hydroxide, ammonium sulfate, ammonium hydroxide, or aqueous ammonia.

In some cases, the treating may be conducted at a temperature of from 30° C. to 180° C.

In some cases, the treating may be conducted for from 10 minutes to 24 hours.

In some cases, the one or more soluble polysaccharides and/or the one or more oligosaccharides are dried prior to step (d).

In some cases, the one or more soluble polysaccharides and/or the one or more oligosaccharides are dried subsequent to step (d).

In some cases, the ingredient may be soluble in water.

In some cases, the solubility of the ingredient in water may be at least 80 g of the ingredient per 100 g of water at 50° C.

In some cases, the method comprises combining the ingredient with a liquid to form a liquid ingredient.

In some cases, a viscosity of the liquid ingredient may be similar to a viscosity of corn syrup.

In some cases, a viscosity of the liquid ingredient may be similar to a viscosity of high-fructose corn syrup.

In some cases, the liquid ingredient has fewer calories per gram than corn syrup or high-fructose corn syrup.

In some cases, the liquid ingredient has a lower glycemic index than corn syrup or high-fructose corn syrup.

In some cases, the liquid comprises water.

In some cases, the liquid ingredient comprises at least 20% by dry weight of the at least one oligosaccharide and at least 2% by dry weight of the at least one polysaccharide.

In some cases, the liquid ingredient has a viscosity of from 5 cps to 100,000 cps, 8,000 cps to 100,000 cps, 10,000 cps to 50,000 cps, or 15,000 cps to 25,000 cps.

In some cases, the liquid ingredient comprises at least 2% by dry weight of xylan.

In some cases, the liquid ingredient comprises at least 2% by dry weight of mannan.

In some cases, the liquid ingredient comprises at least 2% by dry weight of a cellulose derivative.

In some cases, the liquid ingredient has a concentration of polysaccharides of from 0.1% to 50% w/v.

In some cases, the liquid ingredient comprises an amount of polysaccharide and oligosaccharide in a ratio from 1:100 to 1:1.

In some cases, the one or more soluble polysaccharides comprise at least one of a mannan, a xylan, a mixed-linkage glucan, a lignocellulose, a hemicellulose, a cellulose derivative, a chitosan, or a xyloglucan.

In some cases, the cellulose derivative comprises at least one of a cellulose acetate, a hydroxyethylcellulose, or a hydroxymethylcellulose.

In some cases, the biomass comprises at least one of a sugar cane biomass, a corn biomass, a wheat biomass, a hardwood biomass, or a softwood biomass.

In some cases, the one or more oligosaccharides comprise at least one of: i) a cello-oligosaccharide having a degree of polymerization (DP) of from two to six; ii) a xylo-oligosaccharide having a DP of from two to twelve; iii) an arabinoxylo-oligosaccharide having a DP of from three to fifteen; iv) a manno-oligosaccharide having a DP of from two to twelve; v) a mixed-linkage glucan oligosaccharide having a DP of from two to five; vi) a xyloglucan oligosaccharide having a DP of from four to twelve; or vii) a chito-oligosaccharide having a DP of from two to twelve.

In some cases, the ingredient comprises at least two of the oligosaccharides listed in (i) to (vii).

In some cases, the ingredient comprises the at least two oligosaccharides in a ratio from 1:9 to 1:1 in relation to each other.

In some embodiments, described herein are compositions for human consumption.

The composition for human consumption may comprise: a soluble polysaccharide; and an oligosaccharide may comprise at least one of: (i) a cello-oligosaccharide having a degree of polymerization (DP) of from two to six; (ii) a xylo-oligosaccharide having a DP of from two to twelve; (iii) a manno-oligosaccharide having a DP of from two to twelve; (iv) an arabinoxylo-oligosaccharide having a DP of from three to fifteen; (v) a mixed-linkage glucan oligosaccharide having a DP of from two to five; or (vi) a chiton-oligosaccharide having a DP of from two to twelve, wherein the composition comprises less than 5% by dry weight insoluble polysaccharides.

In some cases, the composition may be substantially free of insoluble polysaccharides.

In some cases, the composition may be soluble in water.

In some cases, the solubility of the composition in water may be at least 80 g of the composition per 100 g of water at 50° C.

In some cases, the composition further comprises a liquid, thereby forming a liquid ingredient.

In some cases, the liquid may be water.

In some cases, the liquid ingredient comprises at least 20% by dry weight of the at least one oligosaccharide and at least 2% by dry weight of the at least one polysaccharide.

In some cases, the liquid ingredient has a viscosity of from 5 cps to 100,000 cps, 8,000 cps to 100,000 cps, 10,000 cps to 50,000 cps, or 15,000 cps to 25,000 cps.

In some cases, the liquid ingredient comprises at least 2% by dry weight of xylan.

In some cases, the liquid ingredient comprises at least 2% by dry weight of mannan.

In some cases, the liquid ingredient comprises at least 2% by dry weight of a cellulose derivative.

In some cases, the liquid ingredient has a concentration of polysaccharides of from 0.1% to 50% w/v.

In some cases, the liquid ingredient comprises an amount of polysaccharide and oligosaccharide in a ratio from 1:100 to 1:1.

In some cases, the one or more soluble polysaccharides comprise at least one of a mannan, a xylan, a mixed-linkage glucan, a lignocellulose, a hemicellulose, a cellulose derivative, a chitosan, or a xyloglucan.

In some cases, the cellulose derivative comprises at least one of a cellulose acetate, a hydroxyethylcellulose, or a hydroxymethylcellulose.

In some cases, the biomass comprises at least one of a sugar cane biomass, a corn biomass, a wheat biomass, a hardwood biomass, or a softwood biomass.

In some cases, the one or more oligosaccharides comprise at least one of: i) a cello-oligosaccharide having a degree of polymerization (DP) of from two to six; ii) a xylo-oligosaccharide having a DP of from two to twelve; iii) an arabinoxylo-oligosaccharide having a DP of from three to fifteen; iv) a manno-oligosaccharide having a DP of from two to twelve; v) a mixed-linkage glucan oligosaccharide having a DP of from two to five; vi) a xyloglucan oligosaccharide having a DP of from four to twelve; or vii) a chito-oligosaccharide having a DP of from two to twelve.

In some cases, the composition comprises at least two of the oligosaccharides listed in (i) to (vii).

In some cases, the ingredient comprises the at least two oligosaccharides in a ratio from 1:9 to 1:1 in relation to each other.

In some embodiments, described herein are methods for producing ingredients for human consumption. The method for producing an ingredient for human consumption may comprise: (a) administering a physical pretreatment to a biomass to reduce an average size of the biomass; (b) administering a gentle pretreatment to the physically pretreated biomass, the gentle pretreatment may comprise: (i) incubating the physically pretreated biomass in an aqueous solution to solubilize monosaccharides and/or disaccharides from the physically pretreated biomass; and (ii) removing a portion of the solubilized monosaccharides and/or disaccharides from the aqueous solution; (c) administering a strong pretreatment to the gently pretreated biomass to increase the digestibility of the biomass; (d) contacting, in a solution or suspension, one or more polysaccharide-cleaving enzymes and the strongly pretreated biomass to form one or more oligosaccharides; and (e) enriching the solution or suspension to increase the concentration of the one or more oligosaccharides to form the ingredient.

In some cases, the gentle pretreatment may be an incubation cycle.

In some cases, the strong pretreatment may be a thermochemical treatment may comprise incubating the gently pretreated biomass in one of an acidic solution or an alkali solution.

In some cases, the method may further comprise removing at least 25% or 50% of the solubilized monosaccharides and/or disaccharides from the incubation solution at step (b)(ii).

In some cases, the strongly pretreated biomass composition after step (c) comprises less than 10% w/w monosaccharides.

In some cases, the method may further comprise purifying the one or more oligosaccharides from the solution or suspension.

In some cases, the strongly pretreated biomass composition after step (c) comprises less than 20% w/w monosaccharides.

In some cases, the method may further comprise repeating step (b).

In some cases, the step (b) may be conducted two, three, four, or five times.

In some cases, the method may further comprise repeating step (c).

In some cases, the step (c) may be conducted two, three, four, or five times.

In some cases, the method may further comprise concentrating the portion of the solubilized monosaccharides and/or disaccharides removed in step (b).

In some cases, the method may further comprise discarding the portion of the solubilized monosaccharides and/or disaccharides removed in step (b).

In some cases, the portion of the solubilized monosaccharides and/or disaccharides removed in step (b) may be not combined with the portion of the one or more oligosaccharides of step (e) to form the ingredient.

In some cases, the ingredient comprises less than 15% by dry weight monosaccharides.

In some cases, the ingredient comprises less than 50% by dry weight disaccharides.

In some cases, the ingredient may be substantially free of monosaccharides.

In some cases, the ingredient may be substantially free of disaccharides.

In some cases, the one or more oligosaccharides comprise at least one of: i) a cello-oligosaccharide having a degree of polymerization (DP) of from two to six; ii) a xylo-oligosaccharide having a DP of from two to twelve; iii) an arabinoxylo-oligosaccharide having a DP of from three to fifteen; iv) a manno-oligosaccharide having a DP of from two to twelve; v) a mixed-linkage glucan oligosaccharide having a DP of from two to five; vi) a xyloglucan oligosaccharide having a DP of from four to twelve; or vii) a chito-oligosaccharide having a DP of from two to twelve.

In some cases, the ingredient comprises at least two of the oligosaccharides listed in (i) to (vii).

In some cases, the ingredient comprises the at least two oligosaccharides in a ratio from 1:9 to 1:1 in relation to each other.

In some cases, the ingredient comprises at least one of sucrose, maltose, lactose, glucose, fructose, or galactose at less than 50% total dry w/w of the total dry w/w of all oligosaccharides of i-vii In some cases, the monosaccharides and/or disaccharides comprise at least one of sucrose, maltose, lactose, glucose, fructose, or galactose.

In some cases, the step (b) solubilizes one or more organic acid in addition to the monosaccharides and/or disaccharides.

In some cases, the one or more organic acid comprises at least one of oxalate, tartrate, succinate, formate, citrate, malate, lactate or acetate.

In some cases, the total weight of oxalate, tartrate, succinate, formate, citrate, malate, lactate and acetate may be greater than 10% of the total weight of sucrose, maltose, lactose, glucose, fructose and galactose in the portion solubilized and removed in step b.

In some cases, the physical pretreatment of step (a) comprises at least one of chipping, chopping, milling, ball-milling, grinding, sprucing, or blending the biomass.

In some cases, the gentle pretreatment of step (b) occurs in an aqueous solution may comprise water.

In some cases, the gentle pretreatment of step (b) occurs at a temperature of from 5° C. to 150° C.

In some cases, the gentle pretreatment of step (b) may be conducted from 15 minutes to 1 hour.

In some cases, the strong pretreatment of step (c) comprises heating the gently pretreated biomass in the acidic solution or the alkali solution.

In some cases, the heating may be at a temperature of from 50° C. to 150° C.

In some cases, the heating may be conducted from 30 minutes to 4 hours.

In some cases, the step (c) comprises treating the gently pretreated biomass in an alkali solution having a pH from 8 to 11.

In some cases, the alkali solution comprises at least one of sodium hydroxide, potassium hydroxide, sodium carbonate, calcium carbonate, aqueous ammonia, ammonium sulfate, or ammonium hydroxide.

In some cases, the step (c) comprises treating the gently pretreated biomass in an acidic solution having a pH from 4 to 6.

In some cases, the acidic solution comprises at least one of sulfuric acid, hydrochloric acid, nitric acid, phosphoric acid, acetic acid, maleic acid, fumaric acid, or oxalic acid.

In some cases, the biomass comprises at least one of sugar cane, corn stover, corncob, wheat bran, wheat straw, hardwood, or softwood.

In some cases, the biomass comprises at least one of cellulose, chitin, chitosan, xylan, xyloglucan, mixed-linkage glucan, mannan, or lignocellulose.

In some cases, the one or more polysaccharide-cleaving enzymes comprises at least one of cellulase, xylanase, xyloglucanase, endo-glucanase, cellobiohydrolase, mannanase, lichenase, or lytic polysaccharide monooxygenase (LPMO).

In some cases, the one or more polysaccharide-cleaving enzymes comprises at least one of AA9, AA10, AA11, AA13, AA14, or AA15.

In some cases, the one or more of the polysaccharide-cleaving enzymes may be prepared from a filamentous fungi, such as *Trichoderma reesei*.

In some cases, the one or more polysaccharide-cleaving enzymes may be operably linked to a catalytic module.

In some cases, the one or more polysaccharide-cleaving enzymes may be operably linked to a non-catalytic module.

In some cases, the non-catalytic module may be a carbohydrate-binding module.

In some cases, a water-soluble composition for human consumption may comprise at least one of the following oligosaccharides: i) a cello-oligosaccharide having a degree of polymerization (DP) of from two to six; ii) a xylo-oligosaccharide having a DP of from two to twelve; iii) an arabinoxylo-oligosaccharide having a DP of from three to fifteen; iv) a manno-oligosaccharide having a DP of from two to twelve; v) a mixed-linkage glucan oligosaccharide having a DP of from two to five; vi) a xyloglucan oligosaccharide having a DP of from four to twelve; or vii) a chito-oligosaccharide having a DP of from two to twelve; and at least one of the following monosaccharides or disaccharides: sucrose, maltose, lactose, fructose, or galactose, wherein the total dry weight of the monosaccharides or disaccharides comprises less than 10% of the total dry weight of the oligosaccharides having a DP of from two to twelve.

In some cases, the ingredient may comprise at least two of the oligosaccharides listed in (i) to (vii). In some cases, the ingredient may further comprise at least one of the following organic acids: oxalate, tartrate, succinate, formate, citrate, malate, lactate, or acetate. In some cases, the ingredient may comprise at least two of the organic acids. In some cases, the ingredient may comprise at least two of the oligosaccharides listed in (i) to (vii) in a ratio from 1:9 to 1:1 in relation to each other.

In some cases, a composition may comprise at least one monosaccharide or disaccharide selected from the group consisting of: glucose, fructose, or sucrose; at least one organic acid selected from the group consisting of oxalate, tartrate, succinate, formate, citrate, malate, lactate, or acetate, wherein the total weight of the organic acids is greater than 10% of the total weight of the monosaccharides or disaccharides.

In some cases, a method for producing an ingredient for human consumption may comprise: (a) administering a physical pretreatment to a biomass to reduce an average size of the biomass; (b) administering a gentle pretreatment to the physically pretreated biomass, the gentle pretreatment comprising: (i) incubating the physically pretreated biomass in a water solution to solubilize monosaccharides and/or disaccharides from the physically pretreated biomass; and (ii) removing a portion of the solubilized monosaccharides and/or disaccharides from the water solution; (c) administering a strong pretreatment to the gently pretreated biomass to solubilize polysaccharides and to increase the digestibility of the plant biomass; (d) isolating one or more solubilized polysaccharides from the biomass; (e) contacting the remaining biomass with one or more enzymes to form one or more oligosaccharides; (f) isolating the one or more oligosaccharides; and (g) combining a portion of the one or more soluble polysaccharides from step (d) with a portion of the one or more oligosaccharides from step (f) to form the ingredient.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "figure" and "FIG." herein), of which:

FIG. 10A is a diagram illustrating methods of processing biomass.

DETAILED DESCRIPTION

Introduction

Figure 1:
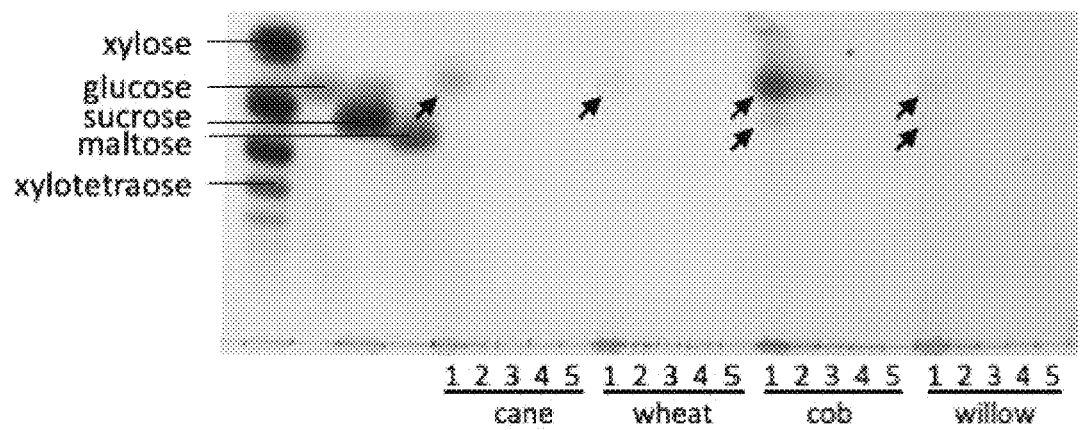
FIG. 1 depicts the results of a thin-layer chromatography (TLC) analysis showing the monosaccharide and disaccharide content of the indicated biomasses after one to five washing cycles (incubation pretreatments).

Provided herein are methods of forming one or more ingredients. The methods may include isolating one or more soluble polysaccharides from a biomass or feedstock (e.g., a plant biomass). The remaining biomass may then be contacted or treated with one or more enzymes to form one or more oligosaccharides and the one or more oligosaccharides may be enriched or isolated. Furthermore, at least a portion of the one or more soluble polysaccharides isolated from the biomass may be combined with a portion of the one or more enriched or isolated oligosaccharides to form the ingredient.

The texture of the ingredient may be consistent and smooth. Furthermore, the ingredient may have certain properties such that the ingredient may be used as a sweetener and/or a sugar substitute. Properties of the ingredient can include sweetness, smooth texture, desirable mouthfeel, ability to bind, ability to glaze or form a glaze, moistness, viscosity, ability to bulk, and/or ability to caramelize. In comparison to corn syrup or high-fructose corn syrup, the ingredient can also have fewer calories, reduced glycemic index, reduced glycemic load, increased fiber, and/or reduced sugar.

Also provided herein are methods for producing an ingredient for incorporation into a foodstuff, a nutraceutical, and/or a cosmetic, wherein the methods may include one or more pretreatment steps performed on a biomass. For example, the method may include a first pretreatment step, a second pretreatment step, a third pretreatment step, or additional pretreatment steps performed on a biomass. The pretreatment steps may be performed in a specified order.

The biomass used to produce one or more oligosaccharides may be a plant biomass. Examples of plant biomass include, but are not limited to, sugar cane, corn stover, corncob, wheat bran, wheat straw, hardwood, or softwood. In some cases, the biomass may comprise cellulose, chitin, chitosan, xylan, xyloglucan, mixed-linkage glucan, mannan, or lignocellulose.

The biomass may be digested into one or more oligosaccharides. The biomass digestion may be performed enzymatically. The enzymatic digestion may be performed after one or more pretreatment steps. The one or more pretreatment steps may be performed to reduce the size of a biomass and/or increase the surface area of the biomass available for digestion. The one or more pretreatment steps may include one or more washing steps, solubilizing steps, or predigestion treatments. In some cases, one or more pretreatment steps may be performed to reduce the monosaccharides and/or disaccharides present in the biomass. In some cases, one or more pretreatment steps may be performed to recover a soluble polysaccharide fraction from the biomass.

During the one or more pretreatment steps, monosaccharides and/or disaccharides may be removed from a starting material (e.g., a biomass). Stated another way, monosaccharides and/or disaccharides may be removed from the biomass during one or more of the pretreatment steps. Accordingly, no, or substantially no, monosaccharides and/or disaccharides may be yielded upon completion of the one or more pretreatment steps. That is, the pretreated biomass may comprise no or substantially no monosaccharides and/or disaccharides. This can improve the efficiency of the method for producing the ingredient for incorporation into a foodstuff, a nutraceutical, and/or a cosmetic as provided herein. For example, as a portion of the monosaccharides and/or disaccharides has already been removed from the biomass during the one or more pretreatment steps, less purification of the ingredient (e.g., to remove monosaccharides and/or disaccharides) may be needed. Specifically, fewer filtration steps, or less stringent filtration steps, may be needed during purification to generate the ingredient as disclosed herein.

A first pretreatment step (pretreatment step 1) may include physically treating a biomass (e.g., chipping the biomass). A second pretreatment step (pretreatment step 2 or gentle pretreatment) may include subjecting the physically treated biomass to an incubation cycle or a washing cycle. The incubation cycle may include incubating the physically treated biomass (from pretreatment step 1) in an aqueous solution to solubilize monosaccharides and/or disaccharides from the physically treated biomass. The incubation cycle may also include removing a portion of the solubilized monosaccharides and/or disaccharides from the aqueous solution. In some cases, the aqueous solution may include water. In some other cases, the incubation cycle may be performed at about 25° C. for a period of about 30 minutes to about 1.5 hours. Pretreatment step 2 may be a gentle pretreatment step. For example, the conditions (e.g., solution, temperature, time, etc.) of pretreatment step 2 may be gentler than the conditions of pretreatment step 3 as described in further detail below.

A third pretreatment step (pretreatment step 3 or strong pretreatment) may include treating the incubated biomass from pretreatment step 2 in one of an acidic solution or an alkali solution. Pretreatment step 3 can improve the digestibility of the biomass (e.g., by an enzyme). Pretreatment step 3 may also improve enzyme access to the biomass. In various instances, pretreatment step 3 may occur in an alkali solution (e.g., a 1% w/v NaOH solution) at a temperature above room temperature (e.g., at from about 90° C. to about 110° C.). Furthermore, pretreatment step 3 may be conducted by being held at the desired temperature for about 30 minutes to 1 hour. For instance, the effective temperature, in this example 90° C., is held for an hour (this can be altered depending on the desired characteristic). The solution in the third pretreatment step can be retained. Stated another way, the solution may not be discarded as the treated biomass moves from the pretreatment steps to the steps after the pretreatment steps as described in further detail below. In some cases, pretreatment step 3 may include a thermochemical treatment. That is, pretreatment step 3 may be performed in an acidic or alkali solution and/or pretreatment step 3 may be performed at a temperature above room temperature.

In various instances, after the one or more pretreatment steps, the method for producing an ingredient for human consumption may include contacting, in a solution or suspension, one or more polysaccharide-cleaving enzymes and the biomass from pretreatment step 3 to form one or more oligosaccharides. The method may further include enriching the solution or suspension to increase the concentration of the one or more oligosaccharides to form the ingredient (e.g., the ingredient for human consumption).

The pretreatment steps may increase the efficiency of the method in comparison to some other methods. The efficiency may be improved insofar as less extensive downstream processing may be needed. In some cases, downstream processing may include the process of removing monosaccharides and/or disaccharides from the pretreated biomass. In some embodiments, it may be difficult to remove disaccharides alone, for example, from an intermediate solution or fraction that is generated by the enzyme digestion. Thus, it may be more efficient to remove the disaccharides during the pretreatment steps.

The steps of the downstream processing can include ion-exchange chromatography, ultrafiltration, microfiltration, nanofiltration, etc. Part of the role of the nanofiltration step may be to remove excess monosaccharides from the oligosaccharide mixture. This nanofiltration may be performed multiple times to arrive at desirable monosaccharide levels. The number of such nanofiltration steps may be reduced when there are fewer monosaccharides in the pretreated biomass (e.g., when the monosaccharides have been removed by washing or incubation). Furthermore, ultrafiltration generally cannot differentiate between desirable disaccharides (e.g., cellobiose) and undesirable disaccharides. Accordingly, removing the undesirable disaccharides during pretreatment and generating the desirable disaccharides during the enzyme treatment step can also reduce the number of steps involved or needed during downstream processing.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

As used in the specification and claims, the singular forms "a," "an," and "the" include plural references unless the context clearly dictates otherwise. For example, the term "a sample" includes a plurality of samples, including mixtures thereof.

The term "about," as used herein, can mean within 1 or more than 1 standard deviation. Alternatively, about can mean a range of up to 10%, up to 5%, or up to 1% of a given value. For example, about can mean up to ±10%, ±9%, ±8%, ±7%, ±6%, ±5%, ±4%, ±3%, ±2%, or ±1% of a given value.

As used herein, "food" and "foodstuff" generally refer to any item destined for consumption, which may be consumption by a human or by any other animal. It may be food, feed, beverage, or an ingredient to be used in the production of any of the above.

As used herein, "nutraceutical" generally refers to any composition introduced into a human or other animal, whether by ingestion, injection, absorption, or any other method, for the purpose of providing nutrition to the human or other animal. Use of such a nutraceutical may take the form of a drink with added dietary fiber, a prebiotic additive, a pill or other capsule, or any other suitable use.

As used herein, "cosmetic" generally refers to any composition which is intended for use on humans or other animals to increase their aesthetic appeal or prevent future loss of aesthetic appeal, as well as any other compositions known in general parlance as cosmetics. Aesthetic appeal is not limited to visual aesthetics but applies as well to textural or any other appeal. The cosmetic may be mascara, foundation, lip gloss, eyeshadow, eyeliner, primer, lipstick, blush, nail polish, bronzer, or any other makeup; shampoo, conditioner, styling mousse, styling gel, hairspray, hair dye, hair wax, or any other hair product; moisturizer, exfoliant, sun cream, cleanser, toothpaste, cream, lotion, ointment, or any other composition effective in modifying teeth, skin, hair, or other parts of the body in some aesthetic way. Further, the cosmetic may be a composition used as a component of a face mask, brush, hair roller, other styling device, other solid structure, or any other suitable composition.

As used herein, "ingredient" generally refers to any composition suitable for incorporation into a foodstuff, cosmetic, or nutraceutical product, which may include those which are used directly as the product itself. It may be a dry or liquid ingredient, unless it is specifically referred to as "dry" or "liquid." This includes compositions that may be deemed to be an intermediate during a method of the disclosure, such as a composition formed after the combining of the one or more oligosaccharides and the one or more soluble polysaccharides prior to any further purification, optimization, drying, dissolving, or any other such steps, as well as including the final composition obtained from the method.

As used herein, "polysaccharide" generally refers to a saccharide polymer of any length greater than about 20 residues. Polysaccharides may be highly branched, lightly branched, or unbranched. Polysaccharides may include any manner of glycosidic bond in any combination; any number of, for example, α or β linkages; and any combination of monomer types, such as glucose, glucosamine, mannose, xylose, galactose, fucose, fructose, glucuronic acid, arabinose, or derivatives thereof, such as any combination of the above monomers decorated with acetyl or other groups. The polysaccharide may be a cellulosic or hemicellulosic polymer. Hemicellulosic polymers envisaged include xylan, glucuronoxylan, arabinoxylan, glucomannan, and xyloglucan. In some embodiments, the cellulosic polymer may be cellulose.

As used herein, "lignocellulose" generally refers to polysaccharide-comprising aggregates that are, or are derived from, plant cell wall material. For example, they may include one or more of the following polysaccharides associated together: cellulose, xylan, mannan, and mixed-linkage glucan.

As used herein "highly branched," "lightly branched," and "unbranched" generally refer to the number of side-chains per stretch of main chain in a saccharide. Highly branched saccharides have on average from 4 to 10 side chains per 10 main-chain residues, slightly branched saccharides have on average from 1 to 3 side chains per 10 main-chain residues, and unbranched saccharides have only one main chain and no side chains. The average is calculated by dividing the number of side chains in a saccharide by the number of main-chain residues.

As used herein, "saccharide" generally refers to any polysaccharide and/or oligosaccharide, such as a monosaccharide and/or a disaccharide.

As used herein, "oligosaccharide" generally refers to saccharide polymers having chain lengths less than or equal to about 20 saccharide residues. Oligosaccharides may be highly branched, lightly branched, or unbranched; and may include glycosidic bonds in any combination, any number of α or β linkages, and any combination of monomer types, such as glucose, glucosamine, mannose, xylose, galactose, fucose, fructose, glucuronic acid, arabinose, or derivatives thereof. Suitable derivatives include the above monomers including acetyl or other groups.

As used herein, "monosaccharide" and "disaccharide" generally refer to saccharide compounds consisting of one or two residues, respectively. Monosaccharides are compounds such as glucose, glucosamine, xylose, galactose, fucose, fructose, glucuronic acid, arabinose, galacturonic acid, or epimers or other derivatives thereof. Suitable derivatives include acetyl or other groups. Disaccharides are compounds consisting of two monosaccharides joined via any glycosidic bond.

As used herein, "cello-oligosaccharides" generally refer to oligosaccharides composed of one or more glucose residues linked by β-1,4-glycosidic bonds, and may be chemically related to that by oxidation, reduction, esterification, epimerization, or another chemical modification.

As used herein, "xylo-oligosaccharides" generally refer to oligosaccharides composed primarily of xylose residues (typically linked by β-1,4-glycosidic bonds) and may also contain glucuronic acid residues and/or arabinose residues and/or acetyl groups and/or any other modification, and may be chemically related to that by oxidation, reduction, esterification, epimerization, further glycosylation, or another chemical modification.

As used herein, "arabinoxylo-oligosaccharides" generally refer to oligosaccharides composed of xylose residues (typically linked by β-(1→4)-bonds substituted with arabinose side-chains), typically linked by (1→2)-bonds or (1→3)-bonds) and may be chemically related to that by oxidation, reduction, esterification, epimerization, further glycosylation, or another chemical modification.

As used herein, "mixed-linkage glucan-oligosaccharides" generally refer to oligosaccharides composed of one or more glucose residues linked by at least one β-1,3-glycosidic bond and at least one β-1,4-glycosidic bond, and may be chemically related to that by oxidation, reduction, esterification, epimerization, or another chemical modification As used herein, "manno-oligosaccharides" generally refer to oligosaccharides composed of one or more mannose residues and optionally containing one or more glucose and/or galactose residues, and may be chemically related to that by oxidation, reduction, esterification, epimerization, or another chemical modification.

As used herein, "chito-oligosaccharides" generally refer to oligosaccharides composed of one or more glucosamine and/or N-acetyl-glucosamine residues, and may be chemically related to that by oxidation, reduction, esterification, epimerization, or another chemical modification.

As used herein, "cellulose" generally refers to polysaccharides composed of glucose residues linked by β-1,4-glycosidic bonds, and derivatives thereof. As used herein, "xylan" generally refers to polysaccharides composed of a backbone of xylose residues and may also contain glucuronic acid residues and/or arabinose residues and/or acetyl groups and/or any other modification. As used herein, "mixed-linkage glucan" generally refers to polysaccharides composed of glucose residues linked by β-1,3-glycosidic bonds and β-1,4-glycosidic bonds. As used herein, "mannan" generally refers to polysaccharides composed of greater than 40% mannose residues and optionally containing glucose and/or galactose residues. As used herein, "chitin" or "chitosan" generally refer to polysaccharides composed of glucosamine and/or N-acetyl-glucosamine residues. The polysaccharides of cellulose, xylan, mixed-linkage glucan, mannan, chitin, or chitosan may include chemical variants that have been modified by oxidation, reduction, esterification, epimerization, or another chemical modification.

As used herein, "soluble," "solubility," and grammatical variants thereof generally refer to solubility in an aqueous solution (e.g., water). As used herein, "solubilize" generally refers to a solid becoming incorporated into an aqueous solution or a liquid so as to form a solution.

As used herein, "suspension" generally refers to a composition comprising at least two immiscible phases, for example, a solid phase and a liquid phase, wherein the weight of the solid phase may be, as a percentage of the weight of the composition, in the range of from about 0.5% to about 30%, about 1% to about 20%, about 2% to about 15%, or about 3% to about 10%. The suspension may comprise a suitable solvent, which may be water.

As used herein, "viscosity" generally refers to a quantity expressing the magnitude of internal friction in a fluid, as measured by the force per unit area resisting uniform flow. The viscosity can be measured by a variety of methods, but the values given herein, unless indicated otherwise, refer to those obtained by using a Brookfield HDB VE roto-viscometer using standard testing procedures, operated as per the manufacturer's instructions with respect to ranges, and with a 400 mL sample taken in a tall-form beaker to ensure that no container effects occur.

As used herein, "dissolved" generally refers to a solid becoming incorporated into a liquid so as to form a solution.

I. Pretreatment

Physical Pretreatment

A mechanical or physical pretreatment may be performed on a biomass for the digestion of the biomass into one or more oligosaccharides. The mechanical and/or physical pretreatment may be the first pretreatment step in the process of biomass digestion. Alternatively, the mechanical or physical pretreatment step may be performed after another pretreatment step. For instance, a mechanical or physical pretreatment step may be performed after another pretreatment step, such as a washing pretreatment step.

A biomass may be mechanically or physically pretreated to reduce the size of the biomass. Examples of mechanical or physical pretreatment steps include, but are not limited to: chipping, chopping, milling, ball-milling, grinding, sprucing, blending, and/or steam explosion of the biomass. More than one physical pretreatment may be performed on the biomass.

Solubilizing Step

The biomass may undergo a solubilizing step. The solubilizing step may be, or be a portion of, a gentle pretreatment step, which solubilizes a polysaccharide fraction or a monosaccharide and/or disaccharide fraction from the biomass. The solubilizing pretreatment step may be a washing step, an incubation step, a thermochemical step, or a chemical treatment step. The solubilizing pretreatment may be performed before a physical or mechanical pretreatment step. The solubilizing pretreatment may be performed after a physical or mechanical pretreatment step.

In some embodiments, the solubilizing step may be performed to remove a fraction of soluble polysaccharides. Soluble polysaccharides can be added to one or more oligosaccharides, for example, upon purification of the soluble polysaccharides. The soluble polysaccharide fraction may be used to produce food types of desired taste, texture, quality, adhesiveness, and smell. Presence of solubilized polysaccharides may also help produce a better-quality product which does not produce sediments (or graininess) in a food product.

The solubilizing step may be a chemical or thermochemical treatment of the biomass. The chemical or thermochemical treatment may comprise one or more aqueous solutions. The aqueous solution may comprise one or more salts, acids, alkalis, or ions. The aqueous solution may comprise one or more of sodium hydroxide, potassium hydroxide, sodium carbonate, calcium carbonate, calcium hydroxide, ammonium sulfate, ammonium hydroxide, aqueous ammonia, dilute sulfuric acid, dilute acetic acid, dilute hydrochloric acid, or dilute phosphoric acid.

The aqueous solution may be an alkali solution with a pH from 10 to 14. The aqueous solution may be an alkali solution with a pH from 10 to 11, 10 to 12, 10 to 13, 10 to 14, 11 to 12, 11 to 13, 11 to 14, 12 to 13, 12 to 14, or 13 to 14. The aqueous solution may be an acid solution with a pH from 2 to 6. The aqueous solution may be an acid solution with a pH from 2 to 3, 2 to 4, 2 to 5, 2 to 6, 3 to 4, 3 to 5, 3 to 6, 4 to 5, 4 to 6, or 5 to 6.

The solubilization step may be performed at a temperature from 30° C. to 180° C. The solubilization step may be performed at a temperature of at least 30° C. The solubilization step may be performed at a temperature of at most 180° C. The solubilization step may be performed at a temperature from 30° C. to 60° C., 30° C. to 90° C., 30° C. to 120° C., 30° C. to 150° C., 30° C. to 180° C., 60° C. to 90° C., 60° C. to 120° C., 60° C. to 150° C., 60° C. to 180° C., 90° C. to 120° C., 90° C. to 150° C., 90° C. to 180° C., 120° C. to 150° C., 120° C. to 180° C., or 150° C. to 180° C. The solubilization step may be performed at a temperature of at least 30° C., 60° C., 90° C., 120° C., 150° C., or 180° C.

The duration of the solubilizing step may be altered according to the biomass being used, the soluble polysaccharide component desired, and/or the complexity of the soluble polysaccharide desired. The solubilizing step may be performed from about 10 minutes to about 24 hours. The solubilization step may be performed for at least 10 minutes. The solubilization step may be performed for at most 60 minutes. The solubilization step may be performed from 10 minutes to 30 minutes, 10 minutes to 60 minutes, or 30 minutes to 60 minutes. The solubilization step may be performed for at least 10 minutes, 30 minutes, or 60 minutes. The solubilization step may be performed for 1 hour to 24 hours. The solubilization step may be performed for at least 1 hour. The solubilization step may be performed for at most 24 hours. The solubilization step may be performed for 1 hour to 4 hours, 1 hour to 8 hours, 1 hour to 12 hours, 1 hour to 16 hours, 1 hour to 20 hours, 1 hour to 24 hours, 4 hours to 8 hours, 4 hours to 12 hours, 4 hours to 16 hours, 4 hours to 20 hours, 4 hours to 24 hours, 8 hours to 12 hours, 8 hours to 16 hours, 8 hours to 20 hours, 8 hours to 24 hours, 12 hours to 16 hours, 12 hours to 20 hours, 12 hours to 24 hours, 16 hours to 20 hours, 16 hours to 24 hours, or 20 hours to 24 hours. The solubilization step may be performed for at least 1 hour, 4 hours, 8 hours, 12 hours, 16 hours, 20 hours, or 24 hours.

Soluble polysaccharides may be removed from the solution after a solubilizing step. A fraction of the solubilized polysaccharides may be removed from the solubilized fraction. In some cases, at least 5% of the solubilized polysaccharides may be removed and/or purified. In some cases, at most 100% of the solubilized polysaccharides may be removed and/or purified. In some cases, 5% to 10%, 5% to 20%, 5% to 30%, 5% to 40%, 5% to 60%, 5% to 80%, 5% to 90%, 5% to 100%, 10% to 20%, 10% to 30%, 10% to 40%, 10% to 60%, 10% to 80%, 10% to 90%, 10% to 100%, 20% to 30%, 20% to 40%, 20% to 60%, 20% to 80%, 20% to 100%, 30% to 40%, 30% to 60%, 30% to 80%, 30% to 100%, 40% to 60%, 40% to 80%, 40% to 100%, 60% to 80%, or 60% to 100% of the solubilized polysaccharides may be removed and purified. In some cases, at least about 5%, 10%, 20%, 30%, 40%, 60%, 80%, or 100% of the solubilized polysaccharides may be removed and purified.

Gentle Pretreatment

The biomass may undergo a gentle pretreatment step. The gentle pretreatment step may solubilize a polysaccharide fraction or a monosaccharide and/or disaccharide fraction from the biomass. In some cases, the gentle pretreatment step may include at least a portion, or all, of the solubilizing step. Stated another way, the solubilizing step may be a portion or sub-step of the gentle pretreatment step. The gentle pretreatment step may be a washing step, an incubation step, a thermochemical step, or a chemical treatment step. The gentle pretreatment may be performed before a physical or mechanical pretreatment step. The gentle pretreatment may be performed after a physical or mechanical pretreatment step. The gentle pretreatment may be performed simultaneously with a physical or mechanical pretreatment step. The gentle pretreatment step may be performed one or more times. The gentle pretreatment may be performed 2, 3, 4, 5, 6, 7, 8, 9, or 10 times.

The gentle pretreatment step may be an incubation step or a washing step. The biomass (physically treated or untreated) may be incubated in an aqueous solution. The aqueous solution may be water, or it may comprise salts, acids, alkali, ions, alcohols, and/or other chemicals. The pH of the aqueous solution may be from 6.2 to 8.5. The pH of the aqueous solution may be at least 6.2. The pH of the aqueous solution may be at most 8.5. The pH of the aqueous solution may be from 6.2 to 6.5, 6.2 to 7, 6.2 to 7.2, 6.2 to 7.5, 6.2 to 7.7, 6.2 to 8, 6.2 to 8.2, 6.2 to 8.5, 6.5 to 7, 6.5 to 7.2, 6.5 to 7.5, 6.5 to 7.7, 6.5 to 8, 6.5 to 8.2, 6.5 to 8.5, 7 to 7.2, 7 to 7.5, 7 to 7.7, 7 to 8, 7 to 8.2, 7 to 8.5, 7.2 to 7.5, 7.2 to 7.7, 7.2 to 8, 7.2 to 8.2, 7.2 to 8.5, 7.5 to 7.7, 7.5 to 8, 7.5 to 8.2, 7.5 to 8.5, 7.7 to 8, 7.7 to 8.2, 7.7 to 8.5, 8 to 8.2, 8 to 8.5, or 8.2 to 8.5. The pH of the aqueous solution may be from 6.2, 6.5, 7, 7.2, 7.5, 7.7, 8, 8.2, or 8.5.

The pH of the aqueous solution may be from 9 to 12. The pH of the aqueous solution may be from at least 9. The pH of the aqueous solution may be from at most 12. The pH of the aqueous solution may be from 9 to 9.5, 9 to 10, 9 to 10.5, 9 to 11, 9 to 11.5, 9 to 12, 9.5 to 10, 9.5 to 10.5, 9.5 to 11, 9.5 to 11.5, 9.5 to 12, 10 to 10.5, 10 to 11, 10 to 11.5, 10 to 12, 10.5 to 11, 10.5 to 11.5, 10.5 to 12, 11 to 11.5, 11 to 12, or 11.5 to 12. The pH of the aqueous solution may be from 9, 9.5, 10, 10.5, 11, 11.5, or 12.

The incubation step may be performed for 15 minutes to 60 minutes. The incubation step may be performed for at least 15 minutes. The incubation step may be performed for at most 60 minutes. The incubation step may be performed for 15 minutes to 30 minutes, 15 minutes to 45 minutes, 15 minutes to 60 minutes, 30 minutes to 45 minutes, 30 minutes to 60 minutes, or 45 minutes to 60 minutes. The incubation step may be performed for at least 15 minutes, 30 minutes, 45 minutes, or 60 minutes. The incubation step may be performed for 1 hour to 24 hours. The incubation step may be performed for at least 1 hour. The incubation step may be performed for at most 24 hours. The incubation step may be performed for 1 hour to 4 hours, 1 hour to 8 hours, 1 hour to 12 hours, 1 hour to 16 hours, 1 hour to 20 hours, 1 hour to 24 hours, 4 hours to 8 hours, 4 hours to 12 hours, 4 hours to 16 hours, 4 hours to 20 hours, 4 hours to 24 hours, 8 hours to 12 hours, 8 hours to 16 hours, 8 hours to 20 hours, 8 hours to 24 hours, 12 hours to 16 hours, 12 hours to 20 hours, 12 hours to 24 hours, 16 hours to 20 hours, 16 hours to 24 hours, or 20 hours to 24 hours. The incubation step may be performed for at least 1 hour, 4 hours, 8 hours, 12 hours, 16 hours, 20 hours, or 24 hours.

Solubilized polysaccharides, monosaccharides, and/or disaccharides may be removed from the aqueous solution after the gentle pretreatment step. In some cases, monosaccharides and/or disaccharides may be removed from the aqueous solution after the gentle pretreatment step.

Soluble polysaccharides may be removed from the solution after a gentle pretreatment step. At least a portion of the solubilized polysaccharides may be removed from the solubilized fraction. In some cases, at least 5% of the solubilized polysaccharides may be removed and/or purified. In some cases, at most 100% of the solubilized polysaccharides may be removed and/or purified. In some cases, 5% to 10%, 5% to 20%, 5% to 30%, 5% to 40%, 5% to 60%, 5% to 80%, 5% to 100%, 10% to 20%, 10% to 30%, 10% to 40%, 10% to 60%, 10% to 80%, 10% to 100%, 20% to 30%, 20% to 40%, 20% to 60%, 20% to 80%, 20% to 100%, 30% to 40%, 30% to 60%, 30% to 80%, 30% to 100%, 40% to 60%, 40% to 80%, 40% to 100%, 60% to 80%, or 60% to 100% of the solubilized polysaccharides may be removed and/or purified. In some cases, at least about 5%, 10%, 20%, 30%, 40%, 60%, 80%, or 100% of the solubilized polysaccharides may be removed and/or purified after the gentle pretreatment step.

Monosaccharides and/or disaccharides may be removed from the solution after a gentle pretreatment step. A fraction of the solubilized monosaccharides and/or disaccharides may be removed from the aqueous solution after the incubation step. In some cases, at least 5% of the solubilized monosaccharides and/or disaccharides may be removed. In some cases, at most 100% of the solubilized monosaccharides and/or disaccharides may be removed. In some cases, 5% to 10%, 5% to 20%, 5% to 30%, 5% to 40%, 5% to 60%, 5% to 80%, 5% to 100%, 10% to 20%, 10% to 30%, 10% to 40%, 10% to 60%, 10% to 80%, 10% to 100%, 20% to 30%, 20% to 40%, 20% to 60%, 20% to 80%, 20% to 100%, 30% to 40%, 30% to 60%, 30% to 80%, 30% to 100%, 40% to 60%, 40% to 80%, 40% to 100%, or 60% to 100% of the solubilized monosaccharides and/or disaccharides may be removed. In some cases, at least about 5%, 10%, 20%, 30%, 40%, 60%, 80%, or 100% of the solubilized monosaccharides and/or disaccharides may be removed and/or purified after the gentle pretreatment step. The monosaccharide and/or disaccharide portion may be discarded after the incubation step. In certain instances, the portion of the solubilized monosaccharides and/or disaccharides removed in this step may not be combined with the portion of the one or more oligosaccharides produced in the biomass treatment.

The aqueous solution may be removed from the biomass after the gentle pretreatment step. A portion of the aqueous solution may be removed from the biomass after the gentle pretreatment step. 5% to 100% of the aqueous solution may be removed from the biomass after the gentle pretreatment step. At least 5% of the aqueous solution may be removed from the biomass after the gentle pretreatment step. At most 98% of the aqueous solution may be removed from the biomass after the gentle pretreatment step. Five percent to 10%, 5% to 20%, 5% to 40%, 5% to 50%, 5% to 60%, 5% to 80%, 5% to 90%, 5% to 98%, 10% to 20%, 10% to 40%, 10% to 50%, 10% to 60%, 10% to 80%, 10% to 90%, 10% to 98%, 20% to 40%, 20% to 50%, 20% to 60%, 20% to 80%, 20% to 90%, 20% to 98%, 40% to 50%, 40% to 60%, 40% to 80%, 40% to 90%, 40% to 98%, 50% to 60%, 50% to 80%, 50% to 90%, 50% to 98%, 60% to 80%, 60% to 90%, 60% to 98%, 80% to 90%, 80% to 98%, or 90% to 98% of the aqueous solution may be removed from the biomass after the gentle pretreatment step. At least 5%, 10%, 20%, 40%, 50%, 60%, 80%, 90%, or 98% of the aqueous solution may be removed from the biomass after the gentle pretreatment step. A portion of the aqueous solution may be removed using a filter press, centrifugation, sedimentation, filtration, and/or any other suitable method.

Strong Pretreatment

The biomass may undergo a strong pretreatment step. The strong pretreatment step may solubilize a polysaccharide fraction or a monosaccharide and/or disaccharide fraction from the biomass. The strong pretreatment step may be performed to make the biomass more digestible by enzymes. The strong pretreatment may help disrupt the hydrogen bonds in the biomass. The strong pretreatment step may be a washing step, a thermochemical step, or a chemical treatment step. The strong pretreatment may be performed before a physical or mechanical pretreatment step. The strong pretreatment step may be performed after a physical or mechanical pretreatment step. The strong pretreatment step may be performed before a gentle pretreatment step. The strong pretreatment step may be performed after a gentle pretreatment step. The strong pretreatment step may be performed one or more times. The strong pretreatment may be performed 2, 3, 4, 5, 6, 7, 8, 9, or 10 times.

The strong pretreatment step may be a thermochemical treatment. The chemical or thermochemical treatment may comprise one or more aqueous solutions. The aqueous solution may comprise one or more salts, acids, alkalis, or ions. The aqueous solution may be an alkali solution comprising one or more of sodium hydroxide, potassium hydroxide, sodium carbonate, calcium carbonate, calcium hydroxide, ammonium sulfate, ammonium hydroxide, or aqueous ammonia. The aqueous solution may be an acidic solution comprising at least one of sulfuric acid, hydrochloric acid, nitric acid, phosphoric acid, acetic acid, maleic acid, fumaric acid, or oxalic acid. In some embodiments, upon completion of the one or more strong pretreatment steps, the aqueous solution may be retained. In other words, the aqueous solution may not be discarded or rejected.

The thermochemical pretreatment may be performed at a pH of from about 2 to 6.5. The thermochemical pretreatment may be performed at a pH of at least 2. The thermochemical pretreatment may be performed at a pH of at most 6.5. The thermochemical pretreatment may be performed at a pH of 2 to 2.5, 2 to 3, 2 to 3.5, 2 to 4, 2 to 4.5, 2 to 5, 2 to 5.5, 2 to 6, 2 to 6.5, 2.5 to 3, 2.5 to 3.5, 2.5 to 4, 2.5 to 4.5, 2.5 to 5, 2.5 to 5.5, 2.5 to 6, 2.5 to 6.5, 3 to 3.5, 3 to 4, 3 to 4.5, 3 to 5, 3 to 5.5, 3 to 6, 3 to 6.5, 3.5 to 4, 3.5 to 4.5, 3.5 to 5, 3.5 to 5.5, 3.5 to 6, 3.5 to 6.5, 4 to 4.5, 4 to 5, 4 to 5.5, 4 to 6, 4 to 6.5, 4.5 to 5, 4.5 to 5.5, 4.5 to 6, 4.5 to 6.5, 5 to 5.5, 5 to 6, 5 to 6.5, 5.5 to 6, 5.5 to 6.5, or 6 to 6.5. The thermochemical pretreatment may be performed at a pH of about 2, 2.5, 3, 3.5, 4, 4.5, 5, 5.5, 6, or 6.5.

The thermochemical pretreatment may be performed at a pH of 7.5 to 12. The thermochemical pretreatment may be performed at a pH of at least 7.5. The thermochemical pretreatment may be performed at a pH of at most 12. The thermochemical pretreatment may be performed at a pH of 7.5 to 8, 7.5 to 8.5, 7.5 to 9, 7.5 to 9.5, 7.5 to 10, 7.5 to 10.5, 7.5 to 11, 7.5 to 11.5, 7.5 to 12, 8 to 8.5, 8 to 9, 8 to 9.5, 8 to 10, 8 to 10.5, 8 to 11, 8 to 11.5, 8 to 12, 8.5 to 9, 8.5 to 9.5, 8.5 to 10, 8.5 to 10.5, 8.5 to 11, 8.5 to 11.5, 8.5 to 12, 9 to 9.5, 9 to 10, 9 to 10.5, 9 to 11, 9 to 11.5, 9 to 12, 9.5 to 10, 9.5 to 10.5, 9.5 to 11, 9.5 to 11.5, 9.5 to 12, 10 to 10.5, 10 to 11, 10 to 11.5, 10 to 12, 10.5 to 11, 10.5 to 11.5, 10.5 to 12, 11 to 11.5, 11 to 12, or 11.5 to 12. The thermochemical pretreatment may be performed at a pH of about 7.5, 8, 8.5, 9, 9.5, 10, 10.5, 11, 11.5, or 12.

The thermochemical pretreatment may be performed at a temperature of 50° C. to 150° C. The thermochemical pretreatment may be performed at a temperature of at least 50° C. The thermochemical pretreatment may be performed at a temperature of at most 150° C. The thermochemical pretreatment may be performed at a temperature of 50° C. to 75° C., 50° C. to 80° C., 50° C. to 90° C., 50° C. to 100° C., 50° C. to 120° C., 50° C. to 130° C., 50° C. to 150° C., 75° C. to 80° C., 75° C. to 90° C., 75° C. to 100° C., 75° C. to 120° C., 75° C. to 130° C., 75° C. to 150° C., 80° C. to 90° C., 80° C. to 100° C., 80° C. to 120° C., 80° C. to 130° C., 80° C. to 150° C., 90° C. to 100° C., 90° C. to 120° C., 90° C. to 130° C., 90° C. to 150° C., 100° C. to 120° C., 100° C. to 130° C., 100° C. to 150° C., 120° C. to 130° C., 120° C. to 150° C., or 130° C. to 150° C. The thermochemical pretreatment may be performed at a temperature of at least 50° C., 75° C., 80° C., 90° C., 100° C., 120° C., 130° C., or 150° C.

The thermochemical treatment may be performed for 0.5 hours to 4 hours. The thermochemical treatment may be performed for at least 0.5 hours. The thermochemical treatment may be performed for at most 4 hours. The thermochemical treatment may be performed for 0.5 hours to 0.75 hours, 0.5 hours to 1 hour, 0.5 hours to 1.5 hours, 0.5 hours to 2 hours, 0.5 hours to 2.5 hours, 0.5 hours to 3 hours, 0.5 hours to 3.5 hours, 0.5 hours to 4 hours, 0.75 hours to 1 hour, 0.75 hours to 1.5 hours, 0.75 hours to 2 hours, 0.75 hours to 2.5 hours, 0.75 hours to 3 hours, 0.75 hours to 3.5 hours, 0.75 hours to 4 hours, 1 hour to 1.5 hours, 1 hour to 2 hours, 1 hour to 2.5 hours, 1 hour to 3 hours, 1 hour to 3.5 hours, 1 hour to 4 hours, 1.5 hours to 2 hours, 1.5 hours to 2.5 hours, 1.5 hours to 3 hours, 1.5 hours to 3.5 hours, 1.5 hours to 4 hours, 2 hours to 2.5 hours, 2 hours to 3 hours, 2 hours to 3.5 hours, 2 hours to 4 hours, 2.5 hours to 3 hours, 2.5 hours to 3.5 hours, 2.5 hours to 4 hours, 3 hours to 3.5 hours, 3 hours to 4 hours, or 3.5 hours to 4 hours. The thermochemical treatment may be performed for at least 0.5 hours, 0.75 hours, 1 hour, 1.5 hours, 2 hours, 2.5 hours, 3 hours, 3.5 hours, or 4 hours.

The thermochemically treated biomass may comprise less than 1% w/w to 30% w/w monosaccharides. The thermochemically treated biomass may comprise less than 1% w/w to 2% w/w, 1% w/w to 5% w/w, 1% w/w to 10% w/w, 1% w/w to 15% w/w, 1% w/w to 20% w/w, 1% w/w to 25% w/w, 1% w/w to 30% w/w, 2% w/w to 5% w/w, 2% w/w to 10% w/w, 2% w/w to 15% w/w, 2% w/w to 20% w/w, 2% w/w to 25% w/w, 2% w/w to 30% w/w, 5% w/w to 10% w/w, 5% w/w to 15% w/w, 5% w/w to 20% w/w, 5% w/w to 25% w/w, 5% w/w to 30% w/w, 10% w/w to 15% w/w, 10% w/w to 20% w/w, 10% w/w to 25% w/w, 10% w/w to 30% w/w, 15% w/w to 20% w/w, 15% w/w to 25% w/w, 15% w/w to 30% w/w, 20% w/w to 25% w/w, 20% w/w to 30% w/w, or 25% w/w to 30% w/w monosaccharides. The thermochemically treated biomass may comprise less than 1% w/w, 2% w/w, 5% w/w, 10% w/w, 15% w/w, 20% w/w, 25% w/w, or 30% w/w monosaccharides.

The thermochemically treated biomass may comprise 5% w/w to 50% w/w disaccharides. The thermochemically treated biomass may comprise 5% w/w to 10% w/w, 5% w/w to 15% w/w, 5% w/w to 20% w/w, 5% w/w to 25% w/w, 5% w/w to 30% w/w, 5% w/w to 35% w/w, 5% w/w to 40% w/w, 5% w/w to 50% w/w, 10% w/w to 15% w/w, 10% w/w to 20% w/w, 10% w/w to 25% w/w, 10% w/w to 30% w/w, 10% w/w to 35% w/w, 10% w/w to 40% w/w, 10% w/w to 50% w/w, 15% w/w to 20% w/w, 15% w/w to 25% w/w, 15% w/w to 30% w/w, 15% w/w to 35% w/w, 15% w/w to 40% w/w, 15% w/w to 50% w/w, 20% w/w to 25% w/w, 20% w/w to 30% w/w, 20% w/w to 35% w/w, 20% w/w to 40% w/w, 20% w/w to 50% w/w, 25% w/w to 30% w/w, 25% w/w to 35% w/w, 25% w/w to 40% w/w, 25% w/w to 50% w/w, 30% w/w to 35% w/w, 30% w/w to 40% w/w, 30% w/w to 50% w/w, 35% w/w to 40% w/w, 35% w/w to 50% w/w, or 40% w/w to 50% w/w disaccharides. The thermochemically treated biomass may comprise less than 5% w/w, 10% w/w, 15% w/w, 20% w/w, 25% w/w, 30% w/w, 35% w/w, 40% w/w, or 50% w/w disaccharides.

II. Enzyme Treatment and Downstream Processing

The methods of the present disclosure may also include contacting, in a solution or suspension, one or more polysaccharide-cleaving enzymes and the thermochemically treated biomass to form one or more oligosaccharides. Furthermore, the methods may include enriching the solution or suspension to increase the concentration of the one or more oligosaccharides to form the ingredient. The one or more oligosaccharides may be purified from the solution or suspension as provided herein.

One or more steps of the method of forming or manufacturing the composition may be an enzymatic reaction, in which one or more enzymes are placed in a suitable reaction vessel together with one or more feedstocks or biomasses (e.g., plant biomasses), which may be soluble or insoluble in water, and a suitable solvent. As used herein, the term "plant biomass" may be replaced with the terms "feedstock" or "biomass" (e.g., a biomass not derived from a plant) unless indicated otherwise.

A variety of enzymes may be suitable for use in the enzymatic reaction. Any enzyme which produces oligosaccharides when acting on a polysaccharide-containing feedstock may be suitable. For example, the enzymatic reaction may comprise a cellulase, an endo-glucanase, a cellobiohydrolase, a lytic polysaccharide monooxygenase (LPMO), a lichenase, a xyloglucan endoglucanase (XEG), a mannanase, a chitinase, a xylanase, and/or one or more suitable enzymes.

In various cases, the enzymatic reaction may comprise a cellulolytic preparation from a species, such as *Trichoderma reesei*, which may be purified and/or pretreated and/or may be supplemented with one or more additional enzymes, for example, adding a beta-glucanase, a beta-xylanase, and a cellobiohydrolase; a beta-glucanase, a beta-xylanase, an LPMO, and a cellobiohydrolase; an LPMO and a xylanase; or an LPMO, a xylanase, and a lichenase. Each enzyme may be provided to the enzymatic reaction as a purified enzyme, a semi-purified mixture derived from some natural source or lab-grown culture, in the form of a microbial strain engineered to produce the enzyme, or in any other suitable manner. Fusions of these enzymes, either with other enzymes or with non-enzymatic modules such as carbohydrate-binding modules (CBMs), are also envisaged. For example, an LPMO fused to a CBM, a xylanase fused to a CBM, or a xylanase fused to an LPMO may be utilized.

Aerobic conditions may be used for the one or more enzymatic reactions. Aerobic condition may comprise the addition of oxygen, which may be provided by aeration of the substrate mixture with an oxygen-comprising gas, such as air. Aeration may be conducted by the introduction of oxygen-comprising air bubbles into the aqueous substrate mixtures by various systems, such as an air-injector, an aeration frit, a membrane system, or an internal-loop airlift reactor. In some cases, the concentration of molecular oxygen in the enzymatic reaction may be from about 4 mg/L to about 14 mg/L.

Another exemplary enzyme is a lichenase, which may be selected from the GH5, GH7, GH8, GH9, GH12, GH16, GH17, or GH26 families. For example, GH16 enzyme such as a GH16 enzyme derived from *Bacillus subtilis* may be utilized. The enzyme may be able to act on, for example, mixed-linkage glucans, which are glucans comprising a mixture of β-1,3 and β-1,4 linkages, and may cleave them at β-1,4 glycosidic bonds. In the case in which the lichenase acts on a mixed-linkage glucan, the β-glucans produced may fall largely within the size range of from 3 to about 7 residues, so they may be particularly useful in the food, cosmetics, and nutraceutical industries. Mixed-linkage glucans are abundant in members of the grass and horsetail families, and as such, grass-based feedstocks such as straw generally have high levels of mixed-linkage glucans and may be acted upon usefully with lichenases. The lichenases may include GH5 lichenase from *Bacillus subtilis*.

Another alternative enzyme is a xylanase, which may act on, for example, feedstocks comprising a xylan backbone. The xylanase may be, for example, a glucuronoxylanase, an arabinoxylanase, or a glucuronoarabinoxylanase. The enzyme may be active on a variety of polymers having a xylan backbone, such as glucuronoxylan, arabinoxylan, and glucuronoarabinoxylan. These polymers are generally abundant in various plant-derived feedstocks, for example, both hardwood and softwood may comprise suitable polysaccharides, with hardwood often comprising glucuronoxylan and softwood often comprising arabinoglucuronoxylan. Xylanases may include GH5 xylanases from *Ruminiclostridium thermocellum* and *Gonapodya prolifera*, and GH30 xylanases from *Dickeya chrysanthemi, Bacillus subtilis, Bacteroides ovatus*, and *Trichoderma reesei*.

Another alternative enzyme is a mannanase, which may act on, for example, feedstocks comprising a mannan backbone. The mannanase may be, for example, a mannanase, an glucomannanase, a galactomannanase or a galactoglucomannanase. The enzyme may be active on a variety of polymers having a mannan backbone, such as mannan, glucomannan, galactomannan, or galactoglucomannan. These polymers are generally abundant in various plant-derived feedstocks, for example, both hardwood and softwood may comprise appropriate polysaccharides. Suitable mannanases can include GH5 mannanases from *Trichoderma reesei* and *Aspergillus niger* and a GH26 mannanase from *Aspergillus niger*.

Other enzymes may include xyloglucanases and xyloglucan endoglucanases (XEGs), which are produced by numerous organisms, including plant-pathogenic microbes. Xyloglucanases and XEGs may be able to act on xyloglucan, a hemicellulosic β-1,4 glucan chain abundant in the primary cell wall of higher plants, which is decorated with xylose, some of the xylose residues being further decorated with other residues, such as galactose. When appropriate xyloglucanases or XEGs act on xyloglucan, the products may comprise xyloglucan oligosaccharides having a main chain of a length useful in the foodstuff, cosmetics, and nutraceutical industries. Suitable xyloglucanases may include a GH5 xyloglucanase from *Bacteroides ovatus* and a GH74 xyloglucanase from *Trichoderma reesei*.

The enzymatic reaction may take place in solution and/or suspension. The enzymatic reaction may take place in a suitable reaction vessel. In some cases, the enzymatic reaction may take place at a temperature or temperature protocol suitable for the particular combination of enzyme and feedstock, the reaction may be allowed to progress for a certain amount of time (e.g., a predetermined amount of time) until the products have reached a desired concentration or until some other requirement has been met.

In order to ensure optimal contact between the enzymes and feedstock, the reaction mixture may be agitated, either constantly or at intervals. The agitation may take the form of (i) rhythmically moving the entire reaction vessel, (ii) a fan or other stirring device, (iii) a bubble sparging, or (iv) any other suitable method of agitation.

The enzymatic reaction may be a microbial fermentation. The temperature and reaction time may be suitable for the growth of the microbial organism used. The microbial organism may be genetically altered to produce an enzyme suitable for the production of an oligosaccharide composition. The microbe may be a bacterium, for example, *Escherichia coli* or a fungus, such as *Saccharomyces cerevisiae* or *Trichoderma reesei*.

In some embodiments, an expression vector suitable for modifying the subject microorganism may be used such that it produces an enzyme or mixture of enzymes as described elsewhere herein. Where desired, the expression vector may be a plasmid or any other nucleic acid able to induce production of the enzyme. In some instances, the expression vector may comprise one or more of the following regulatory sequences so as to control the expression of the exogenous enzyme: regulatory sequences of a heat shock gene, regulatory sequences of a toxicity gene, regulatory sequences of a spore formation gene, or any other suitable regulatory sequence.

The enzymatic reaction can be carried out at a temperature or temperature protocol suitable for the enzymes and substrates used. For example, the enzymatic reaction may be carried out at a constant temperature in the range of from 10° C. to 100° C., from 20° C. to 80° C., or from 40° C. to 60° C. In some cases, if the enzymatic reaction takes the form of a microbial fermentation, wherein the temperature may be appropriate for such. For example, the enzymatic reaction may comprise the growth of *E. coli* and/or the temperature may be substantially constant and at about 37° C.

The pH of the solution or suspension may affect the activity of the enzymes. Control of pH may aid in assuring that an enzymatic reaction proceeds at a suitable rate. The enzymatic reaction may take place at a pH in the range of from 2 to 10, 3 to 8, or 4 to 6.

The enzymatic reaction may be allowed to continue for a certain time period before being quenched and the products isolated or otherwise collected. This time period may be from 1 minute to 6 days, 0.5 days to 5 days, or 16 hours to 96 hours. The reaction may alternatively be allowed to proceed until no further catalysis occurs.

The one or more feedstocks added to the enzymatic reaction may comprise polysaccharides. Such polysaccharides may have been produced by a separate reaction proceeding simultaneously, or substantially simultaneously, in the reaction vessel. The polysaccharides present in the enzymatic reaction may be partially cleaved by enzymes into useful oligosaccharides, leaving partially cleaved or uncleaved polysaccharides, which may include, but are not limited to, cellulose, xylan (such as glucuronoxylan, arabinoxylan, or glucuronoarabinoxylan), mannan (such as glucomannan, galactomannan, or galactoglucomannan), mixed-linkage glucan, xyloglucan chitin, chitosan, or lignocellulose.

The enzymatic reaction may be allowed to continue to run until there is from 5% to 75%, 5% to 70%, 5% to 65%, 5% to 55%, or 10% to 50% undigested polysaccharide-containing feedstocks remaining. This can be monitored or checked by reducing end assays, such as the anthrone assay and/or by chromatographic methods such as thin-layer chromatography and/or high-performance anion exchange chromatography.

Any substance which comprises appropriate polysaccharides may form part of the feedstock. As the foodstuff, cosmetic, and nutraceutical industries generally use a broad variety of oligosaccharides, the polysaccharides appropriate for taking part in the enzymatic reaction are not particularly limited. Feedstocks suitable for producing the oligosaccharide profile may comprise, for example, cellulose, lignocellulose, chitin, chitosan, xylan (such as glucuronoxylan, arabinoxylan, and glucuronoarabinoxylan) and/or mannan (such as glucomannan, galactomannan, or galactoglucomannan), however, any feedstock which can be suitably acted upon is envisaged. The feedstocks may comprise sugar cane, corn stover, corncob, wheat bran, wheat straw, hardwood, softwood, or any other suitable biomass or plant biomass.

The feedstocks comprising such polysaccharides are also not particularly limited, as most plant matter is rich in such polymers. As such, the feedstock may comprise plant biomass such as grain, grain chaff, bean pods, seed coats, and/or other seed materials; seaweeds; corn stover, straw, bagasse, miscanthus, sorghum residue, switch grass, bamboo, and/or other monocotyledonous tissue; water hyacinth, leaf tissue, roots, and/or other vegetative matter; hardwood, hardwood chips, hardwood pulp, softwood, softwood chips, softwood pulp, paper, paper pulp, cardboard, and/or other wood-based feedstocks; crab shells, squid biomass, shrimp shells, and/or other marine biomass, and/or any combination of appropriate feedstocks. The feedstock may comprise wheat straw or wood. As any given natural feedstock is likely to comprise a mixture of different polysaccharides, it will sometimes be the case that a mixture of different enzymes is beneficial. Such a mixture may comprise one or more of any suitable enzyme as discussed herein. For example, such a mixture might comprise an LPMO with an endo-glucanase, a xylanase with a lichenase, a cellobiohydrolase with a mannanase, or an endo-glucanase with a cellobiohydrolase. In some embodiments, the enzyme partners may be present in molar ratios, for example, from 1:100 to 100:1. In addition, as many appropriate feedstocks are recalcitrant, pretreatment of the feedstock is envisaged.

After the enzymatic reaction has progressed to a desired point, the one or more oligosaccharides and the one or more polysaccharides from the enzymatic reaction mixture may be separated. This process can be performed in a variety of ways depending on the composition of the biomass used and the specificity of the enzymes used. As the reaction mixture will often comprise a mixture of soluble oligosaccharides and insoluble polysaccharides, the reaction mixture may be filtered to remove insoluble matter and prepare the soluble oligosaccharide obtained for further processing.

The oligosaccharides may also be separated from the polysaccharides in a number of ways. They may be isolated based on solubility, so that a composition of soluble saccharides only is extracted for further processing, and/or isolated chromatographically to produce a composition with a narrower band of oligosaccharide chain lengths. Isolation may, for example, be based on precipitation, size-exclusion chromatography, ion-exchange chromatography, filtration, ultrafiltration, microfiltration, or nanofiltration. In the case that isolation based on solubility is carried out, the profile of saccharides present in the isolated composition will generally depend on the original enzymatic reaction, as different polysaccharides generally decrease in solubility with length at different rates.

Also envisaged is the further treatment of all or part of the produced oligosaccharides to produce further products before incorporation into a foodstuff, cosmetic, or nutraceutical. This further treatment may comprise any chemical, physical, or enzymatic step, such as reduction, for example, reductive amination where appropriate; oxidation, caramelization, modification with a Schiff base, or via the Maillard reaction, or by any combination of such steps, and may provide different products having properties which are achieved or improved for the desired purpose. For example, the caramelization properties, calorific value, flavor, and color may be modified. The oligosaccharides may also be purified, for example, through precipitation, size-exclusion chromatography, ion-exchange chromatography, filtration, ultrafiltration, microfiltration, or nanofiltration.

Also envisaged is the further treatment of all or part of the produced polysaccharide fraction to produce products with improved properties before incorporation into a foodstuff, cosmetic, or nutraceutical. This further treatment may comprise any chemical, physical, or enzymatic step, such as alkylation or acid-treatment. The polysaccharides may also be purified, for example, through precipitation, size-exclusion chromatography, ion-exchange chromatography, filtration, ultrafiltration, microfiltration, or nanofiltration.

In certain instances, following modification and/or purification of the oligosaccharide and polysaccharide fractions, all or part of the fractions can then be recombined at a ratio of from 1:100 to 1:1 polysaccharide: oligosaccharide, for example, from 1:10 to 1:1, from 1:90 to 1:2, from 1:80 to 1:3, from 1:70 to 1:4, or from 1:60 to 1:5. The specific ratio may depend on the desired properties of the final ingredient as well as the modifications and purifications that have been applied to the fractions. It may not be required to recombine all of the oligosaccharide and polysaccharide isolated from the enzymatic reaction.

The fractions can be recombined in a variety of ways, for example, by mixing a solution comprising all or part of the oligosaccharide fraction and a solution and/or suspension comprising all or part of the polysaccharide fraction, which may further be dried, lyophilized, or condensed in some other way. The fractions may also be recombined by mixing a dry form comprising all or part of the oligosaccharide fraction produced by drying, lyophilization, or condensation in some other way, with a dry form comprising all or part of the polysaccharide fraction, produced by drying, lyophilization, or condensation in some other way.

The oligosaccharide components of the final composition may comprise one or more of any type of oligosaccharide. For example, the oligosaccharide components may comprise cello-oligosaccharides, xylo-oligosaccharides, mixed-linkage glucan oligosaccharides, manno-oligosaccharides, xyloglucan oligosaccharides, chito-oligosaccharides, arabinoxylo-oligosaccharides, or derivatives of any of the aforementioned oligosaccharides.

Any such dry or liquid composition may be deemed an ingredient suitable for incorporation into a foodstuff, cosmetic, or nutraceutical at any stage of this process. This includes compositions that may be deemed to be an intermediate during the method, such as a composition formed after the recombining of the oligosaccharide and polysaccharide fractions prior to any further purification, optimization, drying, dissolving, or any other such steps, as well as including the final composition obtained from the method.

As described herein, dry compositions may be formed by drying and/or lyophilization. The dry compositions can be dissolved into a solution of various liquids including water, syrups, pastes, solvents, alcohols, etc. to form the liquid composition ingredient suitable for incorporation into a foodstuff, cosmetic, or nutraceutical. Liquid compositions may be particularly useful in foods that require a smooth texture such as candy, chocolate, and yogurts.

In some embodiments, following modification and/or purification of the oligosaccharide and polysaccharide fractions, all or part of the fractions may then be recombined at a ratio of from 1:100 to 1:1 polysaccharide:oligosaccharide, for example, from 1:10 to 1:1, from 1:90 to 1:2, from 1:80 to 1:3, from 1:70 to 1:4, or from 1:60 to 1:5. The specific ratio may depend on the desired properties of the final ingredient as well as the modifications and purifications that have been applied to the fractions.

Once a composition of the oligosaccharide products suitable for the application being considered is obtained, and further treatment and/or isolation can be carried out. The derivation of a foodstuff, cosmetic, or nutraceutical from the composition can furnish a broad array of potential uses. The ingredients as described herein, can be useful in applications in which oligosaccharides, sugar, bulking sweeteners, low-intensity sweeteners, or other related food ingredients are conventionally used.

The polysaccharide-cleaving enzymes may be one of cellulase, xylanase, xyloglucanase, endo-glucanase, cellobiohydrolase, mannanase, lichenase, or a lytic polysaccharide monooxygenase (LPMO), for example, selected from the group consisting of AA9, AA10, AA11, AA13, AA14, and AA15. The polysaccharide-cleaving enzyme may be prepared from $T.$ $reesei$ fungi and/or the enzymatic reaction runs until there is 5-75%, 5-65%, or 5-50% undigested polysaccharide-containing feedstocks remaining.

The polysaccharide-cleaving enzymes may be operably linked to a catalytic or non-catalytic module, for example, wherein the polysaccharide-cleaving enzyme may be operably linked to a non-catalytic module and the non-catalytic module is a carbohydrate-binding module.

In various embodiments, after the separating of the one or more oligosaccharides and one or more polysaccharides, the one or more oligosaccharides and one or more polysaccharides may be: purified; and/or undergo chemical, physical, or enzymatic treatment, such as reduction, oxidation, caramelization, or Maillard reaction; and/or may be recombined by combining a dried powder of oligosaccharides with a dried polysaccharide powder.

In some embodiments, the ingredient may comprise three or more oligosaccharides of different molecular weights, wherein the method may comprise forming the three or more oligosaccharides by an enzymatic reaction, wherein the enzymatic reaction comprises the step of contacting, in a solution or suspension, one or more polysaccharide-cleaving enzymes and one or more feedstocks.

III. Foodstuff, Cosmetic, or Nutraceutical Ingredients

Compositions

The polysaccharide components of the composition may comprise one or more of any type of polysaccharide. For example, the polysaccharide may comprise cellulose, lignocellulose, xylan, mixed-linkage glucan, mannan, xyloglucan, chitin, chitosan, or derivatives of any of the aforementioned polysaccharides.

The composition or ingredient may comprise various oligosaccharides. The composition may include the oligosaccharides at varying amounts, for example, depending on the desired properties of the composition. In some instances, the composition may comprise at least 20% by dry weight, for example, at least 30% by dry weight, cello-oligosaccharides having a degree of polymerization of from two to six; and/or the composition may comprise at least 20% by dry weight, for example, at least 30% by dry weight, xylo-oligosaccharides having a degree of polymerization of from two to twelve; and/or the composition may comprise at least 20% by dry weight, for example, at least 30% by dry weight, mixed-linkage glucan oligosaccharides having a degree of polymerization of from two to five; and/or the composition may comprise at least 20% by dry weight, for example, at least 30% by dry weight, manno-oligosaccharides having a degree of polymerization of from two to twelve; and/or the composition may comprise at least 20% by dry weight, for example, at least 30% by dry weight, xyloglucan oligosaccharides having a degree of polymerization of from four to twelve, and/or the composition may comprise at least 20% by dry weight, for example, at least 30% by dry weight, chito-oligosaccharides having a degree of polymerization of from two to twelve; and/or the composition may comprise at least 20% by dry weight, for example, at least 30% by dry weight, arabinoxylo-oligosaccharides having a degree of polymerization of from three to fifteen. In certain embodiments, it may be understand that the composition can comprise a maximum of 100% by dry weight of the above oligosaccharides, therefore, the above embodiment, wherein the oligosaccharides are present in at least 20% by dry weight, does not comprise all seven types of oligosaccharides.

In various embodiments, the composition or ingredient may comprise about 5% to about 50% w/w cello-oligosaccharides with a degree of polymerization of from two to six. In certain embodiments, the composition or ingredient may comprise about 5% to about 50%, about 10% to about 40%, about 15% to about 35% w/w cello-oligosaccharides with a degree of polymerization of from two to six. The composition or ingredient may comprise at least 5%, 8%, 10%, 15%, 20%, or 25% w/w cello-oligosaccharides with a degree of polymerization of from two to six. In some embodiments, the composition or ingredient may comprise about 20% to about 90% w/w cello-oligosaccharides with a degree of polymerization of from two to six. In certain embodiments, the composition or ingredient may comprise about 5% to about 95%, about 10% to about 92.5%, about 30% to about 80%, about 40% to about 70%, or about 50% to about 60% w/w cello-oligosaccharides with a degree of polymerization of from two to six.

In various embodiments, the composition or ingredient may comprise about 20% to about 90% w/w xylo-oligosaccharides with a degree of polymerization of from two to five. In certain embodiments, the composition or ingredient may comprise about 5% to about 95%, about 10% to about 92.5%, about 30% to about 80%, about 40% to about 70%, or about 50% to about 60% w/w xylo-oligosaccharides with a degree of polymerization of from two to five. For example, the composition may comprise at least 30% w/w of xylo-oligosaccharides with a degree of polymerization from two to five. The composition or ingredient may comprise at least 5%, 8%, 10%, 15%, 20%, or 25% w/w xylo-oligosaccharides with a degree of polymerization of from two to five.

In certain embodiments, the composition or ingredient may comprise about 0.1% to about 15% w/w arabinoxylo-oligosaccharides with a degree of polymerization of from three to twelve. The composition or ingredient may comprise at least 0.1%, 0.3%, 0.5%, 0.8%, 1%, 2%, 3%, 4%, 5%, 6%, 7%, 8%, 9%, 10%, or 15% w/w arabinoxylo-oligosaccharides with a degree of polymerization of from three to twelve. In various embodiments, the composition or ingredient may comprise about 0.5% to about 25% w/w arabinoxylo-oligosaccharides with a degree of polymerization of from three to fifteen. The composition or ingredient may comprise at least 0.1%, 0.3%, 0.5%, 0.8%, 1%, 2%, 3%, 4%, 5%, 10%, 15%, 20%, 25%, 30%, or 35% w/w arabinoxylo-oligosaccharides with a degree of polymerization of from three to fifteen.

In some embodiments, provided herein is the use of an oligosaccharide mixture in the formation of a foodstuff, cosmetic, or nutraceutical, wherein the oligosaccharide mixture comprises two oligosaccharides selected from the list consisting of:
  i) cello-oligosaccharides having a degree of polymerization of from two to six;
  ii) xylo-oligosaccharides having a degree of polymerization of from two to twelve;
  iii) mixed-linkage glucan oligosaccharides having a degree of polymerization of from two to five;
  iv) manno-oligosaccharides having a degree of polymerization of from two to twelve;
  v) xyloglucan oligosaccharides having a degree of polymerization of from four to ten;
  vi) chito-oligosaccharides having a degree of polymerization of from two to twelve; and/or
  vii) arabinoxylo-oligosaccharide having a degree of polymerization of from three to fifteen, wherein the two oligosaccharides may be present in a ratio of from 1:9 to 9:1, 1:4 to 4:1, or 2:3 to 3:2 in relation to each other.

In certain cases, the arabinoxylo-oligosaccharides may comprise at least 0.1% arabinosyl residues. The arabinoxylo-oligosaccharides may comprise at least 0.1%, 0.2%, 0.5%, 1%, 5%, or 10% arabinosyl residues.

The amounts of each of the oligosaccharides may be varied depending on the desired properties of the resulting foodstuff, cosmetic, or nutraceutical. For example, the two oligosaccharides may be present in a ratio of 1:9 to 1:1, 1:2 to 1:1, or 2:3 to 1:1 in relation to each other.

The oligosaccharide mixture may further comprise a third oligosaccharide. The oligosaccharide mixture may comprise a third oligosaccharide and a fourth oligosaccharide. The oligosaccharide mixture may comprise a third oligosaccharide, a fourth oligosaccharide, and a fifth oligosaccharide. The oligosaccharide mixture may further comprise a third oligosaccharide, a fourth oligosaccharide, a fifth oligosaccharide, and a sixth oligosaccharide. The oligosaccharide mixture may further comprise a third oligosaccharide, a fourth oligosaccharide, a fifth oligosaccharide, a sixth oligosaccharide, and a seventh oligosaccharide. These oligosaccharides may be selected from the same list as the at least two oligosaccharides as provided above.

Oligosaccharide mixtures of the at least two oligosaccharides may comprise the cello-oligosaccharides, for instance, cello-oligosaccharides in combination with the xylo-oligosaccharides. An alternative composition may comprise cello-oligosaccharides in combination with manno-oligosaccharides. In some embodiments, the oligosaccharide mixtures may include cello-oligosaccharides, xylo-oligosaccharides, and arabinoxylo-oligosaccharides in combination with each other.

The oligosaccharide mixtures of the at least two oligosaccharides may additionally include a polysaccharide, for example, a cellulosic polysaccharide, such as cellulose, or a polysaccharide derivative, for example, a cellulose derivative, such as carboxymethylcellulose, or a polysaccharide aggregate, for example, a portion of lignocellulosic biomass. In some instances, the ratio in the combination may be from 1:100 to 1:1 polysaccharide/polysaccharide derivative/polysaccharide aggregate:oligosaccharide, for example, from 1:90 to 1:2, from 1:80 to 1:3, from 1:70 to 1:4, or from 1:60 to 1:5. As such, the ratio between the first oligosaccharide, the second oligosaccharide, and the polysaccharide may be from 2:2:1 to 30:30:1, for example, about 3:3:1.

Combinations of Oligosaccharides

A composition may comprise a mixture of one or more oligosaccharides. A mixture of oligosaccharides may comprise two forms or types of oligosaccharides, for instance, cello-oligosaccharides and xylo-oligosaccharides. A mixture of oligosaccharides may comprise three forms of oligosaccharides, for instance, cello-oligosaccharides, manno-oligosaccharides, and xylo-oligosaccharides. A mixture of oligosaccharides may comprise four forms of oligosaccharides, for instance, cello-oligosaccharides, manno-oligosaccharides, mixed-linkage glucan oligosaccharides, and chito-oligosaccharides.

An oligosaccharide mixture may comprise two forms of oligosaccharides, for example, a first oligosaccharide and a second oligosaccharide. An oligosaccharide mixture may comprise about 5% of a first oligosaccharide and about 95% of a second oligosaccharide w/w. An oligosaccharide mixture may comprise about 10% of a first oligosaccharide and about 90% of a second oligosaccharide w/w. An oligosaccharide mixture may comprise about 15% of a first oligosaccharide and about 85% of a second oligosaccharide w/w. An oligosaccharide mixture may comprise about 20% of a first oligosaccharide and about 80% of a second oligosaccharide w/w. An oligosaccharide mixture may comprise about 25% of a first oligosaccharide and about 75% of a second oligosaccharide w/w. An oligosaccharide mixture may comprise about 30% of a first oligosaccharide and about 70% of a second oligosaccharide w/w. An oligosaccharide mixture may comprise about 35% of a first oligosaccharide and about 65% of a second oligosaccharide w/w. An oligosaccharide mixture may comprise about 40% of a first oligosaccharide and about 50% of a second oligosaccharide w/w. An oligosaccharide mixture may comprise 45% of a first oligosaccharide and 55% of a second oligosaccharide w/w. An oligosaccharide mixture may comprise 50% of a first oligosaccharide and 50% of a second oligosaccharide w/w. An oligosaccharide mixture may comprise 55% of a first oligosaccharide and 45% of a second oligosaccharide w/w. An oligosaccharide mixture may comprise 60% of a first oligosaccharide and 30% of a second oligosaccharide w/w. An oligosaccharide mixture may comprise 65% of a first oligosaccharide and 35% of a second oligosaccharide w/w. An oligosaccharide mixture may comprise 70% of a first oligosaccharide and 30% of a second oligosaccharide w/w. An oligosaccharide mixture may comprise 75% of a first oligosaccharide and 25% of a second oligosaccharide w/w. An oligosaccharide mixture may comprise 80% of a first oligosaccharide and 20% of a second oligosaccharide w/w. An oligosaccharide mixture may comprise 85% of a first oligosaccharide and 15% of a second oligosaccharide w/w. An oligosaccharide mixture may comprise 90% of a first oligosaccharide and 10% of a second oligosaccharide w/w. An oligosaccharide mixture may comprise 95% of a first oligosaccharide and 5% of a second oligosaccharide w/w. In some cases, a first oligosaccharide may be cello-oligosaccharides and a second oligosaccharide may be xylo-oligosaccharides. In some instances, a first oligosaccharide may be cello-oligosaccharides and a second oligosaccharide may be manno-oligosaccharides. In some embodiments, a first oligosaccharide may be xylo-oligosaccharides and a second oligosaccharide may be manno-oligosaccharides. Other combinations of a first oligosaccharide and a second oligosaccharide are also within the scope of this disclosure.

An oligosaccharide mixture may comprise three forms of oligosaccharides, for example a first oligosaccharide, a second oligosaccharide, and a third oligosaccharide. An oligosaccharide mixture may comprise about 20% of a first oligosaccharide, 40% of a second oligosaccharide, and 40% of a third oligosaccharide w/w. An oligosaccharide mixture may comprise about 30% of a first oligosaccharide, 30% of a second oligosaccharide, and 40% of a third oligosaccharide w/w. An oligosaccharide mixture may comprise about 10% of a first oligosaccharide, 10% of a second oligosaccharide, and 80% of a third oligosaccharide w/w. An oligosaccharide mixture may comprise about 20% of a first oligosaccharide, 20% of a second oligosaccharide, and 60% of a third oligosaccharide w/w. An oligosaccharide mixture may comprise about 20% of a first oligosaccharide, 30% of a second oligosaccharide, and 50% of a third oligosaccharide w/w. In some examples, a first oligosaccharide may be manno-oligosaccharides, a second oligosaccharide may be xylo-oligosaccharides, and a third oligosaccharide may be cello-oligosaccharides. In some examples, a first oligosaccharide may be xyloglucan-oligosaccharides, a second oligosaccharide may be xylo-oligosaccharides, and a third oligosaccharide may be cello-oligosaccharides. Other combinations of a first oligosaccharide, a second oligosaccharide, and a third oligosaccharide are also within the scope of this disclosure.

An oligosaccharide mixture may comprise two or more oligosaccharides, a first oligosaccharide and a second oligosaccharide which is different than the first oligosaccharide. For instance, the first oligosaccharide may be a xylo-oligosaccharide or a cello-oligosaccharide or a manno-oligosaccharide or other oligosaccharide as provided herein, whereas the second oligosaccharide can be a xylo-oligosaccharide or a cello-oligosaccharide or a manno-oligosaccharide or other oligosaccharides not used as the first oligosaccharide. Stated another way, the first oligosaccharide can be different than the second oligosaccharide (e.g., the first oligosaccharide can be of a different type of oligosaccharide than the second oligosaccharide). The ratio of a first oligosaccharide to a second oligosaccharide in the mixture may be about 1:1, 1:2, 1:3, 1:4, 1:5, 1:6, 1:7, 1:8, or 1:9.

The ratio of a first oligosaccharide to a second oligosaccharide in the mixture may be about 2:1, 2:3, 2:5, 2:7, or 2:9. The oligosaccharides may be cello-oligosaccharides, manno-oligosaccharides, xylo-oligosaccharides, xyloglucan-oligosaccharides, mixed-linkage oligosaccharides, chito-oligosaccharides, arabinoxylo-oligosaccharides, or other oligosaccharides as provided herein, wherein the first oligosaccharide is selected to be a different oligosaccharide than the second oligosaccharide. In other words, the first oligosaccharide may be a different type of oligosaccharide than the second oligosaccharide.

The ratio of a first oligosaccharide to a second oligosaccharide in the mixture may be about 3:1, 3:2, 3:4, 3:5, 3:7, or 3:8. The oligosaccharides may be cello-oligosaccharides, manno-oligosaccharides, xylo-oligosaccharides, xyloglucan-oligosaccharides, mixed-linkage oligosaccharides, chito-oligosaccharides, arabinoxylo-oligosaccharides, or other oligosaccharides provided herein, wherein the first oligosaccharide is selected to be a different oligosaccharide than the second oligosaccharide.

The ratio of a first oligosaccharide to a second oligosaccharide in an oligosaccharide mixture comprising two or more oligosaccharides may be from 1:9 to 9:1, from 1:4 to 4:1, from 1:3 to 3:1, or from 2:3 to 3:2. The oligosaccharides may be cello-oligosaccharides, manno-oligosaccharides, xylo-oligosaccharides, xyloglucan-oligosaccharides, mixed-linkage oligosaccharides, chito-oligosaccharides, arabinoxylo-oligosaccharide, or other oligosaccharides provided herein, wherein the first oligosaccharide is selected to be a different oligosaccharide than the second oligosaccharide.

In some cases, the composition or the ingredient may include at least 1% w/w, 2% w/w, 3% w/w, 4% w/w, 5% w/w, 10% w/w, 15% w/w, 20% w/w, 25% w/w, 30% w/w, or more of cellobiose, xylobiose, mannobiose (e.g., Man-β-1, 4-Man), Glc-β-1,4-Man, Man-β-1,4-Glc, laminaribiose, gentiobiose, sophorose, maltose, lactose, or sucrose. In certain cases, the composition or the ingredient may include at least 1% w/w, 2% w/w, 3% w/w, 4% w/w, 5% w/w, 10% w/w, 15% w/w, 20% w/w, 25% w/w, 30% w/w, or more of cellotriose, xylotriose, monoarabinosylated xylobiose, monoglucuronosylated xylobiose, maltotriose, mannotriose (e.g., Man-β-1,4-Man-β-1,4-Man), Glc-β-1,4-Man-β-1,4-Man, Man-β-1,4-Glc-β-1,4-Man, Man-β-1,4-Man-β-1,4-Glc, Man-β-1,4-Glc-β-1,4-Glc, Glc-β-1,4-Man-β-1,4-Glc, Glc-β-1,4-Glc-β-1,4-Man, Glc-β-1,3-Glc-β-1,4-Glc, or Glc-β-1,4-Glc-β-1,3-Glc. In certain instances, the composition or the ingredient may include at least 1% w/w, 2% w/w, 3% w/w, 4% w/w, 5% w/w, 10% w/w, 15% w/w, 20% w/w, 25% w/w, 30% w/w, or more of xylotetraose, cellotetraose, monoarabinosylated xylotriose, monoglucuronosylated xylotriose, diarabinosylated xylobiose, diglucuronosylated xylobiose, maltotetraose, mannotetraose (e.g., Man-β-1,4-Man-β-1,4-Man-β-1,4-Man), Glc-β-1,4-Man-β-1,4-Man-β-1,4-Man, Man-β-1,4-Glc-β-1,4-Man-β-1,4-Man, Man-β-1,4-Man-β-1,4-Glc-β-1,4-Man, Man-β-1,4-Man-β-1,4-Man-β-1,4-Glc, Glc-β-1,4-Glc-β-1,4-Man-β-1,4-Man, Man-β-1,4-Glc-β-1,4-Glc-β-1,4-Man, Man-β-1,4-Man-β-1,4-Glc-β-1,4-Glc, Glc-β-1,4-Man-β-1,4-Glc-β-1,4-Man, Glc-β-1,4-Man-β-1,4-Man-β-1,4-Glc, Man-β-1,4-Glc-β-1,4-Man-β-1,4-Glc, Glc-β-1,3-Glc-β-1,4-Glc-1,4-Glc, Glc-β-1,4-Glc-β-1,3-Glc-1,4-Glc, Glc-β-1,4-Glc-β-1,4-Glc-1,3-Glc, or Glc-β-1,3-Glc-β-1,4-Glc-1,3-Glc. In certain cases, the composition or the ingredient may include at least 0.01% w/w, 0.05% w/w, 0.1% w/w, 0.5% w/w, 1% w/w, 2% w/w, 5% w/w, 10% w/w, 15% w/w, 20% w/w, or more of xylopentaose, cellopentaose, monoarabinosylated xylotetraose, monoglucuronosylated xylotetraose, diarabinosylated xylotriose, diglucuronosylated xylotriose, maltopentaose, mannopentaose (e.g., Man-β-1,4-Man-β-1,4-Man-β-1,4-Man-β-1,4-Man), mixed-linkage glucan-derived pentasaccharide, or mannan-derived pentasaccharide The composition or ingredient may comprise from 1% to 50%, 5% to 40% 10% to 30%, or 15% to 25% w/w of cellobiose. The composition or ingredient may comprise from 2.5% to 90%, 5% to 80% 10% to 70%, or 20% to 60% w/w of xylobiose. The composition or ingredient may comprise from 2.5% to 75%, 5% to 50% 10% to 40%, or 20% to 30% w/w of xylotriose.

Oligosaccharide Compositions with Varying Degrees of Polymerization

The average degree of polymerization of the oligosaccharides in the composition may be from 1 to 50, 1.5 to 25, 2 to 15, 2.1 to 10, 2.1 to 7, or 2.2 to 5.

The concentration of xylo-oligosaccharides with a degree of polymerization of two in a xylo-oligosaccharide mixture may be from about 2% to about 80% w/w. The concentration of xylo-oligosaccharides with a degree of polymerization of two may be at least 2%, 4%, 6%, 8%, 10%, 12%, 15%, 18%, 20%, 25%, or 30% w/w. The concentration of xylo-oligosaccharides with a degree of polymerization of two may be higher in some cases, for instance, up to 35%, 40%, 45%, 50%, 55%, 60%, 65%, 70%, 75%, or 80% w/w.

The concentration of xylo-oligosaccharides with a degree of polymerization of three in a xylo-oligosaccharide mixture may be about 2% to about 20% w/w. The concentration of xylo-oligosaccharides with a degree of polymerization of three may be at least 2%, 4%, 6%, 8%, 10%, 12%, 15%, 18%, or 20% w/w.

The concentration of xylo-oligosaccharides with a degree of polymerization of four in a xylo-oligosaccharide mixture may be about 5% to about 20% w/w. The concentration of xylo-oligosaccharides with a degree of polymerization of four may be at least 5%, 8%, 10%, 12%, 15%, 18%, or 20% w/w.

The concentration of xylo-oligosaccharides with a degree of polymerization of five in a xylo-oligosaccharide mixture may be about 5% to about 20% w/w. The concentration of xylo-oligosaccharides with a degree of polymerization of five may be at least 5%, 7%, 8%, 10%, 12%, 15%, 18%, or 20% w/w.

The concentration of xylo-oligosaccharides with a degree of polymerization of six in a xylo-oligosaccharide mixture may be about 5% to about 25% w/w. The concentration of xylo-oligosaccharides with a degree of polymerization of six may be at least 5%, 8%, 10%, 12%, 15%, 18%, 20%, or 25% w/w.

The concentration of xylo-oligosaccharides with a degree of polymerization of seven in a xylo-oligosaccharide mixture may be about 2% to about 20% w/w. The concentration of xylo-oligosaccharides with a degree of polymerization of seven may be at least 2%, 4%, 6%, 8%, 10%, 12%, 15%, 17%, or 20% w/w.

The concentration of xylo-oligosaccharides with a degree of polymerization of eight in a xylo-oligosaccharide mixture may be about 1% to about 15% w/w. The concentration of xylo-oligosaccharides with a degree of polymerization of eight may be at least 1%, 2%, 3%, 4%, 5%, 6%, 7%, 8%, 9%, 10%, or 15% w/w.

The concentration of xylo-oligosaccharides with a degree of polymerization of nine in a xylo-oligosaccharide mixture may be about 2% to about 15% w/w. The concentration of xylo-oligosaccharides with a degree of polymerization of nine may be at least 1%, 2%, 3%, 4%, 5%, 6%, 7%, 8%, 9%, 10%, or 15% w/w.

The concentration of xylo-oligosaccharides with a degree of polymerization of ten in a xylo-oligosaccharide mixture may be about 2% to about 15% w/w. The concentration of xylo-oligosaccharides with a degree of polymerization of ten may be at least 1%, 2%, 3%, 4%, 5%, 6%, 7%, 8%, 9%, 10%, or 15% w/w.

The concentration of xylo-oligosaccharides with a degree of polymerization of eleven in a xylo-oligosaccharide mixture may be about 2% to about 15% w/w. The concentration of xylo-oligosaccharides with a degree of polymerization of eleven may be at least 1%, 2%, 3%, 4%, 5%, 6%, 7%, 8%, 9%, 10%, or 15% w/w.

The concentration of xylo-oligosaccharides with a degree of polymerization of twelve in a xylo-oligosaccharide mixture may be about 2% to about 15% w/w. The concentration of xylo-oligosaccharides with a degree of polymerization of twelve may be at least 1%, 2%, 3%, 4%, 5%, 6%, 7%, 8%, 9%, 10%, or 15% w/w.

The concentration of cello-oligosaccharides with a degree of polymerization of two in a cello-oligosaccharide mixture may be about 2% to about 80% w/w. The concentration of cello-oligosaccharides with a degree of polymerization of two may be at least 2%, 4%, 6%, 8%, 10%, 12%, 15%, 18%, 20%, 25%, or 30% w/w. The concentration of cello-oligosaccharides with a degree of polymerization of two may be higher in some cases, for instance, at least 35%, 40%, 45%, 50%, 55%, 60%, 65%, 70%, 75%, or 80% w/w.

The concentration of cello-oligosaccharides with a degree of polymerization of three in a cello-oligosaccharide mixture may be about 2% to about 20% w/w. The concentration of cello-oligosaccharides with a degree of polymerization of three may be at least 2%, 4%, 6%, 8%, 10%, 12%, 15%, 18%, or 20% w/w.

The concentration of cello-oligosaccharides with a degree of polymerization of four in a cello-oligosaccharide mixture may be about 5% to about 20% w/w. The concentration of cello-oligosaccharides with a degree of polymerization of four may be at least 5%, 8%, 10%, 12%, 15%, 18%, or 20% w/w.

The concentration of cello-oligosaccharides with a degree of polymerization of five in a cello-oligosaccharide mixture may be about 5% to about 20% w/w. The concentration of cello-oligosaccharides with a degree of polymerization of five may be at least 5%, 7%, 8%, 10%, 12%, 15%, 18%, or 20% w/w.

The concentration of cello-oligosaccharides with a degree of polymerization of six in a cello-oligosaccharide mixture may be about 5% to about 25% w/w. The concentration of cello-oligosaccharides with a degree of polymerization of six may be at least 5%, 8%, 10%, 12%, 15%, 18%, 20%, or 25% w/w.

The concentration of manno-oligosaccharides with a degree of polymerization of two in a manno-oligosaccharide mixture may be about 2% to about 30% w/w. The concentration of manno-oligosaccharides with a degree of polymerization of two may be at least 2%, 4%, 6%, 8%, 10%, 12%, 15%, 18%, 20%, 25%, or 30% w/w.

The concentration of manno-oligosaccharides with a degree of polymerization of three in a manno-oligosaccharide mixture may be about 2% to about 20% w/w. The concentration of manno-oligosaccharides with a degree of polymerization of three may be at least 2%, 4%, 6%, 8%, 10%, 12%, 15%, 18%, or 20% w/w.

The concentration of manno-oligosaccharides with a degree of polymerization of four in a manno-oligosaccharide mixture may be about 5% to about 20% w/w. The concentration of manno-oligosaccharides with a degree of polymerization of four may be at least 5%, 8%, 10%, 12%, 15%, 18%, or 20% w/w.

The concentration of manno-oligosaccharides with a degree of polymerization of five in a manno-oligosaccharide mixture may be about 5% to about 20% w/w. The concentration of manno-oligosaccharides with a degree of polymerization of five may be at least 5%, 7%, 8%, 10%, 12%, 15%, 18%, or 20% w/w.

The concentration of manno-oligosaccharides with a degree of polymerization of six in a manno-oligosaccharide mixture may be about 5% to about 25% w/w. The concentration of manno-oligosaccharides with a degree of polymerization of six may be at least 5%, 8%, 10%, 12%, 15%, 18%, 20%, or 25% w/w.

The concentration of manno-oligosaccharides with a degree of polymerization of seven in a manno-oligosaccharide mixture may be about 2% to about 20% w/w. The concentration of manno-oligosaccharides with a degree of polymerization of seven may be at least 2%, 4%, 6%, 8%, 10%, 12%, 15%, 17%, or 20% w/w.

The concentration of manno-oligosaccharides with a degree of polymerization of eight in a manno-oligosaccharide mixture may be about 1% to about 15% w/w. The concentration of manno-oligosaccharides with a degree of polymerization of eight may be at least 1%, 2%, 3%, 4%, 5%, 6%, 7%, 8%, 9%, 10%, or 15% w/w.

The concentration of manno-oligosaccharides with a degree of polymerization of nine in a manno-oligosaccharide mixture may be about 2% to about 15% w/w. The concentration of manno-oligosaccharides with a degree of polymerization of nine may be at least 1%, 2%, 3%, 4%, 5%, 6%, 7%, 8%, 9%, 10%, or 15% w/w.

The concentration of manno-oligosaccharides with a degree of polymerization of ten in a manno-oligosaccharide mixture may be about 2% to about 15% w/w. The concentration of manno-oligosaccharides with a degree of polymerization of ten may be at least 1%, 2%, 3%, 4%, 5%, 6%, 7%, 8%, 9%, 10%, or 15% w/w.

The concentration of manno-oligosaccharides with a degree of polymerization of eleven in a manno-oligosaccharide mixture may be about 2% to about 15% w/w. The concentration of manno-oligosaccharides with a degree of polymerization of eleven may be at least 1%, 2%, 3%, 4%, 5%, 6%, 7%, 8%, 9%, 10%, or 15% w/w.

The concentration of manno-oligosaccharides with a degree of polymerization of twelve in a manno-oligosaccharide mixture may be about 2% to about 15% w/w. The concentration of manno-oligosaccharides with a degree of polymerization of twelve may be at least 1%, 2%, 3%, 4%, 5%, 6%, 7%, 8%, 9%, 10%, or 15% w/w.

The concentration of xyloglucan-oligosaccharides with a degree of polymerization of four in a xyloglucan-oligosaccharide mixture may be about 5% to about 20% w/w. The concentration of xyloglucan-oligosaccharides with a degree of polymerization of four may be at least 5%, 8%, 10%, 12%, 15%, 18%, or 20% w/w.

The concentration of xyloglucan-oligosaccharides with a degree of polymerization of five in a xyloglucan-oligosaccharide mixture may be about 5% to about 20% w/w. The concentration of xyloglucan-oligosaccharides with a degree of polymerization of five may be at least 5%, 7%, 8%, 10%, 12%, 15%, 18%, or 20% w/w.

The concentration of xyloglucan-oligosaccharides with a degree of polymerization of six in a xyloglucan-oligosaccharide mixture may be about 5% to about 25% w/w. The concentration of xyloglucan-oligosaccharides with a degree of polymerization of six may be at least 5%, 8%, 10%, 12%, 15%, 18%, 20%, or 25% w/w.

The concentration of xyloglucan-oligosaccharides with a degree of polymerization of seven in a xyloglucan-oligosaccharide mixture may be about 2% to about 20% w/w. The concentration of xyloglucan-oligosaccharides with a degree of polymerization of seven may be at least 2%, 4%, 6%, 8%, 10%, 12%, 15%, 17%, or 20% w/w.

The concentration of xyloglucan-oligosaccharides with a degree of polymerization of eight in a xyloglucan-oligosaccharide mixture may be about 1% to about 15% w/w. The concentration of xyloglucan-oligosaccharides with a degree of polymerization of eight may be at least 1%, 2%, 3%, 4%, 5%, 6%, 7%, 8%, 9%, 10%, or 15% w/w.

The concentration of xyloglucan-oligosaccharides with a degree of polymerization of nine in a xyloglucan-oligosaccharide mixture may be about 2% to about 15% w/w. The concentration of xyloglucan-oligosaccharides with a degree of polymerization of nine may be at least 1%, 2%, 3%, 4%, 5%, 6%, 7%, 8%, 9%, 10%, or 15% w/w.

The concentration of xyloglucan-oligosaccharides with a degree of polymerization of ten in a xyloglucan-oligosaccharide mixture may be about 2% to about 15% w/w. The concentration of xyloglucan-oligosaccharides with a degree of polymerization of ten may be at least 1%, 2%, 3%, 4%, 5%, 6%, 7%, 8%, 9%, 10%, or 15% w/w.

The concentration of mixed-linkage glucan-oligosaccharides with a degree of polymerization of two in a mixed-linkage glucan-oligosaccharide mixture may be about 2% to about 30% w/w. The concentration of mixed-linkage glucan-oligosaccharides with a degree of polymerization of two may be at least 2%, 4%, 6%, 8%, 10%, 12%, 15%, 18%, 20%, 25%, or 30% w/w.

The concentration of mixed-linkage glucan-oligosaccharides with a degree of polymerization of three in a mixed-linkage glucan-oligosaccharide mixture may be about 2% to about 20% w/w. The concentration of mixed-linkage glucan-oligosaccharides with a degree of polymerization of three may be at least 2%, 4%, 6%, 8%, 10%, 12%, 15%, 18%, or 20% w/w.

The concentration of mixed-linkage glucan-oligosaccharides with a degree of polymerization of four in a mixed-linkage glucan-oligosaccharide mixture may be about 5% to about 20% w/w. The concentration of mixed-linkage glucan-oligosaccharides with a degree of polymerization of four may be at least 5%, 8%, 10%, 12%, 15%, 18%, or 20% w/w.

The concentration of mixed-linkage glucan-oligosaccharides with a degree of polymerization of five in a mixed-linkage glucan-oligosaccharide mixture may be about 5% to about 20% w/w. The concentration of mixed-linkage glucan-oligosaccharides with a degree of polymerization of five may be at least 5%, 7%, 8%, 10%, 12%, 15%, 18%, or 20% w/w.

The concentration of chito-oligosaccharides with a degree of polymerization of two in a chito-oligosaccharide mixture may be about 2% to about 30% w/w. The concentration of chito-oligosaccharides with a degree of polymerization of two may be at least 2%, 4%, 6%, 8%, 10%, 12%, 15%, 18%, 20%, 25%, or 30% w/w.

The concentration of chito-oligosaccharides with a degree of polymerization of three in a chito-oligosaccharide mixture may be about 2% to about 20% w/w. The concentration of chito-oligosaccharides with a degree of polymerization of three may be at least 2%, 4%, 6%, 8%, 10%, 12%, 15%, 18%, or 20% w/w.

The concentration of chito-oligosaccharides with a degree of polymerization of four in a chito-oligosaccharide mixture may be about 5% to about 20% w/w. The concentration of chito-oligosaccharides with a degree of polymerization of four may be at least 5%, 8%, 10%, 12%, 15%, 18%, or 20% w/w.

The concentration of chito-oligosaccharides with a degree of polymerization of five in a chito-oligosaccharide mixture may be about 5% to about 20% w/w. The concentration of chito-oligosaccharides with a degree of polymerization of five may be at least 5%, 7%, 8%, 10%, 12%, 15%, 18%, or 20% w/w.

The concentration of chito-oligosaccharides with a degree of polymerization of six in a chito-oligosaccharide mixture may be about 5% to about 25% w/w. The concentration of chito-oligosaccharides with a degree of polymerization of six may be at least 5%, 8%, 10%, 12%, 15%, 18%, 20%, or 25% w/w.

The concentration of chito-oligosaccharides with a degree of polymerization of seven in a chito-oligosaccharide mixture may be about 2% to about 20% w/w. The concentration of chito-oligosaccharides with a degree of polymerization of seven may be at least 2%, 4%, 6%, 8%, 10%, 12%, 15%, 17%, or 20% w/w.

The concentration of chito-oligosaccharides with a degree of polymerization of eight in a chito-oligosaccharide mixture may be about 1% to about 15% w/w. The concentration of chito-oligosaccharides with a degree of polymerization of eight may be at least 1%, 2%, 3%, 4%, 5%, 6%, 7%, 8%, 9%, 10%, or 15% w/w.

The concentration of chito-oligosaccharides with a degree of polymerization of nine in a chito-oligosaccharide mixture may be about 2% to about 15% w/w. The concentration of chito-oligosaccharides with a degree of polymerization of nine may be at least 1%, 2%, 3%, 4%, 5%, 6%, 7%, 8%, 9%, 10%, or 15% w/w.

The concentration of chito-oligosaccharides with a degree of polymerization of ten in a chito-oligosaccharide mixture may be about 2% to about 15% w/w. The concentration of chito-oligosaccharides with a degree of polymerization of ten may be at least 1%, 2%, 3%, 4%, 5%, 6%, 7%, 8%, 9%, 10% or 15% w/w.

The concentration of chito-oligosaccharides with a degree of polymerization of eleven in a chito-oligosaccharide mixture may be about 2% to about 15% w/w. The concentration of chito-oligosaccharides with a degree of polymerization of eleven may be at least 1%, 2%, 3%, 4%, 5%, 6%, 7%, 8%, 9%, 10%, or 15% w/w.

The concentration of chito-oligosaccharides with a degree of polymerization of twelve in a chito-oligosaccharide mixture may be about 2% to about 15% w/w. The concentration of chito-oligosaccharides with a degree of polymerization of twelve may be at least 1%, 2%, 3%, 4%, 5%, 6%, 7%, 8%, 9%, 10%, or 15% w/w.

The concentration of arabinoxylo-oligosaccharides with a degree of polymerization of three in an arabinoxylo-oligosaccharide mixture may be about 2% to about 20% w/w. The concentration of arabinoxylo-oligosaccharides with a degree of polymerization of three may be at least 2%, 4%, 6%, 8%, 10%, 12%, 15%, 18%, or 20% w/w.

The concentration of arabinoxylo-oligosaccharides with a degree of polymerization of four in an arabinoxylo-oligosaccharide mixture may be about 5% to about 20% w/w. The concentration of arabinoxylo-oligosaccharides with a degree of polymerization of four may be at least 5%, 8%, 10%, 12%, 15%, 18%, or 20% w/w.

The concentration of arabinoxylo-oligosaccharides with a degree of polymerization of five in an arabinoxylo-oligosaccharide mixture may be about 5% to about 20% w/w. The concentration of arabinoxylo-oligosaccharides with a degree of polymerization of five may be at least 5%, 7%, 8%, 10%, 12%, 15%, 18%, or 20% w/w.

The concentration of arabinoxylo-oligosaccharides with a degree of polymerization of six in an arabinoxylo-oligosaccharide mixture may be about 5% to about 25% w/w. The concentration of arabinoxylo-oligosaccharides with a degree of polymerization of six may be at least 5%, 8%, 10%, 12%, 15%, 18%, 20%, or 25% w/w.

The concentration of arabinoxylo-oligosaccharides with a degree of polymerization of seven in an arabinoxylo-oligosaccharide mixture may be about 2% to about 20% w/w. The concentration of arabinoxylo-oligosaccharides with a degree of polymerization of seven may be at least 2%, 4%, 6%, 8%, 10%, 12%, 15%, 17%, or 20% w/w.

The concentration of arabinoxylo-oligosaccharides with a degree of polymerization of eight in an arabinoxylo-oligosaccharide mixture may be about 1% to about 15% w/w. The concentration of arabinoxylo-oligosaccharides with a degree of polymerization of eight may be at least 1%, 2%, 3%, 4%, 5%, 6%, 7%, 8%, 9%, 10%, or 15% w/w.

The concentration of arabinoxylo-oligosaccharides with a degree of polymerization of nine in an arabinoxylo-oligosaccharide mixture may be about 2% to about 15% w/w. The concentration of arabinoxylo-oligosaccharides with a degree of polymerization of nine may be at least 1%, 2%, 3%, 4%, 5%, 6%, 7%, 8%, 9%, 10%, or 15% w/w.

The concentration of arabinoxylo-oligosaccharides with a degree of polymerization of ten in an arabinoxylo-oligosaccharide mixture may be about 2% to about 15% w/w. The concentration of arabinoxylo-oligosaccharides with a degree of polymerization of ten may be at least 1%, 2%, 3%, 4%, 5%, 6%, 7%, 8%, 9%, 10%, or 15% w/w.

The concentration of arabinoxylo-oligosaccharides with a degree of polymerization of eleven in an arabinoxylo-oligosaccharide mixture may be about 2% to about 15% w/w. The concentration of arabinoxylo-oligosaccharides with a degree of polymerization of eleven may be at least 1%, 2%, 3%, 4%, 5%, 6%, 7%, 8%, 9%, 10%, or 15% w/w.

The concentration of arabinoxylo-oligosaccharides with a degree of polymerization of twelve in an arabinoxylo-oligosaccharide mixture may be about 2% to about 15% w/w. The concentration of arabinoxylo-oligosaccharides with a degree of polymerization of twelve may be at least 1%, 2%, 3%, 4%, 5%, 6%, 7%, 8%, 9%, 10%, or 15% w/w.

The concentration of arabinoxylo-oligosaccharides with a degree of polymerization of thirteen in an arabinoxylo-oligosaccharide mixture may be about 2% to about 15% w/w. The concentration of arabinoxylo-oligosaccharides with a degree of polymerization of thirteen may be at least 1%, 2%, 3%, 4%, 5%, 6%, 7%, 8%, 9%, 10%, or 15% w/w.

The concentration of arabinoxylo-oligosaccharides with a degree of polymerization of fourteen in an arabinoxylo-oligosaccharide mixture may be about 2% to about 15% w/w. The concentration of arabinoxylo-oligosaccharides with a degree of polymerization of fourteen may be at least 1%, 2%, 3%, 4%, 5%, 6%, 7%, 8%, 9%, 10%, or 15% w/w.

The concentration of arabinoxylo-oligosaccharides with a degree of polymerization of fifteen in an arabinoxylo-oligosaccharide mixture may be about 2% to about 15% w/w. The concentration of arabinoxylo-oligosaccharides with a degree of polymerization of fifteen may be at least 1%, 2%, 3%, 4%, 5%, 6%, 7%, 8%, 9%, 10%, or 15% w/w.

The concentration of arabinoxylo-oligosaccharides with a degree of polymerization of from three to twelve in an arabinoxylo-oligosaccharide mixture may be about 0.1% to about 15% w/w. The concentration of arabinoxylo-oligosaccharides with a degree of polymerization of three to twelve may be at least 0.1%, 0.3%, 0.5%, 0.8%, 1%, 2%, 3%, 4%, 5%, 6%, 7%, 8%, 9%, 10%, or 15% w/w.

Compositions with Combinations of Monosaccharides, Polysaccharides, and/or Oligosaccharides In some embodiments, the composition or ingredient (e.g., the ingredient for human consumption) may soluble in water. The solubility of the ingredient in water may be at least 80 g of the ingredient per 100 g of water at 50° C.

The ingredient may be combined with a liquid to form a liquid ingredient. In some cases, a viscosity of the liquid ingredient may be comparable or similar to a viscosity of corn syrup. In some other cases, that viscosity of the liquid ingredient may comparable or similar to a viscosity of high-fructose corn syrup. For example, the liquid ingredient may have a viscosity of from 5 cps to 100,000 cps, 8,000 cps to 100,000 cps, 10,000 cps to 50,000 cps, or 15,000 cps to 25,000 cps. Moreover, the liquid ingredient may have fewer calories per gram than corn syrup or high-fructose corn syrup. The liquid ingredient may have a lower glycemic index than corn syrup or high-fructose corn syrup.

In some embodiments, the liquid may comprise water or any other suitable liquid. The liquid ingredient may comprises at least 5%, 10%, 20%, 30%, 40%, or 50% by dry weight of the at least one oligosaccharide. Furthermore, the liquid ingredient may comprise at least 0.2%, 0.5%, 1%, 2%, 3%, 5%, or 10% by dry weight of the at least one polysaccharide. For example, the liquid ingredient may comprises at least 20% by dry weight of the at least one oligosaccharide and at least 2% by dry weight of the at least one polysaccharide. Other combinations of the at least one oligosaccharide and the at least one polysaccharide are also within the scope of the present disclosure.

The liquid ingredient comprises at least 0.2%, 0.5%, 1%, 2%, 3%, 5%, or 10% by dry weight of xylan. The liquid ingredient may comprise at least 0.2%, 0.5%, 1%, 2%, 3%, 5%, or 10% by dry weight of mannan. The liquid ingredient may comprise at least 0.2%, 0.5%, 1%, 2%, 3%, 5%, or 10% by dry weight of a cellulose derivative.

In various cases, the liquid ingredient may have a concentration of polysaccharides of from 0.1% to 50%, 0.1% to 40%, 0.1% to 30%, 0.1% to 20%, 0.1% to 10%, 0.5% to 50%, or 1% to 50% w/v. For example, the liquid ingredient may have a concentration of polysaccharides of from 0.1% to 50% w/v. The liquid ingredient may comprise an amount of polysaccharide and oligosaccharide in a ratio from 1:200 to 1:1, 1:150 to 1:1, 1:125 to 1:1 1:100 to 1:1, 1:90 to 1:1, 1:80 to 1:1, 1:70 to 1:1, 1:60 and 1:1, 1:50 and 1:1, 1:25 and 1:1, or 1:10 and 1:1. For example, the liquid ingredient may comprises an amount of polysaccharide and oligosaccharide in a ratio from 1:100 to 1:1.

The one or more soluble polysaccharides may comprise at least one of a mannan, a xylan, a mixed-linkage glucan, a lignocellulose, a hemicellulose, a cellulose derivative, a chitosan, a xyloglucan, or any other suitable soluble polysaccharide. The cellulose derivative may comprise at least one of a cellulose acetate, a hydroxyethylcellulose, a hydroxymethylcellulose, or any other suitable cellulose derivative.

The biomass may comprise at least one of a sugar cane biomass, a corn biomass, a wheat biomass, a hardwood biomass, a softwood biomass, or any other suitable biomass.

In certain instances, a composition for human consumption may include a soluble polysaccharide and an oligosaccharide comprising at least one of (i) a cello-oligosaccharide having a degree of polymerization (DP) of from two to six; (ii) a xylo-oligosaccharide having a DP of from two to twelve; (iii) a manno-oligosaccharide having a DP of from two to twelve; (iv) an arabinoxylo-oligosaccharide having a DP of from three to fifteen; (v) a mixed-linkage glucan oligosaccharide having a DP of from two to five; or (vi) a chito-oligosaccharide having a DP of from two to twelve. The composition may include less than 5% by dry weight soluble polysaccharides. In some cases, the composition may include less than 1%, 2%, 5%, 7.5%, 10%, or 20% by dry weight soluble polysaccharides. In some embodiments, the composition may be free, or substantially free, of insoluble polysaccharides.

A composition may comprise a combination of polysaccharides and oligosaccharides. In some embodiments, a composition may comprise a combination of oligosaccharides and soluble polysaccharides. The source of the polysaccharides (or the soluble polysaccharides) in such compositions may contain cellulose, such as biomass, for example, the undigested component of partially digested biomass, such as the undigested biomass from the same reaction as that which produced the oligosaccharides. The polysaccharides in the undigested biomass may comprise lignin, polyphenol, cellulose, lignocellulose, or any other suitable polysaccharides as described herein. Addition of polysaccharides (e.g., soluble polysaccharides) to oligosaccharide mixtures can be done to improve the gastrointestinal tolerance of the oligosaccharide mixtures. Oligosaccharide consumption can cause gastrointestinal distress, including diarrhea, discomfort, and bloating. The compositions described herein may have an improved gastrointestinal tolerance such as, less or no discomfort, bloating, diarrhea, or gastrointestinal distress as compared to a saccharide composition available commercially or a saccharide composition comprising primarily monosaccharides and/or disaccharides. For example, a subject who ingests one or more of the compositions provided herein may have an improved gastrointestinal tolerance such as, less or no discomfort, bloating, diarrhea, or gastrointestinal distress as compared to if, or when, the subject ingests a saccharide composition available commercially or a saccharide composition comprising primarily monosaccharides and/or disaccharides.

The concentration of undigested biomass in a composition may be from 1% to 50% w/w. The concentration of undigested biomass in a composition may be from 1% to 5%, 1% to 10%, 1% to 15%, 1% to 20%, 1% to 25%, 1% to 30%, 1% to 35%, 1% to 40%, 1% to 45%, 1% to 50%, 5% to 10%, 5% to 15%, 5% to 20%, 5% to 25%, 5% to 30%, 5% to 35%, 5% to 40%, 5% to 45%, 5% to 50%, 10% to 15%, 10% to 20%, 10% to 25%, 10% to 30%, 10% to 35%, 10% to 40%, 10% to 45%, 10% to 50%, 15% to 20%, 15% to 25%, 15% to 30%, 15% to 35%, 15% to 40%, 15% to 45%, 15% to 50%, 20% to 25%, 20% to 30%, 20% to 35%, 20% to 40%, 20% to 45%, 20% to 50%, 25% to 30%, 25% to 35%, 25% to 40%, 25% to 45%, 25% to 50%, 30% to 35%, 30% to 40%, 30% to 45%, 30% to 50%, 35% to 40%, 35% to 45%, 35% to 50%, 40% to 45%, 40% to 50%, or 45% to 50% w/w. The concentration of undigested biomass in a composition may be about 1%, 5%, 10%, 15%, 20%, 25%, 30%, 35%, 40%, 45%, or 50% w/w. The concentration of undigested biomass in a composition may be at least 1%, 5%, 10%, 15%, 20%, 25%, 30%, 35%, 40%, or 45% w/w. The concentration of undigested biomass in a composition may be at most 5%, 10%, 15%, 20%, 25%, 30%, 35%, 40%, 45%, or 50% w/w.

The concentration of soluble polysaccharides in a composition may be from 1% to 50% w/w. The concentration of soluble polysaccharides in a composition may be from 1% to 5%, 1% to 10%, 1% to 15%, 1% to 20%, 1% to 25%, 1% to 30%, 1% to 35%, 1% to 40%, 1% to 45%, 1% to 50%, 5% to 10%, 5% to 15%, 5% to 20%, 5% to 25%, 5% to 30%, 5% to 35%, 5% to 40%, 5% to 45%, 5% to 50%, 10% to 15%, 10% to 20%, 10% to 25%, 10% to 30%, 10% to 35%, 10% to 40%, 10% to 45%, 10% to 50%, 15% to 20%, 15% to 25%, 15% to 30%, 15% to 35%, 15% to 40%, 15% to 45%, 15% to 50%, 20% to 25%, 20% to 30%, 20% to 35%, 20% to 40%, 20% to 45%, 20% to 50%, 25% to 30%, 25% to 35%, 25% to 40%, 25% to 45%, 25% to 50%, 30% to 35%, 30% to 40%, 30% to 45%, 30% to 50%, 35% to 40%, 35% to 45%, 35% to 50%, 40% to 45%, 40% to 50%, or 45% to 50% w/w. The concentration of soluble polysaccharides in a composition may be about 1%, 5%, 10%, 15%, 20%, 25%, 30%, 35%, 40%, 45%, or 50% w/w. The concentration of soluble polysaccharides in a composition may be at least 1%, 5%, 10%, 15%, 20%, 25%, 30%, 35%, 40%, or 45% w/w. The concentration of soluble polysaccharides in a composition may be at most 5%, 10%, 15%, 20%, 25%, 30%, 35%, 40%, 45%, or 50% w/w.

The concentration of xylo-oligosaccharides in a composition may be from 1% to 50% w/w. The concentration of xylo-oligosaccharides in a composition may be from 1% to 5%, 1% to 10%, 1% to 15%, 1% to 20%, 1% to 25%, 1% to 30%, 1% to 35%, 1% to 40%, 1% to 45%, 1% to 50%, 5% to 10%, 5% to 15%, 5% to 20%, 5% to 25%, 5% to 30%, 5% to 35%, 5% to 40%, 5% to 45%, 5% to 50%, 10% to 15%, 10% to 20%, 10% to 25%, 10% to 30%, 10% to 35%, 10% to 40%, 10% to 45%, 10% to 50%, 15% to 20%, 15% to 25%, 15% to 30%, 15% to 35%, 15% to 40%, 15% to 45%, 15% to 50%, 20% to 25%, 20% to 30%, 20% to 35%, 20% to 40%, 20% to 45%, 20% to 50%, 25% to 30%, 25% to 35%, 25% to 40%, 25% to 45%, 25% to 50%, 30% to 35%, 30% to 40%, 30% to 45%, 30% to 50%, 35% to 40%, 35% to 45%, 35% to 50%, 40% to 45%, 40% to 50%, or 45% to 50% w/w. The concentration of xylo-oligosaccharides in a composition may be about 1%, 5%, 10%, 15%, 20%, 25%, 30%, 35%, 40%, 45%, or 50% w/w. The concentration of xylo-oligosaccharides in a composition may be at least 1%, 5%, 10%, 15%, 20%, 25%, 30%, 35%, 40%, or 45% w/w. The concentration of xylo-oligosaccharides in a composition may be at most 5%, 10%, 15%, 20%, 25%, 30%, 35%, 40%, 45%, or 50% w/w.

The concentration of cello-oligosaccharides in a composition may be from 1% to 50% w/w. The concentration of cello-oligosaccharides in a composition may be from 1% to 5%, 1% to 10%, 1% to 15%, 1% to 20%, 1% to 25%, 1% to 30%, 1% to 35%, 1% to 40%, 1% to 45%, 1% to 50%, 5% to 10%, 5% to 15%, 5% to 20%, 5% to 25%, 5% to 30%, 5% to 35%, 5% to 40%, 5% to 45%, 5% to 50%, 10% to 15%, 10% to 20%, 10% to 25%, 10% to 30%, 10% to 35%, 10% to 40%, 10% to 45%, 10% to 50%, 15% to 20%, 15% to 25%, 15% to 30%, 15% to 35%, 15% to 40%, 15% to 45%, 15% to 50%, 20% to 25%, 20% to 30%, 20% to 35%, 20% to 40%, 20% to 45%, 20% to 50%, 25% to 30%, 25% to 35%, 25% to 40%, 25% to 45%, 25% to 50%, 30% to 35%, 30% to 40%, 30% to 45%, 30% to 50%, 35% to 40%, 35% to 45%, 35% to 50%, 40% to 45%, 40% to 50%, or 45% to 50% w/w. The concentration of cello-oligosaccharides in a composition may be about 1%, 5%, 10%, 15%, 20%, 25%, 30%, 35%, 40%, 45%, or 50% w/w. The concentration of cello-oligosaccharides in a composition may be at least 1%, 5%, 10%, 15%, 20%, 25%, 30%, 35%, 40%, or 45% w/w. The concentration of cello-oligosaccharides in a composition may be at most 5%, 10%, 15%, 20%, 25%, 30%, 35%, 40%, 45%, or 50% w/w.

In some embodiments, the composition may comprise at least 5% w/w of cello-oligosaccharides and at least 5% w/w of a second oligosaccharides (e.g., at least 5% w/w of xylo-oligosaccharides, manno-oligosaccharides, mixed-linkage glucan oligosaccharides, xyloglucan-oligosaccharides, chito-oligosaccharides, arabinoxylo-oligosaccharides, or any other suitable oligosaccharides).

The concentration of manno-oligosaccharides in a composition may be from 1% to 50% w/w. The concentration of manno-oligosaccharides in a composition may be from 1% to 5%, 1% to 10%, 1% to 15%, 1% to 20%, 1% to 25%, 1% to 30%, 1% to 35%, 1% to 40%, 1% to 45%, 1% to 50%, 5% to 10%, 5% to 15%, 5% to 20%, 5% to 25%, 5% to 30%, 5% to 35%, 5% to 40%, 5% to 45%, 5% to 50%, 10% to 15%, 10% to 20%, 10% to 25%, 10% to 30%, 10% to 35%, 10% to 40%, 10% to 45%, 10% to 50%, 15% to 20%, 15% to 25%, 15% to 30%, 15% to 35%, 15% to 40%, 15% to 45%, 15% to 50%, 20% to 25%, 20% to 30%, 20% to 35%, 20% to 40%, 20% to 45%, 20% to 50%, 25% to 30%, 25% to 35%, 25% to 40%, 25% to 45%, 25% to 50%, 30% to 35%, 30% to 40%, 30% to 45%, 30% to 50%, 35% to 40%, 35% to 45%, 35% to 50%, 40% to 45%, 40% to 50%, or 45% to 50% w/w. The concentration of manno-oligosaccharides in a composition may be about 1%, 5%, 10%, 15%, 20%, 25%, 30%, 35%, 40%, 45%, or 50% w/w. The concentration of manno-oligosaccharides in a composition may be at least 1%, 5%, 10%, 15%, 20%, 25%, 30%, 35%, 40%, or 45% w/w. The concentration of manno-oligosaccharides in a composition may be at most 5%, 10%, 15%, 20%, 25%, 30%, 35%, 40%, 45%, or 50% w/w.

The concentration of chito-oligosaccharides in a composition may be from 1% to 50% w/w. The concentration of chito-oligosaccharides in a composition may be from 1% to 5%, 1% to 10%, 1% to 15%, 1% to 20%, 1% to 25%, 1% to 30%, 1% to 35%, 1% to 40%, 1% to 45%, 1% to 50%, 5% to 10%, 5% to 15%, 5% to 20%, 5% to 25%, 5% to 30%, 5% to 35%, 5% to 40%, 5% to 45%, 5% to 50%, 10% to 15%, 10% to 20%, 10% to 25%, 10% to 30%, 10% to 35%, 10% to 40%, 10% to 45%, 10% to 50%, 15% to 20%, 15% to 25%, 15% to 30%, 15% to 35%, 15% to 40%, 15% to 45%, 15% to 50%, 20% to 25%, 20% to 30%, 20% to 35%, 20% to 40%, 20% to 45%, 20% to 50%, 25% to 30%, 25% to 35%, 25% to 40%, 25% to 45%, 25% to 50%, 30% to 35%, 30% to 40%, 30% to 45%, 30% to 50%, 35% to 40%, 35% to 45%, 35% to 50%, 40% to 45%, 40% to 50%, or 45% to 50% w/w. The concentration of chito-oligosaccharides in a composition may be about 1%, 5%, 10%, 15%, 20%, 25%, 30%, 35%, 40%, 45%, or 50% w/w. The concentration of chito-oligosaccharides in a composition may be at least 1%, 5%, 10%, 15%, 20%, 25%, 30%, 35%, 40%, or 45% w/w. The concentration of chito-oligosaccharides in a composition may be at most 5%, 10%, 15%, 20%, 25%, 30%, 35%, 40%, 45%, or 50% w/w.

The concentration of xyloglucan-oligosaccharides in a composition may be from 1% to 50% w/w. The concentration of xyloglucan-oligosaccharides in a composition may be from 1% to 5%, 1% to 10%, 1% to 15%, 1% to 20%, 1% to 25%, 1% to 30%, 1% to 35%, 1% to 40%, 1% to 45%, 1% to 50%, 5% to 10%, 5% to 15%, 5% to 20%, 5% to 25%, 5% to 30%, 5% to 35%, 5% to 40%, 5% to 45%, 5% to 50%, 10% to 15%, 10% to 20%, 10% to 25%, 10% to 30%, 10% to 35%, 10% to 40%, 10% to 45%, 10% to 50%, 15% to 20%, 15% to 25%, 15% to 30%, 15% to 35%, 15% to 40%, 15% to 45%, 15% to 50%, 20% to 25%, 20% to 30%, 20% to 35%, 20% to 40%, 20% to 45%, 20% to 50%, 25% to 30%, 25% to 35%, 25% to 40%, 25% to 45%, 25% to 50%, 30% to 35%, 30% to 40%, 30% to 45%, 30% to 50%, 35% to 40%, 35% to 45%, 35% to 50%, 40% to 45%, 40% to 50%, or 45% to 50% w/w. The concentration of xyloglucan-oligosaccharides in a composition may be about 1%, 5%, 10%, 15%, 20%, 25%, 30%, 35%, 40%, 45%, or 50% w/w. The concentration of xyloglucan-oligosaccharides in a composition may be at least 1%, 5%, 10%, 15%, 20%, 25%, 30%, 35%, 40%, or 45% w/w. The concentration of xyloglucan-oligosaccharides in a composition may be at most 5%, 10%, 15%, 20%, 25%, 30%, 35%, 40%, 45%, or 50% w/w.

The concentration of mixed-linkage glucan-oligosaccharides in a composition may be from 1% to 50% w/w. The concentration of mixed-linkage glucan-oligosaccharides in a composition may be from 1% to 5%, 1% to 10%, 1% to 15%, 1% to 20%, 1% to 25%, 1% to 30%, 1% to 35%, 1% to 40%, 1% to 45%, 1% to 50%, 5% to 10%, 5% to 15%, 5% to 20%, 5% to 25%, 5% to 30%, 5% to 35%, 5% to 40%, 5% to 45%, 5% to 50%, 10% to 15%, 10% to 20%, 10% to 25%, 10% to 30%, 10% to 35%, 10% to 40%, 10% to 45%, 10% to 50%, 15% to 20%, 15% to 25%, 15% to 30%, 15% to 35%, 15% to 40%, 15% to 45%, 15% to 50%, 20% to 25%, 20% to 30%, 20% to 35%, 20% to 40%, 20% to 45%, 20% to 50%, 25% to 30%, 25% to 35%, 25% to 40%, 25% to 45%, 25% to 50%, 30% to 35%, 30% to 40%, 30% to 45%, 30% to 50%, 35% to 40%, 35% to 45%, 35% to 50%, 40% to 45%, 40% to 50%, or 45% to 50% w/w. The concentration of mixed-linkage glucan-oligosaccharides in a composition may be about 1%, 5%, 10%, 15%, 20%, 25%, 30%, 35%, 40%, 45%, or 50% w/w. The concentration of mixed-linkage glucan-oligosaccharides in a composition may be at least 1%, 5%, 10%, 15%, 20%, 25%, 30%, 35%, 40%, or 45% w/w. The concentration of mixed-linkage glucan-oligosaccharides in a composition may be at most 5%, 10%, 15%, 20%, 25%, 30%, 35%, 40%, 45%, or 50% w/w.

The concentration of arabinoxylo-oligosaccharides in a composition may be from 1% to 50% w/w. The concentration of arabinoxylo-oligosaccharides in a composition may be from 1% to 5%, 1% to 10%, 1% to 15%, 1% to 20%, 1% to 25%, 1% to 30%, 1% to 35%, 1% to 40%, 1% to 45%, 1% to 50%, 5% to 10%, 5% to 15%, 5% to 20%, 5% to 25%, 5% to 30%, 5% to 35%, 5% to 40%, 5% to 45%, 5% to 50%, 10% to 15%, 10% to 20%, 10% to 25%, 10% to 30%, 10% to 35%, 10% to 40%, 10% to 45%, 10% to 50%, 15% to 20%, 15% to 25%, 15% to 30%, 15% to 35%, 15% to 40%, 15% to 45%, 15% to 50%, 20% to 25%, 20% to 30%, 20% to 35%, 20% to 40%, 20% to 45%, 20% to 50%, 25% to 30%, 25% to 35%, 25% to 40%, 25% to 45%, 25% to 50%, 30% to 35%, 30% to 40%, 30% to 45%, 30% to 50%, 35% to 40%, 35% to 45%, 35% to 50%, 40% to 45%, 40% to 50%, or 45% to 50% w/w. The concentration of arabinoxylo-oligosaccharides in a composition may be about 1%, 5%, 10%, 15%, 20%, 25%, 30%, 35%, 40%, 45%, or 50% w/w. The concentration of arabinoxylo-oligosaccharides in a composition may be at least 1%, 5%, 10%, 15%, 20%, 25%, 30%, 35%, 40%, or 45% w/w. The concentration of arabinoxylo-oligosaccharides in a composition may be at most 5%, 10%, 15%, 20%, 25%, 30%, 35%, 40%, 45%, or 50% w/w.

A composition may comprise one or more polysaccharides (e.g., one or more soluble polysaccharides) and one or more oligosaccharides. The composition may comprise a polysaccharide and one type of oligosaccharide. The composition may comprise a polysaccharide or plurality of polysaccharides and two forms of oligosaccharides. The composition may comprise a polysaccharide or plurality of polysaccharides and three forms of oligosaccharides. The composition may comprise a polysaccharide or plurality of polysaccharides and four forms of oligosaccharides. The composition may comprise a polysaccharide or plurality of polysaccharides and five forms of oligosaccharides. The oligosaccharides may be xylo-oligosaccharides, cello-oligosaccharides, manno-oligosaccharides, mixed-linkage glucan oligosaccharides, xyloglucan-oligosaccharides, chito-oligosaccharides, arabinoxylo-oligosaccharides, or any other suitable oligosaccharides described herein.

The composition may comprise from about 1% to 50% polysaccharides w/w, such as in the type of undigested biomass or extracted soluble polysaccharides, and about 5% to about 95% oligosaccharides w/w. The composition of polysaccharides may be at least about 1%, 2%, 2.5%, 3%, 4%, 5%, 10%, 15%, 20%, 25%, 30%, 35%, 40%, 45%, or 50% w/w. Oligosaccharides in such mixtures may be present at greater than 5%, 10%, 15%, 20%, 25%, 30%, 35%, 40%, 45%, 50%, 55%, 60%, 65%, 70%, 75%, 80%, 85%, 90%, or 95% w/w. The oligosaccharides may be a mixture of one or more oligosaccharides. For instance, a composition may comprise 5% undigested biomass and 50% oligosaccharide mixture w/w as described elsewhere herein. In another instance, a composition may comprise 2.5% soluble polysaccharides and 50% oligosaccharide mixture w/w as described elsewhere herein.

The composition may comprise about 5% polysaccharides w/w, such as in the type of undigested biomass, and about 5% to about 95% oligosaccharides w/w. Oligosaccharides in such mixtures may be present at greater than 5%, 10%, 15%, 20%, 25%, 30%, 35%, 40%, 45%, 50%, 55%, 60%, 65%, 70%, 75%, 80%, 85%, 90%, or 95% w/w. The oligosaccharides may be a mixture of one or more oligosaccharides. For instance, a composition may comprise 5% undigested biomass and 50% oligosaccharide mixture w/w as described elsewhere herein. In another instance, a composition may comprise 5% soluble polysaccharide(s) and 50% oligosaccharide mixture w/w as described elsewhere herein.

The composition may comprise about 7% polysaccharides w/w, such as in the type of undigested biomass and about 5% to about 93% oligosaccharides w/w. Oligosaccharides may form at least 5%, 10%, 15%, 20%, 25%, 30%, 35%, 40%, 45%, 50%, 55%, 60%, 65%, 70%, 75%, 80%, 85%, 90%, or 93% w/w of such mixtures. The oligosaccharides may be a mixture of one or more oligosaccharides. For instance, a composition may comprise 7% undigested biomass and 50% oligosaccharide mixture w/w as described elsewhere herein. In another instance, a composition may comprise 7% soluble polysaccharide(s) and 50% oligosaccharide mixture w/w as described elsewhere herein.

The composition may comprise about 10% polysaccharides w/w, such as in the type of undigested biomass and about 5% to about 90% oligosaccharides w/w. Oligosaccharides may form at least 5%, 10%, 15%, 20%, 25%, 30%, 35%, 40%, 45%, 50%, 55%, 60%, 65%, 70%, 75%, 80%, 85%, or 90% w/w of such mixtures. The oligosaccharides may be a mixture of one or more oligosaccharides. For instance, a composition may comprise 10% undigested biomass and 50% oligosaccharide mixture w/w as described elsewhere herein. In another instance, a composition may comprise 10% polysaccharide(s) and 50% oligosaccharide mixture w/w as described elsewhere herein.

The composition may comprise about 12% polysaccharides w/w, such as in the type of undigested biomass and from about 5% to about 95% oligosaccharides w/w. Oligosaccharides may form at least 5%, 10%, 15%, 20%, 25%, 30%, 35%, 40%, 45%, 50%, 55%, 60%, 65%, 70%, 75%, 80%, 85%, or 88% w/w of such mixtures. The oligosaccharides may be a mixture of one or more oligosaccharides. For instance, a composition may comprise 12% undigested biomass and 50% oligosaccharide mixture w/w as described elsewhere herein. In another instance, a composition may comprise 12% soluble polysaccharide(s) and 50% oligosaccharide mixture w/w as described elsewhere herein.

The composition may comprise about 15% polysaccharides w/w, such as in the type of undigested biomass and about 5% to about 85% oligosaccharides w/w. Oligosaccharides may form at least 5%, 10%, 15%, 20%, 25%, 30%, 35%, 40%, 45%, 50%, 55%, 60%, 65%, 70%, 75%, 80%, or 85% w/w of such mixtures. The oligosaccharides may be a mixture of one or more oligosaccharides. For instance, a composition may comprise 15% undigested biomass and 50% oligosaccharide mixture w/w as described elsewhere herein. In another instance, a composition may comprise 15% soluble polysaccharide(s) and 50% oligosaccharide mixture w/w as described elsewhere herein.

The composition may comprise about 20% polysaccharides w/w, such as in the type of undigested biomass and about 5% to about 80% oligosaccharides w/w. Oligosaccharides may form at least 5%, 10%, 15%, 20%, 25%, 30%, 35%, 40%, 45%, 50%, 55%, 60%, 65%, 70%, 75%, or 80% w/w of such mixtures. The oligosaccharides may be a mixture of one or more oligosaccharides. For instance, a composition may comprise 20% undigested biomass and 50% oligosaccharide mixture w/w as described elsewhere herein. In another instance, a composition may comprise 20% soluble polysaccharide(s) and 50% oligosaccharide mixture w/w as described elsewhere herein.

The composition may comprise about 25% polysaccharides w/w, such as in the type of undigested biomass and about 5% to about 75% oligosaccharides w/w. Oligosaccharides may form at least 5%, 10%, 15%, 20%, 25%, 30%, 35%, 40%, 45%, 50%, 55%, 60%, 65%, 70%, or 75% w/w of such mixtures. The oligosaccharides may be a mixture of one or more oligosaccharides. For instance, a composition may comprise 25% undigested biomass and 50% oligosaccharide mixture w/w as described elsewhere herein. In another instance, a composition may comprise 25% soluble polysaccharide(s) and 50% oligosaccharide mixture w/w as described elsewhere herein.

The composition may comprise about 30% polysaccharides w/w, such as in the type of undigested biomass and about 5% to about 70% oligosaccharides w/w. Oligosaccharides may form at least 5%, 10%, 15%, 20%, 25%, 30%, 35%, 40%, 45%, 50%, 55%, 60%, 65%, or 70% w/w of such mixtures. The oligosaccharides may be a mixture of one or more oligosaccharides. For instance, a composition may comprise 30% undigested biomass and 50% oligosaccharide mixture w/w as described elsewhere herein. In another instance, a composition may comprise 30% soluble polysaccharide(s) and 50% oligosaccharide mixture w/w as described elsewhere herein.

The composition may comprise about 40% polysaccharides w/w, such as in the type of undigested biomass and about 5% to about 60% oligosaccharides w/w. Oligosaccharides may form at least 5%, 10%, 15%, 20%, 25%, 30%, 35%, 40%, 45%, 50%, 55%, or 60% w/w of such mixtures. The oligosaccharides may be a mixture of one or more oligosaccharides. For instance, a composition may comprise 40% undigested biomass and 50% oligosaccharide mixture w/w as described elsewhere herein. In another instance, a composition may comprise 40% soluble polysaccharide(s) and 50% oligosaccharide mixture w/w as described elsewhere herein.

The composition may comprise about 50% polysaccharides w/w, such as in the type of undigested biomass and about 5% to about 50% oligosaccharides w/w. Oligosaccharides may form at least 5%, 10%, 15%, 20%, 25%, 30%, 35%, 40%, 45%, or 50% w/w of such mixtures. The oligosaccharides may be a mixture of one or more oligosaccharides. For instance, a composition may comprise 50% undigested biomass and 50% oligosaccharide mixture w/w as described elsewhere herein. In another instance, a composition may comprise 50% soluble polysaccharide(s) and 50% oligosaccharide mixture w/w as described elsewhere herein.

In some embodiments, the composition or ingredient may comprise less than 1%, 5%, 10%, 15%, 20%, 25%, 30%, or 40% w/w monosaccharides. For example, the composition may comprise less than 20% w/w monosaccharides. The composition may include from 10% to 40%, 15% to 30%, 18% to 25%, or about 20% w/w monosaccharides. In some embodiments, the composition or ingredient may comprise less than 1%, 5%, 10%, 15%, 20%, 25%, 30%, or 40% w/w glucose. For example, the composition may comprise less than 10% w/w glucose. The composition may include from 10% to 40%, 15% to 30%, 18% to 25%, or about 20% w/w glucose. In some embodiments, the composition or ingredient may comprise less than 1%, 5%, 10%, 15%, 20%, 25%, 30%, or 40% w/w xylose. For example, the composition may comprise less than 10% w/w xylose. The composition may include from 10% to 40%, 15% to 30%, 18% to 25%, or about 20% w/w xylose.

In certain cases, the ratio of glucose residues to xylose residues (e.g., glucose:xylose) within the composition or ingredient may be from 1:1 and 1:9, 1:1 and 1:7, 1:1 and 1:5, 1:1 and 1:3, or 1:1 and 1:2.

In certain embodiments, the composition may comprise less than 30%, 40%, 50%, 60%, 65%, 70%, 75%, or 80% w/w disaccharides. For example, the composition may comprise less than 70% w/w disaccharides. The composition may include from 10% to 95%, 15% to 90%, 20% to 80%, 30% to 70%, or 40% to 60% w/w disaccharides. The composition may comprise from 5% to 95%, 10% to 92.5%, 15% to 90%, 20% to 70%, 30% to 60%, or 40% to 50% disaccharides. In various embodiments, the composition may comprise at least 0.5%, 1%, 2.5%, 5%, 7.5%, 10%, 15%, or 20% w/w trisaccharides. For example, the composition may comprise at least 5% w/w trisaccharides. In various embodiments, the composition may comprise at least 0.5%, 1%, 2.5%, 5%, 7.5%, 10%, 15%, or 20% w/w trisaccharides. For example, the composition may comprise at least 5% w/w trisaccharides. The composition may comprise from 1% to 75%, 2.5% to 60%, 5% to 50%, 10% to 40%, or 20% to 30% trisaccharides. In some cases, the composition may comprise at least 0.1%, 0.5%, 1%, 2.5%, 5%, 7.5%, 10%, 15%, or 20% w/w tetrasaccharides. For example, the composition may comprise at least 1% w/w tetrasaccharides. In various cases, the composition may comprise at least 0.01%, 0.05%, 0.1%, 0.2%, 0.3%, 0.5%, 0.5%, 1%, 2.5%, 5%, 7.5%, or w/w pentasaccharides. For example, the composition may comprise at least 0.1% w/w pentasaccharides.

Use of Compositions as Ingredients

In some embodiments, the composition is an ingredient (e.g., in a foodstuff). In certain embodiments, the ingredient comprises at least 50%, 60%, 70%, 80%, 90%, 95%, 99%, or 99.5% by dry weight of saccharide present. The ingredient may consist essentially of saccharides. For example, the ingredient may have less than 0.5%, 0.3%, or 0.1% by dry weight of other substances.

The ingredient may comprise an oligosaccharide mixture as described elsewhere herein. The ingredient may comprise at least two of the oligosaccharides. For instance, it may comprise three of the oligosaccharides. It may comprise four oligosaccharides. It may comprise five oligosaccharides. It may comprise six oligosaccharides. It may comprise seven oligosaccharides.

In some embodiments, the ingredient comprises cello-oligosaccharides, for instance, cello-oligosaccharides in combination with xylo-oligosaccharides. An alternative ingredient may comprise cello-oligosaccharides in combination with manno-oligosaccharides.

Ingredients may be used to prepare finished products. The ingredient may also be treated in some physical or chemical way before or during incorporation into a foodstuff, cosmetic, or nutraceutical. It may be directly incorporated into a product, or it may be incorporated into, for example, a dough, cake mixture, chocolate mixture, or other foodstuff precursor; a cosmetic base composition; or a nutraceutical, and, for example, be cooked or otherwise treated in a way which may cause chemical modification, a change of texture, a change of color, or other modification.

A foodstuff, cosmetic, or nutraceutical may be produced from an ingredient described herein. For example, in the food industry, the saccharide formulations produced by the current method may be used as sweeteners, bulking agents, added dietary fiber, or humectants. The ingredient may be used as a sugar substitute. The ingredient may be incorporated into cakes, breads, or other baked goods, or into chocolate or other confectionery such as toffee, fudge, meringue, jam, jelly, or caramel; or drinks, for example, to provide favorable taste or color characteristics or to increase dietary fiber content. In certain instances, the ingredient may be incorporated into animal feed, for example, either as an isolated ingredient or by utilizing the enzymatic reaction mixture directly as feed.

In the cosmetics industry, saccharides can be useful as ingredients, as they may improve texture and moisture retention, act as UV-absorbing molecules, maintain a gel or cream structure, and/or serve as bulking agents. The compositions described herein can be incorporated into nutraceutical compositions, as the dietary fiber they provide can encourage digestive health, well-regulated gut flora, and other benefits to wellbeing. In this context, they may also function as an ingredient in a probiotic drink or other prebiotic or probiotic formulation.

Compositions or ingredients as described herein may be used to alter one or more properties of the finished product. Such properties include, but are not limited to, sweetness, texture, mouthfeel, binding, glazing, smoothness, moistness, viscosity, color, hygroscopicity, flavor, bulking, water-retention, caramelization, surface texture, crystallization, structural properties, and dissolution.

In some cases, the compositions and/or ingredients described herein may provide a property to a finished product which is comparable to or better than the same property as provided by a saccharide mixture comprising primarily monosaccharides and/or disaccharides. The control composition may be a saccharide used commonly in consumables, for instance, a monosaccharide composition such as glucose, fructose, etc., a disaccharide composition such as sucrose or an artificial sugar composition. The control composition may be table sugar, corn syrup, high-fructose corn syrup, or any other suitable composition. The term "comparable," as used herein, generally means that the two compositions may be up to 100%, up to 95%, up to 90%, or up to 80% identical. For instance, comparable can mean that the composition is up to 90% identical to the control composition.

In some cases, the compositions described herein may be used as sweetener compositions. Sweetener compositions may be used by themselves or as an ingredient in a finished product. The compositions described herein may provide about the same level of sweetness or greater sweetness than an identical amount of a control composition wherein the control composition comprises primarily monosaccharides and/or disaccharides. The compositions described herein may be used to replace the control composition as the sweetener in a finished product. In some cases, the sweetness of a composition may be 5%, 10%, 15%, 20%, 30%, 40%, 50%, 70%, 80%, 90%, or 100% more than an identical amount of the control composition.

The compositions described herein may provide a comparable flavor profile or better flavor profile than an identical amount of a control composition wherein the control composition comprises primarily monosaccharides and/or disaccharides. The compositions described herein may be used to replace the control composition as a flavor enhancer in a finished product. In some cases, the flavor of a composition may be 5%, 10%, 15%, 20%, 30%, 40%, 50%, 70%, 80%, 90%, or 100% more than an identical amount of the control composition.

The compositions described herein may provide a comparable texture profile or better texture profile than an identical amount of a control composition wherein the control composition comprises primarily monosaccharides and/or disaccharides. The compositions described herein may be used to replace the control composition as a texture enhancer in a finished product.

The compositions described herein may provide a comparable binding profile or better binding profile than an identical amount of a control composition wherein the control composition comprises primarily monosaccharides and/or disaccharides. The compositions described herein may be used to replace the control composition as a binding enhancer in a finished product.

The compositions described herein may provide a comparable glazing profile or better glazing profile than an identical amount of a control composition wherein the control composition comprises primarily monosaccharides and/or disaccharides. The compositions described herein may be used to replace the control composition as a glazing enhancer in a finished product.

The compositions described herein may provide a comparable moistness or better moistness than an identical amount of a control composition wherein the control composition comprises primarily monosaccharides and/or disaccharides. The compositions described herein may be used to replace the control composition to provide moistness in a finished product.

The compositions described herein may provide a comparable color profile or better color profile than an identical amount of a control composition wherein the control composition comprises primarily monosaccharides and/or disaccharides. The compositions described herein may be used to replace the control composition as a color enhancer in a finished product.

The compositions described herein may provide a comparable dissolution profile or better dissolution profile than an identical amount of a control composition wherein the control composition comprises primarily monosaccharides and/or disaccharides. The compositions described herein may be used to replace the control composition as a dissolution enhancer in a finished product. In some cases, the dissolution of a composition may be 5%, 10%, 15%, 20%, 30%, 40%, 50%, 70%, 80%, 90%, or 100% more than an identical amount of the control composition.

The compositions described herein may provide a comparable mouthfeel or better mouthfeel than an identical amount of a control composition wherein the control composition comprises primarily monosaccharides and/or disaccharides.

The compositions described herein may provide a comparable viscosity or better viscosity than an identical amount of a control composition wherein the control composition comprises primarily monosaccharides and/or disaccharides.

The compositions described herein may provide a comparable hygroscopicity or better hygroscopicity than an identical amount of a control composition wherein the control composition comprises primarily monosaccharides and/or disaccharides. In some cases, the hygroscopicity of a composition may be 5%, 10%, 15%, 20%, 30%, 40%, 50%, 70%, 80%, 90%, or 100% more than an identical amount of the control composition.

The compositions described herein may provide a comparable water-retention or better water-retention than an identical amount of a control composition wherein the control composition comprises primarily monosaccharides and/or disaccharides. In some cases, the water-retention of a composition may be 5%, 10%, 15%, 20%, 30%, 40%, 50%, 70%, 80%, 90%, or 100% more than an identical amount of the control composition.

The compositions described herein may provide a lower calorie composition than an identical amount of a control composition wherein the control composition comprises primarily monosaccharides and/or disaccharides. In some cases, the calorie count of a composition may be 5%, 10%, 15%, 20%, 30%, 40%, 50%, 70%, 80%, 90%, or 100% less than an identical amount of the control composition.

The compositions described herein may provide a lower glycemic index than an identical amount of a control composition wherein the control composition comprises primarily monosaccharides and/or disaccharides. In some cases, the glycemic index of a composition may be 5%, 10%, 15%, 20%, 30%, 40%, 50%, 70%, 80%, 90%, or 100% less than an identical amount of the control composition.

The compositions described herein may provide a comparable bulking or better bulking than an identical amount of a control composition wherein the control composition comprises primarily monosaccharides and/or disaccharides.

The compositions described herein may provide a comparable caramelization or better caramelization than an identical amount of a control composition wherein the control composition comprises primarily monosaccharides and/or disaccharides.

The compositions described herein may provide a comparable surface texture or better surface texture than an identical amount of a control composition wherein the control composition comprises primarily monosaccharides and/or disaccharides.

The compositions described herein may provide a comparable crystallization or better crystallization than an identical amount of a control composition wherein the control composition comprises primarily monosaccharides and/or disaccharides.

The compositions described herein may provide comparable structural properties as an identical amount of a control composition wherein the control composition comprises primarily monosaccharides and/or disaccharides.

The compositions described herein may provide less aftertaste compared to an identical amount of a control composition wherein the control composition comprises primarily monosaccharides and/or disaccharides.

Different compositions of oligosaccharides may have improved dissolution profiles, hygroscopicity profiles, and taste profiles compared to the oligosaccharides used alone.

The compositions or ingredients as described herein may be used to increase the fiber content of a finished product such as a foodstuff or a nutraceutical. The compositions may provide a higher level of fiber in the finished product as compared to an identical amount of a control composition wherein the control composition comprises primarily monosaccharides and/or disaccharides. In some cases, the compositions may improve the fiber content of the finished product without negatively, or substantially negatively, affecting any other properties such as taste, sweetness, mouthfeel, texture, binding, or any other properties described herein. In some cases, the fiber content of a composition may be 5%, 10%, 15%, 20%, 30%, 40%, 50%, 70%, 80%, 90%, or 100% more than an identical amount of the control composition.

Ingredients may be used to alter the properties of a finished product such as foodstuff or nutraceutical or cosmetic. In order to alter the properties of the finished products, the finished products may additionally comprise a polysaccharide, for example, a cellulosic polysaccharide, such as cellulose, or a polysaccharide derivative, for example, a cellulose derivative, such as carboxymethylcellulose, or a polysaccharide aggregate, for example, a portion of lignocellulosic biomass. In some instances, the finished products can comprise from greater than 0% to 40% by dry weight of polysaccharide, polysaccharide derivative, or polysaccharide aggregate, for example, from greater than 1% to 30% by dry weight of polysaccharide, polysaccharide derivative, or polysaccharide aggregate, for example, from greater than 5% to 25% by dry weight of polysaccharide, polysaccharide derivative, or polysaccharide aggregate, for example, from greater than 10% to 20% by dry weight of polysaccharide, polysaccharide derivative, or polysaccharide aggregate.

The concentration of a composition comprising polysaccharides and a mixture of oligosaccharides in a finished product may be anywhere from 0.1% to 40% w/w. The concentration of a composition comprising polysaccharides and a mixture of oligosaccharides in a finished product may be from about 0.1% to about 0.5%, about 0.1% to about 1%, about 0.1% to about 5%, about 0.1% to about 10%, about 0.1% to about 15%, about 0.1% to about 20%, about 0.1% to about 25%, about 0.1% to about 30%, about 0.1% to about 35%, about 0.1% to about 40%, about 0.5% to about 1%, about 0.5% to about 5%, about 0.5% to about 10%, about 0.5% to about 15%, about 0.5% to about 20%, about 0.5% to about 25%, about 0.5% to about 30%, about 0.5% to about 35%, about 0.5% to about 40%, about 1% to about 5%, about 1% to about 10%, about 1% to about 15%, about 1% to about 20%, about 1% to about 25%, about 1% to about 30%, about 1% to about 35%, about 1% to about 40%, about 5% to about 10%, about 5% to about 15%, about 5% to about 20%, about 5% to about 25%, about 5% to about 30%, about 5% to about 35%, about 5% to about 40%, about 10% to about 15%, about 10% to about 20%, about 10% to about 25%, about 10% to about 30%, about 10% to about 35%, about 10% to about 40%, about 15% to about 20%, about 15% to about 25%, about 15% to about 30%, about 15% to about 35%, about 15% to about 40%, about 20% to about 25%, about 20% to about 30%, about 20% to about 35%, about 20% to about 40%, about 25% to about 30%, about 25% to about 35%, about 25% to about 40%, about 30% to about 35%, about 30% to about 40%, or about 35% to about 40% w/w. The concentration of a composition comprising polysaccharides and a mixture of oligosaccharides in a finished product may be about 0.1%, about 0.5%, about 1%, about 5%, about 10%, about 15%, about 20%, about 25%, about 30%, about 35%, or about 40% w/w. The concentration of a composition comprising polysaccharides and a mixture of oligosaccharides in a finished product may be at least 0.1%, 0.5%, 1%, 5%, 10%, 15%, 20%, 25%, 30%, or 35% w/w. The concentration of a composition comprising polysaccharides and a mixture of oligosaccharides in a finished product may be at most 0.5%, 1%, 5%, 10%, 15%, 20%, 25%, 30%, 35%, or 40% w/w.

In cases, the oligosaccharide mixtures (e.g., cello-oligosaccharides and xylo-oligosaccharides) may form at least 20%, 30%, 40%, 50%, 60%, or 70% w/w of the consumable composition or ingredient. For example, 50% w/w of a combination of cello-oligosaccharides and xylo-oligosaccharides may form the consumable composition or ingredient.

In some instances, the ingredient may include a maize cob extract (MCE). The MCE may be a mixture of oligosaccharides composed primarily of arabinoxylo-oligosaccharides, xylo-oligosaccharides, cello-oligosaccharides, and cellulose. In certain instances, the oligosaccharides may be non-digestible or substantially non-digestible. The arabinoxylo-oligosaccharides can be oligomers with xylose backbones linked by $\beta$-(1→4)-bonds substituted with arabinose side-chains. The arabinoxylo-oligosaccharides may be non-digestible. The arabinoxylo-oligosaccharides can be produced by hydrolysis of arabinoxylan (polysaccharide of $\beta$-(1→4)-bonded xylose units substituted with arabinose side-chains). Furthermore, the arabinoxylo-oligosaccharides may have a degree of polymerization (DP) of 3 to 15.

In various instances, the xylo-oligosaccharides may be oligomers with xylose backbones linked by $\beta$-(1→4)-bonds. The xylo-oligosaccharides may be non-digestible. The xylo-oligosaccharides may be produced by hydrolysis of arabinoxylan. Moreover, the xylo-oligosaccharides may have a DP of 2 to 8.

In certain instances, the cello-oligosaccharides may be oligomers with glucose backbones linked by $\beta$-(1→4)-bonds. The cello-oligosaccharides may be non-digestible. The cello-oligosaccharides may be produced by hydrolysis of cellulose (polysaccharide of $\beta$-(1→4)-bonded glucose units). Furthermore, the cello-oligosaccharides may have a DP of 2 to 4, with the majority having a DP of 2.

IV. Exemplary Embodiments

Figure 8:
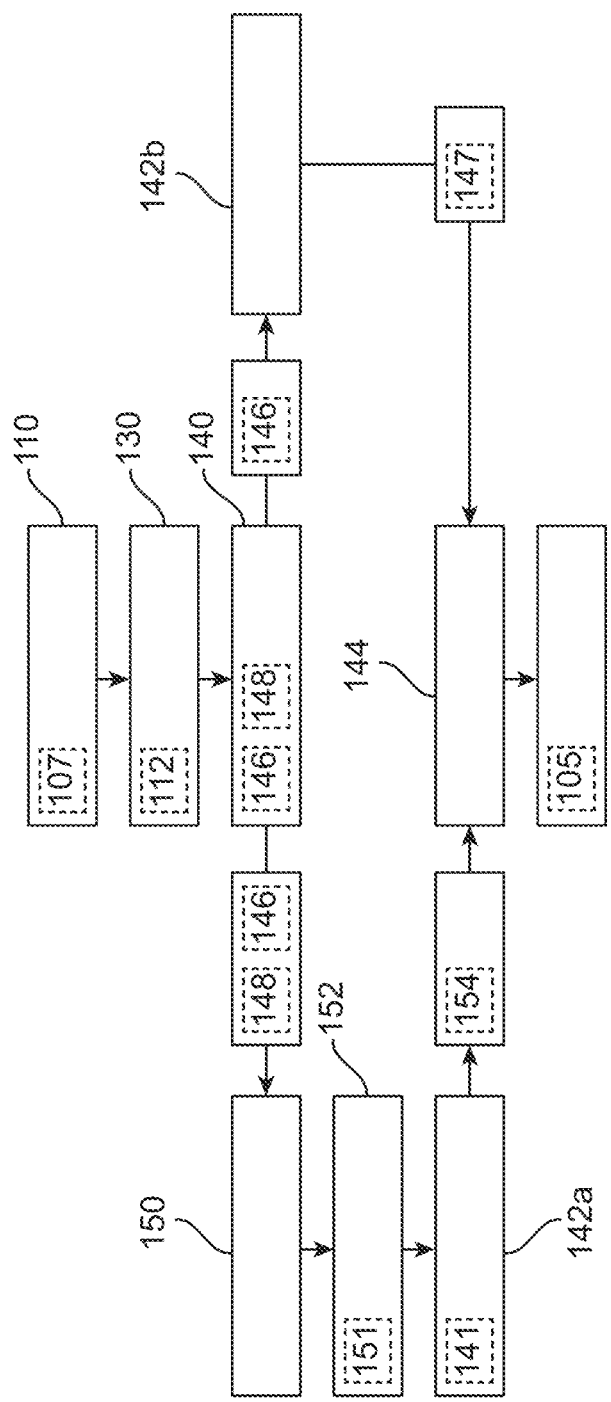
FIG. 8 is a simplified flow diagram depicting a method of treating biomass according to some embodiments of the present disclosure.

Exemplary Method of Extracting Soluble Polysaccharides for Subsequent Combination with Generated Oligosaccharides FIG. 8 is a simplified flow diagram showing an embodiment of a method of extracting soluble polysaccharides for subsequent combination with generated oligosaccharides to form an ingredient.

In the illustrated method, the extraction or removal of at least a portion of the soluble polysaccharides 140 before an enzyme treatment 150 can ensure that at least a portion of the soluble polysaccharides are retained or saved for combination 144 with the generated oligosaccharides to form the ingredient 105. In some other methods (not shown), the soluble polysaccharides can be digested by the one or more enzymes because the soluble polysaccharides are not extracted prior to the enzyme treatment. The ingredient 105 of the illustrated method can be a sweetener or sugar substitute that can remain substantially soluble or entirely soluble. Accordingly, the ingredient 105 can be delivered as a syrup-like product (e.g., a viscous liquid). In some cases, the ingredient 105 can be a replacement or partial replacement for corn syrup, high-fructose corn syrup, maple syrup, honey, treacle, golden syrup, molasses, dextrose syrup, fructose syrup, agave nectar, date syrup, brown rice syrup, coconut syrup, corn syrup or other suitable liquid sweeteners in a foodstuff.

As depicted, biomass 107 (e.g., corncob or any other suitable biomass) can be physically pretreated 110 (e.g., by chipping or any other suitable method of physically pretreating a biomass). The physically treated biomass 112 can then be subjected to or undergo a thermochemical pretreatment 130 (e.g., 15% w/v chipped corncob can be heated in 1% w/v NaOH for one hour). In some embodiments, the thermochemical pretreatment 130 can be followed by a neutralization step (not shown) before extraction of the soluble compounds or material 140 from the physically pretreated biomass 112. Extraction of the soluble compounds or material 140 can include removing a liquid portion (e.g., a supernatant) of the physically pretreated biomass 112. The liquid portion can include soluble compounds 146 from the physically pretreated biomass 112. The soluble compounds 146 can include soluble polysaccharides. In certain embodiments, 15% of the liquid portion (including the soluble compounds or material 146) can then be extracted or removed from the thermochemically pretreated biomass 112. The extracted portion including the soluble compounds or material 146 (e.g., the soluble polysaccharides) can then be subjected to one or more purification steps 142b (e.g., ultrafiltration) to enrich the soluble polysaccharides 147.

Furthermore, the liquid portion that is not extracted at step 140 can include soluble compounds or material 146 and insoluble compounds or material 148. For example, in the case where 15% of the liquid portion is extracted as described above, the remaining portion of the physically pretreated biomass 112 (including 85% of the liquid portion) can include soluble polysaccharides and insoluble polysaccharides. The solution including the soluble compounds or material 146 and insoluble compounds or material 148 can then be subjected to or undergo an enzyme treatment 150, as disclosed herein. For example, one or more polysaccharide-cleaving enzymes can be added to the solution including the soluble compounds or material 146 and insoluble compounds or material 148 to 0.5% w/v and incubated at 50° C. for 24 hours. The enzyme-treated biomass 151 can then be treated (e.g., filtered) 152 to remove at least a portion of the undigested biomass. In certain cases, the removed undigested biomass can be disposed of or rejected. The digested biomass 141 can then be subjected to or undergo purification 142a (e.g., ion-exchange chromatography, nanofiltration, microfiltration, ultrafiltration, or any other suitable method of purification) to enrich for oligosaccharides 154 as described herein. The extracted, isolated, and/or purified oligosaccharides 154 and the extracted, isolated, and/or purified soluble polysaccharides 147 can be combined, mixed, and or spray dried to form the ingredient 105.

Figure 9:
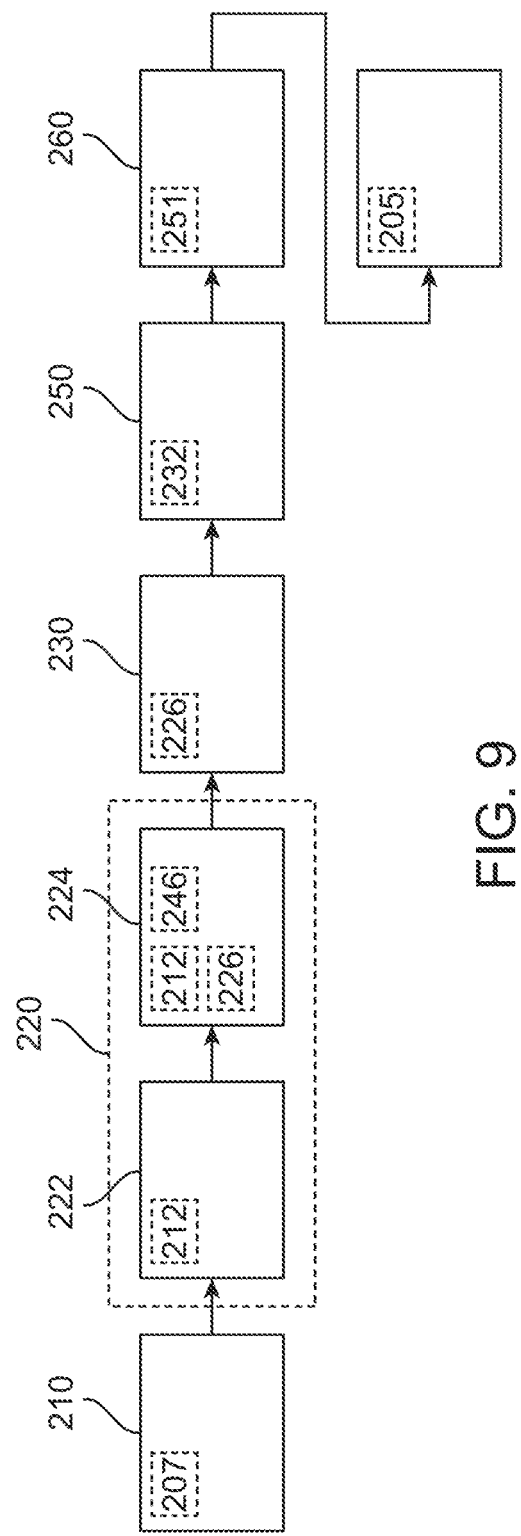
FIG. 9 is a simplified flow diagram depicting another method of treating biomass according to some embodiments of the present disclosure.

Exemplary Method of Pretreating Biomass to Remove Monosaccharides and/or Disaccharides FIG. 9 is a simplified flow diagram showing an embodiment of a method of pretreating biomass to remove monosaccharides and/or disaccharides prior to an enzyme treatment.

The embodiment of FIG. 9 may include components or steps that resemble the components or steps of the embodiment of FIG. 8 in some respects. For example, the embodiment of FIG. 9 includes the step of physically pretreatment 110 that may resemble the physical pretreatment 210 of FIG. 8. It will be appreciated that the illustrated embodiments may have analogous features. Accordingly, like features are designated with like reference numerals, with leading digits added to increment each reference numeral by 100. For instance, the physical pretreatment is designated "110" in FIG. 8 and an analogous physical pretreatment is designated as "210" in FIG. 9. Relevant disclosure set forth above regarding similarly identified features thus may not be repeated hereafter. Moreover, specific features of the method and related components or steps of FIG. 9 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the method and related components or steps of FIG. 9. Any suitable combination of the features, and variations of the same, described with respect to the method illustrated in FIG. 8, can be employed with the method and components or steps of FIG. 9, and vice versa. This pattern of disclosure applies equally to further embodiments depicted in subsequent figures and/or described hereafter.

As illustrated, a gentle pretreatment 220 (e.g., a washing or incubation cycle as provided herein) of a physically pretreated biomass 212 can include removing 224 the soluble compounds 246. In certain cases, the soluble compounds 246 can include monosaccharides and/or disaccharides. The removed soluble monosaccharides and/or disaccharides can then be discarding and/or rejected. Accordingly, the gentle pretreatment 220 can be conducted or performed to remove soluble monosaccharides and/or disaccharides from the biomass 207.

Biomass 207 can be physically pretreated 210 (e.g., chipped) and then the physically pretreated biomass 212 can be subjected to or undergo a gentle pretreatment 220, for example, washed or incubated (e.g., in water at 25° C. for 30 minutes). Soluble saccharides 246 (e.g., soluble monosaccharides and/or disaccharides) can then be removed from the solution including the gently pretreated biomass 226. The gently pretreated biomass 226 can then be subjected to or undergo a strong pretreatment 230. In certain cases, the strong pretreatment 230 can be a thermochemical pretreatment. For example, the gently pretreated biomass 226 can be treated in 1% w/v NaOH at 100° C. for 60 minutes. In some embodiments, the strong pretreatment 230 can be followed by a neutralization step (not shown) before the enzyme treatment 250. The strongly pretreated biomass 232 can then be treated with enzymes 250 as discussed herein. Furthermore, downstream processing 260 can then be conducted on the enzyme-treated biomass 251 to generate the ingredient 205.

Additional Exemplary Embodiments of Extracting Soluble Polysaccharides for Combination with Oligosaccharides In some instances, the disclosure relates to novel methods of treating plant biomass materials for the production of a foodstuff, cosmetic, or nutraceutical ingredient.

Sugary foods and drinks are an important part of culture and lifestyle habits across the world, but the sugar they contain has been linked to obesity, diabetes, poor dental health, and disruptive behavior in people. Because of this, consumer preferences have been shifting away from sugar-containing foods, and governments are increasingly implementing regulation to encourage the consumption of less sugar.

As such, industry has been searching for suitable low-calorie sweeteners for many decades to substitute for sugar in food and beverages. Unfortunately, many sugar substitutes are produced from non-natural resources, and often offer bitter undertones or other unpleasant tastes along with their sweetness, both of which consumers find unappealing. Moreover, while many sweeteners are able to mimic the sweetness of sugar in food and drinks, few are able to mimic the broad range of roles that sugar plays in food, such as adding bulk, modulating texture, providing structure, acting as a preservative, and modulating color and flavor through caramelization and Maillard reactions.

Dietary fiber is an important part of a positive diet, and helps maintain digestive health and a well-regulated gut flora. Such fiber comprises saccharides of varying chain lengths and types. In addition to being found naturally in a wide spectrum of foods, fiber can also be produced separately and added to other foods during their manufacture.

Biomass is a good source of saccharides that can be used to replace sugar and add fiber to food products. However, there remains a need to optimize the process by which these saccharides are obtained from the biomass and processed into the compositions useful as a foodstuff, cosmetic, or nutraceutical ingredient.

Firstly, the saccharides generally need to be produced by controlled breakdown. Different amounts of different sized saccharides in the ingredient can affect its nutritional values, and also other properties such as hygroscopicity which in turn affect properties such as the texture of the product the ingredient is used to make. It can also be desirable for the ingredient to comprise polysaccharide as polysaccharide can improve gastrointestinal tolerance. However, due to the speed at which some particularly desirable polysaccharides break down during the enzymatic reaction of previously known methods, it is difficult to isolate and then incorporate into the ingredient these desirable polysaccharides.

Furthermore, food products that require a smooth texture, such as candy, chocolate, and yoghurt, generally require the ingredient to be soluble to achieve the smooth texture. Ingredients comprising insoluble polymeric material can result in a gritty texture. However, due to the insolubility of certain polysaccharides, it can be difficult to make a composition comprising polysaccharides that is entirely soluble, particularly in a one-pot process from a single piece of biomass. Typically, soluble polysaccharides break down quicker than insoluble polysaccharides so after exposing a plant biomass to enzymes, like of previously known methods, the soluble polysaccharides are entirely broken down and only insoluble polysaccharides are left.

Surprisingly, methods have been identified here that can allow polysaccharides to be isolated and incorporated into a soluble foodstuff, cosmetic, or nutraceutical ingredient comprising oligosaccharides, which thus maintains the benefit of increasing the gastrointestinal tolerance of the ingredient as well as allowing it to be used in food products with a smooth texture. The polysaccharides can be isolated from the same plant biomass as that which the other desired saccharides are obtained from providing an efficient and stream-lined production process.

Accordingly, in a first aspect of the disclosure there is provided a method for producing a foodstuff, cosmetic, or nutraceutical ingredient comprising the steps of:
a) providing a plant biomass comprising one or more soluble polysaccharides and one or more insoluble polysaccharides;
b) treating the plant biomass to dissolve the one or more soluble polysaccharides;
c) removing a portion of the dissolved one or more soluble polysaccharides;
d) reacting the remaining plant biomass with one or more enzymes to form one or more oligosaccharides;
e) removing the one or more oligosaccharides; and
f) combining the portion of the dissolved one or more soluble polysaccharides from step (c) and the one or more oligosaccharides from step (e) to form the ingredient.

As such, there is also provided a foodstuff, cosmetic, or nutraceutical ingredient obtainable by the methods of the disclosure.

In another aspect of the disclosure there is provided a foodstuff, cosmetic, or nutraceutical liquid ingredient comprising at least one oligosaccharide selected from the list consisting of:
i) cello-oligosaccharide having a degree of polymerization of from two to six;
ii) xylo-oligosaccharide having a degree of polymerization of from two to twelve;
iii) manno-oligosaccharide having a degree of polymerization of from two to twelve;
iv) mixed-linkage glucan oligosaccharide having a degree of polymerization of from two to five;
v) xyloglucan oligosaccharide having a degree of polymerization of from four to twelve; and
vi) chito-oligosaccharide having a degree of polymerization of from two to twelve;
and at least one polysaccharide selected from the list consisting of:
i) xylan;
ii) mannan;
iii) cellulose derivative;
iv) mixed-linkage glucan;
v) xyloglucan; and
vi) chitosan;
wherein the liquid ingredient comprises at least 20% by dry weight of the at least one oligosaccharide and at least 2% by dry weight of the at least one polysaccharide and wherein the liquid ingredient has a viscosity of from 5 to 100,000 cps.

Preparing the foodstuff, cosmetic, or nutraceutical ingredient in the manner provided herein can allow efficient use of biomass by incorporating oligomeric and polymeric material from the same biomass source to make a soluble ingredient. Furthermore, the methods can allow for purification, derivatization, or other modification, as well as control of oligomeric and polymeric proportions, which can improve the functional properties, nutritional properties, and tolerance of the ingredient.

Any substance which comprises suitable polysaccharides may be the plant biomass. As the foodstuff, cosmetic, and nutraceutical industries use a broad variety of oligosaccharides, the polysaccharides suitable in the method are not particularly limited. Plant biomass suitable for producing the oligosaccharide profile of the current disclosure may comprise, for example, cellulose, lignocellulose, chitin, chitosan, xylan (such as glucuronoxylan, arabinoxylan, and glucuronoarabinoxylan), xyloglucan, mixed-linkage glucan, and/or mannan (such as glucomannan, galactomannan, or galactoglucomannan), however, any plant biomass which can be suitably acted upon is envisaged. The one or more soluble polysaccharides that the plant biomass comprises may include any one of the following: mannans, mixed-linkage glucans, lignocellulose, hemicellulose, certain cellulose derivatives such as cellulose acetate, hydroxyethylcellulose, and hydroxymethylcellulose, and chitosan. In some embodiments, the plant biomass comprises hemicellulose. In certain embodiments, the hemicellulose comprises xylan and/or mannan.

As such, the plant biomass may be grain, grain chaff, bean pods, seed coats, and/or other seed materials; seaweeds; corn stover, straw, bagasse, miscanthus, sorghum residue, switch grass, bamboo, and/or other monocotyledonous tissue; water hyacinth, leaf tissue, roots, and/or other vegetative matter; and/or any combination of suitable plant biomasses. In some cases, the plant biomass comprises, or suitably consists of, sugar cane biomass (such as sugar cane bagasse), corn biomass (such as corncob or corn stover), wheat biomass (such as wheat straw or wheat bran), hardwood or softwood. In certain cases, the plant biomass comprises corncob, sugar cane bagasse, wheat straw, or rice straw.

In various instances, in step (b) the "treating" is a thermochemical treatment of the plant biomass. "Thermochemical," as used herein, generally refers to heating above room temperature (room temperature can be about 20° C. to 22° C.) the plant biomass in a chemical substance, such as heating in a solution comprising water, alkali, or ionic solvents. The thermochemical step can physically and chemically modify chemical components of the plant biomass. For example, the free hydroxide ions from the water or alkali can disrupt hydrogen bonds between saccharides enabling the solubilization of some types of saccharides, for example, hemicelluloses, and can better enable the enzyme in the subsequent step to more easily break up the saccharides. These disrupted hydrogen bonds may be between monomers of the same saccharide chain which contribute to the chain's tertiary structure. The disrupted hydrogen bonds may also be between monomers of different saccharide chains which contribute to the quaternary structure of more than one chain. Subsequently, the treatment can result in the one or more polysaccharides that are soluble (i.e., the polysaccharides that are particularly susceptible to the disruption of the hydroxide ions, especially, for example, hemicelluloses) to be dissolved into the chemical substance used. The one or more polysaccharides that are insoluble, such as cellulose, do not dissolve into the chemical substance.

The heating of the treatment step (b) may be at a range of temperatures, suitably of from 30° C. to 180° C., 50° C. to 150° C., or from 70° C. to 120° C. Higher temperatures can help the soluble polysaccharides to dissolve quicker, however, temperatures that are too high can be more difficult to achieve in an efficient and cost-effective manner, and can chemically modify the biomass components, including the saccharides (e.g., in an undesirable manner).

The heating may occur for a range of time scales, particularly large amounts of biomass may be exposed to heating for a longer period of time, which can be adjusted accordingly. For example, the heating of the plant biomass can be of from 1 minute to 72 hours, 10 minutes to 24 hours, 20 minutes to 12 hours, or 25 minutes to 8 hours.

In some instances, the thermochemical treatment may comprise heating the plant biomass in water, i.e., at a neutral pH of about pH 7.

In certain instances, the thermochemical treatment may comprise heating the plant biomass in an alkali solution having a pH of from 8 to 14, 9 to 14, or 10 to 14. The solution may comprise, or suitably consist of, any one of the alkalis selected from: sodium hydroxide, potassium hydroxide, sodium carbonate, calcium carbonate, calcium hydroxide, ammonium sulfate, ammonium hydroxide, and aqueous ammonia. In various instances, the alkali may be sodium hydroxide. A combination of the listed alkalis is also envisaged.

Multiple different sequential thermochemical treatment steps are also envisaged. For example, there may be two sequential thermochemical treatments, there may be three sequential thermochemical treatments, or there may be four or more sequential thermochemical treatments. In some cases, the biomass may be thermochemically treated in a neutral aqueous solution and then thermochemically treated in an alkaline aqueous solution.

After the treating step, step (c) can comprise removing a portion of the dissolved one or more soluble polysaccharides. The purpose of this step can be to isolate and remove the soluble polysaccharides from the plant biomass so that they do not get broken down and therefore lost in the subsequent enzymatic reaction. This can enable the use of these polysaccharides when forming the ingredient in a later step. All of the dissolved polysaccharides or a portion of them may be removed dependent on the desired amount in the final ingredient. The soluble polysaccharides can be removed using simple steps such as filtering the chemical substance, of which the soluble polysaccharides are dissolved in.

Step d) comprises reacting the remaining plant biomass, which may be in the form of a solution and/or a suspension, with one or more enzymes to form the one or more oligosaccharides. The soluble and insoluble polysaccharides present in the remaining plant biomass solution and/or suspension can be partially or fully cleaved by the one or more enzymes into oligosaccharides (e.g., useful oligosaccharides), potentially leaving partially cleaved, or uncleaved, polysaccharides, which may include cellulose, xylan (such as glucuronoxylan, arabinoxylan, or glucuronoarabinoxylan), mannan (such as glucomannan, galactomannan, or galactoglucomannan), mixed-linkage glucan, xyloglucan, chitin, chitosan, or lignocellulose.

The enzyme reaction may take place in solution and/or suspension, in a suitable reaction vessel. The enzyme reaction may take place at a temperature or temperature protocol suitable for the particular combination of enzyme and plant biomass, the reaction may be allowed to progress for a certain amount of time, until the products have reached a desired concentration, or until some other requirement has been met.

In order to ensure optimal contact between the enzymes and the plant biomass, the reaction mixture may be agitated, either constantly or at intervals. The agitation may take the form of rhythmically moving the entire reaction vessel, of a fan or other stirring device, of a bubble sparging, or any other method of agitation.

The enzymatic reaction may be a microbial fermentation. The temperature and reaction time can be suitable for the growth of the microbial organism used. The microbial organism may be genetically altered to produce an enzyme suitable for the production of an oligosaccharide of the present disclosure. The microbe may be, for example, a bacterium, for example, *Escherichia coli*, or a fungus, such as *Saccharomyces cerevisiae, Aspergillus niger*, or *Trichoderma reesei*.

Further embodied in the present disclosure is an expression vector suitable for modifying the subject microorganism such that it produces an enzyme or mixture of enzymes of the current disclosure. Where desired, the expression vector, which may be a plasmid or any other nucleic acid able to induce production of the enzyme, may comprise one or more of the following regulatory sequences so as to control the expression of the exogenous enzyme: regulatory sequences of a heat shock gene, regulatory sequences of a toxicity gene, and regulatory sequences of a spore formation gene.

The enzymatic reaction can be carried out at a temperature or temperature protocol suitable to the enzymes and substrates used. For example, it may be carried out at a constant temperature in the range of from about 10° C. to about 100° C., about 20° C. to about 70° C., or about 30° C. to about 60° C. If the enzymatic reaction takes the form of a microbial fermentation the temperature may be suitable for such, for example, the enzymatic reaction may comprise the growth of *E. coli* and/or the temperature may be constant and about 37° C.

The pH of the solution or suspension may affect the activity of the enzymes. Control of pH may assure that an enzymatic reaction proceeds at a suitable rate. The enzymatic reaction of the present disclosure may take place at a pH in the range of from about 2 to about 10, about 3 to about 8, or about 4 to about 6.

The enzymatic reaction can be allowed to continue for a certain time period before being quenched, and the products isolated or otherwise collected. This time period may be from about 1 minute to about 6 days, from about 0.5 days to about 5 days, or from about 16 hours to about 96 hours. The reaction may alternatively be allowed to proceed until no further catalysis occurs.

The enzymatic reaction can be allowed to continue to run until there is less than 75% undigested polysaccharide-containing plant biomasses remaining, less than 70%, less than 65%, less than 55%, or less than 50%. This can be monitored or checked by reducing end assays, such as the anthrone assay and/or by chromatographic methods such as thin-layer chromatography and high-performance anion exchange chromatography. The reaction may run until all polysaccharides are converted to oligosaccharides.

There are many enzymes that are suitable for use in the enzymatic reaction of the present method. For example, "lytic polysaccharide monooxygenase" and "LPMO," which are a class of enzymes able to oxidatively cleave polysaccharides using a copper comprising moiety and using an oxygen source, such as a molecule of dioxygen, peroxide, or any other oxygen source; and a suitable reducing agent. As such, when an LPMO is used, the enzymatic reaction may be carried out under aerobic conditions. Suitable reducing agents are not particularly limited, but examples include ascorbic acid, gallic acid, cysteine, NADH, NADPH, pyrogallol, dithiothreitol, cyanoborohydrides, borohydrides, photosynthetic pigments, lignin, lignols, and a combination of cellobiose and cellobiose dehydrogenase. A wide variety of photosynthetic pigments may be used. In some embodiments, thylakoids and purified fractions, or chlorophyllin may be used, and light may be supplied. LPMOs can be selected from the following families: AA9, AA10, AA11, AA13, AA14, and AA15. In various cases, the LPMO may be PaLPMO9E (SEQ ID NO:1), an AA9 LPMO originally isolated from the ascomycete fungus Podospora anserina or the LPMO may be an AA9 LPMO from Trichoderma reesei (SEQ ID NO:23).

Aerobic conditions may comprise the addition of oxygen, which may be provided by aeration of the substrate mixture with an oxygen-comprising gas, such as air. Aeration may be conducted by the introduction of oxygen-comprising air bubbles into the aqueous substrate mixtures by various systems, such as an air-injector, an aeration frit, a membrane system, or an internal-loop airlift reactor. The concentration of molecular oxygen in the enzymatic reaction may be from about 4 mg/L to about 14 mg/L.

Another type of enzyme that can be used in the method is a "cellulase," which has hydrolytic activity against cellulose, for example, endo-1,4-beta-glucanase, cellobiohydrolase, and/or beta-glucosidase activities. Such enzymes are able to cleave glycosidic bonds in one or more forms of cellulose, including cellulose found in plant biomass. In doing so, they produce products including glucose and cello-oligosaccharides. In certain cases, the beta-glucanases may include enzymes from GH5, GH7, and GH12 enzyme, such as those derived from Aspergillus niger (SEQ ID NO:12, 13 and 14) and Trichoderma reesei (SEQ ID NOs:24 and 25).

Another type of enzyme is "cellobiohydrolase," which has hydrolytic activity against cellulose and produces mainly cellobiose as a product. Cellobiose is a disaccharide and is a cello-oligosaccharide. Such enzymes are able to cleave glycosidic bonds in one or more forms of cellulose, including cellulose found in plant biomass. In various instances, cellobiohydrolases may be from GH6 and GH7 enzyme families, Cel6A or Cel7A enzymes derived from Trichoderma reesei (SEQ ID NOs:10 and 11, respectively).

Another type of enzyme is "beta-glucosidase," which has hydrolytic activity against cellulose and produces mainly glucose as a product. Such enzymes are able to cleave glycosidic bonds in one or more forms of cellulose, including cellulose found in plant biomass. In some embodiments, beta-glucosidases may include GH3 beta-glucosidases, such as one from Trichoderma reesei (SEQ ID NO: 22).

Another type of enzyme is a lichenase, which may be selected from: the GH5, GH7, GH8, GH9, GH12, GH16, GH17, or GH26 families. In some embodiments, the lichenase may be a GH16 enzyme, for example, a GH16 enzyme derived from Bacillus subtilis (SEQ ID NO:2). The enzyme is able to act on, for example, mixed-linkage glucans, which are glucans comprising a mixture of β-1,3 and β-1,4 linkages, and may cleave them at β-1,4 glycosidic bonds. In the case in which the lichenase acts on a mixed-linkage glucan, the β-glucans produced may fall largely within the size range of from about 3 to about 7 residues, so they are particularly useful in the food, cosmetics, and nutraceutical industries. Mixed-linkage glucans are abundant in members of the grass and horsetail families, and as such, grass-based biomasses such as straw have high levels of mixed-linkage glucans, and may be acted upon usefully with lichenases.

Another type of enzyme is a xylanase, which may act on, for example, plant biomass comprising a xylan backbone. The xylanase may be, for example, a glucuronoxylanase, an arabinoxylanase, or a glucuronoarabinoxylanase. The enzyme may be active on a variety of polymers having a xylan backbone, such as glucuronoxylan, arabinoxylan, and glucuronoarabinoxylan. These polymers are abundant in various plant biomass, for example, both hardwood and softwood may comprise suitable polysaccharides, with hardwood often comprising glucuronoxylan and softwood often arabinoglucuronoxylan. In some instances, xylanases may include GH5 xylanases from Ruminiclostridium thermocellum (SEQ ID NO:3) and Gonapodya prolifera (SEQ ID NO:4), and GH30 xylanases from Dickeya chrysanthemi (SEQ ID NO:5), Bacillus subtilis (SEQ ID NO:6), Bacteroides ovatus (SEQ ID NO:7), and Trichoderma reesei (SEQ ID NO: 15).

Other enzymes useful in the disclosure may include xyloglucanases and xyloglucan endoglucanases (XEGs), which are produced by numerous organisms, including plant-pathogenic microbes. They are able to act on xyloglucan, a hemicellulosic β-1,4 glucan chain abundant in the primary cell wall of higher plants, which is decorated with xylose, some of the xylose residues being further decorated with other residues, such as galactose. When suitable xyloglucanases or XEGs act on xyloglucan, the products comprise xyloglucan oligosaccharides having a main chain of a length useful in the foodstuff, cosmetics, and nutraceutical industries. In some cases, xyloglucanases may include a GH5 xyloglucanase from Bacteroides ovatus (SEQ ID NO:8) and a GH74 xyloglucanase from Trichoderma reesei.

As any given natural plant biomass is likely to comprise a mixture of different polysaccharides, sometimes it may be the case that a mixture of different enzymes is beneficial. Such a mixture may comprise one or more of any other enzyme. For example, such a mixture might comprise an LPMO with an endo-glucanase, a xylanase with a lichenase, a cellobiohydrolase with a mannanase, or an endo-glucanase with a cellobiohydrolase in which the enzyme partners are present in molar ratios, for example, from 1:100 to 100:1.

In certain cases, the one or more enzymes may be a cocktail of different enzymes, for example, a crude or semi-crude enzyme preparation. The term "crude enzyme preparation" as used herein generally refers to a soluble preparation extracted from a microbial fermentation that has undergone minimal processing after the extraction, for example, typically the preparation may only undergo filtration in order to remove insoluble components. The term "semi-crude enzyme preparation" as used herein generally refers to a soluble preparation extracted from a microbial fermentation that has undergone some processing after the extraction, for example, the preparation may undergo filtration in order to remove insoluble components, increasing the enzyme concentration and/or nanofiltration to remove small molecular weight compounds.

In certain cases, the crude or semi-crude enzyme preparation may be from a bacteria or a fungus. In some embodiments, the crude or semi-crude enzyme preparation may be from a fungus, such as a filamentous cellulolytic fungus, such as from *Trichoderma* or *Aspergillus* species. In certain embodiments, the enzyme may be a crude or semi-crude enzyme preparation from a *Trichoderma reesei* strain.

In step (e), the one or more oligosaccharides formed in step (d) are removed, which may be done in a number of ways. They may be isolated based on solubility, so that a composition of soluble saccharides only is extracted for further processing, and/or isolated chromatographically to produce a composition with a narrower band of oligosaccharide chain lengths. Isolation may, for example, be based on precipitation, size-exclusion chromatography, ion-exchange chromatography, filtration, ultrafiltration, microfiltration, or nanofiltration. In the case that isolation based on solubility is carried out, the profile of saccharides present in the isolated composition may depend on the original enzymatic reaction, as different saccharides decrease in solubility with length at different rates.

Also envisaged in the scope of the present disclosure is the further treatment of all or part of the removed one or more oligosaccharides to produce further products before combining them with the one or more dissolved polysaccharides to form the ingredient. This further treatment may comprise any chemical, physical, or enzymatic step, such as reduction, for example, reductive amination where suitable; oxidation, caramelization, modification with a Schiff base, or via the Maillard reaction, or by any combination of such steps, and may provide different products having properties which are improved for the desired purpose. For example, the caramelization properties, calorific value, flavor, and color may be modified. The oligosaccharides may also be purified, for example, through precipitation, size-exclusion chromatography, ion-exchange chromatography, filtration, ultrafiltration, microfiltration, or nanofiltration.

Also envisaged in the scope of the disclosure is the further treatment of all or part of the dissolved one or more soluble polysaccharides to produce products with improved properties before combining with the one or more removed oligosaccharides to form the ingredient. This further treatment may comprise any chemical, physical, or enzymatic step, such as alkylation or acid-treatment. The polysaccharides may also be purified, for example, through precipitation, size-exclusion chromatography, ion-exchange chromatography, filtration, ultrafiltration, microfiltration, or nanofiltration.

In certain cases, following modification and/or purification of the oligosaccharides and polysaccharides, all or part of them are then combined, as in step (f), which may be at a ratio of from 1:100 to 1:1 polysaccharide:oligosaccharide, from 1:10 to 1:1, from 1:90 to 1:2, from 1:80 to 1:3, from 1:70 to 1:4, or from 1:60 to 1:5. The specific ratio can depend on the desired properties of the final ingredient as well as the modifications and purifications that have been applied to the saccharides. In certain embodiments, it is not required to recombine all of the removed oligosaccharides and polysaccharides.

In step (f) the combining can be done in a variety of ways, for example, by mixing a solution comprising all or part of the one or more soluble polysaccharides and a solution and/or suspension comprising all or part of the one or more removed oligosaccharides, which may further be spray-dried, lyophilized, or condensed in some other way. The soluble polysaccharides and the removed oligosaccharides may also be combined by mixing a dry form comprising all or part of the one or more removed oligosaccharides produced by spray-drying, lyophilization, or condensation in some other way after removing them in step (e), with a dry form comprising all or part of the one or more soluble polysaccharides, produced by spray-drying, lyophilization, or condensation in some other way after removing them in step (c). Alternatively, one of (i) the one or more soluble polysaccharides or (ii) the removed oligosaccharides may be in dry form and the other in solution when they are combined.

When the ingredient is in a dry form, the method may further comprise a step (g) of mixing and dissolving the ingredient in a liquid to form a liquid ingredient. In various cases, the liquid may be an aqueous solution, such as water.

The ingredient formed in step (f), and the liquid ingredient formed in step (g) and of the second aspect of the disclosure, may comprise various oligosaccharides and at varying amounts depending on the desired properties. In some cases, the ingredient and liquid ingredient may comprise at least 20% by dry weight or at least 30% by dry weight cello-oligosaccharides having a degree of polymerization of from two to six, the ingredient may comprise at least 20% by dry weight or at least 30% by dry weight xylo-oligosaccharides having a degree of polymerization of from two to twelve, the ingredient may comprise at least 20% by dry weight or at least 30% by dry weight mixed-linkage glucan oligosaccharides having a degree of polymerization of from two to five, the ingredient may comprise at least 20% by dry weight or at least 30% by dry weight manno-oligosaccharides having a degree of polymerization of from two to twelve, the ingredient may comprise at least 20% by dry weight or at least 30% by dry weight xyloglucan oligosaccharides having a degree of polymerization of from four to twelve, and/or the ingredient may comprise at least 20% by dry weight or at least 30% by dry weight chito-oligosaccharides having a degree of polymerization of from two to twelve. In some instances, the ingredient can comprise a maximum of 100% by dry weight of the above oligosaccharides and the polysaccharides described herein, therefore the above embodiments, wherein the oligosaccharides are present in at least 20% by dry weight, does not comprise five or six types of oligosaccharides.

The ingredient and liquid ingredient may comprise at least 50%, 60%, 70%, 80%, 90%, 95%, 99%, or 99.5% by dry weight of saccharide present. The ingredient and liquid ingredient may consist essentially of saccharides. For example, the ingredient may have less than 0.5% by dry weight or less than 0.3% by dry weight, for instance, 0.1% by dry weight, of other substances.

In certain cases, the liquid ingredient can have a viscosity of from 5 to 100,000 cps, from 10 to 80,000 cps, from 20 to 60,000 cps, from 30 to 40,000 cps, from 40 to 20,000 cps, or from 50 to 10,000 cps. When the liquid ingredient is to be included into beverages, low syrup viscosities may be desirable, such as about 20 to 300 cps, 50 to 200 cps, or 100 to 150 cps. Higher viscosity values may be desired in applications such as chocolate making, thus where the liquid ingredient is desired to be in a syrup it may have a viscosity in the range of about 8,000 to 100,000, about 10,000 to 50,000 cps, or about 15,000 to 25,000 cps. The viscosity values are in accordance with testing using a Brookfield HDB VE roto-viscometer using standard testing procedures, wherein a 400 mL sample was taken in a tall-form beaker to ensure that no container effects occur. The instrument is operated as per the manufacturer's instructions with respect to ranges (rotoviscometry using spindle code 61, spindle speed 100 rpm, and at 22° C.).

In some instances, the liquid ingredient can have a flow rate of 100 to 350 seconds, 150 to 300 seconds, or 200 to 250 seconds. "Flow rate," as used herein, generally refers to the volume of fluid which passes per unit time. The flow rate values specified herein, unless indicated otherwise, are determined by measuring by timing the flow rate of 5 mL of the liquid ingredient from a vertically stood syringe (BD Plastipak 300613) filled with 20 mL of test liquid under gravity at room temperature.

In various cases, the liquid ingredient may have a concentration of oligo-saccharides of from 1 to 200% w/v, 10 to 150% w/v, 20 to 140% w/v, 30 to 130% w/v, 40 to 120% w/v, 50 to 115% w/v, or 60 to 110% w/v.

In some cases, the liquid ingredient may have a concentration of polysaccharides of from 0.1 to 50% w/v, 0.2 to 40% w/v, 0.3 to 30% w/v, 0.5 to 20% w/v, or 1 to 20% w/v.

In certain cases, the liquid ingredient may have a concentration of the total of oligosaccharides and polysaccharides of from 1 to 200% w/v, 10 to 160% w/v, 20 to 150% w/v, 30 to 140% w/v, 40 to 130% w/v, 50 to 120% w/v, or 60 to 110% w/v. In various cases, the higher the concentration of the oligosaccharides and polysaccharides in the liquid, the thicker and more viscous the liquid may become. The liquid ingredient may be a homogeneous solution.

In another aspect, the ingredient and liquid ingredient may comprise at least two of the oligosaccharides. The amounts of each of the oligosaccharides may be varied depending on the desired properties of the resulting foodstuff, cosmetic, or nutraceutical. The two oligosaccharides may be present in a ratio of 1:9 to 9:1 or 1:2 to 2:1. Further, the ingredient and liquid ingredient may comprise three of the oligosaccharides, they may comprise four oligosaccharides, they may comprise five oligosaccharides, or they may comprise six oligosaccharides.

The ingredient and liquid ingredient can comprise the cello-oligosaccharides, for example, cello-oligosaccharides in combination with the xylo-oligosaccharides. Alternatively, the ingredient and liquid ingredient can comprise the cello-oligosaccharides in combination with the manno-oligosaccharides.

The one or more soluble polysaccharides in the ingredient may be particularly soluble in water or alkali. For example, soluble polysaccharides used in the disclosure can include hemicelluloses such as xylans, mannans, mixed-linkage glucans, and certain cellulose derivatives such as cellulose acetate, hydroxyethylcellulose, and hydroxymethylcellulose, and chitosan. In some embodiments, the one or more soluble polysaccharides can comprise hemicellulose. In certain embodiments, the hemicellulose can comprise xylan and/or mannan.

In some instances, the ingredient and liquid ingredient can comprise at least 2% by dry weight or at least 3% by dry weight of xylan. In various instances, the ingredient and liquid ingredient can comprise at least 2% by dry weight or at least 3% by dry weight of mannan. In certain instances, the ingredient and liquid ingredient can comprise at least 2% by dry weight or at least 3% by dry weight of cellulose derivative. In some cases, the ingredient and liquid ingredient can comprise at least 2% by dry weight or at least 3% by dry weight of mixed-linkage glucan. In various cases, the ingredient and liquid ingredient can comprise at least 2% by dry weight or at least 3% by dry weight of xyloglucan. In certain cases, the ingredient and liquid ingredient can comprise at least 2% by dry weight or at least 3% by dry weight of chitosan.

In certain cases, the ingredient and liquid ingredient can comprise of from 2 to 40% by dry weight of the one or more soluble polysaccharides, which includes polysaccharide derivatives, from 3 to 30% by dry weight of the one or more soluble polysaccharides, from 5 to 25% by dry weight of the one or more soluble polysaccharides, or from 8 to 20% by dry weight of the one or more soluble polysaccharides.

In some cases, the ingredient and liquid ingredient the ratio of polysaccharide:oligosaccharide is from 1:100 to 1:1, from 1:10 to 1:1, from 1:90 to 1:2, from 1:80 to 1:3, from 1:70 to 1:4, or from 1:60 to 1:5.

The produced ingredient and liquid ingredient may be useful in applications in which oligosaccharides, sugar, bulking sweeteners, low-intensity sweeteners, or other related food ingredients are conventionally used. For example, as sweeteners, bulking agents, added dietary fiber, or humectants. Of particular note is the use of reducing cane sugar in food products. It may be incorporated into cakes, bread, or other baked goods; chocolate or other confectionery such as toffee, fudge, meringue, jam, jelly or caramel; or drinks, for example, to provide favorable taste or color characteristics or to increase dietary fiber content. Or the ingredient may be incorporated into animal feed, for example, either as an isolated ingredient or by utilizing the enzymatic reaction mixture directly as feed.

Compositions or ingredients as described herein may be used to alter one or more properties of a finished product. Such properties include, but are not limited to, sweetness, texture, mouthfeel, binding, glazing, smoothness, moistness, viscosity, color, hygroscopicity, flavor, bulking, water-retention, caramelization, surface texture, crystallization, structural properties, reduced calories, reduced glycemic index, reduced glycemic load, increased fiber, reduced sugar, and dissolution. These may be improvements over what is currently possible with saccharides of different types, sugar substitutes, and/or other such compounds.

In the cosmetics industry, the ingredient may improve texture and moisture retention, act as UV-absorbing molecules, maintain a gel or cream structure, and/or serve as bulking agents. Furthermore, the ingredient and liquid ingredient may be useful in nutraceutical compositions, as the dietary fiber it provides has been shown to encourage digestive health, well-regulated gut flora, and other benefits to wellbeing. In this context the ingredients provided herein may also function as an ingredient in a probiotic drink or other prebiotic or probiotic formulation.

The detailed description is further supplemented with reference to the following numbered embodiments. 1) A method for producing a foodstuff, cosmetic, or a nutraceutical ingredient comprising one or more oligosaccharides and one or more soluble polysaccharides comprising the steps of: (a) providing a plant biomass comprising one or more soluble polysaccharides and one or more insoluble polysaccharides; (b) treating the plant biomass to dissolve the one or more soluble polysaccharides; (c) removing a portion of the dissolved one or more soluble polysaccharides; (d) reacting the remaining plant biomass with one or more enzymes to form one or more oligosaccharides; (e) removing the one or more oligosaccharides; and (f) combining the portion of the dissolved one or more soluble polysaccharides from step (c) and the one or more oligosaccharides from step (e) to form the ingredient. 2) The method according to numbered embodiment 1, wherein the treating in step (b) is thermochemical treatment. 3) The method according to numbered embodiment 2, wherein the thermochemical treatment is hot water treatment or hot alkali treatment. 4) The method according to numbered embodiment 3, wherein the alkali treatment uses an alkali with a pH of from 10 to 14.5) The method according to either numbered embodiment 3 or 4, wherein the alkali treatment uses sodium hydroxide, potassium hydroxide, sodium carbonate, calcium carbonate, calcium hydroxide, ammonium sulfate, ammonium hydroxide, and aqueous ammonia. 6) The method according to any preceding numbered embodiment, wherein the treating in step (b) occurs at a temperature of from 30 to 180° C. 7) The method according to any preceding numbered embodiment, wherein the treating in step (b) occurs for 10 minutes to 24 hours. 8) The method of any preceding numbered embodiment, wherein after the removing of the one or more oligosaccharides, the one or more oligosaccharides and/or dissolved one or more soluble polysaccharides undergo chemical, physical, or enzymatic treatment, such as reduction, oxidation, caramelization, or Maillard reaction. 9) The method of any preceding numbered embodiment, wherein the dissolved one or more soluble polysaccharides and/or the one or more oligosaccharides are dried before being combined together in step (f). 10) The method according to numbered embodiment 9, wherein the method further comprises a step: (g) mixing and dissolving the ingredient in a liquid to form a liquid ingredient, wherein the liquid ingredient has a viscosity of from 5 to 100,000 cps. 11) The method according to numbered embodiment 10, wherein the concentration of the oligosaccharides and polysaccharides in the liquid ingredient is of from 1 to 200% w/v. 12) The method according to any preceding numbered embodiment, wherein the one or more soluble polysaccharides comprise at least one selected from the group consisting of: mannans, mixed-linkage glucans, lignocellulose, hemicellulose, certain cellulose derivatives such as cellulose acetate, hydroxyethylcellulose and hydroxymethylcellulose, and chitosan. 13) The method according to numbered embodiment 12, wherein the hemicellulose comprises a xylan and/or a mannan. 14) The method according to any preceding numbered embodiment, wherein the plant biomass comprises a sugar cane biomass, a corn biomass, a wheat biomass, a hardwood, or a softwood. 15) A foodstuff, cosmetic, or a nutraceutical ingredient obtainable by the method of any preceding numbered embodiment. 16) A foodstuff, cosmetic, or nutraceutical liquid ingredient comprising at least one oligosaccharide selected from the list consisting of: i) cello-oligosaccharide having a degree of polymerization of from two to six; ii) xylo-oligosaccharide having a degree of polymerization of from two to twelve; iii) manno-oligosaccharide having a degree of polymerization of from two to twelve; iv) mixed-linkage glucan oligosaccharide having a degree of polymerization of from two to five; v) xyloglucan oligosaccharide having a degree of polymerization of from four to twelve; and vi) chito-oligosaccharide having a degree of polymerization of from two to twelve; and at least one polysaccharide selected from the list consisting of: i) xylan; ii) mannan; iii) cellulose derivative; iv) mixed-linkage glucan; v) xyloglucan; and vi) chitosan; wherein the liquid ingredient comprises at least 20% by dry weight of the at least one oligosaccharide and at least 2% by dry weight of the at least one polysaccharide, and wherein the liquid ingredient has a viscosity of from 5 to 100,000 cps, 8,000 to 100,000 cps, 10,000 to 50,000 cps, or 15,000 to 25,000 cps. 17) The liquid ingredient of numbered embodiment 16, wherein the liquid ingredient comprises at least two of the oligosaccharides listed in (i) to (vi). 18) The liquid ingredient of either numbered embodiment 16 or numbered embodiment 17, wherein the liquid ingredient comprises at least 20% by dry weight of the cello-oligosaccharides having a degree of polymerization of from two to six. 19) The liquid ingredient of any one of numbered embodiments 16 to 18, wherein the liquid ingredient comprises at least 20% by dry weight of the xylo-oligosaccharide having a degree of polymerization of from two to twelve. 20) The liquid ingredient of any one of numbered embodiments 16 to 19, wherein the liquid ingredient comprises at least 20% by dry weight of the manno-oligosaccharide having a degree of polymerization of from two to twelve. 21) The liquid ingredient of any one of numbered embodiments 16 to 20, wherein the liquid ingredient comprises at least 2% by dry weight of the xylan. 22) The liquid ingredient of any one of numbered embodiments 16 to 21, wherein the liquid ingredient comprises at least 2% by dry weight of the mannan. 23) The liquid ingredient of any one of numbered embodiments 16 to 22, wherein the liquid ingredient comprises at least 2% by dry weight of the cellulose derivative. 24) The liquid ingredient of any one of numbered embodiments 16 to 23, wherein the liquid ingredient has a concentration of polysaccharides of from 0.1 to 50% (w/v). 25) The liquid ingredient of any one of numbered embodiments 16 to 24, wherein the liquid ingredient has a concentration of oligosaccharides of from 1 to 200% (w/v). 26) The liquid ingredient of any one of numbered embodiments 16 to 25, wherein the liquid ingredient has a concentration of polysaccharides and oligosaccharides of from 1 to 200% (w/v). 27) The liquid ingredient of any one of numbered embodiments 16 to 26, wherein the liquid ingredient comprises an amount of polysaccharide and oligosaccharide in a ratio from 1:100 to 1:1.28) The liquid ingredient of any one of numbered embodiments 16 to 27, wherein the liquid ingredient comprises two oligosaccharides in a ratio from 1:9 to 9:1 in relation to each other. 29) Use of the liquid ingredient of any of numbered embodiments 16 to 28 in a foodstuff, cosmetic, or nutraceutical product.

Additional Exemplary Embodiments of Pretreating Biomass to Remove Monosaccharides and/or Disaccharides In some cases, the present disclosure relates to novel methods of physically and thermochemically treating plant biomass materials for the production of foodstuff, cosmetic, or nutraceutical ingredients.

Sugary foods and drinks are an important part of culture and lifestyle habits across the world, but the sugar they contain has been linked to obesity, diabetes, poor dental health, and disruptive behavior in people. Because of this, consumer preferences have been shifting away from sugar-containing foods, and governments are increasingly implementing regulation to encourage the consumption of less sugar.

As such, industry has been searching for suitable low-calorie sweeteners for many decades to substitute for sugar in food and beverages. Unfortunately, many sugar substitutes are produced from non-natural resources, and often offer bitter undertones or other unpleasant tastes along with their sweetness, both of which consumers find unappealing. Moreover, while many sweeteners are able to mimic the sweetness of sugar in food and drinks, few are able to mimic the broad range of roles that sugar plays in food, such as adding bulk, modulating texture, providing structure, acting as a preservative, and modulating color and flavor through caramelization and Maillard reactions.

Dietary fiber is an important part of a positive diet and helps maintain digestive health and a well-regulated gut flora. Such fiber comprises saccharides of varying chain lengths and types. In addition to being found naturally in a wide spectrum of foods, fiber can also be produced separately and added to other foods during their manufacture.

Biomass is a good source of saccharides that can be used to replace sugar and add fiber to food products. Compositions made from feedstocks have been provided. However, there remains a need to optimize the process by which these saccharides are obtained from the biomass and processed into the compositions useful as a foodstuff, cosmetic, or nutraceutical ingredient on a large and commercial scale. Enzyme breakdown of a large amount of plant biomass can take a considerable amount of time. Furthermore, the saccharides generally need to be produced by controlled breakdown. Enzyme breakdown can be desirable for this as product sizes can be exquisitely controlled, ensuring no and/or little monosaccharides are yielded.

Methods, as provided herein, can economically and efficiently enable the production of a foodstuff, cosmetic, or nutraceutical ingredient from a plant biomass starting material which is quicker than previously used methods, yields a purer final product, and can be used on a large and commercial scale. The method can do so by performing a prewashing step to remove from biomass endogenous monosaccharides and/or disaccharides, and employing thermochemical pretreatment steps that may ensure controlled breakdown and release of the saccharides that can be needed to manufacture the ingredient. Together, these steps may ensure that no and/or little monosaccharides are yielded during pre-enzyme processing. This can maximize efficiency and limit the amount of post-reaction purification needed.

Accordingly, in another aspect of the disclosure there is provided a method for producing a foodstuff, cosmetic, or nutraceutical ingredient, the ingredient comprising one or more oligosaccharides, wherein the method comprises the steps of:
 a) a physical pretreatment of a plant biomass comprising monosaccharides and/or disaccharides;
 b) a washing cycle (also referred to herein as an incubation cycle) comprising the steps of
  (i) washing (e.g., incubating) the plant biomass to solubilize at least a portion of the monosaccharides and/or disaccharides and (ii) removing the at least a portion of monosaccharides and/or disaccharides;
 c) a thermochemical pretreatment of the plant biomass;
 d) forming the one or more oligosaccharides by an enzymatic reaction, the enzymatic reaction comprising the step of contacting, in a solution or suspension, one or more polysaccharide-cleaving enzymes and the plant biomass;
 e) separating (also referred to herein as enriching for or isolating) the one or more oligosaccharides from the enzymatic reaction mixture and using the one or more oligosaccharides to form the ingredient.

Preparing the foodstuff, cosmetic, or nutraceutical ingredient in the manner provided herein can allow for: efficient use of biomass by incorporating oligomeric and polymeric material from the same biomass source, purification, derivatization or other modification, as well as control of oligomeric and polymeric proportions, which can improve the functional properties, nutritional properties, and tolerance of the ingredient.

Steps (a), (b), and (c) of the method of the disclosure are all "pretreatment" steps which are performed on the plant biomass starting material. "Pretreatment," as used herein, generally refers to steps that are performed on the plant biomass before a polysaccharide-cleaving enzyme is put into contact with the plant biomass.

Step (a) is a physical pretreatment of the plant biomass, which can have the purpose of physically breaking down the plant biomass in preparation for the subsequent steps. The physical step may help speed up the overall method because it may increase the available surface area of the plant biomass enabling the chemicals used in subsequent steps to be active on more of the plant biomass, for example, at one time. The physical pretreatment step may comprise chipping, chopping, milling, ball-milling, grinding, sprucing, blending, or a combination thereof, of the plant biomass.

Any substance which comprises suitable polysaccharides may be the plant biomass. As the foodstuff, cosmetic, and nutraceutical industries use a broad variety of oligosaccharides, the polysaccharides suitable in the method are not particularly limited. Plant biomass suitable for producing the oligosaccharide profile of the current disclosure may comprise, for example, cellulose, lignocellulose, chitin, chitosan, xylan (such as glucuronoxylan, arabinoxylan, and glucuronoarabinoxylan) xyloglucan, and mixed-linkage glucan, and/or mannan (such as glucomannan, galactomannan, or galactoglucomannan). However, any plant biomass which can be suitably acted upon is envisaged.

As such, the plant biomass may be grain, grain chaff, bean pods, seed coats, and/or other seed materials; seaweeds; corn stover, straw, bagasse, miscanthus, sorghum residue, switch grass, bamboo, and/or other monocotyledonous tissue; water hyacinth, leaf tissue, roots, and/or other vegetative matter; and/or any combination of suitable plant biomasses. In some embodiments, the plant biomass can comprise sugar cane, corn stover, corncob, wheat bran, wheat straw, hardwood or softwood. In certain embodiments, the plant biomass can comprise corncob.

Step (b) is a washing cycle (or incubation cycle) pretreatment of the plant biomass that can occur after the physical pretreatment step. The aim of step (b) may be to solubilize and remove monosaccharides and/or disaccharides from the biomass. For example, the monosaccharides and/or disaccharides may include, but are not limited to, free sucrose, maltose, lactose, glucose, fructose, or galactose. Removal of free disaccharides such as sucrose can be of interest, as disaccharides cannot subsequently be easily removed from the oligosaccharide fraction, for example, filtration methods can be used but would generally cause equal loss of other disaccharides.

Step (i) of the washing cycle may occur at a range of temperatures, for example, of from 5 to 150° C., from 10 to 100° C., or from 15 to 50° C. In some cases, the washing cycle can occur at room temperature, for instance, at about 15 to 25° C. or about 20 to 22° C. Higher temperatures may allow for quicker solubilization of the monosaccharides and/or disaccharides, however, too high temperatures can be more difficult to achieve in an efficient and cost-effective manner and may damage the biomass compounds or solubilize compounds that are not desirable to be solubilized during this step.

Step (i) of the washing cycle may occur for a range of time scales, for example, large amounts of biomass may be exposed to this step for a longer period of time, which can be adjusted accordingly. For example, the time scale may be of from 0.5 minutes to 72 hours, from 1 minute to 12 hours, from 5 minutes to 24 hours, or from 10 minutes to 3 hours. In certain embodiments, this step may occur as batch or continuous.

In some embodiments, step (i) of the washing cycle may comprise washing the plant biomass at room temperature in water, i.e., water supplied at a neutral pH of about pH 7. In another aspect, the step (i) of the washing cycle may comprise heating the plant biomass in water, i.e., water supplied at a neutral pH of about pH 7. During the washing cycle, the neutral water supplied may become slightly acidic as monosaccharides and/or disaccharides are solubilized.

In certain embodiments, step (i) of the washing cycle may comprise heating the plant biomass in an alkali solution having a pH of from 7.1 to 14, from 7.5 to 12, or from 8 to 11. The solution may comprise, or suitably consist of, any one of the alkalis selected from: sodium hydroxide, potassium hydroxide, sodium carbonate, calcium carbonate, calcium hydroxide, ammonium sulfate, ammonium hydroxide, and aqueous ammonia. In various embodiments, the alkali may be sodium hydroxide. A combination of the listed alkalis is also envisaged.

In various cases, step (i) of the washing cycle may comprise heating the plant biomass in an acidic solution having a pH of from 1 to 6.9, from 2 to 6.5, or from 4 to 6. The solution may comprise, or suitably consist of, any organic or mineral acids, such as one of the acids selected from: sulfuric acid, hydrochloric acid, nitric acid, phosphoric acid, acetic acid, maleic acid, fumaric acid, and oxalic acid. In certain cases, the acid may be sulfuric acid. A combination of the listed acids is also envisaged.

In certain instances, a portion or all of the monosaccharides and/or disaccharides in the plant biomass are solubilized and removed during step (b). Other contaminants may also be removed during this step, such as other soluble sugars and minerals.

Step (b) may be repeated to remove monosaccharides and/or disaccharides that were not removed from the plant biomass during the washing cycle. In various instances, step (b) may be performed at least two times, at least three times, at least four times, or at least five times. Step (c) is a thermochemical pretreatment of the plant biomass that can occur after the physical and washing pretreatment steps. "Thermochemical," as used herein, generally refers to heating above room temperature (room temperature is, for instance, about 15 to 25° C. or about 20 to 22° C.) the plant biomass in a chemical, such as heating in a solution of water, acid, or alkali. The purpose of the thermochemical step can be to help speed up the overall method because it may chemically modify chemical components of the plant biomass, for example, it can disrupt hydrogen bonds between saccharides enabling the enzyme in the subsequent step to more easily break up the saccharides.

The heating may be at a range of temperatures, for example, from 50 to 150° C., from 60 to 130° C., from 65 to 120° C., or from 70 to 110° C. Higher temperatures can allow for quicker chemical and/or physical modification, however, too high temperatures can be more difficult to achieve in an efficient and cost-effective manner.

The heating may occur for a range of time scales, particularly large amounts of biomass may be exposed to heating for a longer period of time, which can be adjusted accordingly. For example, the heating of the plant biomass can be of from 5 minutes to 72 hours, from 15 minutes to 24 hours, from 30 minutes to 12 hours, or from 1 hour to 4 hours.

In some embodiments, the thermochemical pretreatment may comprise heating the plant biomass in water, i.e., at a neutral pH of about pH 7.

In certain embodiments, the thermochemical treatment may comprise heating the plant biomass in an alkali solution having a pH of from 7.1 to 14, from 9 to 13, or from 10 to 13. The solution may comprise, or suitably consist of, any one of the alkalis selected from: sodium hydroxide, potassium hydroxide, sodium carbonate, calcium carbonate, calcium hydroxide, ammonium sulfate, ammonium hydroxide and aqueous ammonia. In various embodiments, the alkali may be sodium hydroxide. A combination of the listed alkalis is also envisaged.

In some cases, the thermochemical treatment may comprise heating the plant biomass in an acidic solution having a pH of from 1 to 6.9, from 2 to 6.5, or from 4 to 6. The solution may comprise, or suitably consist of, any organic or mineral acids, such as one of the acids selected from: sulfuric acid, hydrochloric acid, nitric acid, phosphoric acid, acetic acid, maleic acid, fumaric acid, and oxalic acid. In certain cases, the acid may be sulfuric acid. A combination of the listed acids is also envisaged.

Multiple different sequential thermochemical treatment steps are also envisaged for step (c). For example, step (c) may be performed at least two times, at least three times, at least four times, or at least five times.

In certain cases, the washing of step (b) may occur in water and the pretreatment of step (c) may occur in alkali.

After the pretreatment steps, step (d) may comprise the enzymatic reaction forming the one or more oligosaccharides from the plant biomass. The polysaccharides present in the plant biomass may be partially cleaved by enzymes into oligosaccharides (e.g., useful oligosaccharides), leaving partially cleaved, or uncleaved, polysaccharides, which may include cellulose, xylan (such as glucuronoxylan, arabinoxylan, or glucuronoarabinoxylan), mannan (such as glucomannan, galactomannan, or galactoglucomannan), mixed-linkage glucan, xyloglucan chitin, chitosan, or lignocellulose.

The reaction may take place in solution and/or suspension. The reaction may take place in a suitable reaction vessel. In some cases, the reaction may take place at a temperature or temperature protocol suitable for the particular combination of enzyme and plant biomass, the reaction may be allowed to progress for a certain amount of time, until the products have reached a desired concentration, or until some other requirement has been met and the products are isolated or otherwise collected. This time period may be from about 1 minute to about 6 days, from about 0.5 days to about 5 days, or from about 16 hours to about 96 hours. The reaction may alternatively be allowed to proceed until no further catalysis occurs.

In order to ensure optimal contact between the enzymes and the plant biomass, the reaction mixture may be agitated, either constantly or at intervals. The agitation may take the form of rhythmically moving the entire reaction vessel, of a fan or other stirring device, of a bubble sparging, or any other method of agitation.

The enzymatic reaction may be a microbial fermentation. The temperature and reaction time may be suitable for the growth of the microbial organism used. The microbial organism may be genetically altered to produce an enzyme suitable for the production of an oligosaccharide of the present disclosure. The microbe may be, for example, a bacterium, for example, *Escherichia coli*, or a fungus, such as *Saccharomyces cerevisiae* or *Trichoderma reesei*.

Further embodied in the present disclosure is an expression vector suitable for modifying the subject microorganism such that it produces an enzyme or mixture of enzymes of the current disclosure. Where desired, the expression vector, which may be a plasmid or any other nucleic acid able to induce production of the enzyme, may comprise one or more of the following regulatory sequences so as to control the expression of the exogenous enzyme: regulatory sequences of a heat shock gene, regulatory sequences of a toxicity gene, and regulatory sequences of a spore formation gene.

The enzymatic reaction can be carried out at a temperature or temperature protocol suitable to the enzymes and substrates used. For example, it may be carried out at a constant temperature in the range of from about 10° C. to about 100° C., about 20° C. to about 70° C., or about 30° C. to about 40° C. If the enzymatic reaction takes the form of a microbial fermentation, the temperature may be suitable for such, for example, the enzymatic reaction may comprise the growth of *E. coli* and/or the temperature may be constant and about 37° C.

The pH of the solution or suspension may affect the activity of the enzymes. Control of pH may assure that an enzymatic reaction proceeds at a suitable rate. The enzymatic reaction of the present disclosure may take place at a pH in the range of from about 2 to about 10, about 3 to about 8, or about 4 to about 6.

The enzymatic reaction may be allowed to continue to run until there is 5-75% undigested polysaccharide-containing plant biomasses remaining, 5-70%, 5-65%, 5-55%, more or 10-50%. This can be monitored or checked by reducing end assays, such as the anthrone assay and/or by chromatographic methods such as thin-layer chromatography and high-performance anion exchange chromatography.

There are many enzymes that may be suitable for use in the enzymatic reaction of the present method. For example, "lytic polysaccharide monooxygenase" and "LPMO" which are a class of enzymes able to oxidatively cleave polysaccharides using a copper comprising moiety and using an oxygen source, such as a molecule of dioxygen, peroxide, or any other oxygen source; and a suitable reducing agent. As such, when an LPMO is used, the enzymatic reaction may be carried out under aerobic conditions. Suitable reducing agents are not particularly limited, but examples include ascorbic acid, gallic acid, cysteine, NADH, NADPH, pyrogallol, dithiothreitol, cyanoborohydrides, borohydrides, photosynthetic pigments, lignin, lignols, and a combination of cellobiose and cellobiose dehydrogenase. A wide variety of photosynthetic pigments may be used, for example, thylakoids and purified fractions or chlorophyllin and light may be supplied. LPMOs can be selected from the following families: AA9, AA10, AA11, AA13, AA14 and AA15. The LPMO may be PaLPMO9E (SEQ ID NO:1), an AA9 LPMO originally isolated from the ascomycete fungus *Podospora anserina*. The LPMO may be an AA9 LPMO from *Trichoderma reesei* (SEQ ID NO:23).

Aerobic conditions may comprise the addition of oxygen, which may be provided by aeration of the substrate mixture with an oxygen-comprising gas, such as air. Aeration may be conducted by the introduction of oxygen-comprising air bubbles into the aqueous substrate mixtures by various systems, such as an air-injector, an aeration frit, a membrane system, or an internal-loop airlift reactor. The concentration of molecular oxygen in the enzymatic reaction may be from about 4 mg/L to about 14 mg/L.

Another type of enzyme that can be used in the method is a "cellulase" which has hydrolytic activity against cellulose, for example, endo-1,4-beta-glucanase, cellobiohydrolase, and/or beta-glucosidase activities. Such enzymes are able to cleave glycosidic bonds in one or more forms of cellulose, including cellulose found in plant biomass. In doing so they produce products including glucose and cello-oligosaccharides. Beta-glucanases include enzymes from GH5, GH7, and GH12 enzyme, such as those derived from *Aspergillus niger* (SEQ ID NOs:12, 13, and 14) and *Trichoderma reesei* (SEQ ID NOs:24 and 25).

Another type of enzyme is "cellobiohydrolase" that has hydrolytic activity against cellulose, and produces mainly cellobiose as a product. Cellobiose is a disaccharide, and is a cello-oligosaccharide. Such enzymes are able to cleave glycosidic bonds in one or more forms of cellulose, including cellulose found in plant biomass. Cellobiohydrolases may be from GH6 and GH7 enzyme families or Cel6A or Cel7A enzymes derived from *Trichoderma reesei* (SEQ ID NOs:10 and 11).

Another type of enzyme is "beta-glucosidase" that has hydrolytic activity against cellulose, and produces mainly glucose as a product. Such enzymes are able to cleave glycosidic bonds in one or more forms of cellulose, including cellulose found in plant biomass. Beta-glucosidases may include GH3 beta-glucosidases, such as from *Trichoderma reesei* (SEQ ID NO: 22).

Another type of enzyme is a lichenase, which may be selected from: the GH5, GH7, GH8, GH9, GH12, GH16, GH17, or GH26 families. In some cases, the lichenase may be a GH16 enzyme. The GH16 enzyme may be derived from *Bacillus subtilis* (SEQ ID NO:2). The enzyme is able to act on, for example, mixed-linkage glucans, which are glucans comprising a mixture of β-1,3 and β-1,4 linkages, and may cleave them at β-1,4 glycosidic bonds. In the case in which the lichenase acts on a mixed-linkage glucan, the β-glucans produced may fall largely within the size range of from about 3 to about 7 residues, so they may be useful in the food, cosmetics, and nutraceutical industries. Mixed-linkage glucans are abundant in members of the grass and horsetail families, and as such, grass-based biomasses such as straw have high levels of it, and may be acted upon usefully with lichenases.

Another type of enzyme is a xylanase, which may act on, for example, plant biomass comprising a xylan backbone. The xylanase may be, for example, a glucuronoxylanase, an arabinoxylanase, or a glucuronoarabinoxylanase. The enzyme may be active on a variety of polymers having a xylan backbone, such as glucuronoxylan, arabinoxylan, and glucuronoarabinoxylan. These polymers are abundant in various plant biomass, for example, both hardwood and softwood may comprise suitable polysaccharides, with hardwood often comprising glucuronoxylan and softwood often comprising arabinoglucuronoxylan. In some embodiments, xylanases may include GH5 xylanases from *Ruminiclostridium thermocellum* (SEQ ID NO:3) and *Gonapodya prolifera* (SEQ ID NO:4), and GH30 xylanases from *Dickeya chrysanthemi* (SEQ ID NO:5), *Bacillus subtilis* (SEQ ID NO:6), *Bacteroides ovatus* (SEQ ID NO:7), and *Trichoderma reesei* (SEQ ID NO:15).

Other enzymes useful in the disclosure may include xyloglucanases and xyloglucan endoglucanases (XEGs), which are produced by numerous organisms, including plant-pathogenic microbes. They are able to act on xyloglucan, a hemicellulosic β-1,4 glucan chain abundant in the primary cell wall of higher plants, which is decorated with xylose, some of the xylose residues being further decorated with other residues, such as galactose. When suitable xyloglucanases or XEGs act on xyloglucan, the products comprise xyloglucan oligosaccharides having a main chain of a length that can be useful in the foodstuff, cosmetics, and nutraceutical industries. Xyloglucanases can include a GH5 xyloglucanase from *Bacteroides ovatus* (SEQ ID NO:8) and a GH74 xyloglucanase from *Trichoderma reesei*.

As any given natural plant biomass is likely to comprise a mixture of different polysaccharides, it can sometimes be the case that a mixture of different enzymes is beneficial. Such a mixture may comprise one or more of any other enzyme. For example, such a mixture might comprise an LPMO with an endo-glucanase, a xylanase with a lichenase, a cellobiohydrolase with a mannanase, or an endo-glucanase with a cellobiohydrolase in which the enzyme partners are present in molar ratios from 1:100 and 100:1.

In some instances, the one or more enzymes may be a cocktail of different enzymes, for example, a crude or semi-crude enzyme preparation. The term "crude enzyme preparation," as used herein, generally refers to a soluble preparation extracted from a microbial fermentation that has undergone minimal processing after the extraction. For example, typically the preparation may only undergo filtration in order to remove insoluble components. The term "semi-crude enzyme preparation," as used herein, generally refers to a soluble preparation extracted from a microbial fermentation that has undergone some processing after the extraction, for example, the preparation may undergo filtration in order to remove insoluble components, increasing the enzyme concentration and/or nanofiltration to remove small molecular weight compounds.

In some cases, the crude or semi-crude enzyme preparation may be from a bacteria or a fungus. For example, the preparation may be from a fungus, such as a filamentous cellulolytic fungus, such as from *Trichoderma* or *Aspergillus* species. The enzyme may be a crude or semi-crude enzyme preparation from a *Trichoderma reesei* strain.

In step (e), the oligosaccharides may be separated from the enzymatic reaction mixture in a number of ways. They may be isolated based on solubility, so that a composition of soluble saccharides only is extracted for further processing, and/or isolated chromatographically to produce a composition with a narrower band of oligosaccharide chain lengths. Isolation may, for example, be based on precipitation, size-exclusion chromatography, ion-exchange chromatography, filtration, ultrafiltration, microfiltration, or nanofiltration. In the case that isolation based on solubility is carried out, the profile of saccharides present in the isolated composition may depend on the original enzymatic reaction, as different saccharides decrease in solubility with length at different rates.

Also envisaged in the scope of the present disclosure is the further treatment of all or part of the produced oligosaccharides to produce further products before incorporation into a foodstuff, cosmetic, or nutraceutical. This further treatment may comprise any chemical, physical, or enzymatic step, such as reduction, for example, reductive amination where suitable; oxidation, caramelization, modification with a Schiff base, or via the Maillard reaction, or by any combination of such steps, and may provide further products having properties which are improved for the desired purpose. For example, the caramelization properties, calorific value, flavor, and color may be modified. The oligosaccharides may also be purified, for example, through precipitation, size-exclusion chromatography, ion-exchange chromatography, filtration, ultrafiltration, microfiltration, or nanofiltration.

The ingredient formed in step (e) may comprise various oligosaccharides and at varying amounts depending on the desired properties. In various cases, the ingredient may comprise at least 20% by dry weight or at least 30% by dry weight cello-oligosaccharides having a degree of polymerization of from two to six, the ingredient may comprise at least 20% by dry weight or at least 30% by dry weight xylo-oligosaccharides having a degree of polymerization of from two to twelve, the ingredient may comprise at least 20% by dry weight or at least 30% by dry weight mixed-linkage glucan oligosaccharides having a degree of polymerization of from two to five, the ingredient may comprise at least 20% by dry weight or at least 30% by dry weight manno-oligosaccharides having a degree of polymerization of from two to twelve, the ingredient may comprise at least 20% by dry weight or at least 30% by dry weight xyloglucan oligosaccharides having a degree of polymerization of from four to twelve, and/or the ingredient may comprise at least 20% by dry weight or at least 30% by dry weight chito-oligosaccharides having a degree of polymerization of from two to twelve. In some embodiments, the ingredient can comprise a maximum of 100% by dry weight of the above oligosaccharides and the polysaccharides described herein, therefore the above embodiment, wherein the oligosaccharides are present in at least 20% by dry weight, does not comprise all six types of oligosaccharides.

In some instances, the ingredient may comprise at least 50%, 60%, 70%, 80%, 90%, 95%, 99%, or 99.5% by dry weight of saccharide present. The ingredient may consist essentially of saccharides. For example, the ingredient may have less than 0.5% by dry weight or less than 0.3% by dry weight, for instance, 0.1% by dry weight, of other substances.

In various instances, the ingredient may comprise at least two of the oligosaccharides. The amounts of each of the oligosaccharides may be varied depending on the desired properties of the resulting foodstuff, cosmetic, or nutraceutical. The two oligosaccharides may be present in a ratio of 1:9 to 9:1 or 1:2 to 2:1. Further, the ingredient may comprise three of the oligosaccharides, four of oligosaccharides, five of the oligosaccharides, or six of the oligosaccharides.

In some embodiments, the ingredient may comprise the cello-oligosaccharides, for instance, cello-oligosaccharides in combination with the xylo-oligosaccharides. In certain embodiments, the ingredient may comprise the cello-oligo-saccharides in combination with the manno-oligosaccharides.

The produced ingredient can be useful in applications in which oligosaccharides, sugar, bulking sweeteners, low-intensity sweeteners, or other related food ingredients are conventionally used. For example, as sweeteners, bulking agents, added dietary fiber, or humectants. Of particular note may be in the use of reducing cane sugar in food products. The ingredient may be incorporated into cakes, bread, or other baked goods; into chocolate or other confectionery such as toffee, fudge, meringue, jam, jelly or caramel; or drinks, for example, to provide favorable taste or color characteristics or to increase dietary fiber content. In some instances, the ingredient may be incorporated into animal feed, for example, either as an isolated ingredient or by utilizing the enzymatic reaction mixture directly as feed.

Compositions or ingredients as described herein may be used to alter one or more properties of a finished product.

Such properties include, but are not limited to, sweetness, texture, mouthfeel, binding, glazing, smoothness, moistness, viscosity, color, hygroscopicity, flavor, bulking, water-retention, caramelization, surface texture, crystallization, structural properties, reduced calories, reduced glycemic index, reduced glycemic load, increased fiber, reduced sugar, and dissolution. These may be improvements over what is currently possible with saccharides of different types, sugar substitutes, and/or other such compounds.

In the cosmetics industry, the ingredient may improve texture and moisture retention, act as UV-absorbing molecules, maintain a gel or cream structure, and/or serve as bulking agents. Furthermore, the ingredient can be useful in nutraceutical compositions, as the dietary fiber it provides has been shown to encourage digestive health, well-regulated gut flora, and other benefits to wellbeing. In this context the ingredients herein may also function as an ingredient in a probiotic drink or other prebiotic or probiotic formulation.

The detailed description is further supplemented with reference to the following numbered embodiments. 1) A method for producing a foodstuff, cosmetic, or nutraceutical ingredient, the ingredient comprising one or more oligosaccharides, wherein the method comprises the steps of: a) a physical pretreatment of a plant biomass comprising monosaccharides and/or disaccharides; b) a washing cycle comprising the steps of (i) washing the plant biomass to solubilize at least a portion of the monosaccharides and/or disaccharides and (ii) removing the at least a portion of monosaccharides and/or disaccharides; c) a thermochemical pretreatment of the plant biomass; d) forming the one or more oligosaccharides by an enzymatic reaction, the enzymatic reaction comprising the step of contacting, in a solution or suspension, one or more polysaccharide-cleaving enzymes and the plant biomass; e) separating the one or more oligosaccharides from the enzymatic reaction mixture and using the one or more oligosaccharides to form the ingredient. 2) The method of numbered embodiment 1, wherein the physical pretreatment step comprises chipping, chopping, milling, ball-milling, grinding, sprucing or blending of the plant biomass. 3) The method of either numbered embodiment 1 or numbered embodiment 2, wherein step (i) of the washing cycle occurs in water, acid, or alkali. 4) The method of any preceding numbered embodiment, wherein step (i) of the washing cycle occurs at a temperature of from 5 to 150° C., from 10 to 100° C., or from 15 to 50° C. 5) The method of any preceding numbered embodiment, wherein step (i) of the washing cycle occurs for a time scale of from 0.5 minutes to 72 hours, of from 1 minute to 12 hours, of from 5 minutes to 24 hours, or from 10 minutes to 3 hours. 6) The method of any preceding numbered embodiment, wherein the thermochemical pretreatment comprises heating the plant biomass in a solution of water, acid, or alkali. 7) The method of numbered embodiment 6, wherein the heating of the plant biomass is at a temperature of from 50 to 150° C., of from 60 to 130° C., of from 65 to 120° C., or of from 70 to 110° C. 8) The method of either numbered embodiment 6 or 7, wherein the heating of the plant biomass is of from 5 minutes to 72 hours, from 15 minutes to 24 hours, from 30 minutes to 12 hours, or from 1 hour to 4 hours. 9) The method of any one of numbered embodiments 6 to 8, wherein the solution has a pH of from 7.1 to 14, 7.5 to 12, or of from 8 to 11.10) The method of numbered embodiment 9, wherein the solution comprises sodium hydroxide potassium hydroxide, sodium carbonate, calcium carbonate, aqueous ammonia, ammonium sulfate, or ammonium hydroxide. 11) The method of any one of numbered embodiments 6 to 8, wherein the solution has a pH of from 1 to 6.9, of from 2 to 6.5, or of from 4 to 6.12) The method of numbered embodiment 11, wherein the solution comprises sulfuric acid, hydrochloric acid, nitric acid, phosphoric acid, acetic acid, maleic acid, fumaric acid, or oxalic acid. 13) The method of any one of numbered embodiments 1 to 12, wherein the plant biomass is sugar cane, corn stover, corncob, wheat bran, wheat straw, hardwood, or softwood. 14) The method of any one of numbered embodiments 1 to 13, wherein the plant biomass comprises cellulose, chitin, chitosan, xylan, xyloglucan, mixed-linkage glucan, mannan, or lignocellulose. 15) The method of any one of numbered embodiments 1 to 14, wherein the one or more of the polysaccharide-cleaving enzymes is one of cellulase, xylanase, xyloglucanase, endo-glucanase, cellobiohydrolase, mannanase, lichenase or a lytic polysaccharide monooxygenase (LPMO), for example, selected from the group consisting of: AA9, AA10, AA11, AA13, AA14, and AA15.16) The method of any one of numbered embodiments 1 to 15, wherein the one or more of the polysaccharide-cleaving enzymes is prepared from *T. reesei* fungi. 17) The method of any one of numbered embodiments 1 to 16, wherein the one or more oligosaccharides comprise one of β-glucans, cello-, MLG-, mannan-, or xylo-oligosaccharide. 18) The method of any one of numbered embodiments 1 to 17, wherein the polysaccharide-cleaving enzyme(s) is operably linked to a catalytic or non-catalytic module, for example, wherein the polysaccharide-cleaving enzyme is operably linked to a non-catalytic module and the non-catalytic module is a carbohydrate-binding module. 19) The method of any one of numbered embodiments 1 to 18, wherein after the separating of the one or more oligosaccharides, the one or more oligosaccharides undergo chemical, physical, or enzymatic treatment, such as reduction, oxidation, caramelization, or Maillard reaction.

The detailed description is further supplemented with reference to the following numbered embodiments. 1) A method for producing an ingredient for human consumption, the method comprising: (a) physically treating a plant biomass; (b) subjecting the physically treated plant biomass to an incubation cycle comprising: (i) incubating the physically treated plant biomass in an incubation solution having a pH from 6.6 to 7.4 to solubilize monosaccharides and/or disaccharides from the physically treated plant biomass; and (ii) removing a portion of the solubilized monosaccharides and/or disaccharides from the incubation solution; (c) thermochemically treating the incubated plant biomass in one of (i) an acidic solution having a pH from 2 to 6.5 or (ii) an alkali solution having a pH from 7.5 to 12; (d) contacting, in a solution or suspension, one or more polysaccharide-cleaving enzymes and the thermochemically treated plant biomass to form one or more oligosaccharides; and (e) enriching the solution or suspension to increase the concentration of the one or more oligosaccharides to form the ingredient. 2) The method of numbered embodiment 1, further comprising removing at least a portion of the monosaccharides and/or disaccharides from the incubation solution at step (b)(ii). 3) The method any preceding numbered embodiment, wherein the thermochemically treated plant biomass comprises no or substantially no monosaccharides. 4) The method of any preceding numbered embodiment, further comprising purifying the one or more oligosaccharides from the solution or suspension. 5) The method of any preceding numbered embodiment, further comprising repeating step (b). 6) The method of numbered embodiment 5, wherein step (b) is conducted two, three, four, or five times. 7) The method of any preceding numbered embodiment, further comprising repeating step (c). 8) The method of numbered embodiment 7, wherein step (c) is conducted two, three, four, or five times. 9) The method of any preceding numbered embodiment, further comprising discarding the portion of the solubilized monosaccharides and/or disaccharides removed in step (b). 10) The method of any preceding numbered embodiment, wherein the portion of the solubilized monosaccharides and/or disaccharides removed in step (b) is not combined with the portion of the one or more oligosaccharides of step (e) to form the ingredient. 11) The method of any preceding numbered embodiment, wherein the ingredient is substantially free of monosaccharides. 12) The method of any preceding numbered embodiment, wherein the ingredient is substantially free of disaccharides. 13) The method of any preceding numbered embodiment, wherein the one or more oligosaccharides comprise at least one of: i) a cello-oligosaccharide having a degree of polymerization (DP) of from two to six; ii) a xylo-oligosaccharide having a DP of from two to twelve; iii) an arabinoxylo-oligosaccharide having a DP of from three to fifteen; iv) a manno-oligosaccharide having a DP of from two to twelve; v) a mixed-linkage glucan oligosaccharide having a DP of from two to five; vi) a xyloglucan oligosaccharide having a DP of from four to twelve; or vii) a chito-oligosaccharide having a DP of from two to twelve. 14) The method of numbered embodiment 13, wherein the ingredient comprises at least two of the oligosaccharides listed in (i) to (vii). 15) The method of numbered embodiment 14, wherein the ingredient comprises the at least two oligosaccharides in a ratio from 1:9 to 1:1 in relation to each other. 16) The method of any preceding numbered embodiment, wherein the monosaccharides and/or disaccharides comprise at least one of sucrose, glucose, maltose, lactose, glucose, fructose, or galactose. 17) The method of any preceding numbered embodiment, wherein the physically treating of step (a) comprises at least one of chipping, chopping, milling, ball-milling, grinding, sprucing, or blending the plant biomass. 18) The method of any preceding numbered embodiment, wherein the incubating of step (b) occurs in an incubation solution comprising water. 19) The method of any preceding numbered embodiment, wherein the incubating of step (b) occurs at a temperature of from 15° C. to 95° C. 20) The method of any preceding numbered embodiment, wherein the incubating of step (b) is conducted from 15 minutes to 1 hour. 21) The method of any preceding numbered embodiment, wherein the thermochemically treating of step (c) comprises heating the physically treated plant biomass in the acidic solution or the alkali solution. 22) The method of numbered embodiment 21, wherein the heating is at a temperature of from 50° C. to 150° C. 23) The method of numbered embodiment 21 or 22, wherein the heating is conducted from 30 minutes to 4 hours. 24) The method of any preceding numbered embodiment, wherein the incubated plant biomass is thermochemically treated in an alkali solution having a pH from 8 to 11.25) The method of numbered embodiment 24, wherein the alkali solution comprises at least one of sodium hydroxide, potassium hydroxide, sodium carbonate, calcium carbonate, aqueous ammonia, ammonium sulfate, or ammonium hydroxide. 26) The method of any preceding numbered embodiment, wherein the incubated plant biomass is thermochemically treated in an acidic solution having a pH from 4 to 6.27) The method of numbered embodiment 26, wherein the acidic solution comprises at least one of sulfuric acid, hydrochloric acid, nitric acid, phosphoric acid, acetic acid, maleic acid, fumaric acid, or oxalic acid. 28) The method of any preceding numbered embodiment, wherein the plant biomass comprises at least one of sugar cane, corn stover, corncob, wheat bran, wheat straw, hardwood, or softwood. 29) The method of any preceding numbered embodiment, wherein the plant biomass comprises at least one of cellulose, chitin, chitosan, xylan, xyloglucan, mixed-linkage glucan, mannan, or lignocellulose. 30) The method of any preceding numbered embodiment, wherein the one or more polysaccharide-cleaving enzymes comprises at least one of cellulase, xylanase, xyloglucanase, endo-glucanase, cellobiohydrolase, mannanase, lichenase, or lytic polysaccharide monooxygenase (LPMO). 31) The method of any preceding numbered embodiment, wherein the one or more polysaccharide-cleaving enzymes comprises at least one of AA9, AA10, AA11, AA13, AA14, or AA15.32) The method of any preceding numbered embodiment, wherein the one or more of the polysaccharide-cleaving enzymes is prepared from *Trichoderma reesei* fungi. 33) The method of any preceding numbered embodiment, wherein the one or more polysaccharide-cleaving enzymes is operably linked to a catalytic module. 34) The method of any preceding numbered embodiment, wherein the one or more polysaccharide-cleaving enzymes is operably linked to a non-catalytic module. 35) The method of numbered embodiment 34, wherein the non-catalytic module is a carbohydrate-binding module. 36) A method for producing an ingredient for human consumption, the method comprising: (a) pretreating a plant biomass, wherein the pretreating comprises: (i) physically treating the plant biomass; (ii) incubating the plant biomass in an incubation solution having a pH from 6.6 to 7.4 to solubilize a portion of the monosaccharides and/or disaccharides and removing a portion of the solubilized monosaccharides and/or disaccharides; and (iii) thermochemically treating the plant biomass in one of (i) an acidic solution having a pH from 2 to 6.5 or (ii) an alkali solution having a pH from 7.5 to 12; (b) contacting, in a solution or suspension, one or more polysaccharide-cleaving enzymes and the pretreated plant biomass to form one or more oligosaccharides; and (c) isolating a portion of the one or more oligosaccharides to form the ingredient.

EXAMPLES

The following illustrative examples are representative of embodiments of the compositions and methods described herein and are not meant to be limiting in any way.

Example 1—Exemplary Process

The following steps can be performed to generate an ingredient as provided herein:
1. Physical pretreatment of a plant biomass: Mix 100 g of milled corncob with water to a 10% (w/w) solids concentration and mix for 60 minutes at room temperature. At the end of the 60 minutes stop mixing and filter out the liquid, while keeping the solids.
2. Re-suspend the solids in water at a concentration of 10% (w/w) solids in suspension. Start mixing, heat to 95° C., and mix for 60 minutes at 95° C.
3. At the end of 60 minutes of heating, add 6 g of sodium hydroxide (0.2-3% by weight of corncob) and continue stirring. Heat to a temperature of 95° C. and mix for 60 minutes to break down the hemicelluloses present in corncob. At the end of the 60 minutes, stop heating and cool down to a temperature of 50° C.
4. Hydrolysis: Add cellulolytic enzymes (e.g., from *Trichoderma reesei*) and incubate at 50° C. at pH 5.5

(adjusted by 1 mol/L sulfuric acid and/or 1 mol/L sodium hydroxide) for 72 hours.
5. Separation of the biomass: At the end of the hydrolysis, separate the liquid from the products through a solid-liquid separator.
6. Enzyme separation following enzymatic hydrolysis: the liquid fraction from the slurry includes enzymes, oligosaccharides, water, and salts that need to be separated. Use a 10 kDa hollow fiber membrane to separate the enzyme proteins and other macromolecules.
7. Salts are removed using ion-exchange columns at ≤45° C.
   a. Cation column: Strongly acidic cation exchange resin, cross-linked polystyrene matrix, sulfonate functional group, $Na^+$ counter-ion.
   b. Anion column: Macroporous, weakly basic anion exchange resin, cross-linked polystyrene matrix, dimethyl-tertiary amine functional group, $OH^-$ counter-ion.
8. Oligosaccharides concentration: The desired oligosaccharides are selectively concentrated through nanofiltration at room temperature.
9. Concentration: Concentrate the liquid to 40-75% at 60-80° C.
10. Spray drying: Spray dry with inlet temperatures of 130-160° C. and outlet temperatures of 65-85° C.

Example 2—Removal of Soluble Saccharides by a Washing Cycle (i.e., Incubation Cycle)

The following steps were performed to remove soluble saccharides from plant biomass:
1. Water was added to 100 mg of four plant biomass types (i.e., cane, wheat, cob, and willow) to a concentration of 10% (w/v) and incubated at 45° C. for 30 minutes, after which suspensions were centrifuged and supernatants were removed.
2. Step 1 was repeated 5 times.
3. 2.5 μl of each supernatant fraction was analyzed by thin-layer chromatography (TLC).

The thin-layer chromatogram of FIG. 1 shows the presence of soluble saccharides washed from four types of plant biomass in the five sequential washing cycles or incubation cycles (1, 2, 3, 4, and 5). Undesired monosaccharides and disaccharides, such as glucose, sucrose, and maltose are arrowed. The results of the TLC showed that for all plant biomasses, the supernatants removed after the first washing cycles have abundant monosaccharides and disaccharides present in them. Thus, the washing cycle successfully removed the monosaccharides and disaccharides from the plant biomass. Supernatants from subsequent washing cycles have significantly fewer monosaccharides and disaccharides present in them, if any at all, showing that the plant biomass has minimal monosaccharides and disaccharides remaining in it after a washing cycle as provided herein.

Example 3—Absence of Washed Soluble Saccharides in Enzyme Hydrolyses

The following steps were performed to show the absence of soluble saccharides in enzyme hydrolyses:
1. The washed cob and willow plant biomasses from Example 2 were each incubated in 1% (w/v) NaOH at 99° C. for 30 minutes and then cooled. 100 mg of unwashed cob and willow biomasses were also each incubated in 1% (w/v) NaOH at 99° C. for 30 minutes and then cooled.
2. 150 μl of the resulting suspensions were each mixed with 150 μl M ammonium acetate (pH 5.5) and 150 μl of an enzyme composition comprising beta xylanase and cellobiohydrolase. Suspensions were then incubated at 50° C. for 16 hours to allow the enzyme reactions with the plant biomasses to occur.
3. 2.5 μl of each supernatant fraction was analyzed by TLC.

Figure 2:
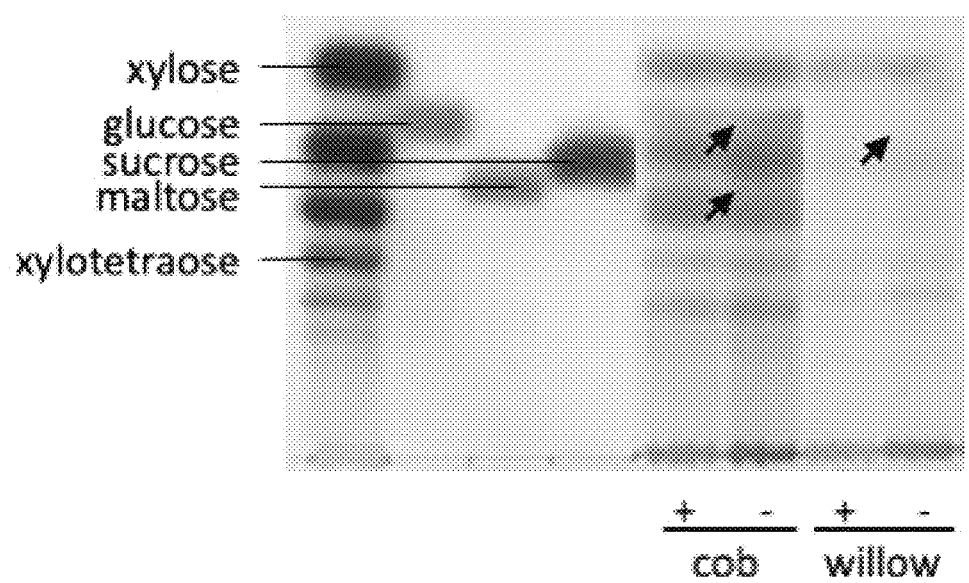
FIG. 2 depicts the results of a TLC analysis comparing the levels of monosaccharides and disaccharides in an enzyme hydrolysate product mixture when washing (incubation pretreatment) has (+) and has not (−) been performed.

The thin layer chromatogram of FIG. 2 shows the products of enzyme digestion of the four types of biomass that have (+) or have not (—) been washed as in Example 2. The results show that after enzyme digestion the end products included glucose, sucrose, and maltose for the unwashed cob and willow plant biomasses. However, the end products after enzyme digestion did not include glucose, sucrose, and maltose for the washed cob and willow plant biomasses.

Figure 3:
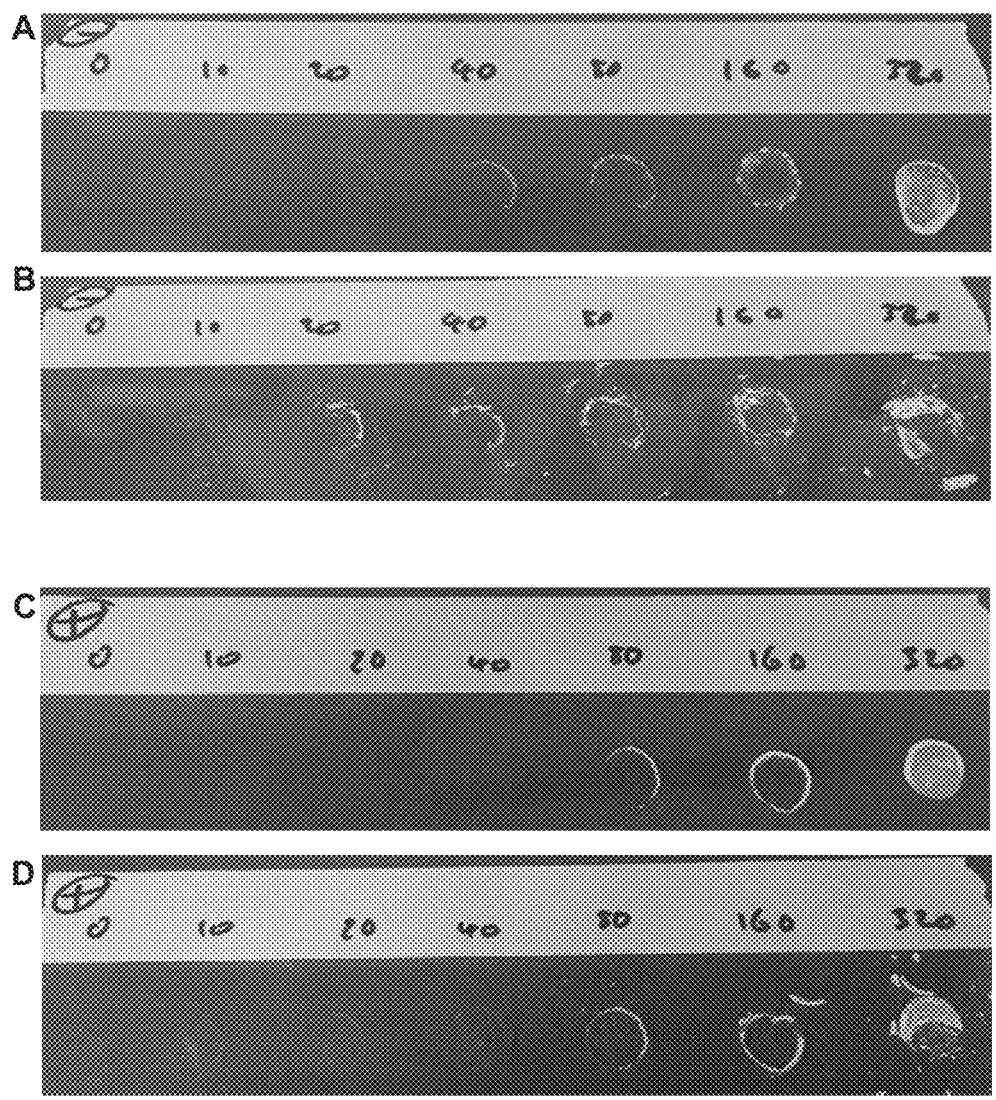
FIG. 3 depicts the results of making a glaze with compositions of the present disclosure and a comparative composition.

Example 4—Adding Polymer to Oligosaccharide Solutions Enables them to Dry into a Hard Glaze The following steps were performed to show that adding polymer to oligosaccharide solutions enables them to dry into a hard glaze:
1. 100 μl of 10-320 mM (10, 20, 40, 80, 160, and 320 mM) cellobiose±1% w/v birchwood xylan was pipetted onto a glass plate.
2. Samples were dried at 37° C.
3. Samples were scored with a knife to test whether or not the ingredient settled into a solid glaze. With cellobiose alone, no firm glaze was formed, and the dried powder readily cracked when pressure was applied with a knife. In contrast, the composition with 1% w/v xylan added and with cellobiose at 80 mM or less the composition dried to form a solid, off-white, translucent surface that was strong enough to be scored with a knife leaving an indentation but without cracking. With a cellobiose concentration of 160 mM or higher (5.5% w/v, or 550% w/w as compared with xylan) the morphology of the glaze reverted to that without xylan present. That is, no firm glaze was formed, and the dried powder readily cracked when pressure was applied with a knife (see FIG. 3).

Example 5—Demonstration of a Composition Comprising Two Oligosaccharides and a Polysaccharide in Food Products The following steps were performed to demonstrate a composition comprising two oligosaccharides and a polysaccharide in food products:
1. 4 g birchwood xylan was dissolved in 75 ml water with boiling.
2. 12 g cellobiose and 24 g xylo-oligosaccharides (primarily degree of polymerization (DP) 2-6) was added in 3 g increments and dissolved with boiling.
3. The mixture was reduced to 50 ml with heating and formed a thick solution with the consistency and appearance of cloudy honey but less sweet.
4. 10 mL of the mixture was mixed with 12 g oats to make a flapjack/cereal bar mixture and separately 10 mL of the mixture was also mixed with 6 g fruit and 6 g nuts to make a cereal bar mixture.
5. Samples were baked at 100° C. for 10 minutes and then left to cool and dry overnight.

Figure 4:
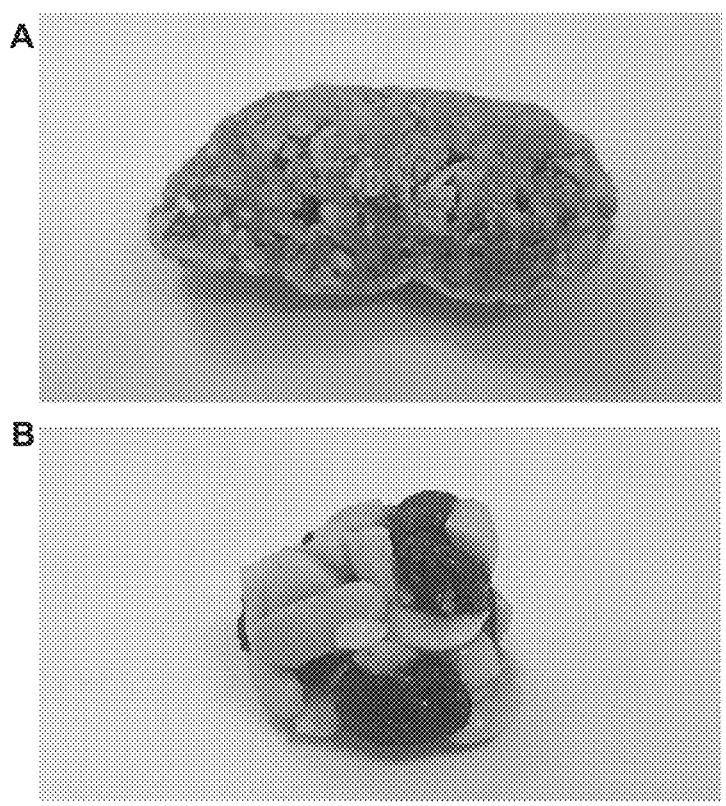
FIG. 4 depicts baked products using a liquid ingredient of the present disclosure.

As shown in FIG. 4, panel A (flapjack/cereal bar) and panel B (fruit and nut bar), the produced flapjack and fruit and nut bar were of a desirable texture and consistency in line with flapjack/cereal bars and fruit and nut bars made with known syrups typically used in baking.

For the flapjack/cereal bar, the thick solution from step 3 helped to bind together the mixture in step 4. The combined effect of the ingredient with the properties of oats yielded a grainy surface texture consistent with flapjack/cereal bars produced using conventional sugar. The ingredient created a firm, chewy, moist, viscous texture yielding a mouthfeel consistent with what is expected from these types of food products, but which is not present in oats alone. The product was mildly sweet and contained no bitter or off-flavors, that can be characteristic of high-intensity sweeteners.

For the fruit and nut bar, the thick solution from step 3 helped to bind together the mixture in step 4. It also added a smooth, shiny glazed surface, which is a core part of the aesthetic qualities of such food products, and which would not be created if the ingredient comprised oligosaccharides alone (i.e., oligosaccharides without the polysaccharides). The ingredient created a firm, chewy, moist, and viscous texture yielding a mouthfeel consistent with what is expected from these types of food products, but which is not present in either the nuts or the fruit alone. The product was mildly sweet and contained no bitter or off-flavors, that can be characteristic of high-intensity sweeteners.

Example 6—Process for Making an Ingredient

The following steps can be performed to make an ingredient as provided herein:
1. Heat 15% w/v of corncob (ground through a 1 mm pore size filter) in 1% w/v NaOH for 1 hour at 90° C., thereby solubilizing a portion of the polymeric components of the biomass.
2. Adjust to pH 5.5 with sulfuric acid.
3. Extract a volume comprising only liquid components of the reaction representing 15% of the total volume of the reaction ("soluble polymers"); retain the remaining 85% volume of the reaction comprising all of the insoluble biomass fraction ("remaining biomass").
4. To the remaining biomass, add a cellulolytic enzyme cocktail (e.g., an enzyme cocktail from *Trichoderma reesei*, including cellulase, xylanase, arabinofuranosidase, LPMO, etc.) to 0.5% w/v and incubate at 50° C. for 24 hours.
5. Separate soluble oligomeric reaction products from undigested insoluble polymeric compounds by filtration.
6. Purify oligomeric reaction products by sequentially employing microfiltration, ultrafiltration, and ion-exchange chromatography (e.g., cross-flow filtration on a ceramic membrane; filtration can be performed using 110 0.45 μm cut-off Inside Ceram candle filters (TiO2, Ø 25 mm×L 1178 mm HD 6 mm, 8 channels per membrane) supplied by TAMI industries at a feed pressure of maximum 3 bar).
7. Purify the soluble polymers by employing ultrafiltration (e.g., 10 kDa spiral wound membranes (Snyder ST-2B-6338, PES, feed spacer thickness 31 mm) run on Alfa Laval ultrafiltration unit).
8. Recombine the solutions formed in steps 6 and 7 and further purify and concentrate by employing nanofiltration to form the ingredient.

Example 7—Viscosity Measurements of Different Solutions

The following steps were performed to measure viscosity of different solutions:
1. Three saccharide solutions comprising cellobiose (Cell$_2$), xylo-oligosaccharides of primarily DP 2-6 (XOS), and polymeric beechwood xylan (BWX) were created by boiling saccharides in water. Final concentrations were:
   a. Sample 1: 0.33 g/ml Cell2, 0.66 g/ml XOS, 0.13 g/ml BWX
   b. Sample 2: 0.17 g/ml Cell2, 0.33 g/ml XOS, 0.07 g/ml BWX;
   c. Sample 3: 0.54 g/ml Cell2, 0.52 g/ml XOS, 0.07 g/ml BWX.
2. The samples were tested using a Brookfield HDB VE roto-viscometer using standard testing procedures. A 400 mL sample was taken in a tall-form beaker to ensure that no container effects occurred. The instrument was operated as per the manufacturer's instructions with respect to ranges: rotoviscometry using spindle code 61, spindle speed 100 rpm, and at 22° C.

| Sample number | Viscosity (cps) |
| --- | --- |
| 1 | 393 |
| 2 | 13 |
| 3 | 26 |

Sample 1 had a consistency like that of thick honey that needed mixing in order to dilute into aqueous solutions. In contrast, Samples 2 and 3 were much runnier and could be readily mixed into aqueous solutions. The results showed that the viscosity of the compositions was affected more by the polysaccharide concentration than the overall concentration of oligosaccharide and polysaccharide. Samples 2 and 3 have the same polysaccharide concentration, but Sample 3 has twice the concentration of total oligosaccharide and polysaccharide than Sample 2. The viscosity of Sample 3 is twice the viscosity of Sample 2, in line with a linear relationship between the overall concentration and viscosity. However, there is an exponential increase in the viscosity values as the concentration of the polysaccharide increases. The polysaccharide concentration of Sample 1 is twice that of Sample 3 and their concentrations of total oligosaccharide and polysaccharide are the same, yet the viscosity of Sample 1 is fifteen (15) times greater than Sample 3.

Example 8—Preparation of Water-Soluble Liquid Product/Ingredient

The following steps were performed to generate a water-soluble liquid product/ingredient (Sample 4):
1. 100 g of milled corncobs were heated in 1 L of deionized water containing 2.5 g of sodium chlorite at 80° C. for 1.5 hours with constant agitation. The residual volume was reconstituted to 900 mL by addition of 200 mL deionized water containing a further 5 g of sodium chlorite and heated at 80° C. for 1 hour with constant agitation.
2. The solution was filtered through a 2 mm pore size ceramic filter funnel with vacuum, until the filtrate was clear.
3. Retained solids were incubated in 1 L 0.5 M sodium hydroxide 0.1% (w/v) sodium borohydride for 17 hours at 50° C. and 115 rpm shaking.
4. The pH was then adjusted to 7 with concentrated sulfuric acid and dialyzed against tap water for 24 hours in 12,000 Dalton cut-off dialysis tubing.

5. The contents of the dialysis tubing were transferred to a 2-L beaker and the insoluble fraction allowed to sediment by gravity.
6. The supernatant was decanted twice and concentrated by evaporation at 80° C. to a volume of 120 mL.
7. Water-soluble polymer was precipitated by centrifugation after addition of 3 volumes of ethanol. The resulting supernatant was discarded and the precipitate air dried to constant weight at room temperature.
8. Oligosaccharides were added to a final w/w of 10% cellobiose, 75% xylo-oligosaccharides, 15% extracted water-soluble polymer, and mixed to homogeneity in a Waring Xtreme blender on the lowest power setting. 94 g solids were recovered from the blender.
9. Unexpectedly, all 94 g solids dissolved in 60 mL water at 50° C. with mild constant agitation (~100 rpm), indicating a solubility of greater than 150 g/100 g.

The sample generated (e.g., at steps 8 and 9 above) is referred to as Sample 4.

Example 9—Physicochemical Properties of the Water-Soluble Liquid Product of Example 8

Flow characteristics: The flow characteristics of the water-soluble liquid product in accordance with the present disclosure (Sample 4) described in Example 8 are detailed in Table 1 along with comparison compositions of water, 20% w/v glucose, 40% w/v glucose, 60% w/v glucose, 80% w/v glucose, and ≥99% glycerol (Fisher G/0650/17 as supplied). The glucose solutions were made by weighing 6, 12, 18, and 24 g D-glucose respectively and making up with 90° C. water to 30 mL. The flow characteristics were measured by timing the flow rate of 5 mL, and where suitable, 20 mL of the liquids from a vertically stood syringe (BD Plastipak 300613) filled with 20 mL of test liquid under gravity at room temperature.

TABLE 1

Flow Characteristics

| Sample | Time for 5 mL flow (seconds) | Time for 20 mL flow (seconds) |
|---|---|---|
| Water | 2 | 13 |
| 20% w/v glucose | 2.3 | 13.5 |
| 40% w/v glucose | 2.5 | 15 |
| 60% w/v glucose | 3 | 20 |
| 80% w/v glucose | 5 | 38 |
| ≥99% Glycerol | 256 | Not Determined |
| Sample 4 | 237 | Not Determined |

The increased time taken for a sample to flow out of the bottom of the syringe (i.e., has a lower flow rate) correlates with increased viscosity of the sample. The lower the flow rate, the more syrup-like/sticky and viscous the liquid sample is. Measured flow rates for Sample 4 are similar to glycerol and lower than all the glucose solutions tested. This property of Sample 4 makes it more useful than the glucose solutions and water as a binder in foodstuffs, such as cereal bars, as well as providing sweetness to the product.

Color: The color of Sample 4 corresponded to No. 30 by the Standard Reference Method (SRM), a method for color assessment of wort or beer as published in the recommended methods of the American Society of Brewing Chemists (ASBC Methods of Analysis, Beer 10. Spectrophotometric Color Method Approved 1958, rev. 2015. American Society of Brewing Chemists, St. Paul, Minn., U.S.A). Briefly, the absorbance of a sample is measured in a cell of path length 1 cm at a wavelength of 430 nm. The resultant absorbance value is multiplied by 12.7 to yield the color value. Given the turbidity of Sample 4, absorbance could not be measured, and an assessment was made by optical comparison to the SRM No. 30 (a dark red/brown color).

Anion exchange chromatography: Analysis of Sample 4 by high-performance anion exchange chromatography (HPAEC) was performed using a Thermo Fisher Scientific DIONEX ICS-6000 system fitted with CarboPac PA200 Analytical column (3×250 mm) and CarboPac PA200G Guard column (3×50 mm) and Dionex ED Electrochemical Detector. Data was acquired with Chromeleon 7 software.

Eluents A (milli Q water), B (250 mM NaOH), and C (250 mM NaOH+1 M Sodium Acetate) were used to produce a mobile phase with the gradient profile shown in Table 2.

TABLE 2

Gradient Profile

| Time (min) | Flow (ml/min) | % A | % B | % C |
|---|---|---|---|---|
| 0 | 0.5 | 75 | 25 | 0 |
| 3 | 0.5 | 75 | 25 | 0 |
| 6 | 0.5 | 50 | 50 | 0 |
| 15 | 0.5 | 50 | 42.5 | 7.5 |
| 20 | 0.5 | 0 | 0 | 100 |
| 23 | 0.5 | 75 | 25 | 0 |
| 26 | 0.5 | 75 | 25 | 0 |

Sample for analysis was prepared by diluting Sample 4 100-fold and passing through a 0.45 μm syringe filter and the injection volume of analyte was 10 μl.

Figure 5:
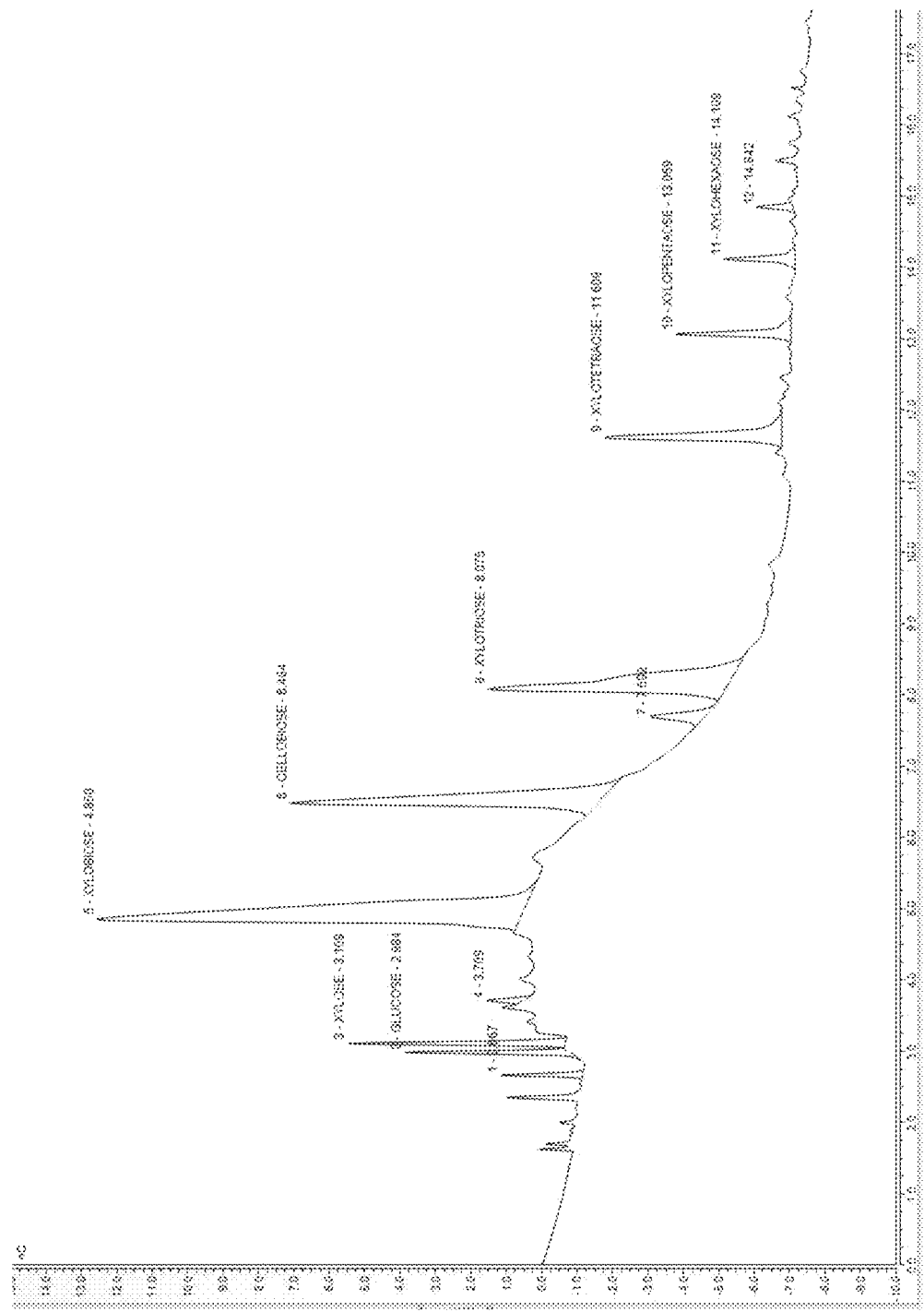
FIG. 5 depicts a high-performance anion exchange chromatography (HPAEC) analysis of Sample 4.

HPAEC analysis (see FIG. 5) confirmed that Sample 4 is a mixture of monosaccharides, disaccharides, and other oligosaccharides composed of glucose and xylose. This is in contrast to syrups typically used in the food industry such as corn syrup and high-fructose corn syrup that contain primarily monosaccharides of glucose and fructose. As a result, the product in Sample 4 when used in foodstuffs is expected to have fewer calories, a lower glycemic index, and contain fiber, in contrast to corn syrup and/or high-fructose corn syrup.

Example 10—Cold-Pressed Fruit Cereal Bar

A cold-pressed fruit cereal bar was made as follows:
1. 120 g of Sample 4 from Example 8 was heated with 30 g coconut oil, and one-quarter (¼) teaspoon of cinnamon was added.
2. Once foaming, the mixture was removed from the heat and 40 g oats, 40 g dried dates, 10 g of crisped rice, and 10 g seeds were added.
3. The ingredients were mixed thoroughly until all components were coated and the mixture was transferred into a freezer bag and into a freezer. The contents of the bag were rolled to a thickness of 7-10 mm and chilled at 4° C. overnight before cutting into rectangles.

Figure 6:
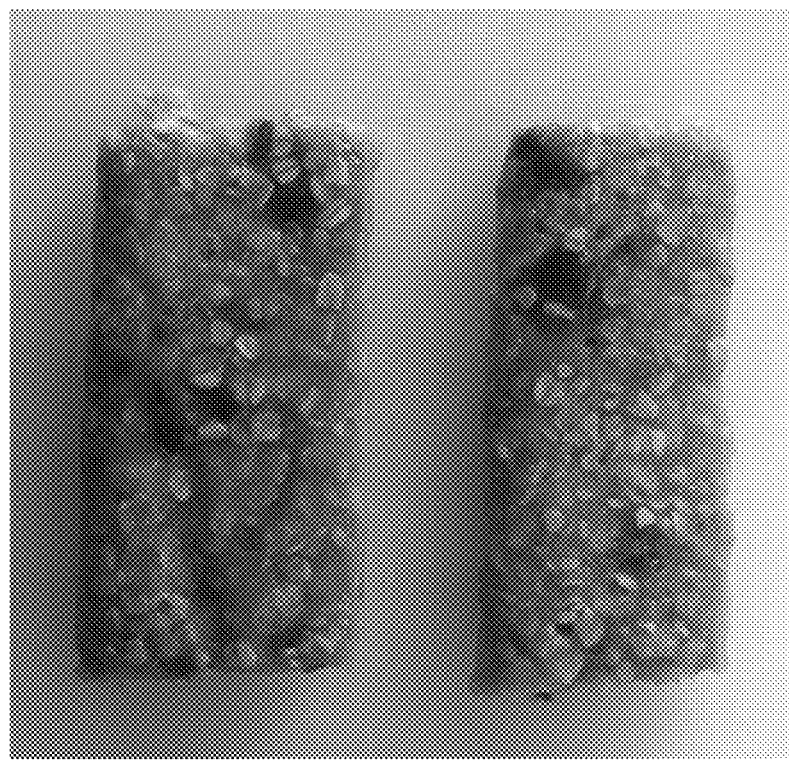
FIG. 6 depicts cereal bars produced using a liquid ingredient of the present disclosure.

The resulting product (shown in FIG. 6) was a chewy, sticky cereal bar, which was loosely set, and containing oats and crisped rice with perceivable sweetness delivered through Sample 4 and chopped dates.

Example 11—Producing the Ingredient in a Large Manufacturing Process

The following steps can be used to produce the ingredient in a large manufacturing process:

1. Physical pretreatment of a plant biomass: Mix 100 kg of milled corncob with water at a concentration of 15% (w/w) solids in suspension. Start mixing and heat to 95° C. and mix for 60 min at 95° C. Add 6 kg of sodium hydroxide (0.2-3% by weight of corncob) and continue stirring. Heat to a temperature of 95° C. and mix for 60 minutes to release the hemicelluloses present in corncob. At the end of the 60 minutes, cool down to 50° C. and adjust pH to 5.5 with sulfuric acid.
2. Removal of portion of soluble polysaccharide: Remove of a portion of the soluble phase corresponding to 5-30% of the total xylan. Neutralize with sulfuric acid and concentrate and purify by ultrafiltration. Remove any precipitated polymer.
3. Hydrolysis: Add cellulolytic enzymes (e.g., from *Trichoderma reesei*) to the milled corncob mixture and incubate at ~50° C. for 12-72 hours.
4. Separation of the biomass: At the end of the hydrolysis, separate the liquid from the products through a solid-liquid separator such as a filter press or decanting centrifuge.
5. Enzyme separation following enzymatic hydrolysis: The liquid fraction from the slurry contains enzymes, oligosaccharides, water, and salts that need to be separated. Use a 3 kDa or 10 kDa hollow fiber membrane to separate the enzyme proteins and other macromolecules.
6. Salts are removed using ion-exchange columns at ≤45° C.
   a. Cation column: Strongly acidic cation exchange resin, cross-linked polystyrene matrix, sulfonate functional group, and $Na^+$ counter-ion.
   b. Anion column: Macroporous, weakly basic anion exchange resin, cross-linked polystyrene matrix, dimethyl-tertiary amine functional group, and $OH^-$ counterion.
7. Oligosaccharides concentration: The desired oligosaccharides are selectively concentrated through nanofiltration at room temperature.
8. Concentration: Optionally concentrate the liquid to 40-75% at 60-80° C.
9. Recombination: Combine purified soluble polymer with enzyme-yielded oligomers at a dry weights ratio of 5:95-20:80.
10. Spray drying: Spray dry the resultant solution with inlet temperatures of 130-160° C. and outlet temperatures of 65-85° C.

Example 12—Use of the Liquid Ingredient to Manufacture an Extruded Cereal Bar The following steps can be performed to use a liquid ingredient as provided herein to manufacture an extruded cereal bar:

1. A 120 kg solution comprising 10.5 kg xylan, 57 kg xylo-oligosaccharides, and 7.5 kg cellobiose is heated with 130 kg coconut oil and transferred into a high-speed mixer. 200 kg rolled oats and 25 kg chopped date/raisin mixture are added and mixed thoroughly. This is pulsed through a dough mixer and set at 20 psi through a dough feed system.
2. The mixture is transferred via belt and ramshorn and baked for 20 minutes at 180° C. The product is then transferred via oven travellator onto a biscuit cutting line and then to variable form fill and seal packaging when cooled to <5° C.
3. The resulting product is a soft, sticky cereal bar that is loosely set and full of oats. Sweetness is delivered through the liquid solution comprising 10.5 kg xylan, 57 kg xylo-oligosaccharides, 7.5 kg cellobiose, and chopped dates in the bar. The liquid solution comprising 10.5 kg xylan, 57 kg xylo-oligosaccharides, 7.5 kg cellobiose, and the coconut oil both act as binders to hold the other ingredients in the bar together and give the bar its structure.

Example 13—Use of the Liquid Ingredient to Manufacture an Extruded Breakfast Cereal The following steps can be performed to use a liquid ingredient as provided herein to manufacture an extruded breakfast cereal:

1. Cereal flours (about 85-75% w/v) are combined with a solution comprising 22.5 g xylan, 30 g cellobiose, and 97.5 g xylo-oligosaccharides per 100 g water (about 15-25% v/v), as well as any additives such as preservatives, and vitamins and minerals for fortification to form a dough. This is extruded using a twin screw extruder, which cooks the product using a combination of heat and moisture addition and/or steam and mechanical sheer, forming the product's shape by pushing it through a nozzle. The product is then puffed until light in texture and golden in color and cooled.
2. The result is a light, crispy, shaped breakfast cereal product. The liquid solution comprising 22.5 g xylan, 30 g cellobiose, and 97.5 g xylo-oligosaccharides gives the product sweetness and helps to form the structure of the dough before extrusion.

Example 14—Use of the Liquid Ingredient to Manufacture a Tomato Ketchup

The following steps can be performed to use a liquid ingredient as provided herein to manufacture a tomato ketchup:

1. 4 onions and 250 g celery are blended until finely chopped in a food processor. They are fried in 5 tbsp vegetable oil on a low heat for 5 minutes. 4 sliced cloves of garlic are added and cooked for a further 5 minutes. 1 tsp ground coriander, 1 short cinnamon stick, 1 tsp all spice, one-half (½) tsp ground black pepper, and 2 tsp celery salt are added and cooked for a further minute.
2. To the mixture, 2 kg ripe, chopped tomatoes, 3 tbsp tomato puree, one-half (½) tsp chili sauce, 200 mL white wine vinegar, and 285 mL of a solution comprising 22.5 g xylan, 30 g cellobiose, and 97.5 g xylo-oligosaccharides per 100 g water, are added. The mixture is brought back to the boil and left uncovered to simmer for an hour until the tomatoes are soft. The cinnamon stick is discarded, the sauce mixture is blended until smooth, and then sieved.
3. The resulting product is a smooth, tangy tomato ketchup. The liquid solution comprising 22.5 g xylan, 30 g cellobiose, and 97.5 g xylo-oligosaccharides sweetens the product and adds body to the sauce, helping to thicken the sauce and bulk the sauce out.

Example 15—HPAEC Chromatography of Saccharides in Water Post Washing of Corncobs Corncobs were incubated at 100 g/L in room temperature water ("Wash" in Table 3), then water was decanted. Water was added to original total volume and heated to 90° C. for 60 minutes ("Wetting" in Table 3) before being heated at 90° C. for 60 minutes in dilute NaOH ("Pretreating" in Table 3).

Figure 7:
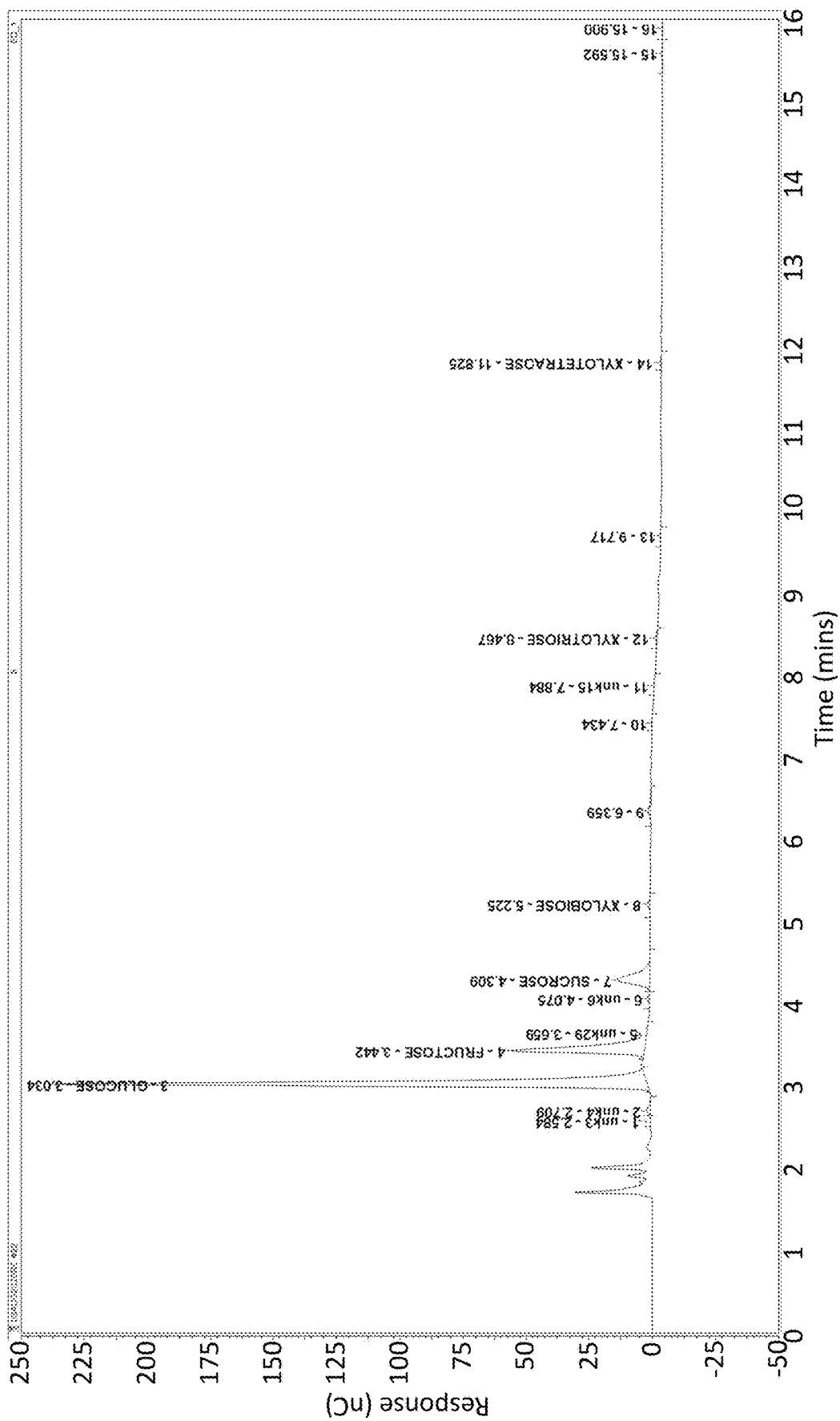
FIG. 7 depicts an HPAEC chromatogram of the saccharides in the water post-washing of corncobs.

HPAEC was performed on the Wash, Wetting, and Pretreating samples and saccharide peaks were identified (see FIG. 7 for example chromatogram from "Wash"). As indicated in Table 3, about 2% of the corncob at the start of the process is glucose that can be washed out and potentially more glucose may be washed out. It was also noted that the pH after the washing step decreased to 4.5.

TABLE 3

| Step | Glucose (g/l) |
| --- | --- |
| Wash | 2.43 g/l |
| Wetting | 1.43 g/l |
| Pretreating | 0.02 g/l |

Example 16—Quantifying Sugars and Organic Acids

Figure 10A:
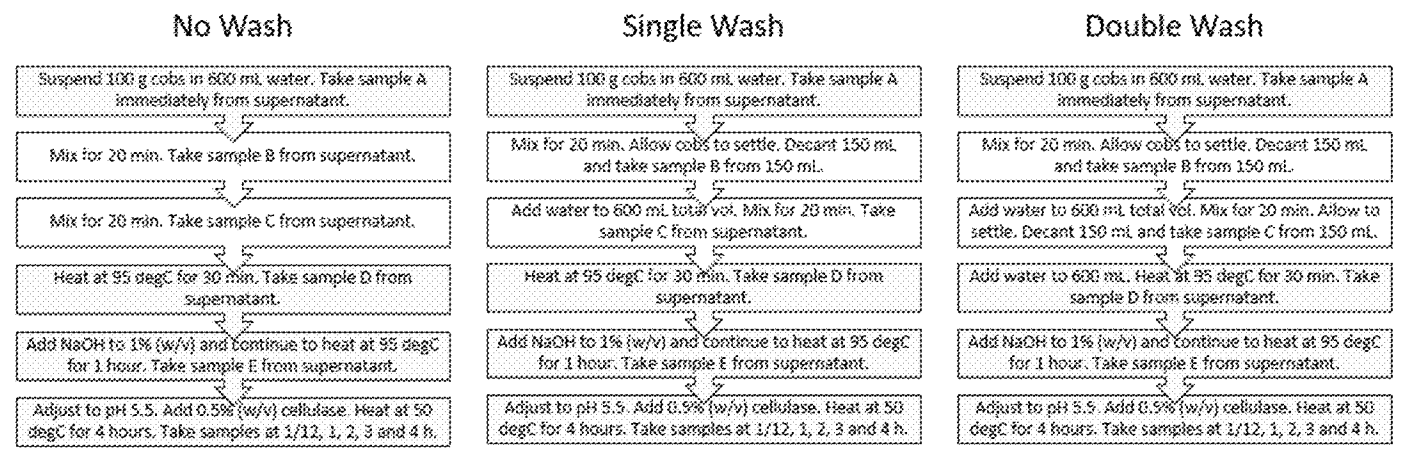
Figure 10B:
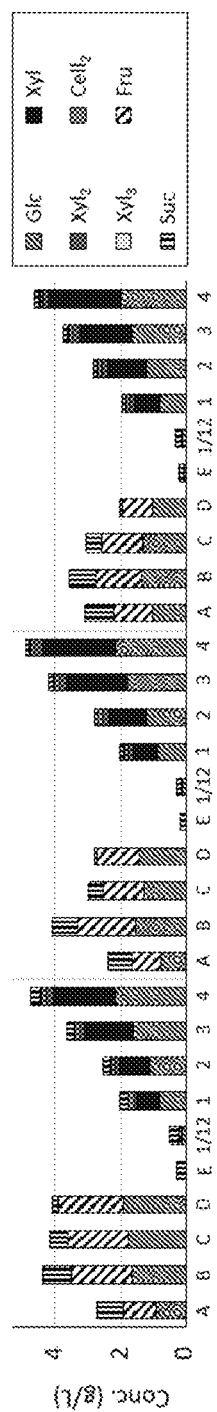
FIG. 10B depicts measurement of saccharides in multiple samples.
Figure 10C:
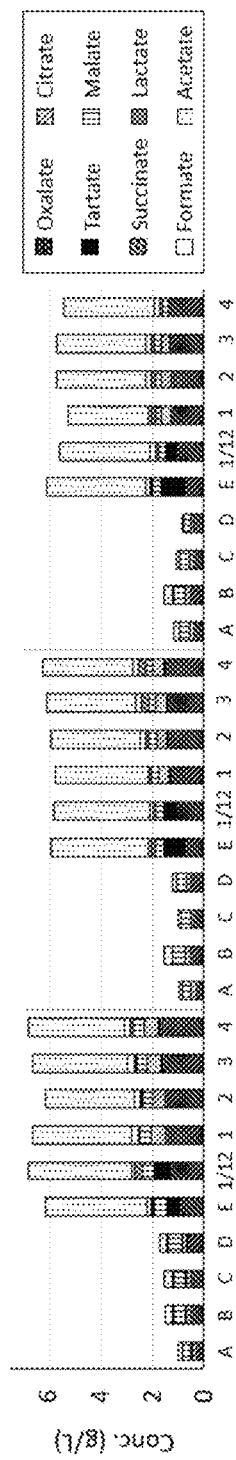
FIG. 10C depicts measurement of organic acids in multiple samples.

To quantify the impact of the prewashing step on the process, three separate batches of corncobs were treated according to the procedures outlined in FIG. 10A. Samples were analyzed by HPLC for saccharides (FIG. 10B) and HPLC for organic acids (FIG. 10C). The differences in the saccharide and organic acid compositions that were isolated from the different samples (Samples A-E and 5 minutes (1/12 hour) to 4 hours) indicate the impact of washing. The impact of the prewashing may have been greater had more than 150 mL of the 600 mL per wash been extracted. Accordingly, these data indicate the direction that washing can take but not washing's limit.

As shown, glucose, fructose, and sucrose all decreased with prewashing. Fructose and glucose are largely broken down during NaOH treatment, but sucrose is resistant to NaOH treatment. Because sucrose cannot generally be removed from other disaccharides through filtration, it can be useful to remove it by washing. Table 4 shows a comparison of the saccharides in Sample Ds ("No Wash" and "Double Wash") and Table 5 shows a comparison of saccharides in the four-hour samples ("No Wash" and "Double Wash").

TABLE 4

| | No Wash (g/L) | Double Wash (g/L) | Change (g/L) | Change (%) |
| --- | --- | --- | --- | --- |
| Glucose | 1.888 | 1.001 | −0.887 | −47.0 |
| Xylose | 0.000 | 0.000 | 0.000 | 0 |
| Xylobiose | 0.000 | 0.000 | 0.000 | 0 |
| Cellobiose | 0.000 | 0.000 | 0.000 | 0 |
| Xylotriose | 0.000 | 0.000 | 0.000 | 0 |
| Fructose | 1.966 | 0.958 | −1.008 | −51.3 |
| Sucrose | 0.232 | 0.045 | −0.188 | −80.6 |

TABLE 5

| | No Wash (g/L) | Double Wash (g/L) | Change (g/L) | Change (%) |
| --- | --- | --- | --- | --- |
| Glucose | 2.132 | 1.987 | −0.145 | −6.8% |
| Xylose | 1.917 | 2.145 | +0.228 | +11.9% |
| Xylobiose | 0.188 | 0.205 | +0.017 | +9.1% |
| Cellobiose | 0.167 | 0.110 | −0.057 | −34.1% |
| Xylotriose | 0.013 | 0.024 | +0.011 | +84.6% |
| Fructose | 0.000 | 0.000 | 0 | 0 |
| Sucrose | 0.292 | 0.125 | −0.167 | −57.19% |

Prior to the start of the "caustic cook" step (e.g., thermochemical step), prewashing lead to a reduction of about 50% of glucose and fructose and about 80% of sucrose. At the end of the hydrolysis, prewashing lead to small differences in small sugars. Xylose-based sugars appear to increase in concentration (as evidenced by the negative change), while glucose and cellobiose decrease in concentration.

A large amount of the organic acids detected are not products of the washing but rather of the pretreatment. However, the unwashed biomass appears to have a higher total loading of organic acids than the two-times washed material.

Acid concentration for the washed biomass also appears lower for the steps leading to the pretreatment stage. Table 6 shows a comparison of the Sample Ds and Table 7 shows a comparison of the four-hour samples.

TABLE 6

| | No Wash (g/L) | Double Wash (g/L) | Change (g/L) | Change (%) |
| --- | --- | --- | --- | --- |
| Oxalate | 0.641 | 0.402 | −0.239 | −37.3% |
| Citrate | 0.186 | 0.092 | −0.094 | −50.5% |
| Tartrate | 0.016 | 0.013 | −0.003 | −18.8% |
| Malate | 0.518 | 0.286 | −0.232 | −44.8% |
| Succinate | 0.063 | 0.002 | −0.061 | −96.8% |
| Lactate | 0.000 | 0.000 | 0 | 0 |
| Formate | 0.000 | 0.000 | 0 | 0 |
| Acetate | 0.295 | 0.003 | −0.292 | −99.0% |

TABLE 7

| | No Wash (g/L) | Double Wash (g/L) | Change (g/L) | Change (%) |
| --- | --- | --- | --- | --- |
| Oxalate | 1.776 | 1.355 | −0.421 | −23.7% |
| Citrate | 0.551 | 0.000 | −0.551 | −100.0% |
| Tartrate | 0.000 | 0.000 | 0 | 0 |
| Malate | 0.403 | 0.240 | −0.163 | −40.4% |
| Succinate | 0.037 | 0.000 | −0.037 | −100.0% |
| Lactate | 0.078 | 0.141 | +0.063 | +80.8% |
| Formate | 0.257 | 0.187 | −0.07 | −27.2% |
| Acetate | 3.727 | 3.512 | −0.215 | −5.8% |

Impact of washing on organic acid content, as shown in "Change" (calculated by "No Wash" minus "Double Wash"), is noticeable both at the end of the wetting stage (Sample D) and at the end of the hydrolysis reaction (4-hour Sample) (see, e.g., Tables 6 and 7). At the end of the wetting stage (Sample D), all other acids except for lactate and formate (n/d) were detected and were at a lower concentration for the material that has been washed twice.

At the end of the hydrolysis, acetate content is higher (hydrolysis releases acetate). Other acids continue to be lower for the washed biomass than the unwashed (with the exception of lactate, which is present in low concentrations).

Figure 10D:
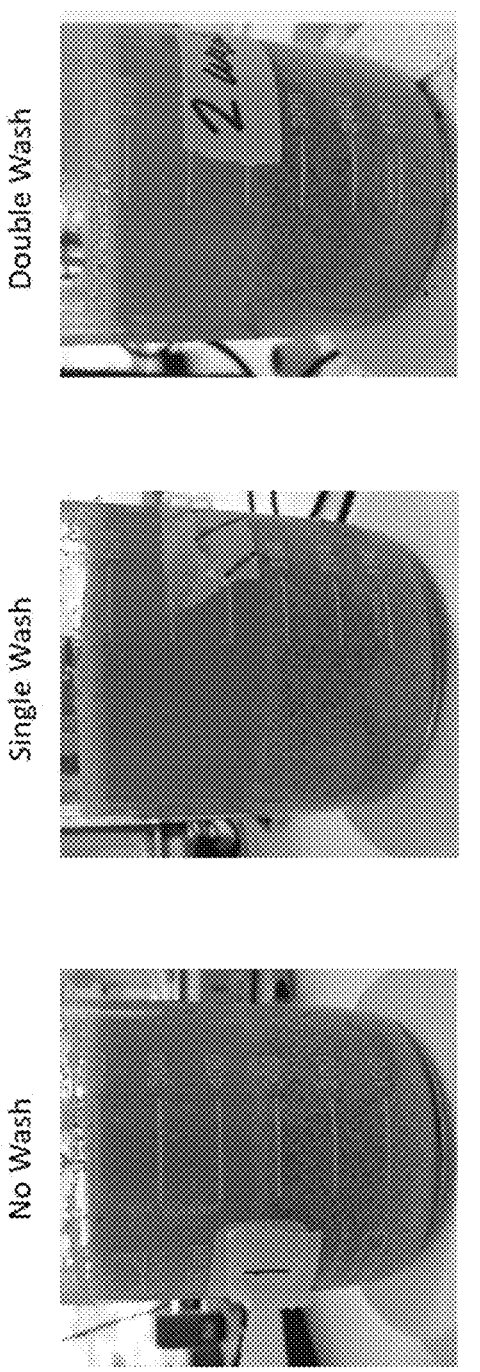
FIG. 10D depicts and visual observation of the samples processed according to the methods of FIG. 10A.

Visual observation of the samples is shown in FIG. 10D. After two washes, the corncobs released fewer colored compounds and the liquor is lighter. Without being bound by any one particular theory, colored compounds are likely phenols and organic acids released during washing.

Example 17—Comparison of Cold-Pressed Cereal Bar

Cold-press cereal bars were prepared according to the recipe as before (see Example 10).

Soluble polysaccharides and insoluble polysaccharides were used in the cereal bars for comparison. The soluble and insoluble polysaccharides were as follows:
- Soluble polysaccharides: 60 mL water containing 94 g dry ingredient with a composition 10% dry w/w cellobiose, 75% xylo-oligosaccharides, and 15% extracted water-soluble polymer (Sample 4 as described above in Example 8).
- Insoluble polysaccharides: 60 mL water containing 94 g dry ingredients with a composition 10% dry w/w cellobiose, 75% xylo-oligosaccharides, and 15% micro-crystalline cellulose.

Figure 11A:
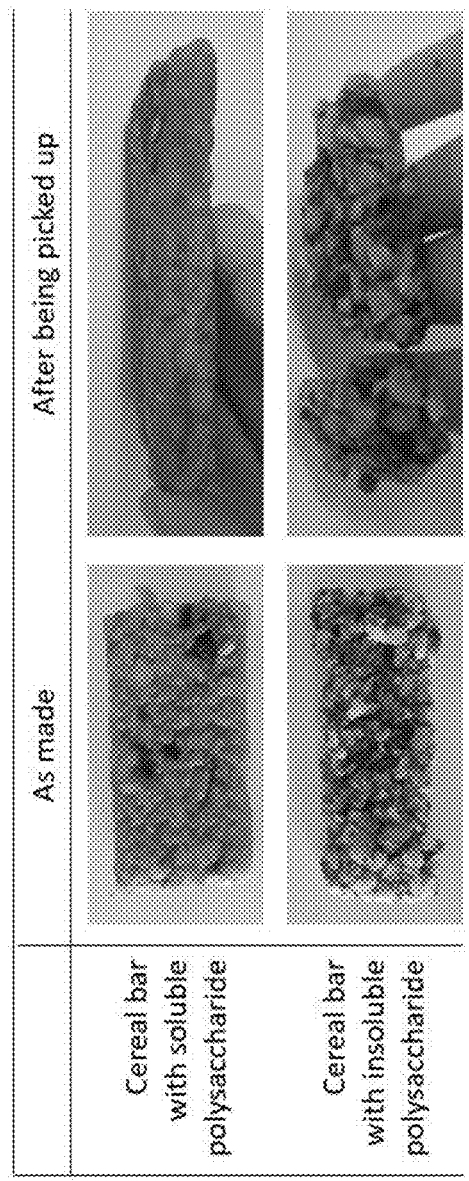
FIG. 11A illustrates a comparison between a cereal bar made using soluble polysaccharides and a cereal bar made using insoluble polysaccharides.

With reference to FIG. 11A, while cereal bars made with insoluble polysaccharide looked like solid bars when placed on the table, they started falling apart as soon as they were lifted from the table and taken in hand due to their soft texture and the ingredients not being bound together well. In contrast, cereal bars made with soluble polysaccharide could be handled with ease and maintained their shape.

Hardness and stickiness of the cereal bars were measured using the TA-XTPlusC Texture Analyser (Stable Microsystems, UK) using the "ExponentC" software. Sample with 9.6 cm×3.8 cm×1 cm dimensions (L×W×H) was placed centrally under the probe. A 6 mm diameter aluminium cylindrical probe was used in a penetration test with "Return To Start" mode and 30 kg load-cell. Once the probe triggered on the surface, it penetrated the 2 mm distance into the sample with 2 mm/s speed. At this point (2 mm depth), the force value was recorded and taken as a measure of "hardness" of the sample. The probe then withdrew from the sample at which point the maximum force to withdraw or "stickiness" was recorded. Pre-test speed was 1 mm/s and post-test speed 10 mm/s.

Figure 11B:
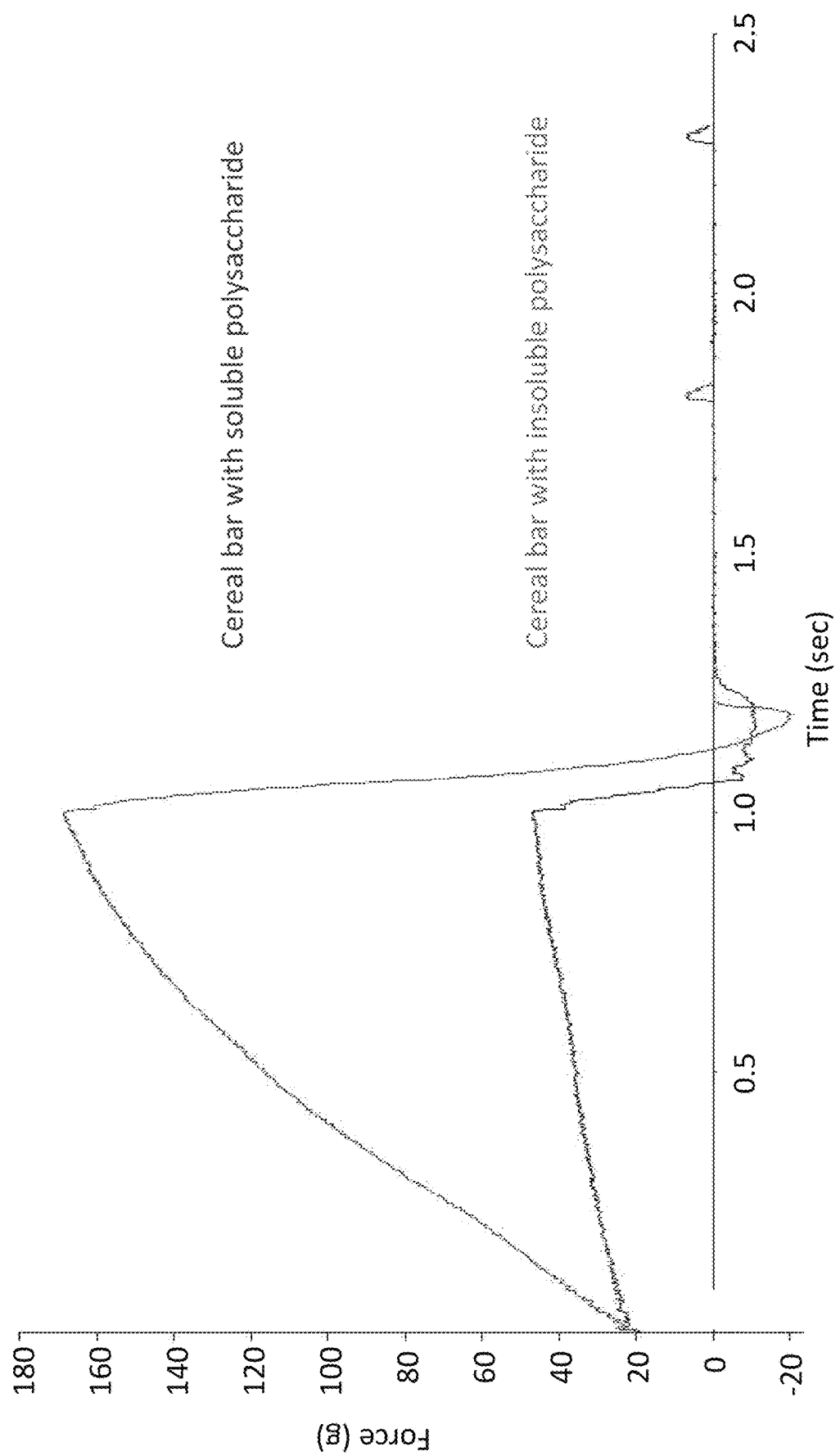
FIG. 11B depicts the hardness and stickiness of the cereal bars of FIG. 11A using a penetration test.

Results showed that the hardest bar was the one made with soluble ingredient, while lower values were obtained for insoluble ingredient (FIG. 11B). Likewise, the soluble polysaccharide-containing bar had higher stickiness and the insoluble polysaccharide-containing bar lower stickiness. These results confirmed visual and tactile observations.

TABLE 8

Results

| Sample | Hardness (g) | Stickiness (g) |
| --- | --- | --- |
| Cereal bar with soluble polysaccharide | 169.19 | −20.33 |
| Cereal bar with insoluble polysaccharide | 47.43 | −11.24 |

TABLE 9

Texture Analyzer Settings

| Mode: | Measure Force in Compression |
| --- | --- |
| Option: | Return To Start |
| Pre-Test Speed: | 1.0 mm/s |
| Test Speed: | 2.0 mm/s |

TABLE 9-continued

Texture Analyzer Settings

| Mode: | Measure Force in Compression |
| --- | --- |
| Post-Test Speed: | 10.0 mm/s |
| Distance: | 2 mm |
| Trigger Type: | Auto - 20 g |
| Tare Mode: | Auto |
| Data Acquisition Rate: | 400 pps |

Hardness of cereal bars was further measured using the TA-XTPlusC Texture Analyser (Stable Microsystems, UK) using the "ExponentC" software. Sample with 9.6 cm×3.8 cm×1 cm (L×W×H) dimensions was placed centrally under the knife. A Knife Edge was used in a cutting test with "Return To Start" mode and 30 kg load-cell. Once the knife triggered on the surface, it penetrated 5 mm into the sample with 2 mm/s test speed. Maximum force measured during the cutting test was recorded as hardness of the sample. Pre-test speed was 1.5 mm/s and post-test speed was 10 mm/s.

Figure 11C:
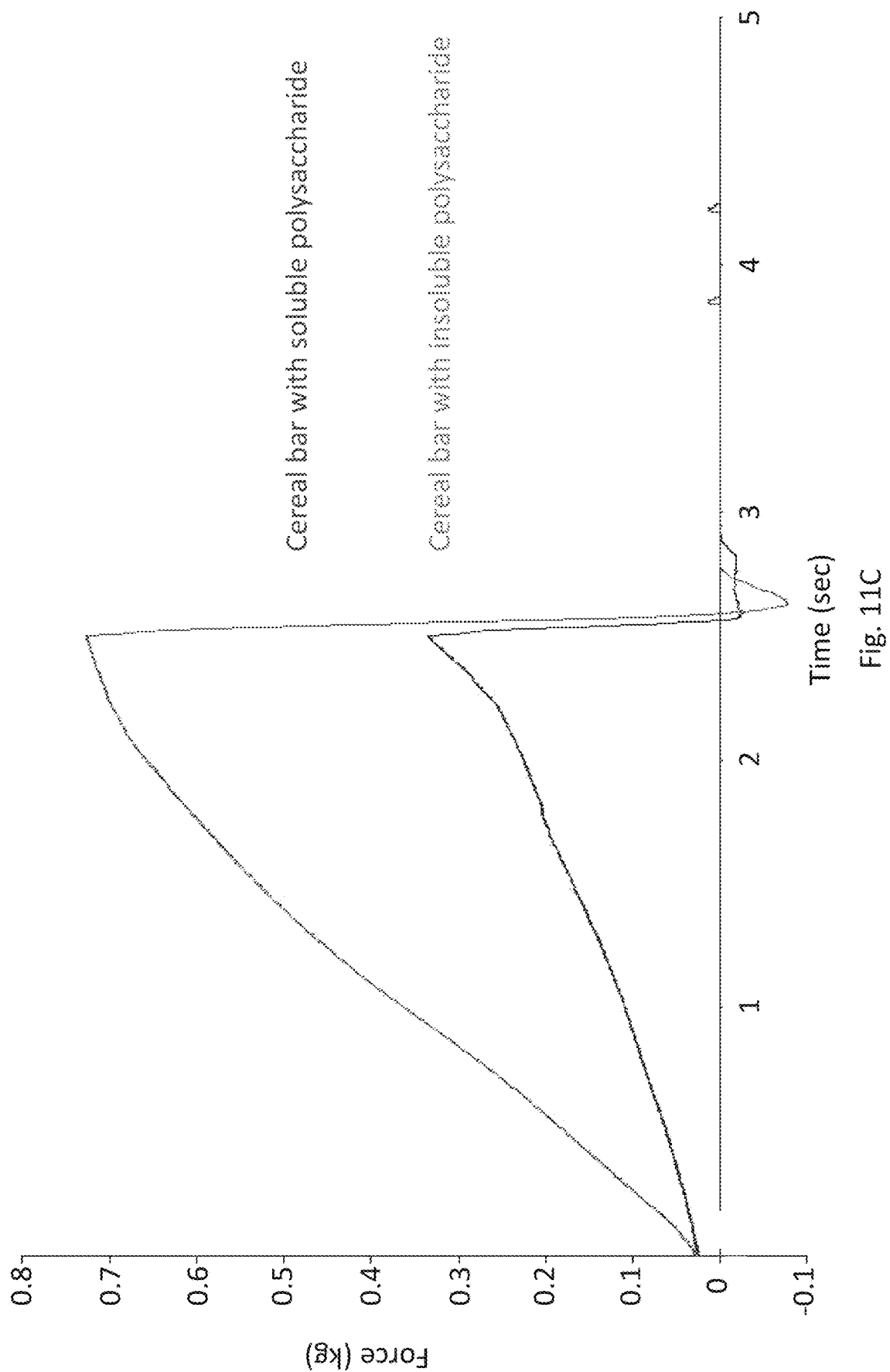
FIG. 11C depicts the hardness of the cereal bars of FIG. 11A using a cutting test.

Results obtained using the cutting method confirm the results obtained using the penetration method described above. Results show that the hardest bar was the one made with soluble polysaccharides, while lower values were obtained for insoluble polysaccharide-containing bars, the insoluble polysaccharide-containing bar being softer (FIG. 11C).

TABLE 10

Results

| Sample | Hardness (kg) |
| --- | --- |
| Cereal bar with soluble polysaccharide | 0.73 |
| Cereal bar with insoluble polysaccharide | 0.34 |

TABLE 11

Texture Analyzer Setting

| Mode: | Measure Force in Compression |
| --- | --- |
| Option: | Return To Start |
| Pre-Test Speed: | 1.5 mm/s |
| Test Speed: | 2.0 mm/s |
| Post-Test Speed: | 10.0 mm/s |
| Distance: | 5 mm |
| Trigger Type: | Auto - 25 g |
| Tare Mode: | Auto |
| Data Acquisition Rate: | 400 pps |

Example 18—Viscosity of Saccharide Composition with Insoluble Polysaccharide vs. Soluble Polysaccharide The following samples were prepared:
Sample 1: 60 mL water containing 94 g dry ingredients with a composition 10% dry w/w cellobiose, 75% xylo-oligosaccharides, and 15% extracted water-soluble polymer.

Sample 2: 60 mL water containing 94 g dry ingredient with a composition 10% dry w/w cellobiose, 75% xylo-oligosaccharides, and 15% micro-crystalline cellulose.

"Sample 4" of Example 8, "Soluble polysaccharides" of Example 17, and "Sample 1" of Example 18 are substantially identical and/or interchangeable. Further, "Sample 2" of Example 18 and "Insoluble polysaccharides" of Example 17 are substantially identical and/or interchangeable.

Sample were analyzed for flow characteristics as described in Example 9. Data confirm that soluble polysaccharides modulate the viscosity of the oligosaccharide composition (Table 12). This can enable fine-tuning of solution viscometric properties in a way not generally possible with oligosaccharide alone.

TABLE 12

| Sample | Time for 5 mL flow (seconds) | Time for 20 mL flow (seconds) |
| --- | --- | --- |
| Water | 2 | 13 |
| 20% w/v glucose | 2.3 | 13.5 |
| 40% w/v glucose | 2.5 | 15 |
| 60% w/v glucose | 3 | 20 |
| 80% w/v glucose | 5 | 38 |
| ≥99% Glycerol | 256 | Not Determined |
| Oligosaccharides with soluble polysaccharide (Sample 1) | 237 | Not Determined |
| Oligosaccharides with insoluble polysaccharide | 29 | 58 |

```
                    Sequence Listing

LPMO
AA9 LPMO from Podospora anserina (SEQ ID NO: 1).
Genbank ID CAP67740
   1 mkgllsvaal slavsevsah yifqqlstgs tkhgvfqyir qntnynspvt dlssndlrcn
  61 eggasgantq tvtvragdsf tfhldtpvyh qgpvsvylsk apgsassydg sgtwfkikdw
 121 gptfpggqwt lagsytaqlp scitdgeyll riqslgihnp ypagtpqfyi scaqikvtgg
 181 gsvnpsgvai pgafkatdpg ytaniysnfn sytvpgpsvf scgsnggqss pvepqpqptt
 241 tlvtstrapv atqpagcava kwgqcggngw tgcttcaags tcntqnayyh qcv Lichenase
GH16 lichenase from Bacillus subtilis subsp. subtilis str. 168 (SEQ ID NO: 2).
GenBank ID CAA86922.1
   1 mpylkrvlll lvtglfmslf avtatasaqt ggsffdpfng ynsgfwqkad gysngnmfnc
  61 twrannvsmt slgemrlalt spaynkfdcg enrsvqtygy glyevrmkpa kntgivssff
 121 tytgptdgtp wdeidieflg kdttkvqfny ytngagnhek ivdlgfdaan ayhtyafdwq
 181 pnsikwyvdg qlkhtatnqi pttpgkimmn lwngtgvdew lgsyngvnpl yahydwvryt
 241 kk Xylanase
GH5 arabinoxylanase from Ruminiclostridium thermocellum (SEQ ID NO: 3).
GenBank ID ABN53395.1
   1 mgasiktsik irtvafvsii aialsilsfi pnrayaspqr grprlnaart tfvgdngqpl
  61 rgpytstewt aaapydqiar vkelgfnavh lyaecfdpry papgskapgy avneidkive
 121 rtrelglylv itigngannq nhnaqwardf wkfyapryak ethvlyeihn epvawgppys
 181 sstanppgav dmeidvyrii rtyapetpvl lfsyavfggk ggaaealkdi rafnkavfgn
 241 enavwtneav afhgyagwqe ttiaveellk agypcfmtey aggawgsgmg gldveltyel
 301 erlgvswltf qyipptgvsd dvtkpeyfsa lvensglswt pdygnwpaar gvygngglar
 361 etatwinnfl tgttrieaed fdwggngvsy ydtdsvnvgg qyrpdegvdi ektsdtgggy
 421 nvgwisegew leytirvrnp gyynlslrva gisgsrvqvs fgnqdktgvw elpatggfqt
 481 wttatrqvfl gaglqklrin alsggfnlnw ielspistgt ipdgtykfln rangktlqev
 541 tgnnsiitad ykgiteqhwk iqhigggqyr issagrgwnw nwwmgfgtvg wwgtgsstcf
 601 iisptgdgyy rivlvgdgtn lqissgdpsk iegkafhgga nqqwailpvs apafptglsa
 661 vldssgntan ltwnaapgan synvkrstks ggpyttiatn itstnytdtg vatgtkyyyv
 721 vsavsngvet lnsaeailqy pkltgtvigt qgswnnignt ihkafdgdln tffdgptang
 781 cwlgldfgeg vrnvitqikf cprsgyeqrm iggifqgank edfsdavtlf titslpgsgt
 841 ltsvdvdnpt gfryvrylsp dgsngniael qffgtpagee nddvhlgdin ddgninstdl
 901 qmlkrhllrs irltekqlln adtnrdgrvd stdlallkry ilrvittl GH5 xylanase from Gonapodya prolifera (SEQ ID NO: 4).
GenBank ID KXS18720.1
   1 marlsslial vlafvavsap alaargrprl ngktfvadsg vplrgpftst ewtpavpaan
  61 ianmrnynfn aihlyaetfd pnypaagsqk pgyaatrvdq ivaatkaanm yvvivlanga
 121 nngkfnlnya kdfwsfyaar yknethviye ihnepvqwgp pyisstqspg avsmnadcyk
 181 iiravapdtp vllftyasig ggssaagavk daqsfntavf gnanaqwtne aiaihgywga
 241 qgasdaakal naagfsvvlt efaaatspts pnggqdtvlt gfmeqqgvsw ltflhvpptg
 301 vsgdvtdpnq ytnrmtaagi gfdrdpglna vgggqaapvp vpapapvpsp vpapvpavpa
 361 vrtttarpap spspvpapvp apapvpapvp apvpapvpap vpapvpaspa attttrhrtr
 421 pprtttapav papppaatpk veg GH30 xylanase from Dickeya chrysanthemi (SEQ ID NO: 5).
GenBank ID AAB53151.1
   1 mngnvslwvr hclhaalfvs atagsfsvya dtvkidanvn yqiiqgfggm sgvgwindlt
  61 teqintaygs gvgqiglsim rvridpdssk wniqlpsarq avslgakima tpwsppaymk
 121 snnslinggr llpanysayt shlldfskym qtngaplyai siqnepdwkp dyescewsgd
 181 efksylksqq skfgslkviv aeslgfnpal tdpvlkdsda skyvsiiggh lygttpkpyp
 241 laqnagkqlw mtehyvdskq sannwtsaie vgtelnasmv snysayvwwy irrsygllte
 301 dgkvskrgyv msqyarfvrp galriqaten pqsnvhltay kntdgkmviv avntndsdqm
 361 lslnisnanv tkfekystsa slnveyggss qvdssgkatv wlnplsvttf vsk
```

Sequence Listing

GH30 xylanase from *Bacillus subtilis* subsp. subtilis str. 168 (SEQ ID NO: 6).
GenBank ID CAA97612.1
```
  1 miprikktic vllvcftmls vmlgpgatev laasdvtvnv saekqvirgf ggmnhpawag
 61 dltaaqreta fgngqnqlgf silrihvden rnnwykevet aksavkhgai vfaspwnpps
121 dmvetfnrng dtsakrlkyn kyaayaqhln dfvtfmknng vnlyaisvqn epdyahewtw
181 wtpqeilrfm renagsinar viapesfqyl knlsdpilnd pqalanmdil gthlygtqvs
241 qfpyplfkqk gagkdlwmte vyypnsdtns adrwpealdv sqhihnamve gdfqayvwwy
301 irrsygpmke dgtiskrgyn mahfskfvrp gyvridatkn pnanvyvsay kgdnkvvviva
361 inksntgvnq nfvlqngsas nvsrwitsss snlqpgtnlt vsgnhfwahl paqsvttfvv
421 nr
```

GH30 xylanase from *Bacteroides ovatus* (SEQ ID NO: 7).
GenBank ID SDY64378.1
```
  1 mknitllfcl flanillgac sggedekkem degkgayalf lkksitvstg esqtdvvvew
 61 aktsweitlg egdivksvtp tsggsntgek qytkvrvscg anstmkkrtq tihlfdktne
121 ttvdllveqe ppfksvtltv dpsvkyqpvv gfggmynpki wcgdnlisas qldkmygagg
181 lgysilrlmi ypnesdwsad veaakaaqan gaiifacpwd ctdaladkit vngkemkhlk
241 kenyeayanh liryvtfmke kgvnlyaisv qnepdmefty wtpsevvdfv kqygariret
301 gvklmspeac gmqpeytdpi innaeafaqt dilaghlyqg ftdlssgyvk nrhdyicgvy
361 sriqgktwwm tehlfndgen sddsskwefl kwqyslnhlg keihmcmegy csayiywylk
421 rfyglmgdtd krsptsegei tkngyimahy aqyatettri kvvtnneevc ataywdektg
481 evtivllnln gasqwleipl agikkasave tnetknmevi dtglmesaeg itvllsansi
541 tsvrltf
```

Xyloglucanase
GH5 xyloglucanase from *Bacteroides ovatus* (SEQ ID NO: 8).
GenBank ID ALJ47680.1
```
  1 mekqsfsdgl fsplgikrvi fmlvllttsf iscsnsdekg gslevaqeyr nlefdargsr
 61 qtiqidgpae whistseswc ksshtigegk qyvnitvean dtqkertatv tvsasgapdi
121 iinvkqslys vpaydeyiap dntgmrdlts mqlsalmkag vnvgntfeav ivgndgslsg
181 detcwgnptp nkvlfegika agfdvvripv ayshqfedaa tykiksawmd kveaavkaal
241 daglyviini hweggwlnhp vdankealde rleamwkqia lrfrdyddrl lfagtnevnn
301 ddangaqpte enyrvqngfn qvfvntvrat ggrnhyrhli vqayntdvak avahftmpld
361 ivqnriflec hyydpydfti mpndenfksq wgaafaggdv satgqegdie atlsslnvfi
421 nnnvpviige ygptlrdqlt gealenhlks rndyieyvvk tcvknklvpl ywdagytekl
481 fdrttgqphn aasiaaimkg ln
```

GH74 xyloglucanase from *Trichoderma reesei* (SEQ ID NO: 9)
GenBank ID AAP57752.1
```
  1 mkvsrvlalv lgavipahaa fswknvklgg gggfvpgiif hpktkgvaya rtdigglyrl
 61 naddswtavt dgiadnagwh nwgidavald pqddqkvyaa vgmytnswdp sngaiirssd
121 rgatwsftnl pfkvggnmpg rgagerlavd pansniiyfg arsgnglwks tdggvtfskv
181 ssftatgtyi pdpsdsngyn sdkqglmwvt fdstssttgg atsrifvgta dnitasvyvs
241 tnagstwsav pgqpgkyfph kaklqpaeka lyltysdgtg pydgtlgsvw rydiaggtwk
301 ditpvsgsdl yfgfgglgld lqkpgtlvva slnswwpdaq lfrstdsgtt wspiwawasy
361 ptetyyysis tpkapwiknn fidvtsesps dglikrlgwm iesleidptd snhwlygtgm
421 tifgghdltn wdtrhnvsiq sladgieefs vqdlasapgg sellaavgdd ngftfasrnd
481 lgtspqtvwa tptwatstsv dyagnsvksv vrvgntagtq qvaissdgga twsidyaadt
541 smnggtvays adgdtilwst assgvqrsqf qgsfasvssl pagaviasdk ktnsvfyags
601 gstfyvskdt gssftrgpkl gsagtirdia ahpttagtly vstdvgifrs tdsgttfgqv
661 staltntyqi algvgsgsnw nlyafgtgps garlyasgds gaswtdiqqs qgfgsidstk
721 vagsgstagq vyvgtngrgv fyaqgtvggg tggtsssstkq ssssstssass sttlrssvvs
781 ttrastvtss rtssaagptg sgvaghyaqc ggigwtgptq cvapyvcqkq ndyyyqcv
```

Cellobiohydrolase
GH7 Cel7A cellobiohydrolase from *Trichoderma reesei* (SEQ ID NO: 10)
GenBank ID CAH10320.1
```
  1 myrklavisa flataraqsa ctlqsethpp ltwqkcssgg tctqqtgsvv idanwrwtha
 61 tnsstncydg ntwsstlcpd netcakncсl dgaayastyg vttsgnslsi gfvtqsaqkn
121 vgarlylmas dttyqeftll gnefsfdvdv sqlpcglnga lyfvsmdadg gvskyptnta
181 gakygtgycd sqcprdlkfi ngqanvegwe pssnnantgi gghgsccsem diweansise
241 altphpcttv gqeicegdgc ggtysdnryg gtcdpdgcdw npyrigntsf ygpgssftld
301 ttkkltvvtq fetsgainry yvqngvtfqq pnaelgsysg nelnddycta eeaefggssf
361 sdkggltqfk katsggmvlv mslwddyyan mlwldstypt netsstpgav rgscstssgv
421 paqvesqspn akvtfsnikf gpigstgnps ggnppggnrg ttttrrpatt tgsspgptqs
481 hygqcggigy sgptvcasgt tcqvlnpyys qcl
```

GH6 Cel6A cellobiohydrolase from *Trichoderma reesei* (SEQ ID NO: 11)
GenBank ID AAA34210.1
```
  1 mivgilttla tlatlaasvp leerqacssv wgqcggqnws gptccasgst cvysndyysq
 61 clpgaassss straasttsr vspttsrsss atpppgsttt rvppvgsgta tysgnpfvgv
121 tpwanayyas evsslaipsl tgamataaaa vakvpsfmwl dtldktplme qtladirtan
181 knggnyagqf vvydlpdrdc aalasngeys iadggvakyk nyidtirqiv veysdirtll
241 viepdslanl vtnlgtpkca naqsayleci nyavtqlnlp nvamyldagh agwlgwpanq
301 dpaaqlfanv yknasspral rglatnvany ngwnitspps ytqgnavyne klyihaigpl
361 lanhgwsnaf fitdqgrsgk qptgqqwgd wcnvigtgfg irpsantgds lldsfvwvkp
421 ggecdgtsds saprfdshca lpdalqpapq agawfqayfv qlltnanpsf l
```

Sequence Listing

Endoglucanase A egl-A-*Aspergillus niger* GH12 (SEQ ID NO: 12)
```
  1 mklpvtlaml aatamgqtmc sqydsassppp ysvnqnlwge yqgtgsqcvy vdklsssgas
 61 whtewtwsgg egtvksysns gvtfnkklvs dvssiptsve wkqdntnvna dvaydlftaa
121 nvdhatssgd yelmiwlary gniqpigkqi atatvggksw evwygsttqa gaeqrtysfv
181 sespinsysg dinaffsylt qnqgfpassq ylinlqfgte aftggpatft vdnwtasvn
```

*Aspergillus niger* endo-β-1,4-glucanase GH5,CBM1 (SEQ ID NO: 13)
```
  1 mrisnlivaa saasmvsalp srqmkkrdsg fkwvgtsesg aefgsalpgt lgtdytwpet
 61 skiqvlrnkg mnifripflm erltpdglts sfastylsdl kstvefvtns gayavldphn
121 ygrfdgsiit stsdfkttwk nvatefadnd kvifdtnney hdmeqslvld lnqaaingir
181 aagattqyif vegnaytgaw dwttyndnls gltdsedkii yemhqyldsd ssgtsetcvs
241 stigqerlek atewlktnnk qgivgefagg vnsvceeave gmlaymsens dvwvgaswws
301 agpwwgtymy sleptdgtay stylpileky fpsgdasass sasvsvaaat stastttaaf
361 eqtttpatqg psatnsagev nqyyqcggin wtgptvcasp ytckvqndyy yqcvae
```

*Aspergillus niger* endo-β-1,4-glucanase B GH5 (SEQ ID NO: 14)
```
  1 mkfqstllla aaagsalavp hgsghkkras vfewfgsnes gaefgtnipg vwgtdyifpd
 61 pstistligk gmnffrvqfm merllpdsmt gsydeeylan lttvvkavtd ggahalidph
121 nygryngeii sstsdfqtfw qnlagqykdn dlvmfdtnne yydmdqdlvl nlnqaaingi
181 raagasqyif vegnswtgaw twvdvndnmk nltdpedkiv yemhqyldsd gsgtsetcvs
241 gtigkeritd atqwlkdnkk vgfigeyagg sndvcrsavs gmleymannt dvwkgaswwa
301 agpwwgdyif sleppdgtay tgmidilety l
```

GH30 Xylanase from *Trichoderma reesei* (SEQ ID NO: 15)
```
  1 mkssisvvla llghsaawsy atksqyrani kinarqtyqt migggcsgaf giacqqfgss
 61 glspenqqkv tqilfdenig glsivrndig sspgttilpt cpatpqdkfd yvvwdgsdncq
121 fnltktalky npnlyvyada wsapgcmktv gtenlggqic gvrgtdckhd wrqayadylv
181 qyvrfykeeg idisllgawn epdfnpftye smlsdgyqak dflevlyptl kkafpkvdvs
241 ccdatgarqe rnilyelqqa ggeryfdiat whnyqsnper pfnaggkpni qtewadgtgp
301 wnstwdysgq laeglqwaly mhnafvnsdt sgythwwcaq ntngdnalir ldrdsyevsa
361 rlwafaqyfr farpgsvrig atsdvenvyv tayvnkngtv aipvinaahf pydltidleg
421 ikkrklseyl tdnshnvtlq srykvsgssl kvtvepramk tfwle
```

*Aspergillus niger* endo-β-1,4-xylanase 1 GH11 (SEQ ID NO: 16)
```
  1 mkvtaafagl ivtafaapvp epvivsrsag inyvqnyngn lgdftydesa gtfsmywedg
 61 vssdfvvglg wttgsskait ysaeysasgs ssylavygwv nypqaeyyiv edygdynpcs
121 satslgtvys dgstyqvctd trtnepsitg tstftqyfsv restrtsgtv tvanhfnfwa
181 qhgfgnsdfn yqvmaveaws gagsasvtis s
```

GH5 mannanase from *Trichoderma reesei* (SEQ ID NO: 17)
```
  1 mmmlsksils aataasalaa vlqpvprass fvtisgtqfn idgkvgyfag tncywcsflt
 61 nhadvdstfs hisssglkvv rvwgfndvnt qpspgqiwfq klsatgstin tgadglqtld
121 yvvqsaeqhn lkliipfvnn wsdygginay vnafggnatt wytntaaqtq yrkyvqavvs
181 ryanstaifa welgneprcn gcstdvivqw atsvsqyvks idsnhlvtlg degiglstgd
241 gaypytygeg tdfaknvqik sldfgtfhly pdswgtnytw gngwiqthaa aclaagkpcv
301 feeygaqqnp ctneapwqtt slttrgmggd mfwqwgdtfa ngaqsnsdpy tvwynssnwq
361 clvknhvdai nggttttpppv ssttttssrt sstppppggs csplygqcgg sgytgptcca
421 qgtciysnyw ysqclnt
```

*Aspergillus niger* endo-β-1,4-mannanase GH26 (SEQ ID NO: 18)
```
  1 mfaklsllsl ifssaalgas nqtlsygnid ksatpearal lkyiqlqygs hyisgqqdid
 61 swnwveknig vapailgsdf tyyspsavah ggkshavedv iqhagrngin alvwhwyapt
121 clldstakepw ykgfyteatc fnvseavndh gngtnyklli rdidaiaaqi krldqakvpi
181 ifrplhepeg gwfwgaqgp apfkklwdil ydritryhnl hnmvwvcnta dpawypgndk
241 cdiatidhyp avgdhgvaad qykklqtvtn nervlamaev gpipdpdkqa renvnwaywm
301 vwsgdfiedg kqnpnqflhk vyndtrvval nwega
```

*Aspergillus niger* β-mannanase GH5 (SEQ ID NO: 19)
```
  1 mklsnalltl aslalanvst alpkaspaps tsssaastsf astsglqfti dgetgyfagt
 61 nsywigfltd nadvdlvmgh ikssglkilr vwgfndvtsq pssgtvwyql hqdgkstint
121 gadglqrldy vvssaeqhdi kliinfvnyw tdyggmsayv sayggsgetd fytsdtmqsa
181 yqtyiktvve rysnssavfa welaneprcp scdtsvlynw iektskfikg ldadrmvcig
241 degfglnids dgsypyqfse glnftmnlgi dtidfgtlhl ypdswgtsdd wgngwitahg
301 aackaagkpc lleeygvtsn hcsvegswqk talsttgvga dlfwqygddl stgkspddgn
361 tiyygtsdyq clvtdhvaai gsa
```

*Aspergillus niger* cellobiohydrolase A GH7 (SEQ ID NO: 20)
```
  1 mhqrallfsa lltavraqqa gtlteevhps ltwqkctseg sctensgsvv idsnwrwths
 61 vndstncytg ntwdaticpd detcaancal dgadyestyg vttdgdsltl kfvtgsnvgs
121 rlylmdtsde gyqtfnllda eftfdvdvsn lpcglngaly ftamdadggw skypankaga
181 kygtgycdsq cprdlkfidg qanvdgweps snndntgign hgsccpemdi weankistal
241 tphpcdsseq tmcegndcgg tysddryggt cdpdgcdfnp yrmgndsfyg pgktidtgsk
301 mtvvtqfitd gsgslseikr yyvqngnvia nadsnisgvt gnsittdfct aqkkafgded
361 ifaehnglag isdamssmvl ilslwddyya smewldsdyp enatatdpgv argtcdsesg
421 vpatvegahp dssvtfsnik fgpinstfsa sa
```

Sequence Listing

Aspergillus niger cellobiohydrolase B GH7,CBM1 (SEQ ID NO: 21)
```
  1 mssfqiyraa lllsilatan aqqvgtytte thpsltwqtc tsdgscttnd gevvidanwr
 61 wvhstssatn cytgnewdts ictddvtcaa ncaldgatye atygvttsgs elrlnfvtqg
121 ssknigsrly lmsddsnyel fkllgqeftf dvdvsnlpcg ingalyfvam dadggtseys
181 gnkagakygt gycdsqcprd ikfingeanc dgwepssnnv ntgvgdhgsc caemdvwean
241 sisnaftahp cdsvsqtmcd gdscggtysa sgdrysgtcd pdgcdynpyr igntdfygpg
301 ltvdtnspft vvtqfitddg tssgtlteik rlyvqngevi angastyssv ngssitsafc
361 esektlfgde nvfdkhggle gmgeamakgm vlvlslwddy aadmlwldsd ypvnssastp
421 gvargtcstd sgvpatveae spnayvtysn ikfgpigsty ssgsssgsgs sssssstttk
481 atsttlktts ttssgsssts aaqaygqcgg qgwtgpttcv sgytctyena yysqcl
```

GH3 beta-glucosidase from Trichoderma reesei (SEQ ID NO: 22)
```
  1 mryrtaaala latgpfarad shstsgasae avvppagtpw gtaydkakaa laklnlqdkv
 61 givsgvgwng gpcvgntspa skisypslcl qdgplgvrys tgstaftpgv qaastwdvnl
121 irergqfige evkasgihvi igpvagplgk tpqggrnweg fgvdpyltgi amgqtingiq
181 svgvqatakh yilneqelnr etissnpddr tlhelytwpf adavqanvas vmcsynkvnt
241 twacedqytl qtvlkdqlgf pgyvmtdwna qhttvqsans gldmsmpgtd fngnnrlwgp
301 altnavnsnq vptsrvddmv trilaawylt gqdqagypsf nisrnvqgnh ktnvraiard
361 givllkndan ilplkkpasi avvgsaaiig nharnspscn dkgcddgalg mgwgsgavny
421 pyfvapydai ntrassqgtq vtlsntdnts sgasaargkd vaivfitads gegyitvegn
481 agdrnnldpw hngnalvqav agansnvivv vhsvgaiile qilalpqvka vvwaglpsqe
541 sgnalvdvlw gdvspsgklv ytiakspndy ntrivsggsd sfseglfidy khfddanitp
601 ryefgyglsy tkfnysrlsv lstaksgpat gavvpggpsd lfqnvatvtv diansgqvtg
661 aevaqlyity pssaprtppk qlrgfaklnl tpgqsgtatf nirrrdlsyw dtasqkwvvp
721 sgsfgisvga ssrdirltst isva
```

AA9 LPMO from Trichoderma reesei (SEQ ID NO: 23)
```
  1 miqklsnllv talavatgvv ghghindivi ngvwyqaydp ttfpyesnpp ivvgwtaadl
 61 dngfvspday qnpdiichkn atnakghasv kagdtilfqw vpvpwphpgp ivdylancng
121 dcetvdkttl effkidgvgl isggdpgtwa sdvlisnnnt wvvkipdnla pgnyvirhei
181 ialhsagqan gaqnypqcfn iavsgsgslq psgvlgtdly hatdpgvlin iytsplnyii
241 pgptvvsglp tsvaqgssaa tatasatvpg ggsgptsrtt ttarttqass rpsstppatt
301 sapaggptqt lygqcggsgy sgptrcappa tcstlnpyya qcln
```

GH7 beta-gluanase (EGI) from Trichoderma reesei (SEQ ID NO: 24)
GenBank: AAA34212.1
```
  1 mapsvtlplt tailaiarlv aaqqpgtstp evhpklttyk ctksggcvaq dtsvvldwny
 61 rwmhdanyns ctvnggvntt lepdeategk ncfiegvdya asgvttsgss ltmnqympss
121 sggyssvspr lylldsdgey vmlklngqel sfdvdlsalp cgengslyls qmdenggganq
181 yntaganygs gycdaqcpvq twrngtlnts hqgfccnemd ilegnsrana ltphsctata
241 cdsagcgfnp ygsgyksyyg pgdtvdtskt ftiitqfntd ngspsgnivs itrkyqqngv
301 dipsaqpggd tisscpsasa ygglatmgka lssgmvlvfs iwndnsqymn widsgnagpc
361 sstegnpsni lannpnthvv fsnirwgdig sttnstappp ppassttfst trrssttsss
421 psctqthwgq cggigysgck tctsgttcqy sndyysqcl
```

GH5 beta-glucanase (EGII) from Trichoderma reesei (SEQ ID NO: 25)
GenBank: ABA64553.1
```
  1 mnksvaplll aasilyggav aqqtvwgqcg gigwsgptnc apgsacstln pyyaqcipga
 61 ttittstrpp sgpttttrat stsssppts sgvrfagvni agfdfgcttd gtcvtskvyp
121 plknftgsnn ypdgigqmqh fvnedgmtif rlpvgwqylv nnnlggnlds tsiskydqlv
181 qgclslgayc ivdihnyarw nggiigqggp tnaqftslws qlaskyasqs rvwfgimnep
241 hdvnintwaa tvqevvtair nagatsqfis lpgndwqsag afisdgsaaa lsqvtnpdgs
301 ttnlifdvhk yldsdnsgth aecttnnidg afsplatwlr qnnrqailte tgggnvqsci
361 qdmcqqiqyl nqnsdvylgy vgwgagsfds tyvltetptg sgnswtdtsl vssclark
```

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

What is claimed is:

1. A soluble sweetener composition, suitable for human consumption, the soluble sweetener composition comprising: one or more polysaccharide(s) comprising one or more soluble polysaccharide(s); and at least two oligosaccharides comprising at least two of oligosaccharides (i)-(vi):
   (i) a cello-oligosaccharide having a degree of polymerization (DP) from two to six;
   (ii) a xylo-oligosaccharide having a DP from two to twelve;
   (iii) a manno-oligosaccharide having a DP from two to twelve;
   (iv) an arabinoxylo-oligosaccharide having a DP from three to fifteen;
   (v) a mixed-linkage glucan oligosaccharide having a DP from two to five; or
   (vi) a chito-oligosaccharide having a DP from two to twelve, wherein the soluble sweetener composition comprises the one or more soluble polysaccharide(s) and the at least two oligosaccharides at a weight ratio from 1:100 to 1:1.

2. The soluble sweetener composition of claim 1, wherein the soluble sweetener composition is substantially free of insoluble polysaccharides.

3. The soluble sweetener composition of claim 1, wherein the soluble sweetener composition comprises from about 1% to about 50% the one or more polysaccharide(s) by weight.

4. The soluble sweetener composition of claim 1, wherein the soluble sweetener composition is soluble in water.

5. The soluble sweetener composition of claim 4, wherein a solubility of the soluble sweetener composition in the water is at least 80 g of the soluble sweetener composition per 100 g of the water at 50° C.

6. The soluble sweetener composition of claim 1, wherein the one or more soluble polysaccharide(s) comprise a xylan or a xyloglucan.

7. The soluble sweetener composition of claim 6, wherein the soluble sweetener composition comprises a cellulose derivative comprising at least one of a carboxymethyl cellulose, a hydroxypropylmethyl cellulose, a cellulose acetate, a hydroxyethylcellulose, or a hydroxymethylcellulose.

8. The soluble sweetener composition of claim 1, wherein the at least two oligosaccharides are independently derived from at least one biomass comprising at least one of a sugar cane biomass, a corn biomass, a wheat biomass, a hardwood biomass, or a softwood biomass.

9. The soluble sweetener composition of claim 1, wherein the at least two oligosaccharides comprise the (iv) arabinoxylo-oligosaccharide having a DP from three to fifteen.

10. The soluble sweetener composition of claim 1, wherein the at least two oligosaccharides comprise at least three of the (i) to (vi).

11. The soluble sweetener composition of claim 10, wherein the composition comprises a first oligosaccharide of the at least three oligosaccharides in a ratio by weight from 1:9 to 1:1 in relation a second of the at least three oligosaccharides.

12. The soluble sweetener composition of claim 1, wherein the cello-oligosaccharide has a degree of polymerization (DP) from two to four.

13. The soluble sweetener composition of claim 1, wherein the cello-oligosaccharide has a degree of polymerization (DP) from two to four and the xylo-oligosaccharide has a degree of polymerization (DP) from two to six.

14. The soluble sweetener composition of claim 1, wherein the soluble sweetener composition comprises less than 20% by dry weight of the one or more soluble polysaccharide(s).

15. The soluble sweetener composition of claim 1, wherein the soluble sweetener composition comprises the one or more soluble polysaccharide(s) and the at least two oligosaccharides at a weight ratio from 1:60 to 1:5.

16. The soluble sweetener composition of claim 1, wherein the soluble sweetener composition comprises from about 10% to about 20% of the one or more soluble polysaccharide(s) by weight.

17. A soluble sweetener composition, suitable for human consumption, the soluble sweetener composition comprising: one or more polysaccharide(s) comprising one or more soluble polysaccharide(s); and at least three oligosaccharides comprising at least three of oligosaccharides selected from the group of:
   a cello-oligosaccharide having a degree of polymerization (DP) from two to six;
   a manno-oligosaccharide having a DP from two to twelve;
   an arabinoxylo-oligosaccharide having a DP from three to fifteen;
   a mixed-linkage glucan oligosaccharide having a DP from two to five; and
   a chito-oligosaccharide having a DP from two to twelve;
   wherein the soluble sweetener composition comprises the one or more soluble polysaccharide(s) and the at least three oligosaccharides at a weight ratio from 1:100 to 1:1.

* * * * *